United States Patent
Zheng et al.

(10) Patent No.: US 9,119,905 B2
(45) Date of Patent: *Sep. 1, 2015

(54) BIODEGRADABLE ENDOPROSTHESES AND METHODS FOR THEIR FABRICATION

(71) Applicant: Elixir Medical Corporation, Sunnyvale, CA (US)

(72) Inventors: Xiaoxia Zheng, Mountain View, CA (US); John Yan, Los Gatos, CA (US); Vinayak Bhat, Cupertino, CA (US)

(73) Assignee: ELIXIR MEDICAL CORPORATION, Sunnyvale, CA (US)

( * ) Notice: Subject to any disclaimer, the term of this patent is extended or adjusted under 35 U.S.C. 154(b) by 0 days.
This patent is subject to a terminal disclaimer.

(21) Appl. No.: 14/461,159

(22) Filed: Aug. 15, 2014

(65) Prior Publication Data
US 2015/0025619 A1 Jan. 22, 2015

Related U.S. Application Data

(60) Continuation of application No. 13/897,302, filed on May 17, 2013, now Pat. No. 8,814,930, which is a continuation-in-part of application No. 13/536,957, filed on Jun. 28, 2012, now abandoned, which is a (Continued)

(51) Int. Cl.
*A61F 2/06* (2013.01)
*A61L 31/14* (2006.01)
(Continued)

(52) U.S. Cl.
CPC .............. *A61L 31/148* (2013.01); *A61F 2/82* (2013.01); *A61F 2/90* (2013.01); *A61F 2/91* (2013.01); *A61F 2/915* (2013.01); *A61L 31/048* (2013.01);

(Continued)

(58) Field of Classification Search
CPC .............. A61F 2/82; A61F 2/91; A61F 2/915; A61F 2/958; A61F 2/07; A61F 2002/82; A61F 2002/91; A61F 2002/07; A61F 2002/30062; A61F 2002/30064; A61L 31/148; A61L 31/06; A61L 31/048
USPC ............................. 623/1.11–1.15, 1.38–1.54
See application file for complete search history.

(56) References Cited

U.S. PATENT DOCUMENTS 3,867,190 A * 2/1975 Schmitt et al. ............... 427/2.25
5,441,483 A * 8/1995 Avitall ....................... 604/95.05
(Continued)

FOREIGN PATENT DOCUMENTS

| CN | 1328853 A | 1/2002 |
|---|---|---|
| CN | 1569270 A | 1/2005 |

(Continued)

OTHER PUBLICATIONS

U.S. Appl. No. 14/604,621, filed Jan. 23, 2015, Zheng et al.
Bae, et al. Drug delivery. Fundamentals and methods of tissue engineering. From 'Frontiers in Tissue Engineering' edited by Patrick et al. Feb. 20, 1998; Ch II.14:263-272.
(Continued)

*Primary Examiner* — Alvin Stewart
(74) *Attorney, Agent, or Firm* — Wilson Sonsini Goodrich & Rosati

(57) ABSTRACT

The disclosure provides biodegradable implantable devices such as a stent comprising a biodegradable polymeric wherein the polymeric material is treated to control crystallinity and/or Tg. The stent is capable to expand at body temperature in a body lumen from a crimped configuration to a deployed diameter and have sufficient strength to support a body lumen.

32 Claims, 41 Drawing Sheets

Related U.S. Application Data continuation-in-part of application No. 13/473,354, filed on May 16, 2012, now Pat. No. 8,323,760, which is a continuation of application No. 12/016,085, filed on Jan. 17, 2008, now Pat. No. 8,182,890, said application No. 13/536,957 is a continuation-in-part of application No. 13/434,555, filed on Mar. 29, 2012, now abandoned, which is a division of application No. 12/016,085, said application No. 13/536,957 is a continuation-in-part of application No. 12/016,077, filed on Jan. 17, 2008.

(60) Provisional application No. 60/885,700, filed on Jan. 19, 2007, provisional application No. 61/503,406, filed on Jun. 30, 2011, provisional application No. 61/540,881, filed on Sep. 29, 2011, provisional application No. 61/545,879, filed on Oct. 11, 2011, provisional application No. 61/555,668, filed on Nov. 4, 2011, provisional application No. 61/595,222, filed on Feb. 6, 2012, provisional application No. 61/645,956, filed on May 11, 2012.

(51) Int. Cl.

| | | |
|---|---|---|
| *A61F 2/82* | (2013.01) | |
| *A61F 2/915* | (2013.01) | |
| *A61L 31/06* | (2006.01) | |
| *A61F 2/91* | (2013.01) | |
| *A61F 2/90* | (2013.01) | |
| *A61L 31/04* | (2006.01) | |

(52) U.S. Cl.
CPC ........ *A61L 31/06* (2013.01); *A61F 2002/91558* (2013.01); *A61F 2002/91575* (2013.01); *A61F 2210/0004* (2013.01); *A61F 2210/0014* (2013.01); *A61F 2210/0019* (2013.01); *A61F 2230/0013* (2013.01); *A61F 2250/0073* (2013.01)

(56) References Cited

U.S. PATENT DOCUMENTS

| | | | |
|---|---|---|---|
| 5,447,724 A * | 9/1995 | Helmus et al. | 424/426 |
| 5,607,466 A * | 3/1997 | Imbert et al. | 623/1.11 |
| 5,670,161 A * | 9/1997 | Healy et al. | 623/1.42 |
| 5,674,286 A * | 10/1997 | D'Alessio et al. | 424/423 |
| 5,741,329 A * | 4/1998 | Agrawal et al. | 424/423 |
| 5,902,333 A * | 5/1999 | Roberts et al. | 606/191 |
| 5,935,119 A * | 8/1999 | Guy et al. | 604/500 |
| 5,957,975 A | 9/1999 | Lafont et al. | |
| 5,964,798 A * | 10/1999 | Imran | 623/1.12 |
| 5,980,564 A * | 11/1999 | Stinson | 623/23.7 |
| 6,039,755 A * | 3/2000 | Edwin et al. | 623/1.15 |
| 6,190,405 B1 * | 2/2001 | Culombo et al. | 623/1.15 |
| 6,224,803 B1 * | 5/2001 | Tiernan | 264/166 |
| 6,245,103 B1 * | 6/2001 | Stinson | 623/1.22 |
| 6,585,755 B2 * | 7/2003 | Jackson et al. | 623/1.15 |
| 6,626,939 B1 * | 9/2003 | Burnside et al. | 623/1.38 |
| 6,652,582 B1 * | 11/2003 | Stinson | 623/1.39 |
| 6,719,934 B2 * | 4/2004 | Stinson | 264/40.1 |
| 6,773,455 B2 * | 8/2004 | Allen et al. | 623/1.15 |
| 6,863,757 B1 * | 3/2005 | Gonzalez et al. | 156/86 |
| 6,896,695 B2 * | 5/2005 | Mueller et al. | 623/1.15 |
| 6,997,948 B2 * | 2/2006 | Stinson | 623/1.38 |
| 7,108,716 B2 * | 9/2006 | Burnside et al. | 623/1.38 |
| 7,258,697 B1 * | 8/2007 | Cox et al. | 623/1.16 |
| 7,279,005 B2 * | 10/2007 | Stinson | 623/1.22 |
| 7,291,166 B2 * | 11/2007 | Cheng et al. | 623/1.15 |
| 7,354,450 B2 * | 4/2008 | Bicek et al. | 623/1.15 |
| 7,377,939 B2 * | 5/2008 | Williams et al. | 623/1.46 |
| 7,390,333 B2 * | 6/2008 | Dutta | 623/1.46 |
| 7,563,277 B2 * | 7/2009 | Case et al. | 623/1.36 |
| 7,572,287 B2 * | 8/2009 | Stinson | 623/1.15 |
| 7,594,928 B2 * | 9/2009 | Headley et al. | 623/1.22 |
| 7,618,448 B2 * | 11/2009 | Schmitz et al. | 623/1.46 |
| 7,622,070 B2 * | 11/2009 | Atladottir et al. | 264/400 |
| 7,666,342 B2 * | 2/2010 | Limon et al. | 264/535 |
| 7,731,890 B2 | 6/2010 | Gale | |
| 7,824,601 B1 * | 11/2010 | Stankus et al. | 264/465 |
| 7,829,008 B2 * | 11/2010 | Gueriguian et al. | 264/454 |
| 7,875,233 B2 * | 1/2011 | Huang et al. | 264/512 |
| 7,964,136 B2 * | 6/2011 | Sabaria | 422/22 |
| 7,971,333 B2 * | 7/2011 | Gale et al. | 29/508 |
| 8,043,553 B1 * | 10/2011 | Durcan | 264/573 |
| 8,062,465 B1 * | 11/2011 | Huang et al. | 156/308.2 |
| 8,172,897 B2 * | 5/2012 | Gale et al. | 623/1.38 |
| 8,173,062 B1 * | 5/2012 | Durcan | 264/573 |
| 8,182,890 B2 * | 5/2012 | Zheng et al. | 428/36.9 |
| 8,241,554 B1 * | 8/2012 | Abbate et al. | 264/573 |
| 8,268,228 B2 * | 9/2012 | Huang et al. | 264/535 |
| 8,323,760 B2 * | 12/2012 | Zheng et al. | 428/36.9 |
| 8,425,587 B2 * | 4/2013 | Trollsas et al. | 623/1.16 |
| 8,501,079 B2 * | 8/2013 | Glauser et al. | 264/573 |
| 8,545,546 B2 * | 10/2013 | Wang | 623/1.15 |
| 8,636,792 B2 * | 1/2014 | Zheng et al. | 623/1.18 |
| 8,778,256 B1 * | 7/2014 | Huang et al. | 264/573 |
| 8,814,930 B2 * | 8/2014 | Zheng et al. | 623/1.38 |
| 8,834,556 B2 * | 9/2014 | Papp et al. | 623/1.16 |
| 8,840,660 B2 * | 9/2014 | Weber | 623/1.38 |
| 8,852,263 B2 * | 10/2014 | Wang | 623/1.15 |
| 9,005,276 B2 * | 4/2015 | Fox et al. | 623/1.44 |
| 2001/0016729 A1 * | 8/2001 | Divino et al. | 604/525 |
| 2001/0016769 A1 * | 8/2001 | Hojeibane | 623/1.15 |
| 2001/0016770 A1 * | 8/2001 | Allen et al. | 623/1.15 |
| 2001/0053929 A1 * | 12/2001 | Vonesh et al. | 623/1.12 |
| 2002/0161430 A1 * | 10/2002 | Jang | 623/1.16 |
| 2002/0165597 A1 * | 11/2002 | Clerc et al. | 623/1.2 |
| 2002/0193336 A1 * | 12/2002 | Elkins et al. | 514/44 |
| 2003/0004563 A1 | 1/2003 | Jackson et al. | |
| 2003/0033007 A1 * | 2/2003 | Sirhan et al. | 623/1.42 |
| 2003/0050692 A1 * | 3/2003 | Sirhan et al. | 623/1.42 |
| 2003/0064097 A1 * | 4/2003 | Patel et al. | 424/465 |
| 2003/0083732 A1 * | 5/2003 | Stinson | 623/1.15 |
| 2003/0093143 A1 * | 5/2003 | Zhao et al. | 623/1.15 |
| 2003/0144726 A1 * | 7/2003 | Majercak et al. | 623/1.15 |
| 2003/0144729 A1 * | 7/2003 | Bicek et al. | 623/1.16 |
| 2003/0199993 A1 * | 10/2003 | Gellman et al. | 623/23.75 |
| 2003/0236320 A1 * | 12/2003 | Martin et al. | 523/124 |
| 2004/0073290 A1 * | 4/2004 | Chouinard | 623/1.15 |
| 2004/0199242 A1 * | 10/2004 | Hong et al. | 623/1.16 |
| 2005/0031704 A1 * | 2/2005 | Ahn | 424/602 |
| 2005/0070991 A1 * | 3/2005 | Pienknagura | 623/1.11 |
| 2005/0075625 A1 * | 4/2005 | Dao et al. | 604/523 |
| 2005/0075716 A1 * | 4/2005 | Yan | 623/1.15 |
| 2005/0123588 A1 * | 6/2005 | Zhu et al. | 424/443 |
| 2005/0125051 A1 * | 6/2005 | Eidenschink et al. | 623/1.12 |
| 2005/0187615 A1 * | 8/2005 | Williams et al. | 623/1.34 |
| 2005/0209680 A1 * | 9/2005 | Gale et al. | 623/1.15 |
| 2005/0216074 A1 * | 9/2005 | Sahatjian et al. | 623/1.11 |
| 2005/0232964 A1 * | 10/2005 | Fennimore, Jr. | 424/423 |
| 2006/0025852 A1 * | 2/2006 | Armstrong et al. | 623/1.17 |
| 2006/0076708 A1 * | 4/2006 | Huang et al. | 264/239 |
| 2006/0100695 A1 * | 5/2006 | Peacock et al. | 623/1.42 |
| 2006/0111485 A1 * | 5/2006 | Laghi | 524/115 |
| 2006/0129222 A1 * | 6/2006 | Stinson | 623/1.2 |
| 2006/0147538 A1 * | 7/2006 | Craig et al. | 424/489 |
| 2006/0229711 A1 * | 10/2006 | Yan et al. | 623/1.38 |
| 2006/0251618 A1 * | 11/2006 | Dennis et al. | 424/85.4 |
| 2006/0265048 A1 * | 11/2006 | Cheng et al. | 623/1.15 |
| 2006/0287710 A1 * | 12/2006 | Lendlein et al. | 623/1.19 |
| 2007/0023974 A1 * | 2/2007 | Wu | 264/491 |
| 2007/0231365 A1 * | 10/2007 | Wang et al. | 424/426 |
| 2007/0253999 A1 * | 11/2007 | Huang et al. | 424/422 |
| 2007/0259099 A1 * | 11/2007 | Van Sciver | 427/2.24 |
| 2007/0270941 A1 * | 11/2007 | Headley et al. | 623/1.15 |
| 2007/0271763 A1 * | 11/2007 | Huang et al. | 29/508 |
| 2007/0278720 A1 * | 12/2007 | Wang et al. | 264/430 |
| 2007/0282426 A1 * | 12/2007 | Wang et al. | 623/1.15 |
| 2007/0282434 A1 * | 12/2007 | Wang et al. | 623/1.38 |
| 2007/0283552 A1 * | 12/2007 | Gale et al. | 29/515 |
| 2007/0290412 A1 * | 12/2007 | Capek et al. | 264/512 |

(56) References Cited

U.S. PATENT DOCUMENTS

| | | | |
|---|---|---|---|
| 2007/0299505 A1* | 12/2007 | Gregorich et al. | 623/1.15 |
| 2008/0051866 A1* | 2/2008 | Chen et al. | 623/1.11 |
| 2008/0081063 A1* | 4/2008 | Wang et al. | 424/426 |
| 2008/0097571 A1* | 4/2008 | Denison et al. | 623/1.11 |
| 2008/0097580 A1* | 4/2008 | Dave | 623/1.16 |
| 2008/0103584 A1 | 5/2008 | Su et al. | |
| 2008/0147165 A1* | 6/2008 | Hossainy et al. | 623/1.15 |
| 2008/0177373 A1* | 7/2008 | Huang et al. | 623/1.15 |
| 2008/0177374 A1* | 7/2008 | Zheng et al. | 623/1.15 |
| 2008/0243243 A1* | 10/2008 | Williams et al. | 623/1.47 |
| 2008/0249608 A1* | 10/2008 | Dave | 623/1.16 |
| 2008/0306579 A1* | 12/2008 | Dolan et al. | 623/1.11 |
| 2009/0095715 A1* | 4/2009 | Sabaria | 216/83 |
| 2009/0096137 A1* | 4/2009 | Williams et al. | 264/540 |
| 2009/0099639 A1* | 4/2009 | Sabaria | 623/1.11 |
| 2009/0105800 A1* | 4/2009 | Sabaria | 623/1.11 |
| 2009/0146348 A1* | 6/2009 | Huang et al. | 264/573 |
| 2009/0208555 A1* | 8/2009 | Kuttler et al. | 424/426 |
| 2009/0228094 A1 | 9/2009 | Yan et al. | |
| 2010/0036478 A1* | 2/2010 | Wang et al. | 623/1.15 |
| 2010/0038822 A1* | 2/2010 | Wang et al. | 264/294 |
| 2010/0198331 A1 | 8/2010 | Rapoza et al. | |
| 2010/0244329 A1* | 9/2010 | Hossainy et al. | 264/479 |
| 2010/0252965 A1* | 10/2010 | Wang et al. | 264/563 |
| 2010/0262224 A1* | 10/2010 | Kleiner | 623/1.15 |
| 2010/0292773 A1* | 11/2010 | Schmid et al. | 623/1.11 |
| 2011/0022163 A1* | 1/2011 | Wang et al. | 623/1.49 |
| 2011/0054591 A1* | 3/2011 | Sahatjian et al. | 623/1.15 |
| 2011/0062638 A1* | 3/2011 | Glauser et al. | 264/532 |
| 2011/0215505 A1* | 9/2011 | Kleiner et al. | 264/346 |
| 2011/0238162 A1* | 9/2011 | Busold et al. | 623/1.46 |
| 2011/0260352 A1* | 10/2011 | Tang et al. | 264/51 |
| 2011/0260358 A1* | 10/2011 | Wang et al. | 264/234 |
| 2012/0071962 A1 | 3/2012 | Huang et al. | |
| 2012/0187606 A1* | 7/2012 | Zheng et al. | 264/400 |
| 2012/0226345 A1* | 9/2012 | Zheng et al. | 623/1.15 |
| 2012/0271396 A1* | 10/2012 | Zheng et al. | 623/1.2 |
| 2012/0290070 A1* | 11/2012 | Wang et al. | 623/1.15 |
| 2012/0290071 A1* | 11/2012 | Wang et al. | 623/1.15 |
| 2013/0084322 A1* | 4/2013 | Wu | 424/426 |
| 2013/0085564 A1* | 4/2013 | Papp et al. | 623/1.15 |
| 2013/0150943 A1* | 6/2013 | Zheng et al. | 623/1.2 |
| 2013/0331927 A1* | 12/2013 | Zheng et al. | 623/1.19 |
| 2014/0004312 A1* | 1/2014 | Foreman et al. | 428/172 |
| 2014/0018903 A1* | 1/2014 | Eli et al. | 623/1.16 |
| 2014/0025161 A1* | 1/2014 | Stankus et al. | 623/1.19 |
| 2014/0121294 A1* | 5/2014 | Huang et al. | 523/113 |
| 2014/0188243 A1* | 7/2014 | Zheng et al. | 623/23.7 |
| 2014/0252683 A1* | 9/2014 | Huang et al. | 264/400 |
| 2014/0277373 A1* | 9/2014 | Huang et al. | 623/1.15 |
| 2014/0350659 A1* | 11/2014 | Zheng et al. | 623/1.15 |
| 2015/0025619 A1* | 1/2015 | Zheng et al. | 623/1.38 |
| 2015/0073536 A1* | 3/2015 | Rapoza et al. | 623/1.38 |

FOREIGN PATENT DOCUMENTS

| | | | | |
|---|---|---|---|---|
| JP | H 11-512626 A | 11/1999 | | |
| JP | 2000-202032 A | 7/2000 | | |
| JP | 2003-500101 A | 1/2003 | | |
| JP | 2004-149692 A | 5/2004 | | |
| JP | 2005-298617 A | 10/2005 | | |
| JP | 2006-192111 | 7/2006 | | |
| JP | 2006-223860 A | 8/2006 | | |
| WO | WO 92/04393 A1 | 3/1992 | | |
| WO | WO 01/95834 A1 | 12/2001 | | |
| WO | WO02/091956 A1 * | 11/2002 | | A61F 2/06 |
| WO | WO 03/034940 A2 | 5/2003 | | |
| WO | WO 2004/052420 A2 | 6/2004 | | |
| WO | WO 2004/080332 A2 | 9/2004 | | |
| WO | WO 2004/110315 A1 | 12/2004 | | |
| WO | WO 2004/110515 A1 | 12/2004 | | |
| WO | WO 2004/080332 A3 | 4/2005 | | |
| WO | WO 2005/096992 A1 | 10/2005 | | |
| WO | WO 2005/115277 A2 | 12/2005 | | |
| WO | WO 2005/115277 A3 | 5/2007 | | |
| WO | WO 2007/126599 A2 | 11/2007 | | |
| WO | WO 2007/146354 A2 | 12/2007 | | |
| WO | WO 2008/002479 A2 | 1/2008 | | |
| WO | WO 2008/002636 A2 | 1/2008 | | |
| WO | WO 2008/005390 A1 | 1/2008 | | |
| WO | WO 2008/008416 A1 | 1/2008 | | |
| WO | WO 2008/011048 A2 | 1/2008 | | |
| WO | WO 2007/146354 A3 | 2/2008 | | |
| WO | WO 2008/016667 A2 | 2/2008 | | |
| WO | WO 2008/016696 A2 | 2/2008 | | |
| WO | WO 2008/016696 A3 | 3/2008 | | |
| WO | WO 2008/033263 A2 | 3/2008 | | |
| WO | WO 2008/002636 A3 | 4/2008 | | |
| WO | WO 2008/051867 A2 | 5/2008 | | |
| WO | WO 2007/126599 A3 | 7/2008 | | |
| WO | WO 2008/051867 A3 | 8/2008 | | |
| WO | WO 2008/002479 A3 | 9/2008 | | |
| WO | WO 2008/016667 A3 | 11/2008 | | |
| WO | WO 2008/137821 A1 | 11/2008 | | |
| WO | WO 2008/011048 A3 | 3/2009 | | |
| WO | WO 2008/033263 A3 | 4/2009 | | |

OTHER PUBLICATIONS

Breiby, et al. Quantification of preferential orientation in conjugated polymers using X-ray diffraction. J. Polymer Science Part B: Polymer Physics. 2003; 41(20):2375-2393.

Cruz, et al. Quantitative mapping of the orientation of fibroin beta-sheets in B. mori cocoon fibers by scanning transmission X-ray microscopy. Biomacromolecules. Mar. 2006;7(3):836-43.

Donald, et al. Electron Microscopy of Banded Structures in Oriented Thermotropic Polymers. J. Materials Science. 1983; 18:1143-1150.

Fuhrman, et al. Central nervous system. From 'Tissue Engineering: From Lab to Clinic' edited by Pallua et al. 2010; Ch12:221-244.

Hacker, et al. Synthetic polymers. From 'Principles of Regenerative Medicine 2nd ed.' Edited by Atala et al. 2011; Ch 33:587-622.

Hara. Ion-containing polymers and their biological interactions. Polyelectrolytes Science and Technology. 1993; Ch 6:321-325.

Hombreiro-Perez, et al. Non-degradable microparticles containing a hydrophilic and/or a lipophilic drug: preparation, characterization and drug release modeling. J Control Release. Mar. 26, 2003;88(3):413-28.

Lamberti, et al. Real-time orientation and crystallinity measurements during the isotactic polypropylene film-casting process. J. Polymer Science Part B: Polymer Physics. 2003; 41(9):998-1008.

Lee, et al. Retardation of enzymatic degradation of microbial polyesters using surface chemistry: effect of addition of non-degradable polymers. Surface Science. 2003; 542(3):235-243.

Ma, et al. Scaffolding in Tissue Engineering. 2005; pp. 78-80.

Majoros, et al. Poly(amidoamine) dendrimer synthesis and characterization. Dendrimer-based Nanomedicine. 2008; Ch 3:35-57.

Qin, et al. Synthesis and Characterization of Unsaturated Thermotropic Polyesters Prepared via Acyclic Diene Metathesis Polymerization. Macromolecules. 2004; 37:5239-5249.

Sanders. Controlled delivery systems for peptides. From 'Peptide and protein drug delivery' Edited by Vincent Lee, Advances in Parenteral science vol. 4. 1990; Ch 19:785-806.

Seal, et al. Polymeric biomaterials for tissue and organ regeneration. Materials Science and Engineering. R34. 2001; 147-230.

Shastri. Non-degradable biocompatible polymers in medicine: past, present, and future. Current Pharmaceutical Biotechnology. 2003; 4:331-337.

Tanimoto, et al. Comparison of in vivo acute stent recoil between the bioabsorbable everolimus-eluting coronary stent and the everolimus-eluting cobalt chromium coronary stent: insights from the Absorb and Spirit trials. Catheter Cardiovasc Interv. Oct. 1, 2007;70(4):515-23.

Valimaa, et al. Viscoelastic memory and self-expansion of self-reinforced bioabsorbable stents. Biomaterials. Sep. 2002;23(17):3575-82.

Weir, et al. Processing, Annealing and Sterilisation of Poly-L-Lactide. Biomaterials. 2004; 25:3939-3949.

\* cited by examiner proximal end                                                               distal end

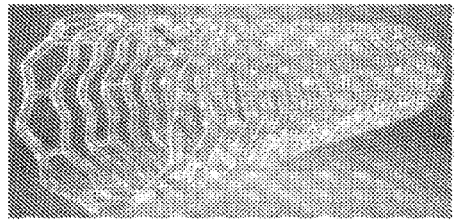 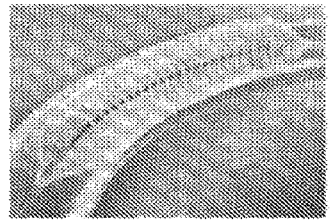
FIGURE 26A   FIGURE 26B
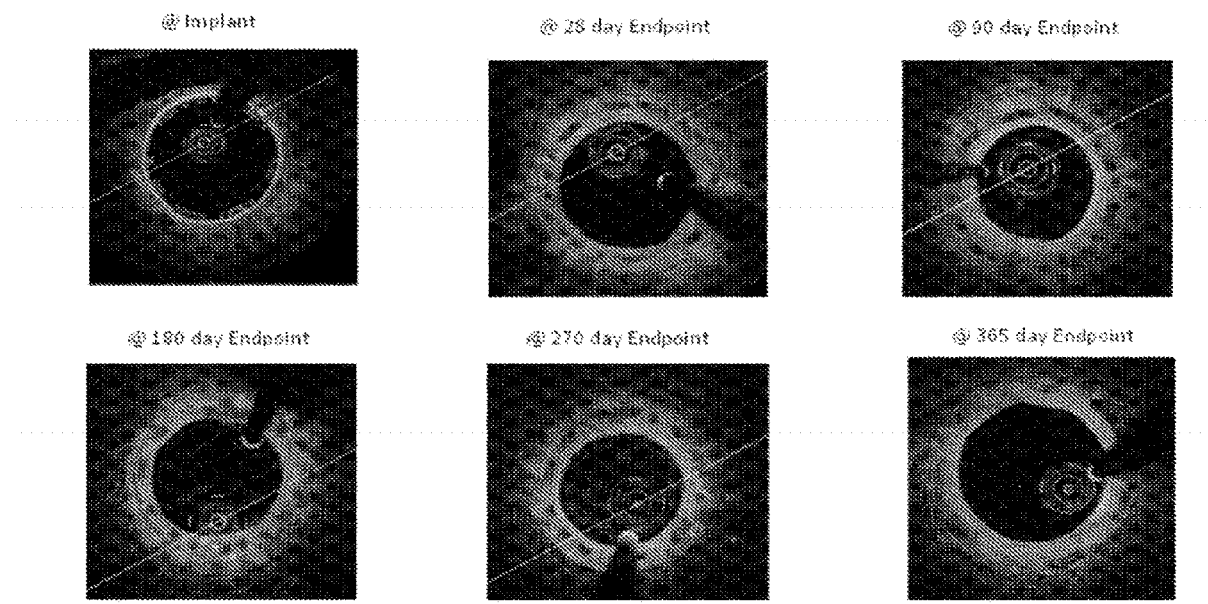
FIGURE 27

BIODEGRADABLE ENDOPROSTHESES AND METHODS FOR THEIR FABRICATION

CROSS-REFERENCE

This application is a continuation of U.S. patent application Ser. No. 13/897,302, filed May 17, 2013, which is a continuation-in-part of U.S. patent application Ser. No. 13/536,957, filed Jun. 28, 2012, which is a continuation-in-part of U.S. patent application Ser. No. 13/473,354, filed May 16, 2012, issued as U.S. Pat. No. 8,323,760, which is in turn a continuation application of U.S. patent application Ser. No. 12/016,085, filed Jan. 17, 2008 and issued as U.S. Pat. No. 8,182,890 on May 22, 2012, which in turn claims the benefit of U.S. Provisional Application 60/885,700 filed on Jan. 19, 2007; U.S. patent application Ser. No. 13/536,957 is also a continuation-in-part of U.S. patent application Ser. No. 13/434,555, filed Mar. 29, 2012, which is a divisional application of U.S. patent application Ser. No. 12/016,085, filed Jan. 17, 2008 and issued as U.S. Pat. No. 8,182,890 on May 22, 2012, which in turn claims the benefit of U.S. Provisional Application 60/885,700 filed on Jan. 19, 2007; and U.S. patent application Ser. No. 13/536,957 is also a continuation-in-part of U.S. patent application Ser. No. 12/016,077, filed Jan. 17, 2008, which claims the benefit of U.S. Provisional Application 60/885,700, filed Jan. 19, 2007. U.S. patent application Ser. No. 13/536,957 also claims the benefit of U.S. Provisional Application 61/503,406, filed Jun. 30, 2011; U.S. Provisional Application 61/540,881, filed Sep. 29, 2011; U.S. Provisional Application 61/545,879, filed Oct. 11, 2011; U.S. Provisional Application 61/555,668, filed Nov. 4, 2011; U.S. Provisional Application 61/595,222, filed Feb. 6, 2012; and U.S. Provisional Application 61/645,956, filed May 11, 2012.

BACKGROUND OF THE INVENTION

1. Field of the Invention

The present invention relates generally to medical devices and methods for their fabrication. In particular, the present invention relates to the fabrication of biodegradable endoprostheses, such as stents, having enhanced strength and controlled persistence after implantation.

Stents are generally tubular-shaped devices which function to hold open or reinforce a segment of a blood vessel or other body lumen, such as a coronary artery, carotid artery, saphenous vein graft, or femoral artery. They also are suitable to support and hold back a dissected arterial lining that could occlude the body lumen, to stabilize plaque, or to support bioprosthetic valves. Stents can be formed from various materials, particularly polymeric and/or metallic materials, and may be non-degradable, biodegradable, or be formed from both degradable and non-degradable components. Stents are typically delivered to the target area within the body lumen using a catheter. With balloon-expandable stents, the stent is mounted to a balloon catheter, navigated to the appropriate area, and the stent is expanded by inflating the balloon. A self-expanding stent is delivered to the target area and released, expanding to the required diameter to treat the disease. Stents may also elute various drugs and pharmacological agents.

Of particular interest to the present invention, biodegradable stents and other endoprostheses are usually formed from polymers which degrade by hydrolysis and other reaction mechanisms in the vascular or other luminal environment over time.

For these reasons, it would be desirable to provide improved endoprostheses and methods for their fabrication.

2. Description of the Background Art

Heat annealing and other treatments of filaments and other components used in stents are described in U.S. Pat. Nos. 5,980,564, 6,245,103, and 6,626,939. Heat treatment of polymeric stent coatings is described in International Application No. PCT/US07/81996, which designates the United States.

Biodegradable implantable devices and methods of making them are also described in commonly owned U.S. Provisional Patent Application No. 60/668,707, filed on Apr. 5, 2005; U.S. Provisional Patent Application No. 60/885,700, filed on Jan. 19, 2007; U.S. patent application Ser. No. 11/398,363, filed on Apr. 4, 2006; U.S. patent application Ser. No. 12/016,077, filed on Jan. 17, 2008; and U.S. patent application Ser. No. 12/016,085, filed on Jan. 17, 2008, the entire disclosure of each of which is incorporated herein by reference.

SUMMARY OF THE INVENTION

In an aspect of the invention, improved biodegradable endoprostheses and methods for their fabrication are provided. The stent prostheses may be formed from one or more amorphous, semi-crystalline, or crystalline biodegradable polymers. The use of amorphous polymers is preferable in some cases since they can provide relatively short periods of biodegradation, usually less than two years, often less than one year, frequently less than nine months, and sometimes shorter than six months, or even shorter.

In some embodiments of the invention, the polymers are modified or treated to introduce a desired degree of crystallinity. In other embodiments, introducing crystallinity into the polymer increases the strength of the polymer so that it is suitable for use as an endoprosthesis and in some cases without substantially lengthening the period of biodegradation after implantation. In other embodiments, the polymeric material is treated to achieve a desired degree of crystallinity. In other embodiments, the polymeric material is treated to control crystallinity.

In an embodiment, treatment comprises a heat treatment of the polymeric material or the tubular body preferably at an initial diameter to a temperature above its glass transition temperature of the polymeric material and below its melting point for a period ranging from a fraction of a second to 7 days. Initial diameter is the diameter of the polymeric material or the tubular body as-formed, or the diameter before patterning, or the diameter after patterning, or the diameter before crimping. The polymeric material or the tubular body in one embodiment may be cooled after heating to a temperature ranging from below ambient temperature to ambient or above temperature over a period ranging from a fraction of a second to 7 days. In a preferred embodiment, the tubular body or polymeric material initial diameter is approximately 1-1.5 times the stent deployment diameter. In one embodiment, the tubular body is treated at diameter below initial diameter, or between initial diameter and crimped diameter. In a further embodiment, the treatment comprises heating the tubular body to a temperature about or below Tg for a period ranging from a fraction of a second to 7 days. In another embodiment, the heat treatment at the below initial diameter comprises heat treatment about or above Tg and below Tm for a period ranging from a fraction of a second to 5 hours, or preferably less than 2 hour, or more preferably less than 60 minutes, or most preferably less than 15 minutes. In another embodiment, the polymeric material or the tubular body after forming is treated comprising heat at temperature about or less than Tg.

In another embodiment, the tubular body after forming and excluding patterning is treated comprising heat at temperature about or less than Tg. Durations are similar to above ranges. Other suitable temperatures and times are described herein. In another embodiment, the initial diameter is 0.9-1.5 times the stent deployment diameter, or the stent nominal diameter. The stent nominal diameter is the labeled deployment stent diameter. The stent deployment diameter usually is the deployed diameter of the stent at nominal or bigger diameter. In another embodiment, the initial diameter is smaller than the deployed stent diameter or smaller than the labeled stent deployed diameter.

In some embodiments, a method according to the present invention for fabricating a biodegradable prosthesis comprises providing a tubular body having an initial diameter, wherein said tubular body is composed at least partially of a substantially amorphous biodegradable polymer, while the diameter remains substantially unchanged; heating the tubular body to a temperature above a glass transition temperature of the polymer and below the melting point of the polymer; cooling the tubular body to increase the crystallinity of the polymer; and patterning the tubular body into a structure capable of radial contraction and expansion.

In one embodiment, the stent prosthesis after deployment from a crimped configuration to an expanded diameter in physiologic environment further expands to a larger diameter. In another embodiment, the stent prosthesis after deployment from a crimped configuration to an expanded diameter in physiologic environment further expands to a larger diameter by at least 0.05 mm within 20 minutes. In another embodiment, the stent prosthesis after deployment from a crimped configuration to an expanded diameter in physiologic environment further expands to a larger diameter by at least 0.1 mm within 20 minutes. In another embodiment, the stent prosthesis after deployment from a crimped configuration to an expanded diameter in physiologic environment further expands to a larger diameter substantially apposing the body lumen. The stent prosthesis after deployment from a crimped configuration to an expanded diameter in physiologic environment further expands to a larger diameter substantially apposing the body lumen within 9 months. In another embodiment, the at least some of the struts of the stent prosthesis after deployment from a crimped configuration to an expanded diameter in physiologic environment further expands to a larger diameter substantially apposing the body lumen.

In some embodiments, the optional heat treatment of the one or more biodegradable polymeric materials, or the tubular body, the stent material, or the stent may occur at a temperature below $T_g$, or at about $T_g$, or at greater than $T_g$ of the one or more biodegradable polymeric materials. In some embodiments, the optional heating may take place at a temperature within 2° C., or within 4° C., or within 6° C., or within 8° C., or within 10° C., or within 12° C., or within 14° C., or within 16° C., or within 18° C., or within 20° C. of $T_g$ of the one or more biodegradable polymeric materials (where "within" may be above or below the $T_g$). In some embodiments the optional treating, such as heating, may take place for at least about $1 \times 10^{-12}$ seconds (s), or at least about $1 \times 10^{-9}$ s, or at least about $1 \times 10^{-6}$ s, or at least about $1 \times 10^{-3}$ s, or at least about $1 \times 10^{-2}$ s, or at least about 0.1 s, or at least about 1 s, or at least about 10 s, or at least about 1 minute (min), or at least about 10 min, or at least about 1 hour (h) or at least about 10 h, or at least about 1 day, or at least about 5 days, or at least about 10 days, or at least about 1 month, or at least about 2 months, or at least about 3 months, or at least about 4 months, or at least about 5 months, or at least about 6 months, or at least about 1 year. In some cases, the treating, such as heating, may take place for about 1 min to about 10 min, or about 3 min to about 10 min, or about 5 min to about 10 min, or about 3 min to about 10 min, or about 30 seconds to about 24 hours.

In some embodiments, the polymers' crystallinity after modification or treatment is increased by at least 10% of the original crystallinity of the polymer material, preferably by at least 20% of the original crystallinity of the polymer material, preferably by at least 50% of the original crystallinity of the polymer material, and more preferably by at least 100% of the original crystallinity of the polymer material.

In other embodiments, the crystallinity of the polymeric material after modification is decreased by at least 10% of the original crystallinity of the polymer material before modification, preferably by at least 20% of the original crystallinity of the polymer material, preferably by at least 50% of the original crystallinity of the polymer material, and more preferably by at least 100% of the original crystallinity of the polymer material, and more preferably by at least 1000% of the original crystallinity of the polymer material. In other embodiments, treatment or modification of the polymeric material has crystallinity that is substantially the same after treatment and before treatment of the polymeric material.

In preferred embodiments, polymer materials will have a crystallinity in the range from 10% to 20% after modification as described herein below. In yet other preferred embodiments, polymer materials will have a crystallinity in the range from 1 to 10%, or 10% to 30% after modification. In yet other preferred embodiments, polymer materials will have a crystallinity between 1% and 35% after modification. In yet other preferred embodiments, polymer materials will have a crystallinity between 1% and 40% after modification. As used herein and as known to skilled in the art, "crystallinity" refers to a degree of structural order or perfection within a polymer matrix as known to someone skilled in the art and methods to measure crystallinity as well such as differential scanning calorimetry.

In some embodiments, the one or more materials comprising the body, or the stent, or the tubular body may have a controlled crystallinity. In some embodiments, the crystallinity is less than 50%, or less than 40%, or less than 35%, or less than 30%, or less than 25%, or less than 20%, or less than 15%, or less than 10%, or less than 5%. In some embodiments, the one or more materials comprising the body, or the stent, or the tubular body, or the polymeric material may have a crystallinity of about 0% or greater than 0%, or greater than 5%, or greater than 10%, or greater than about 15%, or greater than about 20%, or greater than about 25%, or greater than about 30%, or greater than about 35%, or greater than 40%, or greater than 50%. In some embodiments, the one or more materials comprising the body, or the stent, or the tubular body may have a crystallinity of about 0% to less than 60%, or about 0 to less than 55%, or about 0 to less than 50%, or about 0 to less than 40%, or about 0% to less than 35%, or about 0% to less than 30%, or about 0% to less than 25%, or about 0% to less than 20%, or about 0% to less than 15%, or about 0% to less than 10%, or about 0% to less than 5%. In some embodiments, the one or more materials comprising the body, or the stent, or the tubular body or polymeric material may have a crystallinity of about 5% to about 60%, or about 5% to about 55%, or about 5% to about 50%, or about 5% to about 40%, or about 5% to about 45%, or about 5% to about 30%, or about 10% to about 25%, or about 15% to about 20%.

In some embodiments, the polymer or polymeric material after treatment is amorphous, in other embodiments the polymer or polymeric material after treatment is semi-crystalline, yet in other embodiments the polymer or polymeric material after treatment is crystalline. In a preferred embodiment, the polymeric material prior to a treatment is amorphous. In other embodiments, the polymeric material prior to a treatment is semi-crystalline. In a further embodiment, the polymeric material prior to a treatment is crystalline.

Crystallinity can be measured by differential scanning calorimetry (Reading, M. et al, Measurement of crystallinity in polymers using modulated temperature differential scanning calorimetry, in Material Characterization by Dynamic and Modulated Thermal Analytical Techniques, ASTM STP 1402, Riga, A. T. et al. Ed, (2001) pp. 17-31.

In another aspect of the invention, methods for fabricating biodegradable prostheses are provided. The preferred methods comprise providing a tubular body having an initial diameter as-formed, or before patterning, or after patterning, where the tubular body comprises a biodegradable polymeric material. In one embodiment, the polymeric material comprises one or more polymers, or one or more co-polymers, or a combination thereof. In another embodiment, the polymeric material comprises one or more polymers, or one or more co-polymers, or one or more monomers, or a combination thereof. The polymeric material or the tubular body is treated to control crystallinity preferably to between 1% and 50%, or more preferably to between 1% and 35%. In one embodiment the polymeric material or the tubular body treatment comprises a heat treatment preferably at substantially the initial diameter, preferably when the initial diameter is 1-1.5 times the stent deployment diameter, to a temperature above glass transition temperature of the polymeric material and below its melting point for a period ranging from a fraction of a second to 7 days. The polymeric material or the tubular body in one embodiment may be cooled after heating to a temperature ranging from below ambient temperature to ambient or above temperature over a period ranging from a fraction of a second to 7 days. In a preferred embodiment, the polymeric material or the tubular body initial diameter is approximately 1-1.5 times the stent deployment diameter or stent nominal deployment diameter, or stent labeled deployment diameter. In another preferred embodiment, the initial diameter is approximately 0.9-1.5 times the stent deployment diameter or stent nominal deployment diameter, or stent labeled deployment diameter. In another embodiment, the initial diameter is smaller than the stent deployment diameter or stent nominal deployment diameter, or stent labeled deployment diameter. The stent deployment diameter in a preferred embodiment is typically the diameter of the stent deployed to approximately nominal or labeled stent diameter but can also be the deployed diameter above the stent nominal or labeled diameter. Stent nominal deployed diameter can be accomplished in one example by inflating the deploying balloon to nominal or labeled diameter to deploy the stent to nominal or labeled diameter. In a preferred embodiment, the polymeric material or the tubular body is patterned at substantially the initial diameter and is crimped subsequently to a crimped diameter that is smaller than the initial diameter. In one embodiment, the polymeric material or the tubular body is treated at diameter between initial diameter and crimped diameter. In a further embodiment, the treatment comprises heating the tubular body to a temperature about or below Tg for a period ranging from a fraction of a second to 7 days. In another embodiment, the heat treatment at the below initial diameter comprises heat treatment about or above Tg and below Tm for a period ranging from a fraction of a second to 5 hours, or preferably less than 2 hour, or most preferably less than 60 minutes, or most preferably less than 15 minutes. The patterned stent in one embodiment is crimped in one or more steps and fitted onto a delivery system or crimped onto the delivery system at a diameter that is less than the initial diameter. In another embodiment, the crimped diameter is less than 3 mm, in another embodiment, the crimped diameter is less than 2.5 mm, in another embodiment, the crimped diameter is less than 2.0 mm in a third embodiment, the crimped diameter is less than 1.5 mm, in a fourth embodiment, the crimped diameter is less than 1 mm, in a fifth embodiment, the crimped diameter is less than 0.8 mm. In a preferred embodiment, the stent is capable to expand from the crimped diameter to a deployed diameter preferably at about body temperature (in water or dry) and have sufficient strength to support a body lumen. In a further preferred embodiment, the stent is capable to expand from the crimped diameter to a deployed diameter at about body temperature (in aqueous or water or dry) without fracture and have sufficient strength to support a body lumen. In a further preferred embodiment, the stent is capable to crimp from an expanded diameter, wherein the expanded diameter is larger than the crimped diameter, and expand from the crimped diameter to a deployed diameter at about body temperature (in aqueous or water or dry) without fracture and have sufficient strength to support a body lumen.

In some embodiments, sufficient radial strength to support a body lumen is maintained for at least 1 month, or for at least 2 months, for at least 3 months. In some embodiments, the diameter of the scaffold increases after expansion to nominal diameter or between nominal and 1.1 times nominal diameter by 0.1 mm to 0.5 mm between 5 minutes after deployment to an expanded diameter and 1 hour. In other embodiments, the diameter of the scaffold did not substantially decrease over time. In still other embodiments, the diameter of the scaffold did not substantially increase over time.

In some embodiments, an expandable stent comprising a biodegradable polymeric material having an initial configuration is provided. The expandable stent at body temperature can be self-expandable from a crimped configuration and further expandable to a second larger configuration. In further embodiments, the polymeric material has been treated to control one or more of crystallinity, Tg, or molecular weight. In some embodiments, the Tg ranges from about 20° C. to about 50° C. In some embodiments, the second configuration is a deployed configuration. In some embodiments, the stent expands to the first and second configurations without fracture and has sufficient strength to support a body lumen. In some embodiments, the first expanded configuration has a transverse dimension of at least 0.35 times, or at least 0.45 times, or at least 0.55 times, or at least 0.55 times, or at least 0.7 times, or at least 0.8 times, or at least 1 times the transverse dimension of the initial configuration. In some embodiments, the stent expands to the first expanded configuration within a period of 24 hours, or 12 hours, or 4 hours, or 2 hours, or 1 hour, or 30 minutes, or 5 minutes or 30 seconds. In some embodiments, the stent is balloon expandable to the second expanded configuration without fracture and with sufficient strength to support a body lumen.

In some embodiments, an expandable stent comprising a biodegradable polymeric material having an initial configuration is provided. The expandable stent at body temperature can be expandable from a crimped configuration to a first expanded configuration and self expandable to a second larger configuration. In further embodiments, the polymeric material is treated to control one or more of crystallinity, Tg, or molecular weight. In some embodiments, the expandable stent comprises a substantially continuous tubular body. In some embodiments, the stent expands to the first configuration without fracture and has sufficient strength to support a body lumen. In some embodiments, the stent has a nominal expanded configuration with a transverse dimension and the first expanded configuration has a transverse dimension that is at least 1 times the transverse dimension of the transverse dimension of the nominal expanded configuration. In some embodiments, the first expanded configuration is a deployed configuration. In some embodiments, the stent has a nominal expanded configuration with a transverse dimension and the first expanded configuration has a transverse dimension that is 1 time, or 1.1 times, or 1.2 times, or 1.3 times, or 1.35 times, or 1.4 times, or 1.45 times, or 1.5 times the transverse dimension of the transverse dimension of the nominal expanded configuration.

Fabricating a biodegradable stent can be accomplished through a variety of ways. In a preferred embodiment, the biodegradable stent is fabricated by forming a tubular body using extrusion, molding such as injection molding, dipping, spraying such as spraying a tube or mandrel, printing such as 3D printing. The tubular body in a preferred embodiment is formed first and then patterned into a structure capable of radial expansion from a crimped configuration preferably at body temperature. The tubular body in another preferred embodiment is formed first and then patterned into a structure capable of radial expansion from a crimped configuration preferably at body temperature and preferably without fracture. The tubular body in another preferred embodiment is formed first and then patterned into a structure capable of being crimped from an expanded configuration to a crimped diameter (at temperature about Tg or less than Tg), and at body temperature capable to be expanded from the crimped configuration preferably without fracture. In another preferred embodiment the polymeric material is patterned first and then forms a tubular body/stent capable of radial expansion at body temperature and/or capable to be crimped preferably at temperature about Tg or less than Tg. In another preferred embodiment, the biodegradable stent is fabricated from a sheet (such as a flat sheet) joined at ends (such as opposite ends) to form a tubular body capable of radial expansion preferably at body temperature and/or capable to be crimped preferably at temperature about Tg or less than Tg, and patterned before and/or after joining. Joining sheet ends can be accomplished by a variety of methods such as adhesive, ultrasound, welding, melting the ends, chemical means, or treatment such as heating. The tubular body formed from a sheet can be further treated to control crystallinity and Tg as described in this patent application. The tubular body formed form the sheet has an initial diameter, preferably 1-1.5 times the stent deployed diameter. In other preferred embodiment, the biodegradable stent is fabricated from weaving or braiding polymeric material fibers into a tubular body structure capable of expansion at body temperature and/or capable to be crimped at temperature preferably about Tg or less than Tg. Preferably, weaving or braiding of the polymeric material such as fibers into the initial tubular configuration which is capable of radial expansion at body temperature and/or capable of being crimped from an expanded diameter preferably at temperature about Tg or less than Tg (in aqueous or dry environment) wherein the initial diameter is preferably 1-1.5 times the stent deployed diameter (or the stent nominal diameter, or the stent labeled diameter) and preferably treated at the initial tubular diameter, to achieve controlled crystallinity preferably between 0 and 45%, or more preferably between 0 and 35% and a Tg greater than 37° C. and less than 50° C., or more preferably greater than 37° C. and less than 45° C.) and the stent is capable to expand from a crimped configuration to an expanded configuration/diameter at body temperature and has sufficient strength to support a body lumen, and preferably without fracture. In another preferred embodiment, the stent is capable to be crimped (at temperature preferably about Tg or below Tg), and expand from a crimped configuration to an expanded configuration/diameter at body temperature and has sufficient strength to support a body lumen, and preferably without fracture.

In another preferred embodiment, the biodegradable stent is formed using injection molding wherein the polymeric material is loaded inside a mold and the mold is treated once or more to control crystallinity preferably to between 1% and 55% (preferably between 1% and 35%) and treated to control Tg preferably to greater than 37° C. and less than 50° C. (or in another preferred embodiment control Tg to greater than 20° C. and less than 50° C.), or as described within this patent application. The formed patterned tube/stent has an initial diameter, preferably 1-1.5 times the stent deployed diameter, and the treatment can take place before, and/or during, and/or after the molding process and the stent capable to radially expand preferably at body temperature (dry or in aqueous environment). The stent in another embodiment is capable to be expanded from a crimped configuration (which is smaller than the expanded diameter) to an expanded diameter at body temperature and have sufficient strength to support a body lumen, and preferably without fracture. The stent in another embodiment is capable to be crimped from an expanded diameter to a crimped diameter (at temperature preferably about Tg or less than Tg), and expanded from the crimped configuration to an expanded diameter at body temperature and have sufficient strength to support a body lumen, and preferably without fracture. In another preferred embodiment, the biodegradable stent can be fabricated using printing such as 3-D printing wherein the polymeric material is loaded onto the printer and treated to form a patterned tubular body/structure/stent wherein it has an initial diameter, preferably 1-1.5 times the stent deployed diameter, and is treated to control crystallinity and Tg as described within this patent application, and the stent is capable to radially expand at body temperature. The stent in another embodiment is capable to expand from a crimped configuration to an expanded diameter at body temperature and has sufficient strength to support a body lumen, and preferably without fracture. The stent in another preferred embodiment is capable to be crimped from an expanded diameter to a crimped configuration (at temperature preferably about Tg or less than Tg), and expand from the crimped configuration to an expanded diameter at body temperature and has sufficient strength to support a body lumen, and preferably without fracture. Although the preferred embodiment when crimping the stent is at temperature about Tg or less than Tg, crimping the stent can be accomplished at temperature above Tg or within 20° C. above Tg. Although treatment by heat typically ranges from below Tg to below Tm, in some other cases treatment of the polymeric material can be about Tm or above for example when the stent is formed by printing or injection molding. A preferred formation process comprises forming a tube using spraying a polymer or polymeric material comprising one or more polymer, co-polymer- or monomer dissolved in at least one solvent onto a cylindrical mandrel or other structure when the stent prosthesis desired shape is non cylindrical such as oblong shape or other shapes. When the stent prosthesis is not cylindrical, a dimension of the stent may be referred to as "transverse dimension" instead of diameter. Optionally, additives, such as strength-enhancing materials, drugs, or the like, may be dissolved in the solvent or other solvents together with the polymer or polymeric material so that the materials are integrally or monolithically formed with the endoprosthesis tube. Alternatively, methods according to embodiments of the invention may rely on obtaining a pre-formed polymer tube from a supplier or other outside source.

In some embodiments, the polymeric tubular body is usually formed as a substantially continuous cylinder free from holes or other discontinuities. In another embodiment, the tubular body has a foraminous wall. In a third embodiment, the tubular body is formed from a continuous tube. In a fourth embodiment, the tubular body comprises a plurality of fibers woven into an expanded diameter, preferably the initial tubular configuration with a diameter preferably of 1-1.5 times the stent deployed diameter and preferably treated at the initial tubular diameter. The polymeric material or the tubular body or deployed stent typically has an outside or inner diameter in the range from 2 mm to 25 mm, preferably 3 mm to 10 mm, or 3.5 mm to 10 mm, and a thickness preferably in the range from 0.01 mm to 0.5 mm, and may be cut into lengths suitable for individual endoprostheses, typically in the range from 5 mm to 40 mm but can also range from 1 mm to 150 cm.

In an embodiment, the tubular body may be patterned into a suitable endoprosthesis structure, typically by laser cutting or other conventional processes such as milling, chemical etching, stamping, photolithography, etc. In other embodiments, the stent prosthesis is formed by 3D printing which patterns the tubular body/stent as it is being formed and optionally treated to control crystallinity and Tg to facilitate a stent capable to radially expand at body temperature and support a body lumen and preferably without fracture. In another embodiment, the tubular body comprises a plurality of fibers woven into the initial tubular configuration with a diameter preferably of 1-1.5 times the stent deployed diameter and preferably treated at the initial tubular diameter. In another embodiment, the stent tubular body is formed from a sheet joined at opposite ends and patterned either before or after joining.

In some embodiments, as described herein, a biodegradable endoprosthesis (e.g., a stent) is formed from a polymeric tube, wherein the tube is a substantially continuous cylinder. In some cases, the substantially continuous cylinder may be substantially free from holes, gaps, voids or other discontinuities. In other embodiments, the tube may be substantially continues yet include some holes, gaps, voids, or other discontinuities. The tubular body may have an outside diameter in the range from about 2 mm to 10 mm, or about 3 mm to about 9 mm, or about 4 mm to about 8 mm, or about 5 mm to about 7 mm. The tubular body may have a thickness in the range from 0.01 mm to 0.5 mm, or about 0.05 mm to about 0.4 mm, or about 0.1 mm to about 0.3 mm.

In certain embodiments, the tubular body or polymeric material, or the stent has an initial diameter. In one preferred embodiment, the initial diameter is 1-1.5 times the stent deployed diameter. In another preferred embodiment, the initial diameter is 0.9-1.5 times the stent deployed diameter. In a further embodiment, the initial diameter is less than the stent deployed diameter. The initial diameter can be the as-formed diameter, or the diameter before patterning, or the diameter after patterning, or the diameter before crimping. In one embodiment, an endoprosthesis (e.g., a stent) is patterned by laser cutting or other method from a polymeric tube that has a (e.g., inner or outer) diameter substantially equal to or smaller than deployed (e.g., inner or outer) diameter of the endoprosthesis. In other embodiments, an endoprosthesis (e.g., a stent) is patterned from a polymeric tube that has a (e.g., inner or outer) diameter, either when the tube is formed or after the tube is radially expanded to a second larger diameter, larger than deployed (e.g., inner or outer) diameter of the endoprosthesis. Patterning a stent from a polymeric tube having a (e.g., inner or outer) diameter larger than deployed (e.g., inner or outer) diameter of the stent can impart advantageous characteristics to the stent, such as reducing radially inward recoil of the stent after deployment and/or improved strength. In certain embodiments, a stent is patterned from a polymeric tube having a (e.g., inner or outer) diameter about 0.85, 0.90, 1.0, 1.05 to about 1.5 times, or about 1.1 to about 1.5 times, or about 1.1 to about 1.3 times, or about 1.15 to about 1.25 times, smaller, same, or larger than an intended deployed (e.g., inner or outer) diameter of the stent. In an embodiment, the stent is patterned from a polymeric tube having a (e.g., inner or outer) diameter about 1.1 to about 1.3 times larger than an intended deployed (e.g., inner) diameter of the stent. For example, a stent having a deployed (e.g., inner or outer) diameter of about 2.5, 3 or 3.5 mm can be patterned from a tube having a (e.g., inner or outer) diameter of about 2.75, 3.3 or 3.85 mm (1.1 times larger), or about 3.25, 3.9 or 4.55 mm (1.3 times larger), or some other (e.g., inner or outer) diameter larger than the deployed (e.g., inner or outer) diameter of the stent. In preferred embodiments, the initial diameter of the formed tube is larger than the crimped diameter (e.g., crimped diameter on a delivery system) of the stent prosthesis wherein the tubular body is expanded to a second larger diameter than the initial diameter before patterning or before crimping to the crimped diameter; or wherein the tubular body remains substantially the same diameter before patterning or before crimping to a crimped diameter; or wherein the tubular body is crimped to a smaller diameter than the initial formed diameter before patterning or after patterning. In another embodiment, the initial diameter of the formed tube is smaller than the crimped diameter of the stent prosthesis wherein the tubular body is expanded to a second larger diameter than the initial diameter before patterning or before crimping; or wherein the tubular body remains substantially the same diameter before patterning or before crimping; or wherein the tubular body is crimped to a smaller diameter than the crimped diameter of the stent prosthesis before patterning or after patterning. In another embodiment, the initial diameter of the formed tubular body is greater than 0.015 inches, or greater than 0.050 inches, or greater than 0.092 inches, or greater than 0.120 inches, or greater than 0.150 inches, in the as-formed diameter, or before patterning diameter, or after patterning diameter, or before crimping diameter. Stent prosthesis intended deployment diameter is the diameter of the labeled or nominal or higher of the delivery system or balloon catheter, or higher. For example when a stent prosthesis is crimped onto a balloon labeled 3.0 mm diameter (e.g., deployed nominal diameter), the stent prosthesis' deployed diameter or intended deployment diameter is 3.0 mm or higher. Similarly, self expandable stent crimped onto a delivery system is labeled a certain deployment diameter. In a preferred embodiment, a stent prosthesis or tubular body or polymeric material has initial diameter (or initial transverse dimension), preferably 1-1.5 times deployed diameter (deployed transverse dimension) or deployed nominal diameter (e.g., deployed nominal transverse dimension), where in the initial diameter (or initial transverse dimension) is as-formed diameter (or transverse dimension), before patterning diameter (or transverse dimension), or after patterning diameter (or transverse dimension), or before crimping diameter (or transverse dimension), and wherein the initial diameter (or initial transverse dimension) is greater than crimped diameter (or crimped transverse dimension).

In a preferred embodiment, a stent or tubular body first self-expands by at least 0.35 of initial diameter or transverse dimension, and then expands to second larger diameter or transverse dimension, which may be the deployed diameter or transverse dimension, preferably by balloon expansion. In a further preferred embodiment, the stent or tubular body may expand to 1.0 times or more, or 1.1 times or more, or 1.2 times or more, or 1.3 times or more, or 1.4 times or more, or 1.5 times or more the deployed diameter or nominal diameter (or transverse dimension) at body temperature, without fracturing. In a further preferred embodiment, the stent or tubular body or polymeric material is crimped from an expanded diameter to a crimped configuration, and at body temperature expands to 1.0 times or more, or 1.1 times or more, or 1.2 times or more, or 1.3 times or more, or 1.4 times or more, or 1.5 times or more the deployed diameter or nominal diameter (or transverse dimension), without fracturing. In a further preferred embodiment, the stent or tubular body is crimped from an expanded diameter to a crimped configuration wherein the ratio of expanded diameter to crimped configuration is at least 1.5, and at body temperature the stent expands to 1.0 times or more, or 1.1 times or more, or 1.2 times or more, or 1.3 times or more, or 1.4 times or more, or 1.5 times or more the deployed diameter or nominal diameter (or transverse dimension), without fracturing. In a further preferred embodiment, the stent or tubular body is crimped from an expanded diameter to a crimped configuration wherein the ratio of expanded diameter to crimped configuration is at least 2, and at body temperature the stent expands to 1.0 times or more, or 1.1 times or more, or 1.2 times or more, or 1.3 times or more, or 1.4 times or more, or 1.5 times or more the deployed diameter or nominal diameter (or transverse dimension), without fracturing. In a further preferred embodiment, the stent or tubular body is crimped from an expanded diameter to a crimped configuration wherein the ratio of expanded diameter to crimped configuration is at least 2.5, and at body temperature the stent expands to 1.0 times or more, or 1.1 times or more, or 1.2 times or more, or 1.3 times or more, or 1.4 times or more, or 1.5 times or more the deployed diameter or nominal diameter (or transverse dimension), without fracturing. In a further preferred embodiment, the stent or tubular body is crimped from an expanded diameter to a crimped configuration wherein the ratio of expanded diameter to crimped configuration is at least 3, or at least 4, or at least 5, or at least 6, or at least 7, and at body temperature the stent expands to 1.0 times or more, or 1.1 times or more, or 1.2 times or more, or 1.3 times or more, or 1.4 times or more, or 1.5 times or more the deployed diameter or nominal diameter (or transverse dimension), without fracturing. In a further preferred embodiment, the stent or tubular body is crimped from an expanded diameter to a crimped configuration wherein the ratio of expanded diameter to crimped configuration is at least 2, or at least 2.5, or at least 3, or at least 3.5, or at least 4, wherein the stent at body temperature is expandable from the crimped configuration to the deployed configuration without fracture, wherein the deployed configuration is the nominal or higher deployment diameter. In another preferred embodiment, the stent is balloon expanded to its deployed diameter (or transverse dimension) first and then expands, preferably self expands, to a second larger diameter (or transverse dimension) by about 0.1 mm or more, or about 0.2 mm or more, or about 0.3 mm or more, or about 0.4 mm or more, or about 0.5 mm or more, without fracture. In a further preferred embodiment, the balloon expandable stent or tubular body or polymeric material expands to 1.0 times or more, or 1.1 times or more, or 1.2 times or more, or 1.3 times or more, or 1.4 times or more, or 1.5 times or more the deployed diameter or nominal diameter (or transverse dimension) at body temperature, without fracturing. In a further preferred embodiment, the stent or tubular body is crimped from an expanded diameter to a crimped configuration, and at body temperature is balloon expandable to 1.0 times or more, or 1.1 times or more, or 1.2 times or more, or 1.3 times or more, or 1.4 times or more, or 1.5 times or more the deployed diameter or nominal diameter (or transverse dimension), without fracturing. In a further preferred embodiment, the stent or tubular body is crimped from an expanded diameter to a crimped configuration wherein the ratio of expanded diameter to crimped configuration is at least 1.5, and at body temperature the balloon expandable stent expands to 1.0 times or more, or 1.1 times or more, or 1.2 times or more, or 1.3 times or more, or 1.4 times or more, or 1.5 times or more the deployed diameter or nominal diameter (or transverse dimension), without fracturing.

An endoprosthesis (e.g., a stent or a stent delivery system) and/or the polymeric article/material (e.g., a polymeric tube) from which it is formed can be exposed to ionizing radiation such as electron beam or gamma radiation or to ethylene oxide gas (e.g., for purposes of sterilization and/or treatment) as described herein. Such modification or treatment in that it can, e.g., control crystallinity (e.g., degree of crystallinity), control Tg, control molecular weight, control monomer content, and/or enhance the strength of the material (e.g., polymeric material) comprising the polymeric article or the endoprosthesis. In some embodiments, the polymeric article and/or the endoprosthesis are exposed to a single dose or multiple doses of e-beam or gamma radiation totaling about 5 or 10 kGy to about 50 kGy, or about 20 kGy to about 40 kGy of radiation, e.g., a single dose of 30 kGy or multiple smaller doses (e.g., 3×10 kGy doses)], where the polymeric article and/or the endoprosthesis are optionally (cooled to low temperature (e.g., about −10° C. to about −30° C., or about −20° C. to less than ambient temperature) for a period of time (e.g., at least about 1 minute, 20, 30 or 40 minutes) or optionally treated at about ambient temperature) prior to exposure to the single dose or to each of the multiple doses of radiation. In certain embodiments, the polymeric article and/or the endoprosthesis are exposed to a single dose or multiple doses of e-beam or gamma radiation totaling about 10 kGy to about 50 kGy, or about 30 kGy. A polymeric article and/or an endoprosthesis that have been exposed to ionizing radiation or ethylene oxide gas can also undergo one or more other modification treatments (e.g., heating or annealing and/or cooling) described herein.

In some embodiments, the tubular body or polymeric material or stent may be formed from at least one polymer having desired degradation characteristics where the polymer may be modified to have the desired crystallinity, Tg, recoil, strength, shortening, expansion characteristics, crimping characteristics, crystallinity, Tg, molecular weight, and/or other characteristics in accordance with the methods of the present invention. Polymers include one or more polymers, copolymers, blends, and combination thereof of: Lactides, Glycolides, Caprolactone, Lactides and Glycolides, Lactides and Caprolactones: examples poly-DL-Lactide, polylactide-co-glycolactide; polylactide-co-polycaprolactone, poly(L-lactide-co-trimethylene carbonate), polylactide-co-caprolactone, polytrimethylene carbonate and copolymers; polyhydroxybutyrate and copolymers; polyhydroxyvalerate and copolymers, poly orthoesters and copolymers, poly anhydrides and copolymers, polyiminocarbonates and copolymers and the like. A particularly preferred polymer comprises a copolymer of L-lactide and glycolide, preferably with a weight ratio of 85% L-lactide to 15% glycolide.

In one aspect of the invention, the tubular body or polymeric material or stent material comprises a degradable polymeric material wherein the polymeric material comprises one or more polymers; or one or more co-polymers; or one or more blends of monomers, polymers or copolymers; and combination thereof. In another embodiment, the polymeric material comprises one or more polymer or one or more co-polymer. Additionally, at least one monomer, polymer, or co-polymer of similar material (to the one or more polymer or the one or more co-polymer) is blended with the polymeric material. In another embodiment, a different monomer, co-polymer, or polymer is blended with (the one or more polymer or the one or more co-polymer) the polymeric material. In a preferred embodiment, a biodegradable stent comprising a polymeric material comprising a copolymer of lactide and caprolactone in the ratio by weight ranging from 80-99% lactide to 1-20% caprolactone; wherein the polymeric material further comprises a monomer or polymer including copolymer of one or more of the following: lactide, glycolide, lactide glycolide, caprolactone, and lactide caprolactone; wherein the one or more monomer or polymer total amount is 1 to 100 micrograms per milligram of polymeric material, preferably 5 to 75 micrograms per milligram of polymeric material, more preferably 10 to 50 micrograms per milligrams of polymeric material; wherein the stent is capable to be crimped from an expanded configuration to a smaller crimped configuration, and at body temperature expanded to a deployed configuration, and having sufficient strength to support a body lumen, and without fracture of the stent. In another preferred embodiment, a biodegradable stent comprising a polymeric material comprising a copolymer of lactide and caprolactone in the ratio by weight ranging from 80-99% lactide to 1-20% glycolide; wherein the polymeric material further comprises a monomer or polymer including copolymer of one or more of the following: lactide, glycolide, lactide glycolide, caprolactone, and lactide caprolactone; wherein the one or more monomer or polymer total amount is 1 to 100 micrograms per milligram of polymeric material, preferably 5 to 75 micrograms per milligram of polymeric material, more preferably 10 to 50 micrograms per milligrams of polymeric material; wherein the stent is capable to be crimped from an expanded configuration to a smaller crimped configuration, and at body temperature expanded to a deployed configuration, and having sufficient strength to support a body lumen, and without fracture. In a further embodiment, the one or more monomer and/or polymer does not substantially change the crystallinity of the polymeric material. In a further embodiment, the one or more monomer and/or polymer changes (increases or decreases) the crystallinity of the polymeric material by 5% to 150%, preferably by 10% to 75%, more preferably by 10% to 50%. In a further embodiment, the one or more monomer and/or polymer controls the crystallinity of the polymeric material to between 1% and 55%, preferably between 1% and 35%. In a further embodiment, the one or more monomer and/or polymer does not change the crystallinity of the polymeric material from being between 1% and 55%. In a further embodiment, the one or more monomer and/or polymer does not substantially change the Tg of the polymeric material. In a further embodiment, the one or more monomer and/or polymer changes (increases or decreases) the Tg temperature of the polymeric material by 1 C to 15 C, preferably 1° C. to 10° C., more preferably by 1° C. to 5° C. In yet a further embodiment, the one or more monomer and/or polymer controls the Tg temperature of the polymeric material to between 20° C. and 55° C., preferably to between 35° C. and 50° C., more preferably to between 37° C. and 50° C., most preferably between 37° C. and 45° C.

The polymeric material/article and/or the tubular body and/or the prosthesis or device can undergo any of a variety of modification or treatments (e.g., longitudinal extension, longitudinal shrinkage, radial expansion, heating, cooling, quenching, pressurizing, exposure to or humidity, vacuuming, exposure or incorporation or removal of solvents, incorporation of additive, removal of additives, incorporation of or removal of impurities, exposure to radiation, incorporation or exposure or pressurization by gases such as carbon dioxide, or a combination thereof) designed to control or enhance characteristics (e.g., crystallinity, Tg, molecular weight, strength, toughness and degradation, recoil, shortening, expansion) of the article, the tubular body, the polymeric material, and/or the prosthesis or device. The biodegradable implantable device formed from a polymeric article made by spraying, extrusion, dipping, molding, 3D printing, and the like, can have any features of a biodegradable implantable device comprising a body comprising a biodegradable polymer (including homopolymer or copolymer) described herein. In some embodiments, modification or treatment may include heating, and/or pressurizing. In one preferred embodiment, the polymeric material is treated wherein the treatment comprises incorporation of solvents wherein the one or more solvent amounts in the polymeric material or the stent after treatment ranges from 0.001% to 10% by weight, preferably ranges from 0.1% to 5% by weight, more preferably ranges from 0.1% to 3% by weight. In one preferred embodiment, the polymeric material is treated wherein the treatment comprises incorporation of solvents wherein the one or more solvent amounts in the polymeric material or the stent after treatment ranges from 0.001% to 10% by weight, preferably ranges from 0.1% to 3% by weight, more preferably ranges from 0.1% to 2% by weight and wherein the stent at body temperature is capable to expand from a crimped configuration to a deployed diameter without fracture and have sufficient strength to support a body lumen. In one preferred embodiment, the polymeric material is treated wherein the treatment comprises incorporation of solvents wherein the one or more solvent amounts in the polymeric material or the stent after treatment ranges from 0.001% to 10% by weight, preferably ranges from 0.1% to 3% by weight, more preferably ranges from 0.1% to 2% by weight and wherein the one or more solvent substantially does not dissolve the stent (preferably does not dissolve the stent) and wherein the stent at body temperature is capable to expand from a crimped configuration to a deployed diameter without fracture and have sufficient strength to support a body lumen. In one preferred embodiment, the polymeric material is treated wherein the treatment comprises incorporation of solvents wherein the one or more solvent amounts in the polymeric material or the stent after treatment ranges from 0.001% to 10% by weight, preferably ranges from 0.1% to 3% by weight, more preferably ranges from 0.1% to 2% by weight and wherein the one or more solvent preferably substantially does not dissolve the stent (preferably does not dissolve the stent) and wherein the one or more solvent substantially remains in the stent in the ranges described above before deployment of the stent) wherein the stent at body temperature is capable to expand from a crimped configuration to a deployed diameter without fracture and have sufficient strength to support a body lumen. Examples of solvents include DCM, Chloroform to name some. Incorporation of solvents for example by spraying as described in the application. Solvents that can be used for example are ones that dissolves the polymeric material when used in sufficient quantities or solvents that does not dissolve the polymeric material. Preferred solvents are solvents that are retained in the polymeric material or stent after incorporation, or after treatment, or before deployment in the ranges described above. Preferred Tg ranges from 20° C. to 50° C., more preferred from greater than 37° C. to less than 50° C. Preferred crystallinity ranges from 1% to 60%, preferably from 1% to 55%, more preferably from 1% to 45%, most preferably from 1% to 35%. The polymeric material preferably has an initial diameter, preferably 1-1.5 times the deployment diameter of the stent. In a preferred embodiment, the stent is capable of being crimped from an expanded diameter to a crimped diameter, and at body temperature is capable to expand from a crimped configuration to a deployed diameter without fracture and have sufficient strength to support a body lumen. Examples of polymeric material are materials comprising lactide, lactide and glycolide, or lactides and caprolactones, or a combination thereof.

In one preferred embodiment, the polymeric material is treated wherein the treatment comprises inducing or incorporation of monomers or polymers including co-polymers wherein the one or more monomers or polymers amounts in the polymeric material or the stent after treatment ranges from 0.001% to 10% by weight, preferably ranges from 0.1% to 5% by weight, more preferably ranges from 0.1% to 3% by weight. In one preferred embodiment, the polymeric material is treated wherein the treatment comprises inducing or incorporation of monomers or polymers wherein the one or more monomers or polymers amounts in the polymeric material or the stent after treatment ranges from 0.001% to 10% by weight, preferably ranges from 0.1% to 5% by weight, more preferably ranges from 0.1% to 3% by weight and wherein the stent at body temperature is capable to expand from a crimped configuration to a deployed diameter without fracture and have sufficient strength to support a body lumen. In one preferred embodiment, the polymeric material is treated wherein the treatment comprises inducing or incorporation of monomers or polymers wherein the one or more monomers or polymers amounts in the polymeric material or the stent after treatment ranges from 0.001% to 10% by weight, preferably ranges from 0.1% to 5% by weight, more preferably ranges from 0.1% to 3% by weight and wherein the one or more monomers or polymers substantially does not affect degradation of the stent (preferably does not affect degradation the stent. In other embodiments, the monomer or polymer accelerates degradation of the stent) and wherein the stent at body temperature is capable to expand from a crimped configuration to a deployed diameter without fracture and have sufficient strength to support a body lumen. In one preferred embodiment, the polymeric material is treated wherein the treatment comprises inducing or incorporation of monomer or polymer wherein the one or more monomer or polymer amounts in the polymeric material or the stent after treatment ranges from 0.001% to 10% by weight, preferably ranges from 0.1% to 5% by weight, more preferably ranges from 0.1% to 3% by weight and wherein the one or more monomer or polymer preferably substantially does not affect the stent degradation (preferably accelerates the stent degradation) and wherein the one or more monomer or polymer substantially remains in the stent in the ranges described above before deployment of the stent) wherein the stent at body temperature is capable to expand from a crimped configuration to a deployed diameter without fracture and have sufficient strength to support a body lumen. In other embodiments, the one or more monomer or polymer amounts in the polymeric material or the stent after treatment ranges from 0.1% to 10% by weight, preferably ranges from 1% to 5% by weight, more preferably ranges from 2% to 5%. Examples of monomers or polymers include lactides, glycolides, caprolactones, lactides and glycolides, lactides and caprolactones to name a few. Incorporation of monomers can take place, for example by spraying as described herein, or inducing by radiation. Preferred Tg ranges from 20° C. to 50° C., more preferred from greater than 37° C. to less than 50° C. Preferred crystallinity ranges from 1% to 60%, preferably from 1% to 55%, more preferably from 1% to 45%, most preferably from 1% to 35%. The polymeric material preferably has an initial diameter, preferably 1-1.5 times the deployment diameter of the stent. In a preferred embodiment, the stent is capable of being crimped from an expanded diameter to a crimped diameter, and at body temperature is capable to expand from a crimped configuration to a deployed diameter without fracture and have sufficient strength to support a body lumen. Examples of polymeric material are materials comprising lactide, lactide and glycolide, or lactides and caprolactones, or a combination thereof.

Further embodiments of the disclosure relate to a method of making a biodegradable endoprosthesis, comprising providing a polymeric article (e.g., a tubular body, such as a polymeric tube) comprising at least partially a substantially amorphous or semi-crystalline, biodegradable polymeric material, wherein crystallinity (e.g., degree of crystallinity) of the polymeric material increases after the polymeric article undergoes a modification (or treatment), and wherein the endoprosthesis is formed from the polymeric article. The polymeric material is substantially amorphous or semi crystalline prior to the modification, and may or may not be substantially amorphous after the modification. Further embodiments of the disclosure relate to a method of making a biodegradable endoprosthesis, comprising providing a polymeric article (e.g., a tubular body, such as a polymeric tube) comprising at least partially of a substantially amorphous or semi-crystalline biodegradable polymeric material, wherein crystallinity (e.g., degree of crystallinity) of the polymeric material decreases after the polymeric material undergoes a treatment, and wherein the endoprosthesis is formed substantially from the polymeric material. In one embodiment, the polymeric material is substantially amorphous or semi crystalline prior to the modification, and substantially amorphous after the modification. In certain embodiments, the modification comprises heating, cooling, quenching, pressurizing, vacuuming, crosslinking, addition of an additive, or exposure to radiation or carbon dioxide, or a combination thereof. The polymeric article can have any shape, form and dimensions suitable for making the endoprosthesis (e.g., a patterned polymeric tube stent).

In an embodiment, treatment comprises a heat treatment preferably at about initial diameter to a temperature above its glass transition temperature of the polymeric material and below its melting point for a period ranging from a fraction of a second to 7 days. The polymeric material or the tubular body in one embodiment may be cooled after heating to a temperature ranging from below ambient temperature to ambient temperature over a period ranging from a fraction of a second to 7 days. In a preferred embodiment, the polymeric material or the tubular body initial diameter is approximately 1-1.5 times the stent deployment diameter. In one embodiment, the polymeric material or the tubular body is treated at diameter between initial diameter and crimped diameter. In a further embodiment, the treatment comprises heating the tubular body to a temperature about or below Tg for a period ranging from a fraction of a second to 7 days. In another embodiment, the heat treatment at the below initial diameter comprises heat treatment about or above Tg and below Tm for a period ranging from a fraction of a second to 5 hours, or preferably less than 2 hour, or most preferably less than 60 minutes. In another embodiment, the polymeric material or the tubular body after forming is treated comprising heat at temperature about or less than Tg. In another embodiment, the tubular body after forming and excluding patterning is treated comprising heat at temperature about or less than Tg. In some cases, the treatment is about Tm or higher. Examples of methods of forming the stent polymeric material are by injection molding or 3D printing. Durations are similar to above ranges. Other suitable temperatures and times are described herein.

In some embodiments, the diameter of the tubular body or the polymeric material or the stent may, at the time of treatment (e.g., treatment diameter), be optionally smaller or optionally greater than the deployment diameter, where the deployment diameter may include, for example, the diameter of the tubular body or the stent within a lumen. In some embodiments, the treatment diameter may be 1-2 times the deployment diameter, or 1-1.9 times the deployment diameter, or 1-1.8 times the deployment diameter, or 1-1.7 times the deployment diameter, or 1-1.6 times the deployment diameter, or 1-1.5 times the deployment diameter, or 1-1.4 times the deployment diameter, or 1-1.3 times the deployment diameter, or 1-1.2 times the deployment diameter, or 1-1.05 times the deployment diameter. In other embodiments, the treatment diameter may be 0.95-1 times the deployment diameter. In other embodiments, the treatment diameter may be 0.9-1 times the deployment diameter, or 0.8-1 times the deployment diameter, or 0.7-1 times the deployment diameter, or 0.6-1 times the deployment diameter, or 0.5-1 times the deployment diameter, or 0.4-1 times the deployment diameter, or 0.3-1 times the deployment diameter, or 0.2-1 times the deployment diameter. The stent expanded/deployed diameter typically is 2 mm and higher, 2.5 mm and higher, 3 mm and higher, 3.5 mm and higher, 4 mm and higher, 4.5 mm and higher, 5 mm and higher, 5.5 mm and higher. In other embodiments, the stent deployed diameter ranges from 2 mm-25 mm, preferably ranges from 2.5 mm to 15 mm, more preferably from 3 mm to 10 mm. The stent length ranges from 1 mm to 200 cm, preferably from 5 mm to 60 cm, more preferably from 5 mm to 6 cm.

Another aspect of the invention provides biodegradable implantable devices (e.g., stents) comprising a polymeric material, or a body (e.g., a tubular body) that comprises one or more biodegradable polymeric materials to achieve a desired Tg. In another aspect of the invention the treated polymeric material or the tubular body has a desired Tg. In another aspect of the invention the tubular body or polymeric material is treated to control Tg. In another aspect of the invention the tubular body is treated to control Tg and crystallinity. In another aspect of the invention the tubular body is treated to control Tg, crystallinity, and molecular weight. In some embodiments, the one or more materials comprising the body, or the stent, or the stent material, or the tubular body or the polymeric material may have a wet or dry glass transition temperature ($T_g$) greater than 20° C., or greater than 30° C., or greater than 31° C., or greater than 32° C., or greater than 33° C., or greater than about 34° C., or greater than 35° C., or greater than 36° C., or greater than 37° C. In some embodiments, the one or more materials comprising the body, or the stent, or the tubular body have a $T_g$ less than 45° C., or less than 44° C., or less than 43° C., or less than 42° C., or less than 41° C., or less than 40° C., or less than 39° C., or less than 38° C., or less than 37° C., or less than 36° C. In some embodiments, the one or more materials comprising the body, or the stent, or the tubular body have a $T_g$ of about 20° C. to about 55° C., or about 20° C. to about 50° C., or about 31° C. to about 45° C., or about 32° C. to about 45° C., or about 33° C. to about 45° C., or about 34° C. to about 45° C., or about 35° C. to about 45° C., or about 36° C. to about 45° C., or about 37° C. to about 45° C., or about 38° C. to about 45° C., or about 39° C. to about 45° C., or about 40° C. to about 45° C. In some embodiments, the one or more materials comprising the body, or the stent, or the tubular body have a $T_g$ of about 20° C. to about 45° C., or about 30° C. to about 44° C., or about 30° C. to about 43° C., or about 30° C. to about 42° C., or about 30° C. to about 41° C., or about 30° C. to about 40° C., or about 30° C. to about 39° C., or about 30° C. to about 38° C., or about 30° C. to about 37° C. In some embodiments, the one or more materials comprising the body, or the stent, or the tubular body has a $T_g$ greater than 37° C. and less than 45° C., or greater than 37° C. and less than 40° C., or greater than 37° C. to less than 50° C., or greater than 37° C. to less than 55° C., or greater than 38° C. to less than 50° C., or greater than 40° C. and less than 50° C., or greater than 45° C. and less than 50° C.

In some embodiments, the one or more materials comprising the body, or the polymeric material, or the stent, or the stent material, or the tubular body has a $T_g$ greater than 35° C. and less than 45° C., or greater than 36° C. and less than 45° C., or greater than 37° C. and less than 45° C., or greater than 37° C. and less than 40° C. or greater than 20° C. and less than 45° C., or greater than 35° C. and less than or equal to 45° C.

In some embodiments, the one or more biodegradable polymeric materials or the tubular body or the stent material has elastic modulus at body temperature (in aqueous or water or dry) of 0.2 GPa to 20 GPa, or of 0.3 GPa to 5 Pa, or greater than 0.35 GPa and less than 3 GPa, or of 0.4 GPa to 2.5 GPa, or of about 0.5 Pa to about 1 GPa, or of about 0.35 GPa to about 0.85 GPa, or of about 0.40 GPa to about 0.75 GPa, or of about 0.45 Pa to about 0.70 Pa, or of about 0.50 GPa to about 0.65 GPa, or at least 0.2 GPa, or at least 0.3 GPa, or at least 0.4 GPa, or at least 0.5 GPa. In some embodiments, the one or more biodegradable polymeric materials, or the tubular body or the stent may have a percent elongation at break at body temperature (in aqueous or water or dry) of 20% to 800%, or of about 20% to about 300%, or of about 20% to about 200%, or of about 20% to about 100%, or of about 20% to about 50%, or of about 10% to about 600%, or of about 10% to about 300%, or of about 5% to about 600%, or of about 5% to about 300%, or of about 1% to about 600%, or of about 1% to about 300%, or of about 1% to about 200%, or of about 1% to about 150%;

In yet further embodiments, the polymeric material comprising the body of the device or the biodegradable polymer, or copolymer or polymer blend, or the tubular body comprising the biodegradable polymeric material or the stent material; has a tensile yield strength of at least 1500 psi, or at least 2000 psi, or at least 2500 psi, or at least 3000 psi, or at least 4000 psi, or at least 5000 psi. In yet further embodiments, the polymeric stent material has a tensile yield strength ranging from 1500 psi to 6000 psi, or between 200 psi and 5000 psi. In another embodiment, the biodegradable polymeric material or the tubular body or the stent material; has stiffness of at least 1000 MPa, or at least 1500 MPa, or at least 2000 MPa, or at least 2500 MPa, or at least 3000 MPa, or at most 5000 MPa, or at most 4000 MPa; when measured at body temperature (in aqueous or water or dry). In yet further embodiments, the biodegradable polymeric material or the tubular body or the stent material; has elastic modulus of at least 250 MPa, or at least 350 MPa, or at least 400 MPa, or at least 450 MPa, or at least 500 MPa; when measured at body temperature (in aqueous or water or dry). In yet another embodiment, the material comprising the body or the biodegradable polymer or copolymer or polymer blend, or the tubular body comprising the biodegradable polymer, or the stent; has a percent elongation at break when measure at body temperature (wet or dry) of about 20% to about 800%, or of about 20% to about 300%, or of about 20% to about 200%, or of about 20% to about 100%, or of about 20% to about 50%, or of about 10% to about 600%, or of about 10% to about 300%, or of about 5% to about 600%, or of about 5% to about 300%, or of about 1% to about 600%, or of about 1% to about 300%, or of about 1% to about 200%, or of about 1% to about 150%. In other embodiments, the biodegradable polymer, copolymer or polymer blend or tubular body comprising the biodegradable polymer material or stent prosthesis material has stiffness at body temperature (in aqueous or water or dry) of about 0.4 N/mm2 to about 2 N/mm2, or of about 0.5 N/mm2 to about 1.5 N/mm2, or of about 0.7 N/mm2 to about 1.4 N/mm2, or of about 0.8 N/mm2 to about 1.3 N/mm2. In other embodiments, the biodegradable polymer or copolymer or polymer blend or tubular body comprising the biodegradable polymer material or prosthesis; has elastic modulus at body temperature, of about 0.2 GPa to about 20 GPa, or of about 0.3 GPa to about 5 PGa, or of about 0.4 GPa to about 2.5 GPa, or of about 0.5 GPa to about 1 GPa, or at least 0.2 GPa, or at least 0.3 GPa, or at least 0.4 GPa, or at least 0.5 GPa. In other embodiments, the biodegradable polymer or copolymer or polymer blend or tubular body comprising the biodegradable polymer material or prosthesis material; has yield strain at body temperature of at most 20%, or at most 15%, preferably at most 10%, more preferably at most 5%, at body temperature (in aqueous or water or dry). In yet another embodiment, the prosthesis has radial strength sufficient to support a body lumen. In yet another embodiment, the biodegradable polymer or copolymer or tubular body or stent prosthesis; has a radial strength in an aqueous environment at about 37° C. (e.g., body temperature) of about 2 psi to about 25 psi, or of about 5 psi to about 22 psi, or of about 7 psi to about 20 psi, or of about 9 psi to about 18 psi. In yet another embodiment, the biodegradable polymer or copolymer or tubular body or stent prosthesis; has a radial strength at body temperature (in aqueous or water or dry) of greater than 2 psi, or greater than 8 psi, or greater than 10 psi, or greater than 15 psi. Radial strength can be measured in a variety of methods known in the art. For example the flat plate method or iris method or other known methods. Radial force can be measured with several methods known in the art. For example when the stent radial strength is not sufficient to support a body lumen, or the expanded diameter is reduced by a substantial amount, or reduced by at least 15%, or reduced by at least 20%, or reduced by at least 25%, or reduced by at least 50%. In other embodiments, the biodegradable copolymer, or polymer blend, or polymer, or tubular body comprising the biodegradable polymer, or prosthesis has a % recoil in an aqueous environment at 37° C. of about −20% to about 20%, or of about −15% to about 15%, or of about −10% to about 10%, or of about −10% to about 0%, or of about 0% to about 10%, or of about 3% to about 10%, or of about 4% to about 9%, or less than 25%, or less than 20%, or less than 15%, or less than 10%, or less than 5%; after expansion from a crimped state. % recoil is measured in a variety of ways in-vitro or in-vivo with methods known in the art. For example in-vitro % recoil can be measured by expanding the stent in an aqueous environment at about 37° C. inside a tube or unconstrained and measuring % recoil after expansion using laser micrometer. For an example for in-vivo % recoil measurement using QCA see, e.g., Catheterization and Cardiovascular Interventions, 70:515-523 (2007). In yet another embodiment, the biodegradable polymer or copolymer or tubular body or prosthesis, has a radial strength (in an aqueous environment or dry at 37° C. from about 1 minute to about 1 day after expansion) of about 2 psi to about 25 psi; wherein the radial strength increases by about 1 psi to about 20 psi, or by about 2 psi to about 15 psi, or by about 3 psi to about 10 psi, or by about 4 psi to about 8 psi, after being in such an aqueous or dry environment for about 1 day to about 60 days. In other embodiments, the biodegradable, polymer, or copolymer, or polymer blend, or tubular body, or stent material; is substantially amorphous, or substantially semi crystalline, or substantially crystalline; after modification, or before modification, or after radiation, or before implantation into a mammalian body lumen. In other embodiments, the biodegradable polymer, or copolymer or polymer blend, or tubular body, or stent; is substantially amorphous before and after modification, or substantially amorphous before a modification and substantially semi crystalline after modification, or substantially amorphous before a modification and substantially crystalline after modification, or substantially semi crystalline before a modification and substantially amorphous after modification, or substantially semi crystalline before a modification and substantially semi crystalline after modification, or substantially semi crystalline before a modification and crystalline after modification, or substantially crystalline before modification and substantially semi crystalline after a modification, or substantially crystalline before a modification and substantially amorphous after a modification, or substantially crystalline before a modification and after modification.

In other embodiments, the biodegradable polymer or copolymer or polymer blend or tubular body or stent has longitudinal shrinkage of about 0% to about 30%, or of about 5% to about 25%, or of about 7% to about 20%, or of about 10% to about 15%; when heated (e.g. in an oven) at temperatures ranging from about 30° C. to about 150° C. (with or without a mandrel inserted into the copolymer or tubular body or prosthesis for a time ranging from about 30 minutes to about 24 hours); or upon or after expansion of the stent from a crimped state to an expanded state at body temperature. In yet another embodiment, the longitudinal shrinkage is less than 30%, or less than 25%, or less than 20%, or less than 15%, or less than 10%, of the original length upon or after expansion of the stent from a crimped state to an expanded state at body temperature. In yet another embodiment, the stent or polymer material or polymer tube has longitudinal shrinkage of less than about 25% or less, or about 15% or less, or about 10% or less, or about 5% or less, or about 1-25%, or about 5-15%, after being in aqueous condition at about 37° C. in vitro or in vivo for about 1 minute or less, or about 5 minutes or less, or about 15 minutes or less, or after expansion from the crimped state at body temperature. In other embodiments the stent or polymer material or polymer tube has longitudinal shrinkage of less than about 25% or less, or about 15% or less, or about 10% or less, or about 5% or less, or about 1-25%, or about 5-15%, after being in aqueous condition at about 37° C. in vitro or in vivo for about 1 minute or less, or about 5 minutes or less, or about 15 minutes or less, or after expansion from the crimped state. In yet another embodiment, the stent or polymeric material or tubular body has longitudinal lengthening of less than 25%, or 15% or less, or 10% or less, or 5% or less, or 1-25%, or 5-15%, after being in aqueous condition at about 37° C. in vitro or in vivo for about 1 minute or less, or about 5 minutes or less, or about 15 minutes or less, or after expansion from the crimped state at body temperature. In yet another embodiment, the amorphous, or semicrystalline, or crystalline polymeric material has internal stresses, or longitudinal shrinkage of no more than 15% from before a modification to after modification. In yet another embodiment, the polymer comprises a polymer, or a co-polymer, or a blend of polymers, or a mixture of polymers, or a blend of polymer and at least one monomer, or a blend of co-polymer and at least one monomer, or a combination thereof. In yet another embodiment, the polymer blend, copolymer, or mixture of polymers, substantially does not exhibit phase separation. In yet another embodiment, the polymer or tubular body or prosthesis, is porous; such that it will grow in the radial direction by about 0.025 mm to about 1 mm when soaked in an aqueous or dry environment at about 37° C. from about 1 minute to about 15 minutes. In another embodiment, the copolymer material, or tubular body, or prosthesis, has a textured surface, or non uniform surface, or surface with ridges, or bumpy surface, or surface with grooves, or wavy surface. The distance between the peak and trough of the surface texture range from about 0.01 micron to about 30 micron, or from about 0.1 micron to about 20 micron, or from about 1 micron to about 15 micron.

In some embodiments, the one or more biodegradable polymeric materials, or the tubular body or the stent may have a radial strength in an aqueous environment at about 37° C. of about 2 psi to about 25 psi, or of about 5 psi to about 22 psi, or of about 7 psi to about 20 psi, or of about 9 psi to about 18 psi. In yet another embodiment, the biodegradable polymer or copolymer or tubular body or prosthesis; has a radial strength in an aqueous or dry environment at body temperature of, greater than 3 psi, or greater than 5 psi, or greater than 8 psi, or greater than 10 psi, or greater than 15 psi.

In some embodiments, the biodegradable copolymer, or polymer blend, or polymer, or tubular body comprising the biodegradable polymer, or prosthesis has a % recoil in an aqueous or dry environment at 37° C. of about −20% to about 20%, or of about −15% to about 15%, or of about −10% to about 10%, or of about −10% to about 0%, or of about 0% to about 10%, or of about 3% to about 10%, or of about 4% to about 9%, or about 10% to about 20%, or about 15% to about 20%, or about 10% to about 15% or less than 25%, or less than 20%, or less than 15%, or less than 10%, or less than 5% after expansion to a deployed configuration from a crimped state.

The one or more biodegradable polymeric materials, or the tubular body, or the stent may optionally undergo treatment such as heating. In some embodiments, the one or more biodegradable polymeric materials, or the tubular body, or the stent may undergo longitudinal shrinkage of about 0% to about 30%, or of about 5% to about 25%, or of about 7% to about 20%, or of about 10% to about 15%. In other embodiments, the longitudinal (e.g., scaffold) shrinkage is less than 30%, or less than 25%, or less than 20%, or less than 15%, or less than 10%, of the original length. In other embodiments, the stent or polymer material or polymer tube has longitudinal shrinkage of about 25% or less, or about 15% or less, or about 10% or less, or about 5% or less, or about 0-30%, or about 1-25%, or about 5-15%. In some embodiments, treatment may include heating (e.g. in an oven) at temperatures ranging from about 30° C. to about 150° C. (with or without a mandrel inserted into the polymer or copolymer or tubular body or stent for a time ranging from about 30 minutes to about 24 hours); or expansion of the one or more biodegradable polymeric materials, or the tubular body, or the stent from a crimped state to an expanded state in an aqueous or dry environment at about 37° C. in vitro or in vivo for about 1 minute or less, or about 5 minutes or less, or about 15 minutes or less.

In further embodiments, the material comprising the body of the device or the biodegradable polymer, copolymer or polymer blend, or the tubular body comprising the biodegradable polymer, or the stent; is, or has crystals, crystalline regions, or polymer chains that are: substantially not uniaxially oriented, or not circumferentially oriented, or not longitudinally oriented, or not biaxially oriented. In other embodiments, the biodegradable copolymer has crystals, crystalline regions, molecular architecture, structural order, orientation, or polymer chains that are: substantially not uniform, or has low degree of order, or has varying degree of order, or is not substantially oriented as a result of not performing at least one of pressurizing and stretching of the tubular body, or is at least partially oriented as a result of spraying or dipping or crystallization or recrystallization, or radiation, or is at least partially oriented as a result of solvent evaporation or annealing or radiation, or is substantially not oriented, or not uniformly oriented, or low order oriented, or varying degree oriented, or randomly oriented, as a result of spraying or dipping, or solvent evaporation, or annealing, or radiation, or crystallization or recrystallization. In yet another embodiment, the biodegradable copolymer has crystals, crystalline regions, molecular architecture, structural order, orientation, or polymer chains that are: substantially oriented, or oriented, or biaxially oriented, or uniaxially oriented, or oriented in a direction that is longitudinal, or oriented in a direction that is circumferential, or oriented in a direction that is not longitudinal or circumferential, or oriented as a result of at least one of pressurizing the tube or stretching or drawing the tube, or oriented as a result of modification or treatment.

In further embodiments, the material comprising the body of the device or the biodegradable polymer, copolymer or polymer blend, or the tubular body comprising the biodegradable polymer, or the stent; is, or has crystals, crystalline regions, or polymer chains that are: substantially not uniaxially oriented, or circumferentially oriented, or longitudinally oriented, or biaxially oriented. In other embodiments, the biodegradable copolymer has crystals, crystalline regions, molecular architecture, structural order, orientation, or polymer chains that are: substantially not uniform, or has low degree of order, or has varying degree of order, or is not substantially oriented as a result of not performing at least one of pressurizing and stretching of the tubular body, or is at least partially oriented as a result of spraying or dipping or crystallization or recrystallization, or radiation, or is at least partially oriented as a result of solvent evaporation or annealing or radiation, or is substantially not oriented, or not uniformly oriented, or low order oriented, or varying degree oriented, or randomly oriented, as a result of spraying or dipping, or solvent evaporation, or annealing, or radiation, or crystallization or recrystallization. In yet another embodiment, the biodegradable copolymer has crystals, crystalline regions, molecular architecture, structural order, orientation, or polymer chains that are: substantially oriented, or oriented, or biaxially oriented, or uniaxially oriented, or oriented in a direction that is longitudinal, or oriented in a direction that is circumferential, or oriented in a direction that is not longitudinal or circumferential, or oriented as a result of at least one of pressurizing the copolymer tube or stretching or drawing the tube, or oriented as a result of modification or treatment.

In one embodiment, controlling the orientation of the polymeric material achieves the desired crystallinity, or Tg. In another embodiment, the polymeric material orientation is controlled such that the stent is capable to be crimped from an expanded condition to a crimped condition. In another embodiment, the polymeric material orientation is controlled such that the stent is capable to be expanded to a deployed diameter from a crimped configuration. In another embodiment, the polymeric material orientation is controlled such that the stent is capable to be expanded from a crimped configuration to a deployed configuration without fracture. In another embodiment, the polymeric material orientation is controlled such that the material has sufficient strength to support a body lumen. In a preferred embodiment, the polymeric material orientation is controlled by pressurizing the polymeric material with a medium such as gas such as $CO_2$ wherein the orientation control affects crystallinity to a range from 1% to 35%, or 1% to 45%, or 1% to 55%.

In some embodiments, the material (e.g., polymeric material) comprising the body of the device or the biodegradable copolymer or polymer has a weight-average molecular weight ($M_W$) of at least about 30,000 daltons (30 kDa), 60,000 daltons, 90 kDa, 120 kDa, 150 kDa, 180 kDa, 210 kDa, or 240 kDa, or 500 kDa, or 750 kDa, or 1000 kDa. In an embodiment, the material (e.g., polymeric material) comprising the body of the device or the biodegradable copolymer or polymer has an $M_W$ of at least about 120 kDa. In further embodiments, the material (e.g., polymeric material) comprising the body of the device or the biodegradable copolymer or polymer has an $M_W$ of about 30 kDa to about 800 kDa, or about 30 kDa to about 700 kDa, or about 30 kDa to about 600 kDa, or about 30 kDa to about 500 kDa, or about 30 kDa to about 400 kDa, or about 30 kDa to about 300 kDa, or about 60 kDa to about 900 kDa, or about 90 kDa to about 600 kDa, or about 120 kDa to about 400 kDa, or about 150 kDa to about 250 kDa, or about 80 kDa to about 250 kDa; before treatment, or after treatment, of the stent prosthesis or the polymeric material. In an embodiment, the material (e.g., polymeric material) comprising the body of the device or the biodegradable copolymer or polymer has a $M_W$ of about 120 kDa to about 250 kDa; before treatment, or after treatment, of the stent prosthesis.

In some embodiments, biodegradable polymeric materials may be copolymers, such as block copolymers or random copolymers. In some embodiments, two or more biodegradable polymeric materials may be used as part of a tubular body or prosthesis or stent (e.g., as a polymer blend). In some cases, co-polymeric and homopolymeric materials may be blended. Biodegradable polymeric materials may include poly-DL-lactide, polylactide-co-glycolactide, or other polymers as described herein. In some embodiments, the tubular body or prosthesis or stent may also include one or more monomers of the polymers that comprise the stent, or of other polymers. In some cases, the one or more monomers may be covalently bonded to the one or more polymers. In some embodiments, the two or more biodegradable polymeric materials may remain in substantially the same phase after about 1 second, or 10 seconds, or 1 minute, or 10 minutes, or 1 hour, or 10 hours, or 1 day, or 10 days, or 1 month, or 6 months, or 1 year, or 2 years, or 5 years of deployment and/or treatment. In some embodiments, the two or more biodegradable polymeric materials may have a $T_g$ within 2° C., or within 4° C., or within 6° C., or within 8° C., or within 10° C., or within 12° C., or within 14° C., or within 16° C., or within 18° C., or within 20° C. of each other.

In some embodiments, the polymeric material comprises monomer. In further embodiments, the polymeric material comprises less than 10% (by weight), or less than 5% (by weight), or less than 1% (by weight), or less than 0.5% (by weight), or less than 0.25% (by weight) monomer. In other embodiments, the polymeric material comprises 0-10% (by weight) of monomer.

In a preferred embodiment, the polymeric material comprises one or more co-polymers, and to this polymeric material is added about 0.1% or less, or about 0.5% or less, or about 1% or less, or about 2% or less, or about 3% or less, or about 4% or less, or about 5% or less, or about 6% or less, or about 7% or less, or about 8% or less, or about 9% or less, or about 10% or less monomer. In another embodiment, the polymeric material further comprising one or more of the co-polymers, or another monomer, or another polymer, or another co-polymer. In further preferred embodiments, the addition of monomer, polymer or copolymer does not change the Tg of the polymeric material substantially. In other preferred embodiments, the addition of monomer, polymer, or copolymer does not change the Tg of the polymeric material by more than 10° C., or by more than 5° C., or by more than 3° C. than the polymeric material without added monomer, polymer, or copolymer. In other preferred embodiments, the addition of monomer, polymer, or copolymer does not exhibit phase separation from the polymeric material after treatment and/or before deployment. In other preferred embodiments, the polymeric material comprises less than about 100 micrograms, or less than about 50 micrograms, or less than about 25 micrograms or monomer (such as unreacted monomer), polymer, or copolymer per milligram of stent. In other preferred embodiments, the addition of monomer, polymer or copolymer does not interfere with the expansion of stent from crimped state to expanded state, and the expansion can occur without fracture. In other preferred embodiments, the addition of monomer, polymer, or copolymer does not change crystallinity of the polymeric material, which may be more than about 1% and less than about 30%, or more than about 0% and less than about 35%, or less than 35%, or less than 30%, or less than 25%, or less than 20%, or less than 15%, or less than 10%, or less than 5%, or greater than 0%, or greater than 5%, or greater than 10%, or greater than about 15%, or greater than about 20%, or greater than about 25%, or greater than about 30%, or greater than about 35%. In other preferred embodiments, combination of polymeric material and monomer, polymer, or copolymer comprising the body, or the stent, or the tubular body may have a crystallinity of about 0% to less than 35%, or about 0% to less than 30%, or about 0% to less than 25%, or about 0% to less than 20%, or about 0% to less than 15%, or about 0% to less than 10%, or about 0% to less than 5%. In other preferred embodiments, addition of monomer, polymer or copolymer does not change the molecular weight of the polymeric material, which can be in the range from about 30 kDa to about 700 kDa. In further preferred embodiments, the unreacted monomer, polymer or copolymer comprises glycolic acid, lactide, polyglycolic acid, lactide-co-glycolide, caprolactone, polycaprolactone, lactide-co-caprolactone, and combinations thereof.

In some embodiments, the biodegradable stent or tube comprises a body which comprises a biodegradable polymer, or copolymer, polymer blends, copolymers, and/or polymer/monomer mixtures wherein the polymer material is configured to be capable of being balloon expandable and self-expanding at body temperature of about 37° C. In one embodiment, prior to being balloon-expanded, the stent may self-expand by about 0.001-0.025 inches, or about 0.003-0.015 inches, or about 0.005-0.10 inches, or about 0.001 inches or more, or 0.003 inches or more, or 0.005 inches or more, or 0.010 inches or more, or 0.025 inch or more, or by about 0.05%, or about 0.1%, or about 0.25%, or about 0.5%, or about 1%, or more than an initial crimped diameter of the stent, after being in aqueous condition at about 37° C. in vitro or in vivo for about 1 minute or less, or about 5 minutes or less, or about 15 minutes or less, or about 30 minutes or less, or about 1 hour or less, or about 2 hours or less, or about 3 hours or less, or about 4 hours or less, or about 6 hours or less, or about 12 hours or less, or about one day or less. Optionally, the stent is constrained from self-expanding using a sheath or other means and then such constraining means is removed, disengaged, or withdrawn, or released after the stent is positioned for deployment, allowing the stent to self-deploy. The stent in a preferred embodiment further self expands after balloon deployment by about 0.01 mm to about 0.5 mm, or about 0.05 mm to about 0.3 mm, within about 30 seconds or more, or about 1 minute or more, or about 10 minutes or more, or about 1 hour or more, or about 12 hours or more, or about 24 hours or more.

In some embodiments, the one or more biodegradable polymeric materials, or the tubular body, or the stent degrade over time. Degradation may occur in vitro or in vivo. Degradation may occur after about 1 day, or about 5 days, or about 10 days, or about 1 month, or about 2 months, or about 6 months, or about 1 year in aqueous condition (e.g., in aqueous solution, water, saline solution or physiological conditions) at about 37° C. in vitro or in vivo. The one or more biodegradable polymeric materials or the tubular body may substantially degrade within 2 years, or 1.5 years, or 1 years, or 9 months, or 6 months.

In some embodiments, the body of the device, or the stent, or the material comprising the body of the device, or the material comprising one or more layers of the body of the device, comprises one or more biologically active agents. In some embodiments, the biologically active agent(s) are selected from the group consisting of anti-proliferative agents, anti-mitotic agents, cytostatic agents, anti-migratory agents, immunomodulators, immunosuppressants, anti-inflammatory agents, anticoagulants, anti-thrombotic agents, thrombolytic agents, anti-thrombin agents, anti-fibrin agents, anti-platelet agents, anti-ischemia agents, anti-hypertensive agents, anti-hyperlipidemia agents, anti-diabetic agents, anti-cancer agents, anti-tumor agents, anti-angiogenic agents, angiogenic agents, anti-bacterial agents, anti-fungal agents, anti-chemokine agents, and healing-promoting agents. In certain embodiments, the body of the device comprises an anti-proliferative agent, anti-mitotic agent, cytostatic agent or anti-migratory agent. In further embodiments, the body of the device comprises an anticoagulant, anti-thrombotic agent, thrombolytic agent, anti-thrombin agent, anti-fibrin agent or anti-platelet agent in addition to an anti-proliferative agent, anti-mitotic agent, cytostatic agent or anti-migratory agent. It is appreciated that specific examples of biologically active agents disclosed herein may exert more than one biological effect. Examples of anti-proliferative agents, anti-mitotic agents, cytostatic agents and anti-migratory agents include without limitation rapamycin and its derivatives and metabolites.

In some embodiments, the stent or body of the device can comprise one or more biologically active agents, and/or one or more additives such as carbon nano fibers or tubes. The additives can serve any of a variety of functions, including controlling degradation, increasing the strength, increasing elongation, controlling Tg, or/and increasing toughness of the material (e.g., polymeric material) comprising the body of the device (or the material comprising a coating on the body), and/or increasing crystallinity.

In another embodiment, the stent or tubular body comprises radiopaque markers. Radiopaque markers can be metallic such as gold, platinum, iridium, bismuth, or combination thereof, or alloys thereof. Radiopaque markers can also be polymeric material. Radiopaque markers can be incorporated in the stent or tubular body when it is being formed or incorporated into the stent or the tubular body after forming.

In some embodiments, one or more coatings can be applied onto the body of the device. Each of the coatings can contain one or more biodegradable polymers, one or more non-degradable polymers, one or more metals or metal alloys, one or more biologically active agents, or one or more additives, or a combination thereof. The coating(s) can serve any of a variety of functions, including controlling degradation of the body of the device, improving or controlling physical characteristics (e.g., strength, recoil, toughness) of the device, and delivering one or more biologically active agents to a site of treatment.

In some embodiments, depending in part on the type of device it is, the biodegradable implantable device described herein can be used to treat or prevent a wide variety of diseases, disorders and conditions, or promote a wide variety of therapeutic effects. In some embodiments, the biodegradable device is implanted in a subject for treatment or prevention of a disorder or condition, or delivery or a drug, or promotion of a therapeutic effect, selected from the group consisting of wound healing, hyper-proliferative disease, cancer, tumor, vascular disease, cardiovascular disease, coronary artery disease, peripheral arterial disease, ENT or nose disorder, atherosclerosis, thrombosis, vulnerable plaque, stenosis, restenosis, ischemia, myocardial ischemia, peripheral ischemia, limb ischemia, hyper-calcemia, vascular obstruction, vascular dissection, vascular perforation, aneurysm, vascular aneurysm, aortic aneurysm, abdominal aortic aneurysm, cerebral aneurysm, chronic total occlusion, patent foramen ovale, hemorrhage, claudication, diabetic disease, pancreas obstruction, kidney obstruction, bile duct obstruction, intestine obstruction, duodenum obstruction, colon obstruction, ureter obstruction, urethra obstruction, sphincter obstruction, airway obstruction, anastomosis, anastomotic proliferation of artery, vein or artificial graft, bone injury, bone crack, bone fracture, osteoporosis, skeletal defect, bone defect, weak bone, bone thinning, improper bone union or healing, fusing bone, fusion of adjacent vertebrae, osteochondral defect, chondral defect, cranial defect, scalp defect, calvarial defect, craniofacial defect, craniomaxillofacial defect, segmental bone loss, thoracic cage defect, cartilage defect, cartilage repair, cartilage regeneration, bone-cartilage bridging, bone-tendon bridging, spinal disorder, scoliosis, nerve damage, nerve injury, nerve defect, nerve repair, nerve reconstruction, nerve regeneration, herniation, abdominal herniation, disc herniation, acute or chronic low back pain, discogenic pain, trauma, abdominal wall defect, septal repair, burn injury, facial reconstruction, facial regeneration, aging, and contraception. The biodegradable device can also be used outside the body, e.g., in tissue engineering to generate tissue.

When the biodegradable device is a stent, the stent can also be used to treat or prevent a wide variety of diseases, disorders and conditions. In some embodiments, the biodegradable stent is implanted in a subject for treatment or prevention of obstruction, occlusion, constriction, stricture, narrowing, stenosis, restenosis, intimal hyperplasia, collapse, dissection, thinning, perforation, kinking, aneurysm, failed access graft, cancer or tumor of a vessel, passage, conduit, tubular tissue or tubular organ, such as an artery, vein, peripheral artery, peripheral vein, subclavian artery, superior caval vein, inferior caval vein, popliteal artery, popliteal vein, arterial duct, coronary artery, carotid artery, brain artery, aorta, ductus arteriosus, right ventricular outflow tract conduit, transitional atrioventricular canal, interatrial septum, iliac artery, common iliac artery, external iliac artery, internal iliac artery, iliac vein, internal pudendal artery, mammary artery, femoral artery, superficial femoral artery, femoral vein, pancreatic artery, pancreatic duct, renal artery, hepatic artery, splenic artery, biliary artery, bile duct, stomach, small intestine, duodenum, jejunum, ileum, large intestine, cecum, colon, rectosigmoid colon, sphincter, rectum, colorectum, ureter, urethra, prostatic duct, pulmonary artery, aortopulmonary collateral artery, aortopulmonary collateral vessel, airway, nasal passage, nostril, throat, pharynx, larynx, esophagus, epiglottis, glottis, trachea, carina, bronchus, bilateral main bronchus, intermediate branch bronchus, transbronchial passage, or tracheobronchus.

In certain embodiments, the biodegradable device is an endoprosthesis or stent. Non-limiting examples of stents include vascular stents, coronary stents, coronary heart disease (CHD) stents, carotid stents, brain aneurysm stents, peripheral stents, peripheral vascular stents, venous stents, femoral stents, superficial femoral artery (SFA) stents, pancreatic stents, renal stents, biliary stents, intestinal stents, duodenal stents, colonic stents, ureteral stents, urethral stents, prostatic stents, sphincter stents, airway stents, tracheobronchial stents, tracheal stents, laryngeal stents, esophageal stents, single stents, segmented stents, joined stents, overlap stents, tapered stents, and bifurcated stents. In certain embodiments, the biodegradable device is a vascular or coronary stent.

In some embodiments, the endoprosthesis design and pattern can be any suitable pattern of the type employed in conventional endoprostheses to serve the intended purpose of the device. A variety of exemplary patterns are set forth in (but not limited to) U.S. patent application Ser. No. 12/016,077, which is incorporated herein by reference in its entirety.

In certain embodiments, the material (e.g., polymeric material) comprising or comprising the body of the biodegradable implantable device or the biodegradable copolymer or polymer:

has a degree of crystallinity, or % crystallinity by XRD or DSC, of about 5% to about 30% by weight or volume;
has a $T_g$ of greater than 37° C. and less than 50° C.;
has a tensile yield strength of at least about 1500 psi;
Mw of 30 kDa to 600 kDa; and
has a % elongation at break or failure or yield of about 15% to about 300%; and radially expandable from crimped configuration to expanded configuration without fracture at body temperature.

In certain embodiments, the material (e.g., polymeric material) comprising the body of the biodegradable implantable device or the biodegradable copolymer or polymer:

has a degree of crystallinity, or % crystallinity by XRD or DSC, of about 30%;
has a $T_g$ of greater than 37° C. to less than 47° C.;
has a tensile yield strength of at least about 1500 psi; and
has a % elongation at break or failure or yield of about 15% to about 300%.

In certain embodiments, the biodegradable devices and the biodegradable polymers have a rough exterior, or texture as depicted in FIG. 5A for example. The preferred texture is such that the surface has several bumps, or/and such bumps are not oriented in an uniform manner. This texture can be achieved in a variety of ways including spraying as an example. Such texture is different from the texture show in FIG. 5B, wherein the texturing has an orientation, in this case the orientation being in the horizontal direction. Such horizontally oriented texturing is in some embodiments can be achieved by die extrusion. In certain other embodiments, the biodegradable devices and the biodegradable polymers have both types of texturing described herein. In a preferred embodiment, orientation of the device may be controlled.

In some embodiments, the stent is deployed in a main vessel across a side branch, and the stent of the invention allows for insertion of a guidewire and/or balloon catheter through openings between stent struts, and enabling inflation through the openings of stent struts to increase or expand interstrut opening to the branch. The stent allows for a guidewire and/or balloon catheter through the opening to expand at least one transverse dimension to access and treat the side branch with balloon inflation, or additional stent implantation or drug delivery treatments. The stent expanded diameter/transverse dimension in one embodiment is substantially maintained after balloon expansion and removal of the balloon. In another embodiment, the expanded diameter/transverse dimension is decreased after balloon expansion and removal of the balloon. In a preferred embodiment, the decrease is at least 20% from the expanded transverse dimension. In a preferred embodiment, the decrease is at least 20% from the expanded transverse dimension and less than 75%. In a third embodiment, the expanded transverse dimension becomes larger after balloon expansion and removal of the balloon, preferably larger by at least 1%, or by at least 5%, or by at least 10% from the balloon expanded transverse dimension. Typically, changes in the transverse dimension occur within 24 hours or less, or 12 hours or less, or 9 hours or less, or 6 hours or less, or 3 hours or less, or 1 hour or less, or 30 minutes or less.

In one embodiment, the stent struts are capable of expanding along one or more than one dimension or directional dimension upon balloon inflation through the stent strut openings along the longitudinal, radial, or circumferential dimensions. In a preferred embodiment, the stent struts are capable to expand in one or more transverse dimensions without fracture. In a preferred embodiment, the expanded transverse dimension of the stent struts remains substantially the same, and without fracture. In a preferred embodiment, the expanded transverse dimension of the stent struts further expands or increase, and without fracture. In a preferred embodiment, the expanded transverse dimension of the stent struts further contracts or decrease, and without fracture.

In another embodiment, the balloon expands stent struts in at least the radial transverse dimension, further self expands to align with vessel wall, or self expand to oppose the vessel wall, or self expands by at least 0.01 mm.

The invention provides polymeric materials, including biodegradable stents, and methods of their fabrication. Various aspects of the invention described herein may be applied to any of the particular applications set forth below or in any other type of setting. The invention may be applied as a standalone system or method, or as part of an integrated system or method. It shall be understood that different aspects of the invention can be appreciated individually, collectively, or in combination with each other.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

BRIEF DESCRIPTION OF THE DRAWINGS

FIGS. 26A and 26B depict the DESolve™ Bioresorbable Coronary Stent Scaffold used in the DESolve 1 clinical trial;

FIG. 27 depicts preclinical optical coherence tomography (OCT) images of the scaffold at different time points;

FIG. 39 shows slides at 28 days, six months, and two years. FIG. 40 shows slides at nine months.

Table 29 provides an incomplete scaffold apposition (USA) analysis.

Figure 49:
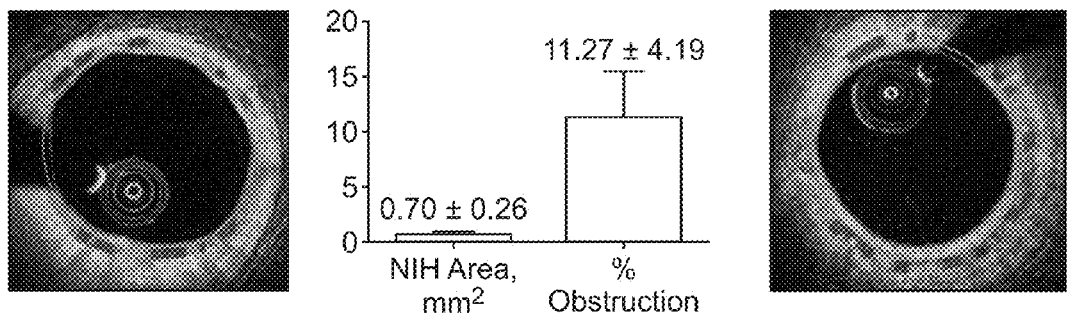
Figure 50:
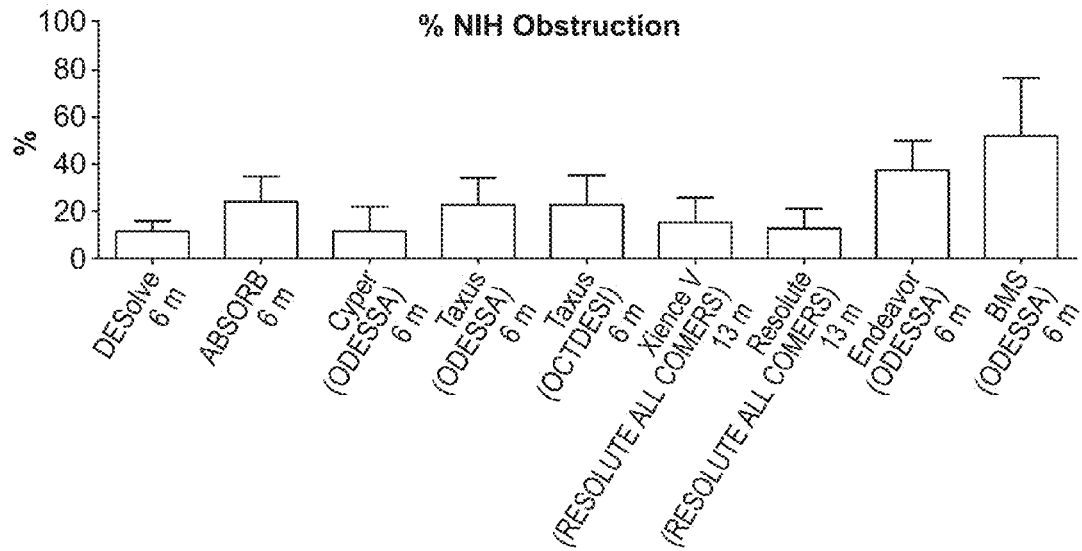

FIGS. 49 and 50 provide an NIH quantification by OCT.

Figure 51:
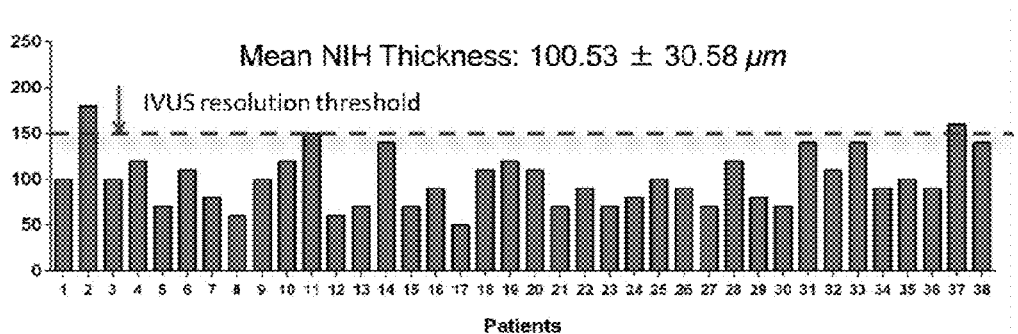
Figure 52:
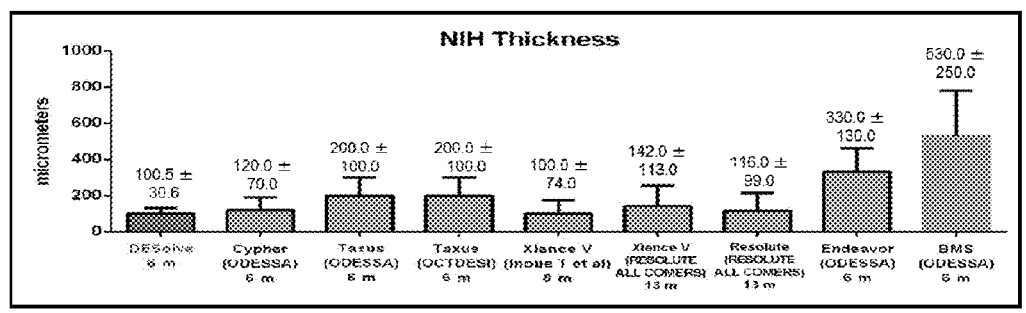

FIGS. 51 and 52 provide an NIH thickness and distribution analysis.

Figure 53:
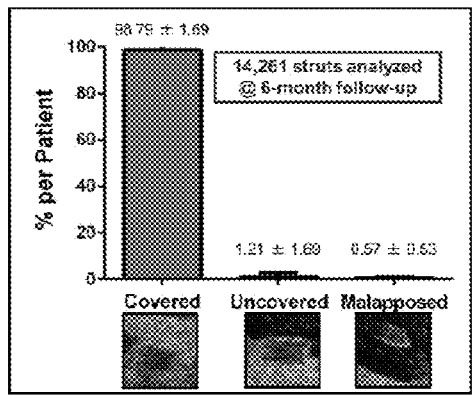
Figure 54:
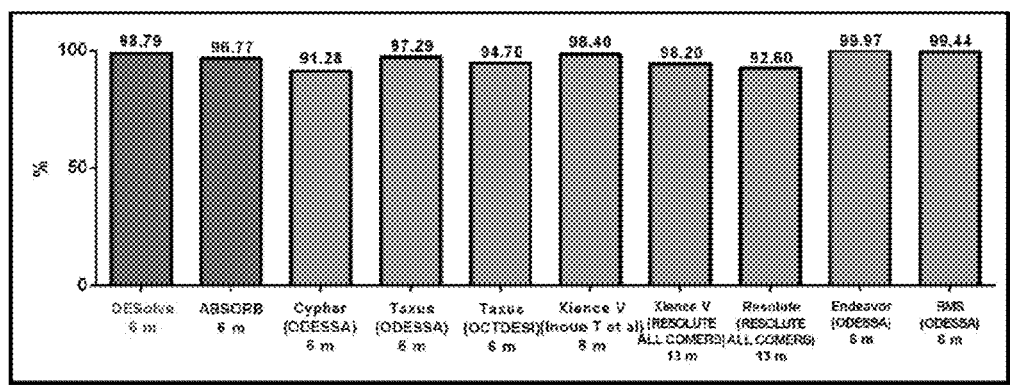

FIGS. 53 and 54 provide a strut coverage (safety surrogate) analysis.

DETAILED DESCRIPTION OF THE INVENTION

In preferred embodiments, improved biodegradable endoprostheses and methods for their fabrication are provided. The stent prostheses may be formed from one or more amorphous, semi-crystalline, or crystalline biodegradable polymers.

In some embodiments of the invention, the polymers are modified or treated to introduce a desired degree of crystallinity. In other embodiments, introducing crystallinity into the polymer increases the strength of the polymer so that it is suitable for use as an endoprosthesis and in some cases without substantially lengthening the period of biodegradation after implantation. In other embodiments, the polymeric material is treated to achieve a desired degree of crystallinity. In other embodiments, the polymeric material is treated to control crystallinity.

Some embodiments of the disclosure relate to a biodegradable implantable device comprising a body comprising a material which comprises a biodegradable copolymer or polymer blend or mixture. It is appreciated that any copolymer or polymer blends or mixture described herein can be formed from one, two, three, four or more different monomers or polymers, where each of the monomers or polymers comprising the copolymer or the polymer can be in any amount (e.g., about 0.1% to about 99.9%, or about 0.5% to about 99.5%, or about 1% to about 99%, or about 2% to about 98%, by weight or molarity).

The substantially amorphous or semi-crystalline polymeric material or the tubular body formed there from can be modified to control crystallinity (e.g., degree of crystallinity) of the polymeric material. In certain embodiments, the substantially amorphous or semi-crystalline polymeric material or the tubular body formed therefrom undergoes a modification treatment to introduce a desired degree of crystallinity into the polymeric material to increase the strength of the polymeric material without substantially lengthening its degradation time.

Additional embodiments of the disclosure relate to biodegradable endoprostheses (e.g., stents) formed at least partially from a substantially amorphous, biodegradable polymer, and to biodegradable endoprostheses comprising a tubular body formed at least partially from a substantially amorphous, biodegradable polymer. In some embodiments, the biodegradable endoprostheses are comprised of a material which comprises a biodegradable polymer, or the biodegradable endoprostheses comprise a tubular body comprised of a material which comprises a biodegradable polymer, wherein the material or the polymer is substantially amorphous or semi-crystalline prior to a modification (or treatment), and crystallinity (e.g., degree of crystallinity) of the material or the polymer increases after the material, the polymer, the tubular body, or the endoprosthesis undergoes the modification. In one embodiment, the crystallinity increases by about 1% to about 40%, or by about 5% to about to about 35%, or by about 10% to about 30, or by about 10% to about 25%, of the original crystallinity prior to modification. In another embodiment, the crystallinity after treatment (modification) is less than about 40%, or less than about 35%, or less than about 30%, or less than about 25%. In one embodiment, the substantially amorphous polymeric material or semi-crystalline material can decrease the period of degradation of the endoprosthesis or the tubular body to, e.g., less than about four years, or less than about three years, or less than about two years, or less than about one year, or less than about nine months, or less than about six months, or shorter.

In some embodiments, amorphous biodegradable polymers having less than 10% crystallinity can degrade faster than crystalline polymers but are weaker than crystalline polymers and hence are not typically suitable for vascular implants, such as stents, which need sufficient strength to provide support to the blood vessel. The present invention provides for the modification of polymeric materials to make them suitable for use as biodegradable stents and other endoprostheses. Materials suitable for modification according to the present invention include but are not limited to poly-DL-Lactide, polylactide-co-glycolactide; polylactide-co-polycaprolactone, poly(L-lactide-co-trimethylene carbonate), polytrimethylene carbonate and copolymers; polyhydroxybutyrate and copolymers; polyhydroxyvalerate and copolymers, poly orthoesters and copolymers, poly anhydrides and copolymers, polyiminocarbonates and copolymers and the like. An exemplary stent is made from amorphous material of a copolymer of 85/15 Poly(L-Lactide-co-Glycolide) and processed to increase crystallinity by at least 20% of original crystallinity, preferably by at least 100%, more preferably by at least 1000% of original crystallinity. In one embodiment, the biodegradable stent substantially degrades in less than 2 years, preferable less than 1 year, more preferable less than 9 months.

In some embodiments, the polymers' crystallinity of the polymeric material after modification or treatment is increased by at least 10% of the original crystallinity of the polymer material, preferably by at least 20% of the original crystallinity of the polymer material, preferably by at least 50% of the original crystallinity of the polymer material, and more preferably by at least 100% of the original crystallinity of the polymer material.

In another embodiment, the initial diameter is 0.9-1.5 times the stent deployment diameter, or the stent nominal diameter. The stent nominal diameter is the labeled deployment stent diameter. The stent deployment diameter usually is the deployed diameter of the stent at nominal or bigger diameter. In another embodiment, the initial diameter is smaller than the deployed stent diameter or smaller than the labeled stent deployed diameter.

In a preferred embodiment, the polymeric material prior to a treatment is amorphous. In other embodiments, the polymeric material prior to a treatment is semi-crystalline. In a further embodiment, the polymeric material prior to a treatment is crystalline.

In certain embodiments, the material (e.g., polymeric material) comprising the body of the device or the biodegradable polymer or copolymer has a crystallinity or percent crystallinity by X-ray diffraction (XRD) or differential scanning calorimetry (DSC), by weight or volume of about 0%, 1%, 2%, 5% or 10% to about 70%; or about 0%, 1%, 2%, 5% or 10% to about 60%; or about 0%, 1%, 2%, 5% or 10% to about 55%; or about 0%, 1%, 2%, 5% or 10% to about 50%; or about 0%, 1%, 2%, 5% or 10% to about 40%; or about 0%, 1%, 2%, 5% or 10% to about 30%; or about 0%, 1%, 2%, 5% or 10% to about 25%; or about 0%, 1%, 2%, 5% or 10% to about 20%. In certain embodiments, the material (e.g., polymeric material) comprising the body of the device or the biodegradable polymer copolymer has a degree of crystallinity, or % crystallinity by XRD or DSC, of about 5% to about 30%, or about 7% to about 22%, by weight or volume.

In some embodiments, the amorphous biodegradable polymeric material is processed to increase its crystallinity. Increased crystallinity may increase the strength, storage shelf life, and hydrolytic stability of the polymer stent material. The process initiates and/or enhances crystallinity in the polymeric material by nucleating and/or growing small size spherulite crystals in the material. Since the amorphous regions of the modified polymer in some embodiments are preferentially broken down by hydrolysis or enzymatic degradation in biological environment, the modified amorphous biodegradable polymer in those embodiments has increased crystallinity and increased material strength post processing. The increase in crystallinity can be achieved by modifications described in present invention which include at least one of heating, cooling, pressurizing, addition of additives, crosslinking and other processes.

The polymer material can be made into a tube by spraying, extrusion, molding, dipping or printing or other process from a selected amorphous copolymer. The amorphous polymer tubing is optionally vacuumed to at least −25 in. Hg, annealed, and quenched to increase crystallinity. In one embodiment, the tube is vacuumed at or below 1 torr at ambient temperature to remove water and solvent. It is then annealed by heating to a temperature above the glass transitional temperature but below melting temperature of the polymer material. Preferably, the annealing temperature is at least 10° C. higher than the glass transitional temperature (Tg), more preferably being at least 20° C. higher, and still more preferably being at least 30° C. higher than the Tg. The annealing temperature is usually at least 5° C. below the melting point (Tm), preferably being at least 20° C. lower, and more preferably being at least 30° C. lower than the Tm of the polymer material. The annealing time is between 1 minute to 10 days, preferably from 30 minutes to 3 hours, and more preferably from 1.5 hours to 2.5 hours.

In another embodiment, the treatment comprising heating ranges from a fraction of a second to seven days, preferably from 30 seconds to 3 days, more preferably from 1 minute to 24 hours, and most preferably from 2 minutes to 10 hours.

In one embodiment, the heated (annealed) tube is quenched by fast cooling from the annealing temperature to a temperature at or below ambient temperature over a period from 1 second to 1 hour, preferably 1 minute to 30 minutes, and more preferably 5 minutes to 15 minutes. In another embodiment the annealed tune is quenched by slow cooling from the annealing temperature to at or below ambient temperature within 1 hour to 24 hours, preferably 4 hours to 12 hours, and more preferably 6 hours to 10 hours. In some instances the heat treated tube is cooled to a temperature below ambient temperature for a period from 1 minute to 96 hours, more preferably 24 hours to 72 hours, to stabilize the crystals and/or terminate crystallization. This annealing and quenching process initiates and promotes nucleation of crystals in the polymer and increases the mechanical strength of the material. The initial annealing temperature and the cooling rate can be controlled to optimize the size of the crystals and strength of the material. In a further embodiment, the unannealed and/or annealed tube is exposed to ebeam or gamma radiation, with single or multiple doses of radiation ranging from 5 kGy to 100 kGy, more preferably from 10 kGy to 50 kGy.

In another embodiment, the biodegradable polymeric stent material can have increased crystallinity by cross-linking such as exposure to radiation such as gamma or ebeam. The cumulative radiation dose can range from 1 kGy to 1000 KGy, preferably 5 to 100 KGy, more preferably 10 to 30 KGy.

Crystallinity (e.g., degree of crystallinity) of the material (e.g., polymeric material) comprising a polymeric material (e.g., a tube) can be controlled by exposure of the polymeric article to carbon dioxide gas or liquid, e.g., under conditions used for controlling solvents and monomers as described herein. When the degree of crystallinity of the polymeric material comprising the polymeric article is relatively low, exposure of the polymeric material to carbon dioxide gas or liquid can control crystallinity by decrease or increase the degree of crystallinity. When the degree of crystallinity of the polymeric material is relatively high, exposure of the polymeric article to carbon dioxide gas or liquid can potentially decrease the degree of crystallinity.

Some embodiments of the disclosure relate to biodegradable implantable devices (e.g., a stent) comprising a body (e.g., a tubular body) comprising a material which comprises a biodegradable polymer, copolymer, or polymer blend, wherein the material comprising the body, or the biodegradable polymer, copolymer, or polymer blend, or the stent, has a degree of crystallinity of about 0% to about 70%, or of about 0% to about 55%, or of about 0% to about 30%, or of about 0% to about 25%, or of about 5% to about 70%, or of about 5% to about 55%, or of about 5% to about 30%, or of about 5% to about 25%, or of about 10% to about 70%, or of about 10% to about 55%, or of about 10% to about 30%, or of about 10% to about 25%; or of about 15% to about 70%, or of about 15% to about 55%, or of about 15% to about 30%, or of about 15% to about 25%, or of about 0% to about 40%, or of about 0% to about 35%, or of about 0% to about 25%, or of about 0% to about 20%, or of about 0% to about 15%, or of about 5% to about 40%, or of about 5% to about 35%, or of about 5% to about 25%, or of about 5% to about 20%, or of about 5% to about 15%, or greater than 0% to about 10%, or greater than 1% to about 10%; before modification or treatment, or after modification or treatment, or with a modification or treatment, or without a modification or treatment, or prior to implant, or after sterilization, or before patterning, or after patterning, or the stent, or the tubular body.

In yet another preferred embodiment, the stent or body or biodegradable material, is substantially amorphous. In yet another preferred embodiment, the stent or body or biodegradable material, is substantially amorphous prior to treatment. In yet another preferred embodiment, the stent or body or biodegradable material, is substantially amorphous prior to treatment and substantially amorphous after treatment. In yet another preferred embodiment, the stent or body or biodegradable material, is substantially amorphous prior to treatment and substantially semi-crystalline after treatment. In yet another embodiment, the stent or tubular body or biodegradable material, has crystallinity that is higher prior to treatment than the crystallinity after treatment. In yet another embodiment, the stent or tubular body or biodegradable material, has crystallinity that is higher prior to treatment than the crystallinity after treatment wherein the stent or tubular body or biodegradable material, is in an amorphous state prior to said treatment. In yet another embodiment, the stent or tubular body or biodegradable material, has crystallinity that is substantially similar prior to treatment to the crystallinity after treatment wherein the stent or tubular body or biodegradable material, is in an amorphous state prior to said treatment. In yet another embodiment, the stent or tubular body or biodegradable material, has crystallinity of about 0% to about 50% prior to treatment and has crystallinity of about 0% to about 50% after treatment. In yet another embodiment, the stent or tubular body or biodegradable material, has crystallinity of about 0% to about 45% prior to treatment and has crystallinity of about 0% to about 45% after treatment. In yet another embodiment, the stent or tubular body or biodegradable material, has crystallinity of about 0% to about 40% prior to treatment and has crystallinity of about 0% to about 40% after treatment. In yet another embodiment, the stent or tubular body or biodegradable material, has crystallinity of about 0% to about 35% prior to treatment and has crystallinity of about 0% to about 35% after treatment. In yet another embodiment, the stent or tubular body or biodegradable material, has crystallinity of about 0% to about 35% prior to treatment and has crystallinity of about 0% to about 35% after treatment. In yet another embodiment, the stent or tubular body or biodegradable material, has crystallinity of about 0% to about 30% treatment and has crystallinity of about 0% to about 30% after treatment. In yet another embodiment, the stent or tubular body or biodegradable material, has crystallinity of about 0% to about 25% prior to treatment and has crystallinity of about 0% to about 25% after treatment. In yet another embodiment, the stent or tubular body or biodegradable material, has crystallinity of about 0% to about 20% prior to treatment and has crystallinity of about 0% to about 20% after treatment. In yet another embodiment, the stent or tubular body or biodegradable material, has crystallinity of about 0% to about 15% prior to treatment and has crystallinity of about 0% to about 15% after treatment. In yet another embodiment, the stent or tubular body or biodegradable material, has crystallinity of about 0% to about 25% prior to treatment and has crystallinity of about 0.3% to about 40% after treatment. In yet another embodiment, the stent or tubular body or biodegradable material, has crystallinity of about 0% to about 25% prior to treatment and has crystallinity of about 0% to about 20% after treatment. In certain embodiments, the material comprising the body of the device or the biodegradable polymer, copolymer or the stent, has a degree of crystallinity of about 5% to about 30% and a $T_g$ of about 35° C. to about 70° C.

In certain embodiments, the biodegradable copolymer is a polylactide copolymer, where lactide includes L-lactide, D-lactide and D,L-lactide. In another embodiment, the biodegradable polymer or tubular body or prosthesis comprises a poly-l-lactide acid (PLLA) polymer that is substantially amorphous or substantially semi crystalline. In another embodiment, the biodegradable polymer or tubular body or prosthesis comprises a PLLA polymer that is substantially amorphous or substantially semi crystalline, wherein the tubular body is substantially randomly oriented, or substantially not oriented, or non uniformly oriented, or not biaxially oriented. In another embodiment, the biodegradable polymer is PLLA polymer that is substantially amorphous or substantially semi crystalline, and/or having a % crystallinity ranging from about 0% to about 30%. In another embodiment, the biodegradable polymer is PLLA polymer that is substantially amorphous or substantially semi crystalline, and/or having a % crystallinity ranging from about 0% to about 30% after a modification. In another embodiment, the biodegradable polymer is PLLA polymer that is substantially amorphous before and after modification. In another embodiment, the biodegradable polymer is PLLA polymer that is substantially amorphous before modification and semi crystalline after modification. In another embodiment, the biodegradable polymer is PLLA polymer that is substantially semi crystalline before modification and crystalline after modification. In another embodiment, the biodegradable polymer is PLLA polymer that is substantially amorphous or substantially semi crystalline and/or having a % crystallinity ranging from about 0% to about 30% after a modification and/or having % elongation or shrinkage of about 10% to about 50% after treatment; or of less than 10% after treatment. In another embodiment, the biodegradable polymer is PLLA polymer that is substantially amorphous or substantially semi crystalline, and/or having a % crystallinity ranging from about 0% to about 30% after a modification, and/or having % elongation or shrinkage of about 10% to about 50% after treatment, and/or capable of radial expansion from a crimped state to an expanded state in an aqueous environment at about 37° C. In yet another embodiment, various combinations of the embodiments are included.

In another embodiment, it is desired to control crystallinity in a manner to preserve the material properties after forming. For example it is desirable to treat the tubular body or the biodegradable polymeric material wherein the crystallinity of the tubular body after forming is substantially unchanged from the crystallinity of the stent prosthesis material prior to implant. In such cases, the treatment(s) of the biodegradable polymeric material controls maintaining crystallinity to be substantially the same.

In another embodiment, it is desired to control crystallinity in a manner to lower crystallinity after forming or after treatment. For example it is desirable to treat the tubular body or the biodegradable polymeric material wherein the crystallinity of the stent prosthesis material prior to implant is lower than the crystallinity of the tubular body after forming.

The biodegradable stent prosthesis comprising a tubular body comprising a biodegradable polymeric material, wherein the tubular body has been formed using extrusion, molding, dipping, or spraying, said biodegradable polymeric material has an initial crystallinity and has a Tg greater than 37° C. and the stent prosthesis has a crystallinity (biodegradable stent material) that is substantially the same as the initial crystallinity and at body temperature is radially expandable and has sufficient strength to support a body lumen.

In certain embodiments, the material (e.g., polymeric material) comprising the body of the device or the biodegradable polymer or copolymer has a crystallinity or percent crystallinity by X-ray diffraction (XRD) or differential scanning calorimetry (DSC), by weight or volume of about 0%, 1%, 2%, 5% or 10% to about 70%; or about 0%, 1%, 2%, 5% or 10% to about 60%; or about 0%, 1%, 2%, 5% or 10% to about 55%; or about 0%, 1%, 2%, 5% or 10% to about 50%; or about 0%, 1%, 2%, 5% or 10% to about 40%; or about 0%, 1%, 2%, 5% or 10% to about 30%; or about 0%, 1%, 2%, 5% or 10% to about 25%; or about 0%, 1%, 2%, 5% or 10% to about 20%. In certain embodiments, the material (e.g., polymeric material) comprising the body of the device or the biodegradable polymer copolymer has a degree of crystallinity, or % crystallinity by XRD or DSC, of about 5% to about 30%, or about 7% to about 22%, by weight or volume.

In a preferred embodiment, there is a desire to minimize the amount of heat and/or duration the tubular body or the stent or the biodegradable material sees after forming. Examples include treating the tubular body by heating the tubular body after forming to temperature at about Tg or lower than Tg or within 10° C. higher than Tg, of the biodegradable polymeric material Tg, for duration ranging from a fraction of a second to 7 days, or 5 seconds to 7 days, preferably from 15 seconds to 1 day, more preferably from 30 seconds to 5 hours, and optionally cooling or quenching after heating to above ambient temperature, ambient temperature or below ambient temperature. The heating can take place once or more than once at various stages of the tubular body or stent prosthesis fabrication. In one embodiment, the biodegradable stent prosthesis comprising a tubular body comprising a biodegradable polymeric material, wherein the tubular body has been formed using extrusion, molding, dipping, or spraying and has been treated by heating the tubular body at about Tg or lower of the biodegradable polymeric material Tg, said biodegradable polymeric material is substantially amorphous after said treatment and has a Tg greater than 37° C. and the stent prosthesis at body temperature is radially expandable and has sufficient strength to support a body lumen. In another embodiment, the biodegradable stent prosthesis comprising a tubular body comprising a biodegradable polymeric material, wherein the tubular body has been formed using extrusion, molding, printing, dipping, or spraying and has been treated by heating the tubular body at about Tg or lower of the biodegradable polymeric material Tg, said biodegradable polymeric material has crystallinity of 10%-60% (or 10%-

50% or 10%-40% or 10% to 30% or 10%-20% or 0%-10% or 0% to 30%) after said treatment and has a Tg greater than 37° C. and the stent prosthesis at body temperature is radially expandable and has sufficient strength to support a body lumen. In one embodiment, the Tg is greater than 37° C. and less than 60° C., preferably greater than 37° C. and less than 55° C., more preferably greater than 37° C. and less than 45° C., more preferably greater than 35° C. and less than 45° C.

In certain embodiments, the degree of crystallinity is controlled in the polymeric material to about 40% or less, or about 35% or less, or about 30% or less, or about 25% or less, or about 20% or less, or about 15% or less, or about 10% or less, or about 8% or less, or about 6% or less, or about 4% or less, or about 2% or less, prior to a modification (or treatment) or after modification. In an embodiment, the degree of crystallinity of a polymeric material is about 10% or less prior to a modification.

In some embodiments, after a substantially amorphous or semi crystalline or crystalline polymeric material or a tubular body formed therefrom undergoes a modification, the degree of crystallinity of the polymeric material is controlled such as to increases or decrease by at least about 5%, 10%, 20%, 30%, 40%, 50%, 100%, 150%, 200%, 300%, 400%, 500%, 600%, 700%, 800%, 900% or 1000% (e.g., of the initial degree of crystallinity or before treatment). In an embodiment, after a substantially amorphous or semi crystalline or crystalline polymeric material or a tubular body formed therefrom undergoes a modification, the degree of crystallinity of the polymeric material increases by at least about 50%.

In further embodiments, polymeric material or a tubular body formed therefrom undergoes a modification, the polymeric material has a degree of crystallinity of about 2%, 5% or 10% to about 70%; or about 2%, 5% or 10% to about 60%; or about 2%, 5% or 10% to about 50%; or about 2%, 5% or 10% to about 40%; or about 2%, 5% or 10% to about 30%; or about 2%, 5% or 10% to about 20%. In an embodiment, the polymeric material or a tubular body formed therefrom undergoes a modification, the polymeric material has a degree of crystallinity of about 10% to about 40%. In another embodiment, the polymer material or tubular body or stent comprises PLLA/PCL (polymer blend or copolymers), wherein the tubular body is substantially oriented, or at least axially oriented, or biaxially oriented, or substantially randomly oriented, or substantially not oriented. In another embodiment, the polymer material is PLLA/PCL (polymer blend or copolymers) and an additive of carbon nano tube or fibers are added to it. The amounts of carbon nano tube or fibers ranges from about 0.1% to about 15%. In another embodiment, the polymer material comprises PLLA/PCL/PGA (polymer blend or copolymers or a mixture of copolymers and polymer blend) and an additive of carbon nano tube or fibers added to it. The amounts of carbon nano tube or fibers ranges from about 0.1% to about 15%. In some embodiments, crystallinity of the tubular body after modification ranges from about 10% to about 70% and % elongation ranges from about 10% to about 200%, and Tg ranges from about 35° C. to about 60° C., or a Tg greater than 37° C. to about 55° C., or a Tg greater than 37° C. to about 45° C., or a Tg greater than 35° C. to about 45° C.

In further embodiments, the material (e.g., polymeric material) comprising the body of an endoprosthesis (e.g., a stent), or comprising the polymeric article/material (e.g., a polymeric tube) from which the endoprosthesis is formed, has a degree of crystallinity of about 2%, 5% or 10% to about 70%, or about 2%, 5% or 10% to about 60%, or about 2%, 5% or 10% to about 50%, or about 2%, 5% or 10% to about 40%, or about 2%, 5% or 10% to about 30%, or about 2%, 5% or 10% to about 20%, or has a degree of crystallinity of at least about 2%, 5%, 10%, 20%, 25%, 30%, 40%, 50%, 60% or 70%, after the polymeric article and/or the endoprosthesis undergo the modification or treatment. In certain embodiments, the material (e.g., polymeric material) comprising the polymeric article or the body of the endoprosthesis has a degree of crystallinity of about 5% to about 50%, or about 10% to about 40%, after the polymeric article and/or the endoprosthesis undergo the modification.

Increased crystallinity may increase the strength, storage shelf life, and/or hydrolytic stability of the polymeric material or the endoprosthesis formed therefrom. The modification may introduce or enhance crystallinity in the polymeric material by nucleating or growing small spherulite crystals in the polymeric material. Modification of a polymeric material can include longitudinal extension, radial expansion, heating, cooling, pressurizing, vacuuming, addition of an additive, crosslinking, exposure to radiation (e.g., e-beam or gamma radiation), exposure to carbon dioxide gas or liquid, or other modifications described herein, or a combination thereof.

Additional embodiments of the disclosure relate to biodegradable endoprostheses comprised of a material which comprises a biodegradable polymer, or biodegradable endoprostheses comprising a tubular body comprised of a material which comprises a biodegradable polymer, wherein the material or the polymer is substantially amorphous or semi crystalline or crystalline prior to a modification (or treatment), and crystallinity (e.g., degree of crystallinity) of the material or the polymer increases or decreases after the material, the polymer, the tubular body or the endoprosthesis undergoes the modification. In one embodiment, the crystallinity increases or decreases from about 1% to about 30%, in another embodiment, the crystallinity increases from about 1% to about 20%, or from about 1% to about 10%, or no more than 10%.

Substantially amorphous or semi-crystalline, biodegradable polymers having a degree of crystallinity of, e.g., about 30% or less, or 20% or less, or 10% or less may degrade faster than crystalline polymers. The present disclosure provides for modifications (or treatments) of polymers, preferably substantially amorphous or semi crystalline polymeric materials to increase crystallinity of biodegradable endoprostheses, e.g., or by increasing the strength of the polymeric material without substantially increasing its degradation time. In certain embodiments, a biodegradable endoprosthesis (e.g., a stent) formed from a substantially amorphous or semi crystalline polymeric material that has undergone a modification substantially completely degrades in less than about four years, or less than about three years, or less than about two years, or less than about one year, or less than about nine months, or less than about six months.

In some embodiments, a biodegradable endoprosthesis (e.g., a stent) is formed from a biodegradable polymeric material, wherein crystallinity (e.g., degree of crystallinity) of the polymeric material is controlled by increasing or decreasing after the polymeric material undergoes a modification (or treatment). In certain embodiments, the degree of crystallinity of the polymeric material increases or decreases by at least about 10%, 20%, 25%, 30%, 40%, 50%, 75%, 100%, 150%, 200%, 300%, 400%, 500%, 600%, 700%, 800%, 900% or 1000% after the polymeric material undergoes the modification. In certain embodiments, the degree of crystallinity of polymeric material increases by at least about 25% or 50% after the polymeric material undergoes the modification.

In one embodiment, the biodegradable polymeric stent material has increased crystallinity by using a combination of solvents, with one solvent having solubility parameter within 10% of the solubility parameter of the polymer and the second solvent having solubility parameter at least 10% different than the solubility parameter of the polymer in the solvent.

In one embodiment the biodegradable polymer stent material has a crystallinity of greater than 10%, preferably greater than 25%, more preferably greater than 50%. In other embodiments, treatment to control crystallinity takes place in such a way as to decrease it after treatment. Examples include decreasing the crystallinity by at least 5%-50%, preferably by at least 10% to 30%.

In some embodiments, the invention also provides means to improve consistency of strength, recoil or degradation rate of a biodegradable polymer stent material.

Another way to control crystallinity of the material (e.g., polymeric material) comprising the body of an endoprosthesis (e.g., a stent), or comprising the polymeric article/material (e.g., a tube) from which the endoprosthesis is formed, is to use a combination of solvents in which the polymeric material has different solubilities (e.g., when the polymeric article is being formed). For example, one solvent can have a solubility parameter within about 20% (or 10%) of the solubility parameter of the polymeric material, and the second solvent can have a solubility parameter at least about 20% (or 10%) different than the solubility parameter of the polymeric material in the solvent.

In some embodiments, the first biodegradable polymer or the material (e.g., polymeric material) comprising the polymeric article or the body of the device has a degree of crystallinity, or percent crystallinity by X-ray diffraction (XRD) or differential scanning calorimetry (DSC), of about 20%, 15%, 10% or 5% or less by weight or volume before the polymeric article or the device undergoes a treatment (e.g., heating or exposure to radiation), and the degree of crystallinity, or % crystallinity by XRD or DSC, of the first biodegradable polymer or the material (e.g., polymeric material) comprising the polymeric article or the body of the device increases by at least about 10%, 20%, 30%, 40%, 50%, 100%, 200%, 300%, 400% or 500% after the polymeric article or the device undergoes the treatment. In certain embodiments, the first biodegradable polymer or the material (e.g., polymeric material) comprising the polymeric article or the body of the device has a degree of crystallinity, or % crystallinity by XRD or DSC, of about 15% or less by weight or volume before the polymeric article or the device undergoes a treatment (e.g., heating or exposure to radiation), and the degree of crystallinity, or % crystallinity by XRD or DSC, of the first biodegradable polymer or the material (e.g., polymeric material) comprising the polymeric article or the body of the device increases by at least about 20% after the polymeric article or the device undergoes the treatment.

In further embodiments, the first biodegradable polymer or the material (e.g., polymeric material) comprising the polymeric article or the body of the device has a degree of crystallinity, or % crystallinity by XRD or DSC, of about 20%, 15%, 10% or 5% or less by weight or volume before the polymeric article or the device undergoes a treatment (e.g., heating or exposure to radiation), and the first biodegradable polymer or the material (e.g., polymeric material) comprising the polymeric article or the body of the device has a degree of crystallinity, or % crystallinity by XRD or DSC, by weight or volume of about 2%, 5% or 10% to about 70%, or about 2%, 5% or 10% to about 60%, or about 2%, 5% or 10% to about 50%, or about 2%, 5% or 10% to about 40%, or about 2%, 5% or 10% to about 30%, or about 2%, 5% or 10% to about 20%, after the polymeric article or the device undergoes the treatment. In certain embodiments, the first biodegradable polymer or the material (e.g., polymeric material) comprising the polymeric article or the body of the device has a degree of crystallinity, or % crystallinity by XRD or DSC, of about 15% or less by weight or volume before the polymeric article or the device undergoes a treatment (e.g., heating or exposure to radiation), and the first biodegradable polymer or the material (e.g., polymeric material) comprising the polymeric article or the body of the device has a degree of crystallinity, or % crystallinity by XRD or DSC, of about 10% to about 50% by weight or volume after the polymeric article or the device undergoes the treatment.

In yet further embodiments, the first biodegradable polymer or the material (e.g., polymeric material) comprising the polymeric article or the body of the device has a degree of crystallinity, or % crystallinity by XRD or DSC, of about 15% or less, or about 10% or less, by weight or volume before the polymeric article or the device is exposed to radiation (e.g., e-beam or gamma radiation), and the first biodegradable polymer or the material (e.g., polymeric material) comprising the polymeric article or the body of the device has a degree of crystallinity, or % crystallinity by XRD or DSC, of about 10% to about 40%, or about 10% to about 30%, or about 10% to about 20%, by weight or volume after the polymeric article or the device is exposed to the radiation. In certain embodiments, the first biodegradable polymer or the material (e.g., polymeric material) comprising the polymeric article or the body of the device has a degree of crystallinity, or % crystallinity by XRD or DSC, of about 10% or less by weight or volume before the polymeric article or the device is exposed to radiation (e.g., e-beam or gamma radiation), and the first biodegradable polymer or the material (e.g., polymeric material) comprising the polymeric article or the body of the device has a degree of crystallinity, or % crystallinity by XRD or DSC, of about 10% to about 30% by weight or volume after the polymeric article or the device is exposed to the radiation.

In still further embodiments, the first biodegradable polymer or the material (e.g., polymeric material) comprising the polymeric article has a degree of crystallinity, or % crystallinity by XRD or DSC, of about 15% or less, or about 10% or less, by weight or volume before the device is formed from the polymeric article (e.g., by laser or mechanical cutting), and the first biodegradable polymer or the material (e.g., polymeric material) comprising the body of the device has a degree of crystallinity, or % crystallinity by XRD or DSC, of about 10% to about 40%, or about 10% to about 30%, or about 10% to about 20%, by weight or volume after the device undergoes a treatment (e.g., heating or exposure to radiation). In certain embodiments, the first biodegradable polymer or the material (e.g., polymeric material) comprising the polymeric article has a degree of crystallinity, or % crystallinity by XRD or DSC, of about 10% or less by weight or volume before the device is formed from the polymeric article (e.g., by laser or mechanical cutting), and the first biodegradable polymer or the material (e.g., polymeric material) comprising the body of the device has a degree of crystallinity, or % crystallinity by XRD or DSC, of about 10% to about 30% by weight or volume after the device undergoes a treatment (e.g., heating or exposure to radiation).

In additional embodiments, the first biodegradable polymer or the material (e.g., polymeric material) comprising the polymeric article or the body of the device has a degree of crystallinity, or % crystallinity by XRD or DSC, by weight or volume of about 2%, 5% or 10% to about 70%, or about 2%, 5% or 10% to about 60%, or about 2%, 5% or 10% to about 55%, or about 2%, 5% or 10% to about 50%, or about 2%, 5% or 10% to about 40%, or about 2%, 5% or 10% to about 30%, or about 2%, 5% or 10% to about 25%, or about 2%, 5% or 10% to about 20%, or about 7% to about 22%, before and/or after the polymeric article or the device undergoes a treatment (e.g., heating or exposure to radiation). In certain embodiments, the first biodegradable polymer or the material (e.g., polymeric material) comprising the polymeric article or the body of the device has a degree of crystallinity, or % crystallinity by XRD or DSC, of about 5% to about 30%, or about 10% to about 25%, or about 7% to about 22%, by weight or volume after the polymeric article or the device undergoes a treatment (e.g., heating or exposure to radiation).

The teachings disclosed herein can be applied to make any appropriate implantable device from a polymeric article comprised of a biodegradable polymeric material. The implantable device can be any implantable device described herein, and may have a tubular body (e.g., a stent) or may not have a tubular body. The polymeric article can have any shape, form and dimensions suitable for making the device (e.g., a polymeric tube from which a stent is patterned).

In another aspect of the invention, methods for fabricating biodegradable prostheses are provided. The preferred methods comprise providing a tubular body having an initial diameter as-formed, or before patterning, or after patterning, where the tubular body comprises a biodegradable polymeric material. In one embodiment, the polymeric material comprises one or more polymers, or one or more co-polymers, or a combination thereof. In another embodiment, the polymeric material comprises one or more polymers, or one or more co-polymers, or one or more monomers, or a combination thereof. The polymeric material or the tubular body is treated to control crystallinity preferably to between 1% and 50%, or more preferably to between 1% and 35%. In one embodiment the polymeric material or the tubular body treatment comprises a heat treatment preferably at substantially the initial diameter, preferably when the initial diameter is 1-1.5 times the stent deployment diameter, to a temperature above glass transition temperature of the polymeric material and below its melting point for a period ranging from a fraction of a second to 7 days. The polymeric material or the tubular body in one embodiment may be cooled after heating to a temperature ranging from below ambient temperature to ambient or above temperature over a period ranging from a fraction of a second to 7 days. In a preferred embodiment, the polymeric material or the tubular body initial diameter is approximately 1-1.5 times the stent deployment diameter or stent nominal deployment diameter, or stent labeled deployment diameter. In another preferred embodiment, the initial diameter is approximately 0.9-1.5 times the stent deployment diameter or stent nominal deployment diameter, or stent labeled deployment diameter.

The biodegradable implantable device can be made using any suitable method, such as spraying, dipping, extrusion, molding, injection molding, compression molding or 3-D printing, using, e.g., BFB3000 from Bits From Bytes company (UK), or a combination thereof. In some embodiments, the body of the device is formed from a polymeric article made by spraying a solution or mixture containing the biodegradable copolymer or polymer and a solvent onto a structure. In a preferred embodiment, the biodegradable stent is fabricated by forming a tubular body using extrusion, molding such as injection molding, dipping, spraying such as spraying a tube or mandrel, printing such as 3D printing. The tubular body in a preferred embodiment is formed first and then patterned into a structure capable of radial expansion from a crimped configuration preferably at body temperature. The tubular body in another preferred embodiment is formed first and then patterned into a structure capable of radial expansion from a crimped configuration preferably at body temperature and preferably without fracture. The tubular body in another preferred embodiment is formed first and then patterned into a structure capable of being crimped from an expanded configuration to a crimped diameter (at temperature about Tg or less than Tg), and at body temperature capable to be expanded from the crimped configuration preferably without fracture. In another preferred embodiment the polymeric material is patterned first and then forms a tubular body/stent capable of radial expansion at body temperature and/or capable to be crimped preferably at temperature about Tg or less than Tg.

In certain embodiments, the tubular body or polymeric material, or the stent has an initial diameter. In one preferred embodiment, the initial diameter is 1-1.5 times the stent deployed diameter. In another preferred embodiment, the initial diameter is 0.9-1.5 times the stent deployed diameter. In a further embodiment, the initial diameter is less than the stent deployed diameter. The initial diameter can be the as-formed diameter, or the diameter before patterning, or the diameter after patterning, or the diameter before crimping. In one embodiment, an endoprosthesis (e.g., a stent) is patterned by laser cutting or other method from a polymeric tube that has a (e.g., inner or outer) diameter substantially equal to or smaller than deployed (e.g., inner or outer) diameter of the endoprosthesis. In other embodiments, an endoprosthesis (e.g., a stent) is patterned from a polymeric tube that has a (e.g., inner or outer) diameter, either when the tube is formed or after the tube is radially expanded to a second larger diameter, larger than deployed (e.g., inner or outer) diameter of the endoprosthesis. Patterning a stent from a polymeric tube having a (e.g., inner or outer) diameter larger than deployed (e.g., inner or outer) diameter of the stent can impart advantageous characteristics to the stent, such as reducing radially inward recoil of the stent after deployment and/or improved strength.

In a preferred embodiment, a stent prosthesis or tubular body or polymeric material has initial diameter (or initial transverse dimension), preferably 1-1.5 times deployed diameter (deployed transverse dimension) or deployed nominal diameter (e.g., deployed nominal transverse dimension), where in the initial diameter (or initial transverse dimension) is as-formed diameter (or transverse dimension), before patterning diameter (or transverse dimension), or after patterning diameter (or transverse dimension), or before crimping diameter (or transverse dimension), and wherein the initial diameter (or initial transverse dimension) is greater than crimped diameter (or crimped transverse dimension). In a preferred embodiment, a stent or tubular body first self-expands by at least 0.35 of initial diameter or transverse dimension, and then expands to second larger diameter or transverse dimension, which may be the deployed diameter or transverse dimension, preferably by balloon expansion. In a further preferred embodiment, the stent or tubular body may expand to 1.0 times or more, or 1.1 times or more, or 1.2 times or more, or 1.3 times or more, or 1.4 times or more, or 1.5 times or more the deployed diameter or nominal diameter (or transverse dimension) at body temperature, without fracturing. In a further preferred embodiment, the stent or tubular body or polymeric material is crimped from an expanded diameter to a crimped configuration, and at body temperature expands to 1.0 times or more, or 1.1 times or more, or 1.2 times or more, or 1.3 times or more, or 1.4 times or more, or 1.5 times or more the deployed diameter or nominal diameter (or transverse dimension), without fracturing.

In some embodiments, an expandable stent comprising a biodegradable polymeric material having an initial configuration is provided. The expandable stent at body temperature can be self-expandable from a crimped configuration and further expandable to a second larger configuration. In further embodiments, the polymeric material has been treated to control one or more of crystallinity, Tg, or molecular weight. In some embodiments, the Tg ranges from about 20° C. to about 50° C. In some embodiments, the second configuration is a deployed configuration. In some embodiments, the stent expands to the first and second configurations without fracture and has sufficient strength to support a body lumen. In some embodiments, the first expanded configuration has a transverse dimension of at least 0.35 times, or at least 0.45 times, or at least 0.55 times, or at least 0.55 times, or at least 0.7 times, or at least 0.8 times, or at least 1 times the transverse dimension of the initial configuration. In some embodiments, the stent expands to the first expanded configuration within a period of 24 hours, or 12 hours, or 4 hours, or 2 hours, or 1 hour, or 30 minutes, or 5 minutes or 30 seconds. In some embodiments, the stent is balloon expandable to the second expanded configuration without fracture and with sufficient strength to support a body lumen.

In some embodiments, an expandable stent comprising a biodegradable polymeric material having an initial configuration is provided. The expandable stent at body temperature can be expandable from a crimped configuration to a first expanded configuration and self expandable to a second larger configuration. In further embodiments, the polymeric material is treated to control one or more of crystallinity, Tg, or molecular weight. In some embodiments, the expandable stent comprises a substantially continuous tubular body. In some embodiments, the stent expands to the first configuration without fracture and has sufficient strength to support a body lumen. In some embodiments, the stent has a nominal expanded configuration with a transverse dimension and the first expanded configuration has a transverse dimension that is at least 1 times the transverse dimension of the transverse dimension of the nominal expanded configuration. In some embodiments, the first expanded configuration is a deployed configuration. In some embodiments, the stent has a nominal expanded configuration with a transverse dimension and the first expanded configuration has a transverse dimension that is 1 time, or 1.1 times, or 1.2 times, or 1.3 times, or 1.35 times, or 1.4 times, or 1.45 times, or 1.5 times the transverse dimension of the transverse dimension of the nominal expanded configuration.

In certain embodiments, the body of the biodegradable implantable device is formed from a polymeric article made by:

(i) spraying a solution or mixture containing the biodegradable copolymer or polymer and a solvent onto a structure to form a first layer containing the biodegradable copolymer or polymer, and spraying a solution or mixture containing a second biodegradable polymer and a solvent over at least a portion of the first layer containing the biodegradable copolymer or polymer to form a second layer containing the second biodegradable polymer; or (ii) spraying a solution or mixture containing a second biodegradable polymer and a solvent onto a structure to form a first layer containing the second biodegradable polymer, and spraying a solution or mixture containing the biodegradable copolymer or polymer and a solvent over at least a portion of the first layer containing the second biodegradable polymer to form a second layer containing the biodegradable copolymer. the polymer, copolymers, and/or solvents can be the same or different for the first and second layers.

In some embodiments, the solution or mixture containing the biodegradable copolymer contains an additional biodegradable polymer or a non-degradable polymer or both. In certain embodiments, the solution or mixture containing the biodegradable copolymer contains one or more biologically active agents, or one or more additives, or both biologically active agent(s) and additive(s).

In further embodiments, the solution or mixture containing the second biodegradable polymer contains an additional biodegradable polymer or a non-degradable polymer or both. In certain embodiments, the solution or mixture containing the second biodegradable polymer contains one or more biologically active agents, or one or more additives, or both biologically active agent(s) and additive(s).

In additional embodiments, the biodegradable copolymer contains about 5, 4, 3, 2, 1, 0.5 or 0.1 wt % or less of each of water, solvent(s), monomer(s), low molecular weight oligomer(s) or particulate(s), or a combination thereof, prior to preparation of the solution or mixture containing the biodegradable copolymer, or after spraying of the solution or mixture, or both. In further embodiments, the second biodegradable polymer contains about 5, 4, 3, 2, 1, 0.5 or 0.1 wt % or less of each of water, solvent(s), monomer(s), low molecular weight oligomer(s) or particulate(s), or a combination thereof, prior to preparation of the solution or mixture containing the second biodegradable polymer, or after spraying of the solution or mixture, or both. Low content of water, solvent(s), monomer(s), low molecular weight oligomer(s) or particulate(s), or a combination thereof, in a polymeric material can be achieved by methods described herein.

The biodegradable implantable devices described herein can be made using any suitable method or technique, including without limitation spraying, dipping, extrusion, molding, injection molding, compression molding or 3-D printing, or a combination thereof.

Some embodiments of the present disclosure relate to a method of making a biodegradable implantable device comprising a body comprised of a material which comprises a first biodegradable polymer, the method comprising:

spraying a first solution or mixture containing the first biodegradable polymer and a first solvent onto a structure to form a polymeric article;

optionally removing the polymeric article from the structure; and forming the implantable device from the polymeric article.

In certain embodiments, the polymer solution or mixture is sprayed onto the structure at ambient temperature. In other embodiments, the polymer solution or mixture is sprayed onto the structure at a temperature below or above ambient temperature. In further embodiments, the polymer solution or mixture is sprayed onto the structure in ambient environment. In other embodiments, the polymer solution or mixture is sprayed onto the structure in a substantially inert environment (e.g., in the presence of nitrogen or argon gas). In additional embodiments, the polymer solution or mixture is sprayed onto the structure in an environment having a relative humidity of about 70% or less, or about 60% or less, or about 50% or less, or about 40% or less, or about 30% or less. In certain embodiments, the polymer solution or mixture is sprayed onto the structure in an environment having a relative humidity of about 50% or less.

The first biodegradable polymer can be any biodegradable polymer (including homopolymer or copolymer) described herein. In some embodiments, the first biodegradable polymer is a polylactide homopolymer or copolymer, wherein lactide includes L-lactide, D-lactide and D,L-lactide. In certain embodiments, the first biodegradable polymer is a poly (L-lactide) copolymer. The poly(L-lactide) copolymer can comprise L-lactide and one or more other monomers selected from any of the monomers described herein. In some embodiments, the biodegradable poly(L-lactide) copolymer comprises L-lactide in at least about 70%, 75%, 80%, 85%, 90%, 95%, 96%, 97%, 98%, 99%, 99.5% or 99.9% by weight or molarity, and each of the one or more other monomers in no more than about 0.1%, 0.5%, 1%, 1.5%, 2%, 2.5%, 3%, 3.5%, 4%, 4.5%, 5%, 6%, 7%, 8%, 9%, 10%, 15%, 20%, 25% or 30% by weight or molarity. In certain embodiments, the biodegradable poly(L-lactide) copolymer comprises L-lactide in at least about 90%, 95% or 99% by weight or molarity, and each of the one or more other monomers in no more than about 1%, 5% or 10% by weight or molarity.

In certain embodiments, the first biodegradable polymer is selected from the group consisting of poly(L-lactide), poly(D-lactide), poly(D,L-lactide), polydioxanone, poly(4-hydroxybutyrate), polysalicylate/polysalicylic acid, poly(propylene carbonate), poly(tyrosine carbonate), poly(cellulose acetate butyrate), poly(L-lactide-co-D-lactide), poly(L-lactide-co-D,L-lactide), poly(L-lactide-co-glycolide), poly(L-lactide-co-ε-caprolactone), poly(L-lactide-co-dioxanone), poly(L-lactide-co-3-hydroxybutyrate), poly(L-lactide-co-4-hydroxybutyrate), poly(L-lactide-co-4-hydroxyvalerate), poly(L-lactide-co-ethylene carbonate), poly(L-lactide-co-propylene carbonate), poly(L-lactide-co-trimethylene carbonate), and poly(L-lactide-co-cellulose acetate butyrate).

In further embodiments, the first biodegradable polymer is a block or random copolymer of L-lactide and ε-caprolactone in a weight or molar ratio of about 70:30 to about 99.9:0.1, or about 80:20 to about 99.9:0.1, or about 85:15 to about 99.9:0.1, or about 85:15 to about 95:5, or about 87:13 to about 93:7, or about 90:10. In an embodiment, the first biodegradable polymer is a random copolymer of L-lactide and ε-caprolactone in a weight or molar ratio of about 90:10. In other embodiments, the first biodegradable polymer is a block or random copolymer of L-lactide and glycolide in a weight or molar ratio of about 70:30 to about 99.9:0.1, or about 75:25 to about 95:5, or about 80:20 to about 90:10, or about 82:18 to about 88:12, or about 85:15. In an embodiment, the first biodegradable polymer is a random copolymer of L-lactide and glycolide in a weight or molar ratio of about 85:15.

The first solvent can be any solvent (a single solvent or a mixture of solvents) that dissolves to a suitable extent, and is compatible with, the first biodegradable polymer and any additional material (e.g., an additional polymer, a biologically active agent or an additive, or a combination thereof) in the first solution or mixture, and results in suitable characteristics of the polymeric article (e.g., minimal amount of residual solvent after removal of the solvent, if desired). Non-limiting examples of solvents include hydrocarbon solvents, toluene, xylenes, 1,2-xylene, 1,3-xylene, 1,4-xylene, halogenated hydrocarbon solvents, dichloromethane, chloroform, trichlorofluoromethane, (1,1,1,3,3,3)-hexafluoro-2-propanol, ethers, diethyl ether, methyl tert-butyl ether, tetrahydrofuran, ketones, acetone, esters, ethyl acetate, tert-butyl acetate, alcohols, methanol, ethanol, isopropanol, tert-butanol, amines, diethylamine, and mixtures thereof. In certain embodiments, the first solvent is dichloromethane, or tetrahydrofuran, or acetone.

The choice of concentration of a polymer in a spray solution or mixture may be based on various factors, such as the viscosity of the polymer, the type of solvent and the type of spray equipment used. Examples of spray equipments that can be used include, but are not limited to, MicroMist™ sprayers from Sono-Tek (New York) and 784S-SS Aseptic sprayers from EFD (Rhode Island). In some embodiments, the concentration of the first biodegradable polymer in the first solution or mixture is about 0.1 or 1 mg/mL to about 20 mg/mL, or about 0.5 or 1 mg/mL to about 15 mg/mL, or about 1 or 2 mg/mL to about 10 mg/mL, or about 3 mg/mL to about 7 mg/mL, or about 4 mg/mL to about 6 mg/mL. In certain embodiments, the concentration of the first biodegradable polymer in the first solution or mixture is about 1 mg/mL to about 10 mg/mL, or about 5 mg/mL.

In some embodiments, the structure onto which the polymer solution or mixture is sprayed has a substantially flat surface or a contour surface, or both. In further embodiments, the structure has an irregular surface, or a surface having surface features. In certain embodiments, the irregular surface, or the surface having surface features, of the structure has one or more protrusions, and/or one or more indentations, where the protrusions and/or the indentations can be arranged in a regular or irregular manner on the surface. The protrusions and/or the indentations on the surface of the structure can be formed as indentations and/or protrusions, respectively, on the corresponding (e.g., inner) surface of the polymeric article spray coated on the structure for any of a variety of purposes. For example, a polymeric article having indentations and/or protrusions on a surface can be used to make a device that has a variable thickness along its length, which can, e.g., increase its longitudinal flexibility. As another example, indentations and/or protrusions on a surface of a device can promote endothelialization of the device with the surrounding tissue after implantation of the device. As a further example, indentations on a surface of a device can contain one or more biologically active agents, or one or more additives, or both.

The structure onto which the polymer solution or mixture is sprayed can have any shape, configuration or form suitable for making a polymeric article. In certain embodiments, the structure is a substantially cylindrical or tubular structure (e.g., a mandrel, rod, tube or balloon), which can be used to make a polymeric article from which, e.g., a single stent, segmented stent, joined stent or overlap stent can be patterned. In further embodiments, the structure is a tapered tubular structure (e.g., a tapered mandrel, rod, tube or balloon), which can be used to make a polymeric article from which, e.g., a tapered stent can be patterned. In additional embodiments, the structure is a substantially Y-shaped cylindrical or tubular structure (e.g., a substantially Y-shaped mandrel, rod or tube), which can be used to make a polymeric article from which, e.g., a bifurcated stent can be patterned.

Further, the polymeric article can have any shape, configuration or form suitable for making an implantable device from the polymeric article. In certain embodiments, the polymeric article is a polymeric sheet. In other embodiments, the polymeric article is a polymeric tube.

When the polymeric article is a polymeric tube, in some embodiments the polymeric tube is substantially concentric. If a stent is patterned from a polymeric tube, a more concentric tube can result in more uniform thickness of struts, crowns and links of the stent. In some embodiments, the polymeric tube has a concentricity of about 0.0025 inch (about 64 microns) or less, or about 0.002 inch (about 51 microns) or less, or about 0.0015 inch (about 38 microns) or less, or about 0.001 inch (about 25 microns) or less, or about 0.0005 inch (about 13 microns) or less. In further embodiments, the polymeric tube has a percent concentricity of at least about 75%, 80%, 85%, 90%, 91%, 92%, 93%, 94%, 95%, 96%, 97%, 98% or 99%. In certain embodiments, the polymeric tube has a concentricity of about 0.001 inch (about 25 microns) or less, or a percent concentricity of at least about 90%.

A substantially concentric polymeric tube can be made by, e.g., slowly forming a tube thickness by spraying a solution or mixture of relatively low polymer concentration onto a mandrel that is constantly rotating (clockwise and counter-clockwise) and moving axially (back and forth over the length of the mandrel).

In some embodiments, the first solution or mixture containing the first biodegradable polymer contains an additional biodegradable polymer or a non-degradable polymer, or both. The additional biodegradable polymer can be any biodegradable polymer described herein, and the non-degradable polymer can be any non-degradable polymer described herein. In some embodiments, the first solution or mixture contains poly(L-lactide) or a poly(L-lactide) copolymer, and an additional biodegradable polymer or a non-degradable polymer or both. In certain embodiments, the first solution or mixture contains poly(L-lactide) and poly($\epsilon$-caprolactone).

The first biodegradable polymer, and any optional additional biodegradable polymer and/or any optional non-degradable polymer, can be treated prior to preparation of the first solution or mixture to remove substantially residual water, solvent(s), monomer(s), low molecular weight oligomer(s) and/or particulate(s) from the polymer(s). In further embodiments, the first biodegradable polymer, and any optional additional biodegradable polymer and/or any optional non-degradable polymer, are exposed to an extracting solvent (e.g., an alcohol, such as methanol or ethanol), or to carbon dioxide gas or liquid under elevated pressure (e.g., at least about 500, 600, 700, 800 900 or 1000 psi for carbon dioxide gas, or at least about 500, 1000, 2000, 3000, 4000 or 5000 psi for carbon dioxide liquid) and optionally under a flow of carbon dioxide, e.g., at least about 10, 20, 30, 40 or 50 ccm (cubic centimeter per minute), optionally at reduced or elevated temperature, for a period of time (e.g., at least about 1, 6, 12, 24, 36 or 48 hours) prior to preparation of the first solution or mixture containing the polymer(s).

In additional embodiments, the first solution or mixture containing the first biodegradable polymer contains one or more biologically active agents, or one or more additives, or both. The biologically active agent(s) can be any biologically active agent described herein, and the additive(s) can be any additive described herein. In certain embodiments, the biologically active agent(s) include myolimus or novolimus.

Applying a mixture containing two or more substances or materials having significantly different surface tensions can result in phase separation of the substances or materials. The following provides embodiments of ways for minimizing or preventing phase separation of substances or materials. Substances or materials having a substantially similar surface tension are applied. If the substances or materials have significantly different surface tensions, a surfactant can be added to the mixture. Exposure of the polymeric article to heat (in terms of, e.g., temperature and exposure time) is minimized during processing and during any sterilization or storage of the article, and exposure of the device formed from the polymeric article to heat is minimized during processing, sterilization and storage (e.g., the device is frozen during sterilization with radiation and during storage).

In some embodiments, the method of making the device comprises:
(i) spraying the first solution or mixture containing the first biodegradable polymer and the first solvent onto the structure to form a first layer containing the first biodegradable polymer, and
spraying a second solution or mixture containing a second biodegradable polymer and a second solvent over at least a portion of the first layer containing the first biodegradable polymer to form a second layer of the polymeric article which contains the second biodegradable polymer; or (ii) spraying a second solution or mixture containing a second biodegradable polymer and a second solvent onto the structure to form a first layer containing the second biodegradable polymer, and
spraying the first solution or mixture containing the first biodegradable polymer and the first solvent over at least a portion of the first layer containing the second biodegradable polymer to form a second layer of the polymeric article which contains the first biodegradable polymer.

The second biodegradable polymer can be any biodegradable polymer described herein. In certain embodiments, the second solution or mixture containing the second biodegradable polymer contains an additional biodegradable polymer or a non-degradable polymer, or both. The additional biodegradable polymer can be any biodegradable polymer described herein, and the non-degradable polymer can be any non-degradable polymer described herein. Prior to preparation of the second solution or mixture, the second biodegradable polymer, and any optional additional biodegradable polymer and/or any optional non-degradable polymer, can be treated as described herein, e.g., to remove residual water, solvent(s), monomer(s), low molecular weight oligomer(s) and/or particulate(s) from the polymer(s). In certain embodiments, the second solution or mixture containing the second biodegradable polymer contains one or more biologically active agents, or one or more additives, or both. The biologically active agent(s) can be any biologically active agent described herein, and the additive(s) can be any additive described herein.

The method of making the device can also comprise spraying a third solution or mixture containing a third biodegradable polymer and a third solvent, a fourth solution or mixture containing a fourth biodegradable polymer and a fourth solvent, a fifth solution or mixture containing a fifth biodegradable polymer and a fifth solvent, or additional polymer solution or mixture to form a third layer containing the third biodegradable polymer, a fourth layer containing the fourth biodegradable polymer, a fifth layer containing the fifth biodegradable polymer, or additional polymer layer of the polymeric article, where the first layer, the second layer, the third layer, the fourth layer, the fifth layer, or additional layer can be in any order. The optional third biodegradable polymer, the optional fourth biodegradable polymer and the optional fifth biodegradable polymer can independently be any biodegradable polymer described herein.

The optional third solution or mixture containing the third biodegradable polymer, the optional fourth solution or mixture containing the fourth biodegradable polymer, and the optional fifth solution or mixture containing the fifth biodegradable polymer can each optionally and independently contain an additional biodegradable polymer or a non-degradable polymer, or both. The additional biodegradable polymer and/or the non-degradable polymer optionally in the third solution or mixture, the fourth solution or mixture, and/or the fifth solution or mixture can independently be any biodegradable polymer described herein and any non-degradable polymer described herein. Prior to preparation of the optional third solution or mixture, the optional fourth solution or mixture, and/or the optional fifth solution or mixture, the third biodegradable polymer, the fourth biodegradable polymer, and/or the fifth biodegradable polymer, and any optional additional biodegradable polymer and/or any optional non-degradable polymer, can be treated as described herein, e.g., to remove residual water, solvent(s), monomer(s), low molecular weight oligomer(s) and/or particulate(s) from the polymer(s). The optional third solution or mixture containing the third biodegradable polymer, the optional fourth solution or mixture containing the fourth biodegradable polymer, and the optional fifth solution or mixture containing the fifth biodegradable polymer can each optionally and independently contain one or more biologically active agents, or one or more additives, or both. The biologically active agent(s) and/or the additive(s) optionally in the third solution or mixture, the fourth solution or mixture, and/or the fifth solution or mixture can independently be any biologically active agent described herein and any additive described herein.

In some embodiments, the method of making the device comprises crosslinking the first biodegradable polymer, the optional second biodegradable polymer, the optional third biodegradable polymer, the optional fourth biodegradable polymer, or the optional fifth biodegradable polymer, or any optional additional biodegradable polymer or any optional non-degradable polymer in the first layer, the optional second layer, the optional third layer, the optional fourth layer, or the optional fifth layer of the polymeric article, or crosslinking any combination of the aforementioned polymers. In certain embodiments, the polymer(s) are crosslinked by exposure to radiation (e.g., ultraviolet, e-beam or gamma radiation), exposure to heat, use of a degradable or non-degradable crosslinker, or use of a crosslinking agent and an initiator, as described herein.

The method of making the device can also comprise forming one or more layers comprising a corrodible metal or metal alloy, and optionally a non-corrodible metal or metal alloy, to form the polymeric article. The polymeric article can comprise one or more polymer layers and one or more metal layers in any order. For example, a metal layer, or each of multiple metal layers, or multiple metal layers, can lie between polymer layers of the polymeric article. Further, the one or more metal layers can be applied as a first outer layer, and/or as a second outer layer, of the polymeric article. For example, when the device is a stent, the one or more metal layers can be applied as a first outer layer, and/or as a second outer layer, of the polymeric tube which correspond to the luminal surface and the abluminal surface of the stent.

A metal layer can be applied using any suitable method, e.g., by applying a metal film, foil or tube onto the structure (e.g., a structure having a flat surface and/or a contour surface) or over a polymer layer. If the implantable device is a stent, a stent can be patterned from the polymeric article comprising one or more polymer layers and one or more metal layers using any suitable method (e.g., laser or mechanical cutting). Alternatively, a metal film, foil or tube having the desired stent pattern can be applied onto a mandrel or over a polymer layer (e.g., a metal tube having the desired stent pattern and a slightly larger diameter than the polymeric article can be crimped onto the polymeric article). To enhance adhesion of a metal layer to a polymer layer and/or prevent separation or delamination thereof, the metal layer can be textured or treated, before and/or after being applied onto the structure or over a polymer layer, to form surface roughness, surface irregularities or surface features on one or more surfaces of the metal layer. Surface roughness, surface irregularities and surface features of the metal layer can include, but are not limited to, protrusions, spikes, pillars, ridges, mounds, bumps, textures, scratches, scores, streaks, dents, indentations, recesses, trenches, pores, pits, holes and cavities. Surface roughness, surface irregularities or surface features can be formed on the metal layer, before and/or after the metal layer is applied, by any suitable method, such as microblasting, beadblasting, sandblasting, treatment with a corrosive agent, treatment with an acid or base, treatment with water, chemical etching, physical or mechanical etching, or laser treatment, or a combination thereof.

The specific corrodible metal or metal alloy in a metal layer and the thickness of the metal layer can be selected to control characteristics of the device, e.g., strength and degradation. If a non-corrodible metal or metal alloy is used in a metal layer, the specific non-corrodible metal or metal alloy and the amount thereof can be selected to impart desired characteristics (e.g., enhanced strength and/or radiopacity) without unduly prolonging the degradation time of the device. In some embodiments, the thickness (e.g., average thickness) of a metal layer is about 100 microns or less, or about 80 microns or less, or about 60 microns or less, or about 50 microns or less, or about 40 microns or less, or about 30 microns or less, or about 20 microns or less, or about 10 microns or less, or about 5 microns or less. In certain embodiments, the thickness (e.g., average thickness) of a metal layer is about 30 microns or less, or about 20 microns or less.

As a non-limiting example of potential benefits of a metal layer, the presence of one or more metal layers comprising a corrodible metal or metal alloy, and optionally a non-corrodible metal or metal alloy, in the body of a stent can enhance the strength of the stent and allow the struts, crowns and/or links of the stent to have a smaller thickness and/or a smaller width, thereby decreasing the amount of polymeric material used to make the body. In addition to increasing the strength of the device, use of a non-corrodible metal or metal alloy in a metal layer, or as an additive, in the body of the device or in a coating on the device can increase the radiopacity of the device, which may dispense with the use of a radiopaque marker.

Non-limiting examples of corrodible metals and metal alloys that can independently comprise any metal layer(s) of the body of the device include cast ductile irons (e.g., 80-55-06 grade cast ductile iron), corrodible steels (e.g., AISI 1010 steel, AISI 1015 steel, AISI 1430 steel, AISI 5140 steel and AISI 8620 steel), melt-fusible metal alloys, bismuth-tin alloys (e.g., 40% bismuth-60% tin and 58% bismuth-42% tin), bismuth-tin-indium alloys, magnesium alloys, tungsten alloys, zinc alloys, shape-memory metal alloys, and super-elastic metal alloys. Examples of non-corrodible metals and metal alloys that can optionally and independently comprise any metal layer(s) include without limitation stainless steels (e.g., 316L stainless steel), cobalt-chromium alloys (e.g., L-605 and MP35N cobalt-chromium alloys), nickel-titanium alloys, gold, palladium, platinum, tantalum, and alloys thereof.

The polymeric article, whether associated with the structure or removed from the structure, can be treated to remove residual water, solvent(s), monomer(s), low molecular weight oligomer(s) and/or particulate(s) from the article. In some embodiments, the polymeric article is subjected to reduced pressure or heated at elevated temperature (e.g., at least about 50, 60, 70, 80, 90 or 100° C.), or both, for a period of time (e.g., at least about 0.5, 1, 6, 12, 24, 36 or 48 hours). In further embodiments, the polymeric article is exposed to an extracting solvent (e.g., an alcohol, such as methanol or ethanol), or to carbon dioxide gas or liquid under elevated pressure (e.g., at least about 500, 600, 700, 800, 900 or 1000 psi for carbon dioxide gas, or at least about 500, 1000, 2000, 3000, 4000 or 5000 psi for carbon dioxide liquid) and optionally under a flow of carbon dioxide (e.g., at least about 10, 20, 30, 40 or 50 ccm), optionally at reduced or elevated temperature, for a period of time (e.g., at least about 0.5, 1, 6, 12, 24, 36 or 48 hours). In certain embodiments, the material (e.g., polymeric material) comprising the polymeric article or the body of the device, or the material (e.g., polymeric material) comprising each layer of the polymeric article or the body of the device, comprises about 5, 4, 3, 2, 1.5, 1, 0.5 or 0.1 wt % or less of each of water, solvent(s), monomer(s), low molecular weight oligomer(s) or particulate(s), or a combination thereof. In an embodiment, the material (e.g., polymeric material) comprising the polymeric article or the body of the device, or the material (e.g., polymeric material) comprising each layer of the polymeric article or the body of the device, comprises about 2 wt % or less of each of water, solvent(s), monomer(s), low molecular weight oligomer(s) or particulate(s), or a combination thereof.

The polymeric article, whether associated with the structure or removed from the structure, can also undergo any of a variety of treatments designed, e.g., to control crystallinity, enhance the strength or toughness of the material (e.g., polymeric material) comprising the article, and/or reduce residual or internal stress in the polymeric article. Control of crystallinity (e.g., degree of crystallinity) of the polymeric material can achieve a suitable balance between the radial strength (important for, e.g., support of the treated tubular tissue in the subject) and the toughness (important for, e.g., resistance to cracking and fatigue) of the polymeric material. In certain embodiments, the polymeric article is removed from the structure prior to undergoing a modification or treatment. In some other embodiments, it is not removed for at least one modification.

The polymeric article can also be deformed (e.g., contracted or expanded) in any direction. Deforming the polymeric article in a direction can increase its strength along that direction (e.g., increase its resistance to force applied in that direction). Furthermore, deforming the polymeric article in a direction can align polymer chains substantially in that direction and can induce crystallization and increase crystallinity of the material (e.g., polymeric material) comprising the polymeric article, or can align amorphous polymer chains substantially in that direction without necessarily inducing crystallization of the amorphous polymer region or increasing crystallinity of the material (e.g., polymeric material). In certain embodiments, the polymeric article is expanded in a direction (e.g., longitudinal, circumferential or other direction) while being heated at elevated temperature (e.g., at or above the $T_g$ of the polymeric material comprising the polymeric article), and then the expanded polymeric article is cooled to a lower temperature (e.g., below $T_g$).

The polymeric article can be longitudinally extended by any suitable method. For example, if the polymeric article is a tube, a tubular structure whose diameter is slightly less than the inner diameter of the polymeric tube can be placed inside the tube, one end of the tube can be held in place, and force can be applied to the other end of the tube to stretch the polymeric tube while maintaining the diameter of the tube relatively uniform along the length of the tube. Moreover, the polymeric article can be radially expanded by any suitable method. For example, if the polymeric article is a tube, an expandable pressure vessel can be placed inside the tube and then gas or fluid, optionally heated, can be introduced into the vessel to radially expand the polymeric tube to the desired diameter. The expandable pressure vessel can optionally have heating elements for heating the polymeric tube. An alternative method of radial expansion of the polymeric tube is blow molding. The polymeric tube can be placed inside a molding tube having an inner diameter equal to the desired expanded outer diameter of the polymeric tube. Pressurized inert gas (e.g., nitrogen or argon), optionally heated, can be introduced into the molding tube to radially expand the polymeric tube to the inner diameter of the molding tube. The molding tube can optionally have heating elements for heating the polymeric tube.

In some embodiments, the polymeric article is longitudinally extended and/or radially expanded, optionally while the polymeric article is heated at elevated temperature (e.g., at or above the $T_g$ of the polymeric material comprising the polymeric article) and optionally with cooling of the longitudinally extended and/or radially expanded polymeric article to a lower temperature (e.g., below $T_g$), which can increase the strength of the polymeric article and can induce or increase orientation of crystals, crystalline regions or polymer chains substantially in the longitudinal direction, the circumferential direction, and/or a biaxial direction. In certain embodiments, the polymeric article is radially expanded while being heated at elevated temperature (e.g., at or above the $T_g$ of the polymeric material comprising the polymeric article) and then the radially expanded polymeric article is cooled to a lower temperature (e.g., below $T_g$), which can increase the strength of the polymeric article and can induce or increase orientation of crystals, crystalline regions or polymer chains substantially in the circumferential direction or a biaxial direction. In some embodiments, the polymeric article is longitudinally extended by at least about 25%, 50%, 75%, 100%, 200%, 300%, 400% or 500% of its initial length, and/or radially expanded by at least about 25%, 50%, 75%, 100%, 200%, 300%, 400% or 500% of its initial diameter. In certain embodiments, the polymeric article is longitudinally extended by at least about 50% of its initial length, or radially expanded by at least about 50% of its initial diameter, or both. In further embodiments, the polymeric article is longitudinally extended by at least about 100% of its initial length, or radially expanded by at least about 100% of its initial diameter, or both.

Furthermore, the polymeric article can be rotated at a certain rate and for a certain period of time, optionally with heating, to induce circumferentially oriented stress, which can increase the radial strength of the polymeric article and/or impart substantially circumferential or biaxial orientation to the polymeric material comprising the polymeric article. For example, a mandrel having a polymeric tube formed on it can be rotated at a certain rate and for a certain period of time, optionally with heating.

Another treatment that can, e.g., control crystallinity of the material (e.g., polymeric material) comprising the polymeric article is exposure of the polymeric article to radiation (e.g., ionizing radiation, such as e-beam radiation or gamma radiation). Ionizing radiation can be used to control physical characteristics (e.g., control crystallinity or promote crosslinking) of the material (e.g., polymeric material) comprising the polymeric article without necessarily sterilizing the article, or to control physical characteristics of the material and sterilize the polymeric article. In some embodiments, the polymeric article is exposed to a single dose or multiple doses of e-beam or gamma radiation at ambient temperature, or below or above ambient temperature, where a dose of radiation is at least about 0.1, 1, 5, 10, 20, 30, 40 or 50 kGray (kGy), or the total dose of radiation is about 1 or 5 kGy to about 100 kGy, or about 5 or 10 kGy to about 60 kGy, or about 10 or 20 kGy to about 50 kGy, or about 20 or 30 kGy to about 40 kGy. In certain embodiments, the polymeric article is cooled to reduced temperature (e.g., below 0° C.) and then is exposed to a single dose or multiple doses of e-beam or gamma radiation totaling about 10 kGy to about 50 kGy.

The strength and/or toughness of the material(s) (e.g., polymeric material(s)] comprising the implantable device can also be enhanced by incorporation of one or more additives in the polymeric article from which the device is formed, and/or by incorporation of one or more additives in a coating on the device. As an example, one or more additives (e.g., nanotubes, carbon nanotubes, fullerenes, nanoparticles, nanospheres, nanopowders, nanoclay, zeolites, exfoliates, fibers, whiskers, platelets, monomers, polymers, etc.) can be incorporated in the polymeric article and/or a coating on the device to reinforce and strengthen the material(s), e.g., polymeric material(s), comprising the polymeric article and/or the coating. For example, fibers, particles or the like comprised of the same polymer or a different biodegradable or non-degradable polymer can be incorporated in the polymeric article and/or a coating on the device to reinforce and strengthen the material(s), e.g., polymeric material(s), comprising the polymeric article and/or the coating. In certain embodiments, the amount of each of the one or more additives (e.g., nanotubes, carbon nanotubes, fullerenes, nanoparticles, nanospheres, nanopowders, nanoclay, zeolites, exfoliates, fibers, whiskers, platelets, monomers, polymers, etc.) incorporated in the polymeric article and/or a coating on the device is about 0.1 or 0.5 wt % to about 10 wt %, or about 0.1 or 0.5 wt % to about 5 wt %, or about 0.1, 0.5, 1, 1.5, 2, 2.5, 3, 3.5, 4, 4.5, 5, 6, 7, 8, 9 or 10 wt %. As a further example, one or more additives, e.g., solvents (e.g., dichloromethane and dimethylsulfoxide), glucosemonoesters, citrate esters, adipate esters, epoxidized soy oil, acetyl-tri-n-butyl citrate (ATBC), buturyl-tri-n-hexyl citrate (BTHC), di-iso-nonyl 1,2-cyclohexanedicarboxylate (DINCH), dioctyl terephthalate (DOTP), monomers (e.g., monomer(s) of the polymer(s) comprising the polymeric article and/or the coating), and polymers (e.g., polyethylene carbonate, polyethylene glycol, polyvinylpyrrolidone, and polydimethylsiloxane), can be incorporated in the polymeric article and/or a coating on the device to plasticize or soften the material(s), e.g., polymeric material(s) comprising the polymeric article and/or the coating and make those material(s), e.g., polymeric material(s), more ductile and/or tougher.

If a solvent (e.g., dichloromethane or dimethylsulfoxide) is utilized as an additive, a controlled amount of the solvent (e.g., about 0.5 wt % to about 5 wt %, or about 1 wt % to about 3 or 4 wt %, of the solvent relative to the weight of the material (e.g., polymeric material) comprising the body of the device or a coating on the device, or relative to the weight of the device) can be incorporated in the body of the device and/or a coating on the device by, e.g., incorporating the solvent in the polymeric article and/or a coating and controlling the parameters of any treatments (e.g., heating, vacuuming and/or exposure to carbon dioxide gas or liquid) that the polymeric article and/or the device undergo. In certain embodiments, about 1.5 or 2 wt % of a solvent (e.g., dichloromethane or dimethylsulfoxide) relative to the weight of the material (e.g., polymeric material) comprising the body of the device or a coating on the device, or relative to the weight of the device, is incorporated in the body of the device and/or a coating on the device as an additive.

Depending on the type of device it is, the biodegradable implantable device may be able to be formed from the polymeric article when the polymeric article is associated with the structure or removed from the structure. For example, a stent can be patterned from a polymeric tube (e.g., by laser or mechanical cutting) when the tube is either associated with a mandrel or removed from the mandrel. In certain embodiments, the polymeric article is removed from the structure prior to formation of the device from the polymeric article.

The implantable device can be formed from the polymeric article using any suitable method or technique. In certain embodiments, the device is formed from the polymeric article by cutting the polymeric article with a laser to form a pattern of the device. The heat-affect zone and recasting of the material (e.g., polymeric material) comprising the polymeric article can be minimized by employing a laser having a short pulse duration (e.g., a pulse duration in the nanoseconds or femtoseconds). Non-limiting examples of lasers that can be used to cut the polymeric article include excimer lasers and diode-pumped solid-state lasers operating at a wavelength of about 157 nm to about 351 nm, or at about 193 nm, and femtosecond lasers and ultrafast lasers operating at a wavelength of about 600 nm to about 1000 nm, or at about 800 nm.

The implantable device can be any device described herein. When the device is a stent, the stent can be any stent described herein, and can have any pattern and design suitable for its intended use, including any stent pattern and design described herein.

When the device is a stent, in some embodiments the stent is patterned from a polymeric tube that has a (e.g., inner) diameter substantially equal to an intended deployment (e.g., inner) diameter or the maximum allowable expansion (e.g., inner) diameter of the stent. In other embodiments, the stent is patterned from a polymeric tube that has a (e.g., inner) diameter greater than (e.g., at least about 5%, 10%, 15%, 20%, 25%, 30%, 35%, 40%, 45% or 50% greater than) an intended deployment (nominal or labeled) (e.g., inner) diameter or the maximum allowable expansion (e.g., inner) diameter of the stent. In an embodiment, the stent is patterned from a polymeric tube that has a (e.g., inner) diameter at least about 10% greater than an intended (labeled or nominal) deployment (e.g., inner) diameter or the maximum allowable expansion (e.g., inner) diameter of the stent. In some embodiments, the stent is patterned from a polymeric tube that has a (e.g., inner) diameter of about 2 mm to about 9 mm, or about 2 mm to about 7 mm, or about 2 mm to about 5 mm, or about 2.5 mm to about 4.5 mm, or about 2.75 mm to about 4.5 mm, or about 3 mm to about 4.5 mm, or about 2.75 mm to about 4 mm, or about 3 mm to about 4 mm, or about 3.3 mm to about 3.8 mm. In certain embodiments, the stent is patterned from a polymeric tube that has a (e.g., inner) diameter of about 2.75 mm to about 4.5 mm, or about 2.75 mm to about 4 mm. In some embodiments, prior to patterning the stent from a polymeric tube, the diameter (e.g., inner diameter) of the polymeric tube is set by heating the tube at a temperature within about 10° C. or 5° C. of the $T_g$, or at or above the $T_g$, of the material (e.g., polymeric material) comprising the tube, and optionally cooling the tube to a temperature below the $T_g$ (e.g., at least about 5, 10, 15 or 20° C. below the $T_g$, or to ambient temperature or below).

In some embodiments, the method of making the biodegradable implantable device comprises applying a first coating solution or mixture containing a biodegradable polymer or a non-degradable polymer, or both, and a solvent to the device to form a first coating disposed over or adjacent to at least a portion of the device. The biodegradable polymer of the first coating can be any biodegradable polymer described herein, and the non-degradable polymer of the first coating can be any non-degradable polymer described herein. In some embodiments, the biodegradable polymer of the first coating is a polylactide homopolymer or copolymer, wherein lactide includes L-lactide, D-lactide and D,L-lactide. In certain embodiments, the biodegradable polymer of the first coating is a poly(L-lactide) homopolymer or copolymer. In further embodiments, the biodegradable polymer of the first coating is a copolymer of L-lactide and glycolide in a weight or molar ratio of about 70:30 to about 99.9:0.1, or about 75:25 to about 95:5, or about 80:20 to about 90:10, or about 82:18 to about 88:12. In an embodiment, the biodegradable polymer of the first coating is a copolymer of L-lactide and glycolide in a weight or molar ratio of about 85:15.

The solvent of the first coating solution or mixture can be any suitable solvent for applying a polymer as described herein. In an embodiment, the solvent is dichloromethane. In some embodiments, the concentration of the biodegradable polymer or the non-degradable polymer, or both individually or combined, in the first coating solution or mixture is about 0.1 mg/mL to about 15 mg/mL, or about 0.5 mg/mL to about 10 mg/mL, or about 0.5 mg/mL to about 5 mg/mL, or about 1 mg/mL to about 3 mg/mL. In certain embodiments, the concentration of the biodegradable polymer or the non-degradable polymer, or both individually or combined, in the first coating solution or mixture is about 1 mg/mL to about 3 mg/mL, or about 2 mg/mL.

In further embodiments, the first coating solution or mixture contains one or more biologically active agents, or one or more additives, or both. The biologically active agent(s) of the first coating can be any biologically active agent described herein, and the additive(s) of the first coating can be any additive described herein. In an embodiment, the biologically active agent(s) of the first coating include myolimus or novolimus. In some embodiments, the weight percentage of the biologically active agent(s), individually or combined, relative to the amount of the biologically active agent(s) and the polymer(s) in the first coating solution or mixture is about 10% to about 60%, or about 20% to about 60%, or about 30% to about 60%, or about 30% to about 50%, or about 40% to about 50%. In certain embodiments, the weight percentage of the biologically active agent(s), individually or combined, relative to the amount of the biologically active agent(s) and the polymer(s) in the first coating solution or mixture is about 30% to about 50%, or about 40%.

In additional embodiments, the method of making the device comprises applying a second coating solution or mixture containing a biodegradable polymer or a non-degradable polymer, or both, and a solvent to the device to form a second coating disposed over or adjacent to at least a portion of the first coating. The second coating solution or mixture can contain one or more biologically active agents, or one or more additives, or both. The method can also comprise applying one or more additional coatings to the device. The biodegradable polymer, the non-degradable polymer, the biologically active agent(s) and the additive(s) of the second coating and any additional coating(s) can independently be any biodegradable polymer described herein, any non-degradable polymer described herein, any biologically active agent described herein, and any additive described herein.

The first coating and any additional coating(s) can be applied to the implantable device using any suitable method, e.g., by spraying the respective coating solution or mixture onto the device or dipping the device in the respective coating solution or mixture.

The coated device can be treated to incorporate or remove any residual water, solvent(s), monomer(s), low molecular weight oligomer(s) and/or particulate(s) from the coating(s) or the device. In some embodiments, the coated device is subjected to reduced or elevated pressure or heated at elevated temperature (e.g., at least about 50, 60, 70, 80, 90 or 100° C.), or both, for a period of time (e.g., at least about 0.5, 1, 6, 12, 24, 36 or 48 hours).

The coated device can also be treated to stabilize the coating(s) and prevent their smearing (e.g., upon expansion of the device). In some embodiments, the coated device is heated at about 50° C., 60° C., 70° C., 80° C., 90° C. or 100° C. or above, at ambient pressure or under reduced pressure, for a period of time (e.g., at least about 10 min, 30 min, 1 hr, 4 hr, 8 hr or 12 hr). In certain embodiments, the coated device is heated at about 60° C. or above, at ambient pressure or under reduced pressure, for at least about 10 min. To minimize degradation of any biologically active agent(s) present in a coating or in the body of the device, the coated device can be heated in an inert environment (e.g., under nitrogen, argon or other inert gas).

In some embodiments, after the coated device undergoes any vacuum and/or heat treatments, the thickness (e.g., average thickness) of each of the first coating and any additional coating(s) independently is about 20 microns or less, or about 15 microns or less, or about 10 microns or less, or about 5 microns or less, or about 4 microns or less, or about 3 microns or less, or about 2 microns or less, or about 1 micron or less. In certain embodiments, after the coated device undergoes any vacuum and/or heat treatments, the thickness (e.g., average thickness) of each of the first coating and any additional coating(s) independently is about 10 microns or less, or about 5 microns or less. In further embodiments, after the coated device undergoes any vacuum and/or heat treatments, the thickness (e.g., average thickness) of the first coating is about 5 microns or less, or about 3 microns or less.

As described herein, the body of the implantable device can comprise features in and/or on the body, and/or a coating on the device can comprise features in and/or on the coating, that promote degradation of the body and/or the coating. Examples of degradation-promoting features include without limitation openings, pores (including partial pores and through pores), holes (including partial holes and through holes), recesses, pits, cavities, trenches, reservoirs and channels.

Such degradation-promoting features can be formed by any of a variety of ways. For example, incorporation of an additive in the polymeric article and/or a coating on the device and subsequent removal of the additive by exposure of the polymeric article and/or the device to a solvent that dissolves the additive but does not substantially dissolve the polymer(s) comprising the polymeric article and/or the coating can form pores in and/or on the body and/or the coating of the device. As another example, incorporation of an additive (e.g., a blowing agent, a gas, a solvent or water) in the polymeric article and/or a coating on the device and subsequent removal of the additive by exposure of the polymeric article and/or the device to heat and/or reduced pressure can form pores in and/or on the body and/or the coating of the device. As still another example, incorporation of an additive (e.g., a substance having a relatively low molecular weight of about 2,000 daltons or less) in the polymeric article and/or a coating on the device and subsequent removal of the additive by exposure of the polymeric article and/or the device to carbon dioxide gas or liquid under elevated pressure, optionally under a flow of carbon dioxide, can form pores in and/or on the body and/or the coating of the device. As yet another example, an additive (e.g., a blowing agent) incorporated in the polymeric article and/or a coating on the device can leach out from the polymeric article, the body of the device and/or the coating before and/or after the device is implanted in a subject to form pores in and/or on the body and/or the coating of the device. As a further example, a certain amount of an additive (e.g., about 4-10 wt %, or about 5 wt %, of carbon nanotubes) can be incorporated in the polymeric article and/or a coating on the device to form pores in and/or on the body and/or the coating of the device.

After a device is formed from the polymeric article, the device can undergo any of a variety of treatments designed, e.g., to control or reduce residual or internal stress in the device and/or to control crystallinity and/or control or enhance the strength or toughness of the material(s), e.g., polymeric material(s), comprising the body of the device and/or a coating on the device. In some embodiments, the device undergoes one or more cycles of heating and cooling to anneal the material(s), e.g., polymeric material(s). In certain embodiments, the device is heated at a temperature equal to or greater than the $T_g$ of the first biodegradable polymer or the material (e.g., polymeric material) comprising the body of the device for a period of time (e.g., at least about 0.1, 0.25, 0.5, 1, 4, 8, 12 or 24 hours), and then quickly or slowly cooled to a lower temperature (e.g., at least about 10° C., 20° C., 30° C., 40° C. or 50° C. below the $T_g$, or to ambient temperature or below) over a period of time (e.g., about 10 sec, 30 sec, 1 min, 10 min, 30 min, 1 hr, 4 hr, 8 hr or 12 hr). In further embodiments, the device is heated at a temperature above the $T_g$ and below the $T_m$ of the first biodegradable polymer or the material (e.g., polymeric material) comprising the body of the device for a period of time (e.g., at least about 0.1, 0.25, 0.5, 1, 4, 8, 12 or 24 hours), and then quickly or slowly cooled to a lower temperature (e.g., at least about 10° C., 20° C., 30° C., 40° C. or 50° C. below the $T_g$, or to ambient temperature or below) over a period of time (e.g., about 10 sec, 30 sec, 1 min, 10 min, 30 min, 1 hr, 4 hr, 8 hr or 12 hr). In certain embodiments, the device is heated at a temperature within the cold crystallization temperature range of the first biodegradable polymer or the material (e.g., polymeric material) comprising the body of the device for a period of time (e.g., at least about 0.1, 0.25, 0.5, 1, 4, 8, 12 or 24 hours), and then quickly or slowly cooled to a lower temperature (e.g., at least about 10° C., 20° C., 30° C., 40° C. or 50° C. below the $T_g$, or to ambient temperature or below) over a period of time (e.g., about 10 sec, 30 sec, 1 min, 10 min, 30 min, 1 hr, 4 hr, 8 hr or 12 hr). In still further embodiments, the device is heated at a temperature equal to or greater than the $T_m$ of the first biodegradable polymer or the material (e.g., polymeric material) comprising the body of the device for a period of time (e.g., at least about 0.1, 0.25, 0.5, 1, 4, 8, 12 or 24 hours) to melt crystalline regions of the first biodegradable polymer or the material (e.g., polymeric material), and then quickly or slowly cooled to a lower temperature (e.g., at least about 10° C., 20° C., 30° C., 40° C. or 50° C. below the $T_g$, or to ambient temperature or below) over a period of time (e.g., about 10 sec, 30 sec, 1 min, 10 min, 30 min, 1 hr, 4 hr, 8 hr or 12 hr).

Another treatment that can, e.g., control crystallinity of the material(s), e.g., polymeric material(s) comprising the body of the device and/or a coating on the device is exposure of the device to radiation (e.g., ionizing radiation, such as e-beam radiation or gamma radiation). Ionizing radiation can be used to control physical characteristics (e.g., control crystallinity or promote crosslinking) of the material(s), e.g., polymeric material(s), comprising the body of the device and/or a coating on the device without necessarily sterilizing the device, or to control physical characteristics of the material(s) and sterilize the device. In some embodiments, the device is exposed to a single dose or multiple doses of e-beam or gamma radiation at ambient temperature, or below or above ambient temperature, where a dose of radiation is at least about 0.1, 1, 5, 10, 20, 30, 40 or 50 kGy, or the total dose of radiation is about 1 or 5 kGy to about 100 kGy, or about 5 or 10 kGy to about 60 kGy, or about 10 or 20 kGy to about 50 kGy, or about 20 or 30 kGy to about 40 kGy. In certain embodiments, the device is cooled to reduced temperature (e.g., below 0° C.) and then is exposed to a single dose or multiple doses of e-beam or gamma radiation totaling about 10 kGy to about 50 kGy, or about 30 kGy.

Furthermore, the device can be rotated at a certain rate and for a certain period of time, optionally with heating, to induce circumferentially oriented stress, which can increase the radial strength of the device and/or impart substantially circumferential or biaxial orientation to the polymeric material comprising the body of the device. For example, a mandrel having a stent associated with it can be rotated at a certain rate and for a certain period of time, optionally with heating.

When the implantable device is a stent, the stent can be crimped to a reduced diameter so that the stent can be delivered through a vessel or passage of a subject. In some embodiments, the stent is crimped to an inner diameter of about 0.4 mm, 1 mm to about 2 mm, or about 1.2 mm to about 1.6 mm, or about 1.3 mm to about 1.5 mm. In certain embodiments, the stent is crimped to an inner diameter of about 1.3 mm to about 1.5 mm, or about 1.4 mm.

In some embodiments, the stent is crimped at ambient temperature, or is crimped at a temperature (crimping temperature) of at least about 30° C., 35° C., 40° C., 45° C. or 50° C., and the stent crimped at elevated temperature is then cooled to a lower temperature (e.g., at least about 5° C., 10° C., 15° C., 20° C., 25° C. or 30° C. below the crimping temperature, or to ambient temperature or below). In certain embodiments, the stent is crimped at about 40° C. or above, and the crimped stent is then cooled to a temperature at least about 5° C. below the crimping temperature. Radially inward recoil of the stent after it is deployed can be reduced by crimping the stent at a temperature at about the $T_g$ or below the $T_g$ of the material (e.g., polymeric material) comprising the stent body. In certain embodiments, the stent is crimped at an elevated temperature that is at about the $T_g$ or at least about 1° C., 5° C., 10° C., 15° C., 20° C., 25° C., 30° C., 35° C., 40° C., 45° C. or 50° C. below the $T_g$ of the material (e.g., polymeric material) comprising the stent body. In an embodiment, the stent is crimped at an elevated temperature that is at least about 5° C. below the $T_g$ of the material (e.g., polymeric material) comprising the stent body.

Furthermore, the conditions in which the crimped stent is treated and handled can affect cracking, recoil, radial strength and uniformity of radial expansion of the stent. Minimizing exposure of the crimped stent to heat (in terms of, e.g., temperature and exposure time) can decrease cracking and recoil and improve radial strength and uniformity of radial expansion. Heat may promote generation of a crimped-state memory and may promote erasure of some amount of the as-cut tube memory (the diameter of the tube used to pattern the stent). For example, cracking and recoil can be decreased and radial strength and uniformity of radial expansion can be improved by exposing the crimped stent to a temperature not exceeding the $T_g$, or at least about 1° C., 5° C., 10° C., 15° C., 20° C., 25° C. or 30° C. below the $T_g$ of the material (e.g., polymeric material) comprising the stent body during, e.g., stabilization of the stent in the crimped state, mounting of the crimped stent onto a balloon-catheter, sterilization of the stent delivery system (e.g., with e-beam), and storage.

During storage of a crimped stent, the presence of heat (whether added or not) may induce crystallization of the polymeric material comprising the stent body over time. Crystallization of the polymeric material may or may not be accompanied by increase in the glass transition temperature of the polymeric material, and may render the polymeric material more brittle. Greater brittleness of the polymeric material may increase cracking of crowns of the stent upon radial expansion of the stent. Crystallization of the polymeric material during storage may also strengthen the crimped-state memory and may weaken the as-cut tube memory of the stent, which may result in less uniform radial expansion of the stent and greater radially inward recoil of the stent after expansion.

Crystallization of the polymeric material comprising the body of the crimped stent during storage can be reduced by any of a variety of ways. As a non-limiting example, the stent body can be comprised of a polymeric material that does not crystallize or increase in crystallinity over time and/or in the presence of heat (whether added or not). For example, the stent polymeric material can already be at its maximum % crystallinity prior to storage of the crimped stent, provided that the polymeric material is not too brittle and is sufficiently tough. As another example, one or more crystallization-inhibiting additives can be incorporated in the material (e.g., polymeric material) comprising the stent body. In certain embodiments, the crystallization-inhibiting additive(s) leach out from the stent material after exposure of the stent to physiological conditions. As yet another example, the crimped stent (or stent delivery system) can be stored at reduced temperature (e.g., at about 10° C., 5° C., 0° C., −5° C., −10° C. or −20° C. or below). Or the stent can be formed from a polymeric tube comprised of a polymeric material that has a low % crystallinity, so that any increase in crystallinity of the polymeric material during storage of the crimped stent does not result in a final % crystallinity that may adversely affect physical properties of the stent.

In some embodiments, prior to sterilization the crimped stent is stabilized in the crimped state at about 20° C. to about 35° C., or at about 25° C. to about 30° C., or at about 30° C., or at about 30° C. to about 35° C., or at about 35° C. to about 45° C.; for at least about 0.1 hr, 1 hr, 2 hr, 3 hr, 4 hr, 8 hr, 12 hr, 16 hr or 24 hr, or longer. The crimped stent can be mounted onto a balloon-catheter to provide a stent delivery system. In certain embodiments, after sterilization (e.g., with e-beam) the crimped stent, or the stent mounted on a balloon-catheter, is stabilized in the crimped state at about 20° C. to about the $T_g$ of the material (e.g., polymeric material) comprising the body of the stent, or at about 5° C., 10° C., 15° C., 20° C., 25° C. or 30° C. below the $T_g$, or at about 20° C. to about 30° C., or at about 25° C., or at about 30° C. to about 35° C., or at about 35° C. to about 45° C.; for at least about 0.1 hr, 1 hr, 4 hr, 6 hr, 12 hr, 24 hr, 36 hr, 48 hr, 60 hr, 72 hr, 84 hr or 96 hr, or longer. Stabilization of the mounted stent in the crimped state can enhance or control its retention on the balloon or delivery system during delivery through a vessel or a passage in a subject or upon expansion inside a blood vessel.

Retention of a stent on a balloon-catheter can also be enhanced by forming the inner (luminal) layer of the stent body from, or coating the luminal surface of the stent with, an elastomeric polymeric material, e.g., poly(ε-caprolactone), with a relatively high coefficient of friction. The relatively high-friction polymeric material can minimize movement of the stent on the balloon.

Additional ways for improving retention of a stent on a balloon-catheter include use of a non-permanent adhesive applied to the balloon or the luminal surface of the stent, or both. In some embodiments, the adhesive is made from a hydrophobic material that can resist water and lose its tackiness when exposed to water. In certain embodiments, the adhesive has weak bond force in the shear direction.

Figure 2:
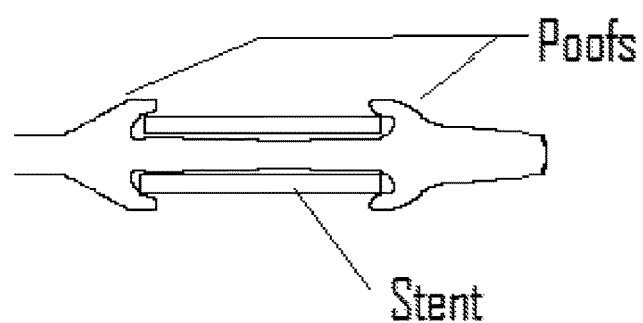
FIG. 2 illustrates an example of raised portions (poofs) formed on the balloon of a balloon-catheter which hold, cap and/or extend over the proximal and/or distal ends of a stent to retain the stent substantially in place on the balloon during delivery.

Raised portions (poofs) formed on the balloon of a balloon-catheter and located at the proximal and distal ends of a stent can maintain the stent on the balloon. Poofs located above the balloon markers of the catheter can be formed on the balloon (see, e.g., Example 1). For example, the balloon poofs can be designed to cap the proximal and distal ends of the stent (FIG. 2).

Furthermore, the abluminal surface, the luminal surface and both side surfaces of a crimped stent can be partially or fully covered by a water-soluble or non soluble material that dissolves away after a certain period of time. Coverage of the stent by the water-soluble or non soluble material reduces permeation of water into the body of the stent, which prevents the stent from growing or swelling above the balloon poofs, thereby helping to retain the stent on the balloon.

Cap(s) can be placed on the proximal end and/or the distal end of a crimped stent to maintain the stent on a balloon-catheter. A major portion of the cap can be on the balloon-catheter, and a minor portion of the cap can be extended over the stent. In certain embodiments, the cap covers at most one full crown of the stent, or at most half a crown. The cap can be fitted tightly against the balloon portion of the catheter or be bonded to the catheter. Prior to radial expansion of the stent, the cap maintains the stent on the balloon-catheter. During radial expansion of the stent, the cap recesses, allowing the stent to expand without hindrance. The cap can be solid and be substantially free of holes, or can be a mesh or have holes.

Figure 3:
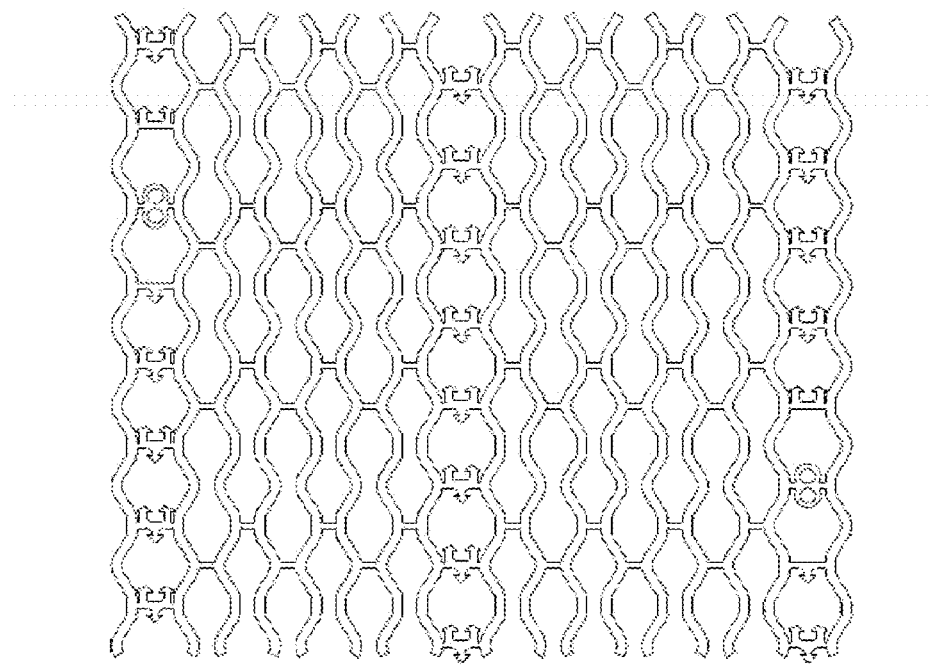
FIG. 3 depicts an example of stent pattern having lockable elements that are designed to retain the stent on a balloon-catheter.

Moreover, a stent can have locks or lockable elements that help to retain the stent on a balloon-catheter. FIG. 3 illustrates a non-limiting example of a stent pattern having lockable elements. When the stent is crimped, the arrow or male on one side of a lockable element engages with the other side or female of an adjacent lockable element and locks in place. Locking of the lockable elements prevents the stent from growing, thereby helping to retain the stent on the balloon.

A crimped stent can also be maintained on a balloon-catheter by placing a retractable sheath or sleeve over the stent. The sheath or sleeve can end at or beyond the proximal end and/or the distal end of the stent, or over the stent. The sheath or sleeve can be physically or mechanically retracted from the stent prior to radial expansion of the stent.

In addition, a stent can be retained on a balloon by placing or crimping a protector stent over the main stent. In certain embodiments, the protector stent is thin (e.g., about 0.001 inch thick) and has a relatively high degree of crystallinity or a relatively high $T_g$. The protector stent may not grow when exposed to physiological conditions, may not expand evenly or may crack, but the main stent is the stent that is designed to expand substantially evenly and support the treated vessel.

In some embodiments, the biodegradable stent is retained on a balloon-catheter by any suitable means, including any means described herein, and is configured not to move on the balloon-catheter in at least one longitudinal direction by more than about 5 mm, 4 mm, 3 mm, 2 mm, 1 mm or 0.5 mm, e.g., during delivery of the stent-catheter system through a vessel or passage of a subject. In an embodiment, the stent is configured not to move on the balloon-catheter in at least one longitudinal direction by more than about 1 mm.

The device (e.g., a crimped or uncrimped stent or a stent delivery system) can be subjected to a sterilization condition. Subjecting the device to a sterilization condition can serve purposes in addition to sterilization of the device, such as controlling crystallinity of the material(s), e.g., polymeric material(s), comprising the device. Non-limiting examples of sterilization conditions include radiation, ionizing radiation, e-beam radiation, gamma radiation, and ethylene oxide gas. In some embodiments, the device is exposed to a single dose or multiple doses of e-beam or gamma radiation at ambient temperature, or below or above ambient temperature, where a dose of radiation is at least about 0.1, 1, 5, 10, 20, 30, 40 or 50 kGray (kGy), or the total dose of radiation is about 1 or 5 kGy to about 100 kGy, or about 5 or 10 kGy to about 60 kGy, or about 10 or 20 kGy to about 50 kGy, or about 20 or 30 kGy to about 40 kGy.

For sterilization the device (e.g., a crimped or uncrimped stent or a stent delivery system) can also be exposed to ethylene oxide gas in a suitable environment (e.g., a sealed bag or a chamber). As a non-limiting example of sterilization with ethylene oxide gas, the device is preconditioned for about 1 hr at a relative humidity of at least about 35% and at a temperature of about ambient temperature to about 33° C. The device is exposed to ethylene oxide gas at a temperature of about ambient temperature to about 33° C., or at about 25° C., or between about 20° C. to about 40° C.; for at least about 4 hr, 8 hr, 12 hr, 16 hr, 24 hr or 30 hr. Sterilization can be conducted in the presence of water chips (e.g., two 4 g water chips) to increase humidity. As another example of sterilization with ethylene oxide gas, the device is exposed to ethylene oxide gas at a temperature of about 35° C. to about 50° C., or about 35° C. to about 45° C., and at a relative humidity of about 20% to about 80%, or about 30% to about 70%, for at least about 4 hr, 8 hr, 12 hr, 16 hr or 24 hr. To avoid generation of a crimped-state memory at higher temperature, a stent can be mounted onto an inflated balloon prior to sterilization, sterilized with ethylene oxide gas at elevated temperature, and then crimped onto the deflated balloon in an aseptic or semi-aseptic environment. The stent-balloon-catheter delivery system can be terminally sterilized by exposure to nitrogen dioxide at about ambient temperature or below for at least about 10, 30, 60, 90 or 120 minutes, using, e.g., a system developed by Noxilizer (Baltimore, Md.).

In addition to spraying, the biodegradable implantable devices such as the stent (scaffold) described herein can be made by other suitable methods, such as dipping, extrusion, molding, injection molding, compression molding and 3-D printing. For example, a polymeric article/material (e.g., a polymeric tube) can be made by dipping a structure (e.g., a substantially cylindrical structure) in a solution or mixture containing one or more biodegradable polymers and a solvent, and optionally one or more non-degradable polymers, one or more biologically active agents, and one or more additives. A device (e.g., a stent) can be formed from the polymeric article (e.g., by laser or mechanical cutting) while the article is associated with the structure or after the article is removed from the structure. A polymeric article made by dipping, and/or a device formed from such a polymeric article, can undergo any one or more of the processing steps and treatments described herein (e.g., longitudinal extension, radial expansion, heating, pressurizing, vacuuming, or exposure to radiation or carbon dioxide, or a combination thereof).

Dipping can also be performed to make a polymeric article (e.g., a polymeric tube) comprising two or more polymer layers, where each layer independently contains one or more biodegradable polymers, and optionally one or more non-degradable polymers, one or more biologically active agents, and one or more additives. After a structure (e.g., a substantially cylindrical structure) is dipped in and then removed from a first solution or mixture containing one or more biodegradable polymers and optional additional material(s) or substance(s), the coated structure is suitably dried by any of various treatments described herein (e.g., vacuuming, heating, and/or exposure to carbon dioxide gas or liquid). The coated structure is dipped in and then removed from a second solution or mixture containing one or more biodegradable polymers and optional additional material(s) or substance(s), and is suitably dried to form a second polymer layer of the polymeric article. The dipping and drying process can be repeated a desired number of times to form a desired number of polymer layers of the polymeric article.

Moreover, a polymeric article (e.g., a polymeric tube) comprising one or more polymer layers and one or more metal layers can be made by dipping. For example, a metal film, foil or tube comprising a corrodible metal or metal alloy, and optionally a non-corrodible metal or metal alloy, can be applied to a coated structure made by dipping the structure (e.g., a substantially cylindrical structure) in a first solution or mixture containing one or more biodegradable polymers, and optionally one or more non-degradable polymers, one or more biologically active agents, and one or more additives. The metal film, foil or tube can be pre-textured or pre-treated (e.g., by microblasting) prior to its application to form surface roughness on one side of the metal film, foil or tube to enhance its adhesion to the first polymer layer. A second polymer layer can be applied to the metal layer, the other side of the metal film, foil or tube can be pre-textured or pre-treated, or can be treated after its application to the first polymer layer, to form surface roughness on the uncoated side of the metal layer before the structure is dipped in a second solution or mixture containing one or more biodegradable polymers and optional additional material(s) or substance(s).

The following provides embodiments of ways for making a polymeric tube by dipping. A mandrel, whose diameter can be substantially equal to or larger than an intended deployment inner diameter of a stent to be formed from the tube, is dipped in a solution or mixture containing one or more biodegradable polymers and a solvent, and optionally one or more non-degradable polymers, one or more biologically active agents, and one or more additives. The concentration of the material(s) in the solution or mixture can be about 1 or 5 mg/mL to about 100 mg/mL, or about 10 or 20 mg/mL to about 50 mg/mL. The mandrel can be dipped in the polymer solution or mixture with or without rotation of the mandrel. After the mandrel is dipped in the polymer solution or mixture for a period of time (e.g., at least about 1, 2, 3, 4, 5, 10 or 15 seconds), the mandrel is removed from the polymer solution or mixture at a certain rate that may depend on the desired thickness of the coating/layer or tube (if the tube contains only one polymer layer). More than one cycle of dipping and removal can be performed depending on, e.g., the concentration of the polymer solution or mixture and the desired thickness of the coating/layer or tube. After removal of the mandrel from the polymer solution or mixture, the coated mandrel can be rotated (e.g., held and rotated in a horizontal position) or not rotated. The coated mandrel can undergo vacuuming and/or heating to remove, e.g., any residual solvent(s) and monomer(s). The coated mandrel can also be exposed to carbon dioxide gas or liquid under elevated pressure to remove, e.g., any residual solvent(s), monomer(s), low molecular weight oligomer(s) and/or particulate(s). The thickness and physical characteristics of the coating/layer or tube can be controlled by controlling various parameters, such as the composition and concentration of the polymer solution or mixture, the number of times the mandrel is dipped in the polymer solution or mixture, the duration of each dip, the rate of removal of the mandrel from the polymer solution or mixture, and the conditions and duration of drying after each dip. If the polymeric tube is to comprise a second polymer layer, the suitably dried coated mandrel is dipped in a second solution or mixture containing one or more biodegradable polymers and a solvent, and optionally one or more non-degradable polymers, one or more biologically active agents, and one or more additives. A stent can be patterned from the polymeric tube by, e.g., laser or mechanical cutting while the tube remains on the mandrel or after the tube is removed from the mandrel.

Dipping can provide a polymeric tube comprised of a polymeric material that is, or has crystals, crystalline regions or polymer chains that are, substantially randomly oriented or substantially not uniaxially oriented, circumferentially oriented, longitudinally oriented or biaxially oriented, if desired. To promote formation of a polymeric tube comprised of a polymeric material that is substantially not uniaxially oriented or biaxially oriented, certain parameters of the dipping process can be controlled, such as the concentration of the polymer solution or mixture, the rate and direction of dipping (e.g., the length of the mandrel is dipped in the polymer solution or mixture horizontally, vertically or at an angle), the rate of rotation, if any, of the mandrel while dipped in the polymer solution or mixture, the rate of removal of the mandrel from the polymer solution or mixture, and the rate of rotation, if any, of the coated mandrel after removal from the polymer solution or mixture.

Extrusion is another non-limiting example of a method for making biodegradable implantable devices described herein. For example, one or more biodegradable polymers, and optionally one or more non-degradable polymers, one or more additives, and one or more biologically active agents [if the heating is compatible with the bioactive agent(s)], can be heated and drawn through a die to make a polymeric article (e.g., a polymeric tube). A device (e.g., a stent) can be formed from the polymeric article using any suitable method (e.g., laser or mechanical cutting). To make a polymeric tube comprising two or more polymer layers, two or more tubings can be co-drawn, where each tubing independently contains one or more biodegradable polymers, and optionally one or more non-degradable polymers, one or more additives, and one or more biologically active agents.

Drawing the extruded material in a particular direction, optionally at elevated temperature, may induce or increase orientation of the material, or its crystals, crystalline regions or polymer chains, substantially in that direction. If desired, the following provides embodiments of ways for making a polymeric article (e.g., a polymeric tube) by extrusion, where the article is comprised of a polymeric material that is, or has crystals, crystalline regions or polymer chains that are, substantially randomly oriented or substantially not uniaxially oriented, circumferentially oriented, longitudinally oriented or biaxially oriented. As a first embodiment, a polymeric material is extruded at elevated temperature in the presence of a crystallization inhibitor that inhibits crystallization of the polymeric material while the material cools down after it exits the hot extruder nozzle.

As a second embodiment, a polymeric material is extruded at elevated temperature. Immediately after the polymeric material exits the hot extruder nozzle, the polymeric material is rapidly cooled below its crystallization temperature ($T_c$) or glass transition temperature ($T_g$), or to ambient temperature or below, to prevent or minimize crystallization of the polymeric material. The resulting polymeric article (e.g., polymeric tube) can be formed into a device (e.g., a stent).

As a third embodiment, a polymeric material is extruded at elevated temperature with a minimal drawing ratio. The resulting polymeric article (e.g., polymeric tube) is heated to about or above the melting temperature ($T_m$) of the polymeric material comprising the article. The polymeric material is rapidly cooled below its $T_c$ or $T_g$, or to ambient temperature or below, to prevent or minimize crystallization of the polymeric material. The resulting polymeric article can be formed into a device (e.g., a stent).

One embodiment is a process for making a biodegradable polymeric stent (or other endoprosthesis having a tubular body) according to the present teachings. A tubular body (e.g., a tube) comprised of a biodegradable polymeric material (having a degree of crystallinity of about 30%, 20%, 15%, 10% or 5% or less) is made by any suitable method, such as spraying, dipping, extrusion, molding, injection molding, compression molding or 3-D printing, e.g., by spraying onto a mandrel. The polymeric tube undergoes one or more cycles of heating and cooling (or step-wise heating and then cooling) as described herein, e.g., to increase crystallinity and/or strength of the material (e.g., polymeric material) the tube, and/or to reduce residual or internal stress in the polymeric tube. After the one or more cycles of heating and cooling or radiation, the degree of crystallinity of the material (e.g., polymeric material) is about 2%, 5% or 10% to about 70%, or about 2%, 5% or 10% to about 60%, or about 2%, 5% or 10% to about 50%, or about 2%, 5% or 10% to about 40%, or about 2%, 5% or 10% to about 30%, or about 2%, 5% or 10% to about 20%, or increases by at least about 10%, 20%, 25%, 30%, 40%, 50%, 75%, 100%, 150%, 200%, 300%, 400%, 500%, 600%, 700%, 800%, 900% or 1000%. The heat-treated or radiated polymeric tube is patterned into a stent or other endoprosthesis having a tubular body using any suitable method (e.g., laser or mechanical cutting). Alternatively, a stent or other endoprosthesis can be patterned from a polymeric tube that has not undergone a heat treatment, and the stent or other endoprosthesis can undergo one or more cycles of heating and cooling. As a further alternative, both the polymeric tube and the stent or other endoprosthesis can each undergo one or more cycles of heating and cooling.

Residual or internal stress may arise during processing of a polymeric article (e.g., a polymeric tube) or a device (e.g., a stent) formed from the polymeric article. Residual/internal stress may cause failure (e.g., substantial shortening, shrinkage, warping or the like) of the device if the level of residual/internal stress is high enough to overcome the structural integrity of the device. A polymeric article (e.g., a polymeric tube) made by extrusion or molding or spraying may require stabilization (which can include heating and pre-shrinkage) to relieve residual/internal stress and minimize shortening, shrinkage, warping or the like. Preparation of a polymeric article (e.g., a polymeric tube) by spraying can decrease the level of residual/internal stress in the article without resorting to stabilization.

Further embodiments of the disclosure relate to a method of making a biodegradable endoprosthesis, comprising providing a polymeric article (e.g., a tubular body, such as a polymeric tube) composed at least partially of a substantially amorphous or semi-crystalline, biodegradable polymeric material, wherein crystallinity (e.g., degree of crystallinity) of the polymeric material increases after the polymeric article undergoes a modification (or treatment), and wherein the endoprosthesis is formed from the polymeric article. The polymeric material is substantially amorphous or semi crystalline or crystalline prior to the modification, and may or may not be substantially amorphous after the modification. Further embodiments of the disclosure relate to a method of making a biodegradable endoprosthesis, comprising providing a polymeric article (e.g., a tubular body, such as a polymeric tube) comprising at least partially of a substantially amorphous or semi-crystalline biodegradable polymeric material, wherein crystallinity (e.g., degree of crystallinity) of the polymeric material decreases after the polymeric material undergoes a treatment, and wherein the endoprosthesis is formed substantially from the polymeric material. In one embodiment, the polymeric material is substantially amorphous or semi crystalline or crystalline prior to the modification, and substantially amorphous after the modification. In certain embodiments, the modification comprises heating, cooling, quenching, pressurizing, vacuuming, crosslinking, addition of an additive, or exposure to radiation or carbon dioxide, or a combination thereof. The polymeric article can have any shape, form and dimensions suitable for making the endoprosthesis (e.g., a patterned polymeric tube stent).

In some embodiments, a biodegradable endoprosthesis (e.g., a stent) is formed from a polymeric tube, wherein the tube is a substantially continuous cylinder that is substantially free from holes, gaps, voids or other discontinuities. In some embodiments, the polymeric tube has an outside diameter of about 2 mm to about 10 mm, or about 2 mm to about 5 mm; a thickness of about 0.01 mm to about 0.5 mm, or about 0.05 mm to about 0.3 mm; and a length of about 2 or 5 mm to about 20, 30, 40 or 80 mm. In certain embodiments, the polymeric tube has an outside diameter of about 2 mm to about 5 mm, a thickness of about 0.05 mm to about 0.3 mm, and a length of about 5 mm to about 30 mm.

In certain embodiments, an endoprosthesis (e.g., a stent) is patterned by laser cutting or other method from a polymeric tube that has a (e.g., inner or outer) diameter substantially equal to or smaller than an intended deployed (e.g., inner or outer) diameter of the endoprosthesis. In other embodiments, an endoprosthesis (e.g., a stent) is patterned from a polymeric tube that has a (e.g., inner or outer) diameter, either when the tube is formed or after the tube is radially expanded to a second larger diameter, larger than an intended deployed (e.g., inner or outer) diameter of the endoprosthesis. Patterning a stent from a polymeric tube having a (e.g., inner or outer) diameter larger than an intended deployed (e.g., inner or outer) diameter of the stent can impart advantageous characteristics to the stent, such as reducing radially inward recoil of the stent after deployment. In certain embodiments, a stent is patterned from a polymeric tube having a (e.g., inner or outer) diameter about 0.85, 0.90, 1.0, 1.05 to about 1.5 times, or about 1.1 to about 1.5 times, or about 1.1 to about 1.3 times, or about 1.15 to about 1.25 times, smaller, same, or larger than an intended deployed (e.g., inner or outer) diameter of the stent. In an embodiment, the stent is patterned from a polymeric tube having a (e.g., inner or outer) diameter about 1.1 to about 1.3 times larger than an intended deployed (e.g., inner) diameter of the stent. For example, a stent having a deployed (e.g., inner or outer) diameter of about 2.5, 3 or 3.5 mm can be patterned from a tube having a (e.g., inner or outer) diameter of about 2.75, 3.3 or 3.85 mm (1.1 times larger), or about 3.25, 3.9 or 4.55 mm (1.3 times larger), or some other (e.g., inner or outer) diameter larger than the deployed (e.g., inner or outer) diameter of the stent. In other embodiments, the initial diameter of the formed tube is larger than the crimped diameter (e.g., crimped diameter on a delivery system) of the stent prosthesis wherein the tubular body is expanded to a second larger diameter than the initial diameter before patterning or before crimping to the crimped diameter; or wherein the tubular body remains substantially the same diameter before patterning or before crimping to a crimped diameter; or wherein the tubular body is crimped to a smaller diameter than the initial formed diameter before patterning or after patterning. In another embodiment, the initial diameter of the formed tube is smaller than the crimped diameter of the stent prosthesis wherein the tubular body is expanded to a second larger diameter than the initial diameter before patterning or before crimping; or wherein the tubular body remains substantially the same diameter before patterning or before crimping; or wherein the tubular body is crimped to a smaller diameter than the crimped diameter of the stent prosthesis before patterning or after patterning. In another embodiment, the initial diameter of the formed tubular body is greater than 0.015 inches, or greater than 0.050 inches, or greater than 0.092 inches, or greater than 0.120 inches, or greater than 0.150 inches. Stent prosthesis intended deployment diameter is the diameter of the labeled delivery system or balloon catheter. For example when a stent prosthesis is crimped onto a balloon labeled 3.0 mm diameter, the stent prosthesis' intended deployment diameter is 3.0 mm. Similarly, self expandable stent crimped onto a delivery system is labeled a certain deployment diameter.

The stent cut from a polymeric tube can be any kind of stent and can have any pattern and design suitable for its intended use, including any kind of stent and any pattern and design described herein. Further, the stent can be a fully self-expandable stent, a balloon-expandable stent, or a stent capable of radially self-expanding prior to balloon expansion to an intended deployed diameter.

The degree of crystallinity of the material (e.g., polymeric material) of which an endoprosthesis (e.g., a stent) is comprised may decline as a result of cutting of the polymeric article (e.g., a polymeric tube). In some embodiments, a stent is annealed and quenched one or more times after cutting of the polymeric tube, as described herein for annealing and quenching a polymeric article or tube, to increase the degree of crystallinity of the polymeric material (and/or reduce residual/internal stress in the polymeric material or the stent). In certain embodiments, a heat-treated stent is cooled to a temperature below ambient temperature for a period of about 1 minute to about 96 hours, or about 24 hours to about 72 hours, or about 30 minutes to about 48 hours, or about 1 hour to about 48 hours, or about 1 hour to about 36 hours, or about 1 hour to about 24 hours, or about 1 hour to about 12 hours, or about 4 hours to about 12 hours, to stabilize the stent, and/or stabilize the crystals and/or terminate crystallization in the polymeric material.

In further embodiments, an unannealed or annealed stent is exposed to ionizing radiation (e.g., e-beam or gamma radiation) at, above or below ambient temperature, with a single dose or multiple doses of radiation totaling about 5 kGy to about 100 kGy, or about 10 kGy to about 50 kGy, or about 10 kGy to about 30 kGy, or about 20 kGy to about 60 kGy, or about 20 kGy to about 40 kGy. In certain embodiments, an unannealed or annealed stent is cooled to reduced temperature (e.g., below 0° C.) and then is exposed to a single dose or multiple doses of ionizing radiation (e.g., e-beam or gamma radiation) totaling about 10 kGy to about 50 kGy, or about 30 kGy.

The body of the device can be formed from a polymeric material made by any suitable method, such as spraying, dipping, extrusion, molding, injection molding, compression molding, or three-dimensional (3-D) printing, or a combination thereof. In certain embodiments, the body of the device is formed from a polymeric article made by spraying a solution or mixture containing at least the biodegradable copolymer or polymer and at least one solvent onto a structure. When the device is a stent, a stent can be laser-cut from a polymeric tube made by spraying the polymer solution or mixture onto a mandrel. In another embodiment, the polymeric material or tubular body comprising the biodegradable polymer is patterned into a stent using (3-D) printing or laser cut. In another embodiment, the polymeric material or tubular body comprising the biodegradable polymer is formed using extrusion or spraying or dipping, or molding, and is patterned into a stent. In certain embodiments, the stent or body of the device comprises one or more additional polymer layers, and/or one or more metal or metal alloy layers, the additional polymer layer(s) of the polymeric material can be formed by spraying additional solution(s) or mixture(s) containing a biodegradable polymer, and/or the metal layer(s) can be formed by applying metal film(s), foil(s) or tube(s). In some embodiments, a polymer solution or mixture can contain one or more additional biodegradable polymers and/or one or more non-degradable polymers, and can also contain one or more biologically active agents and/or one or more additives. In another embodiment, the stent or tubular body comprises radiopaque markers. Radiopaque markers can be metallic such as gold, platinum, iridium, bismuth, or combination thereof, or alloys thereof. Radiopaque markers can also be polymeric material. Radiopaque markers can be incorporated in the stent or tubular body when it is being formed or incorporated into the stent or the tubular body after forming.

In some embodiments, the tubular body or polymeric material or stent may be formed from at least one polymer having desired degradation characteristics where the polymer may be modified to have the desired crystallinity, Tg, recoil, strength, shortening, expansion characteristics, crimping characteristics, crystallinity, Tg, molecular weight, and/or other characteristics in accordance with the methods of the present invention. Polymers include one or more polymers, copolymers, blends, and combination thereof of: Lactides, Glycolides, Caprolactone, Lactides and Glycolides, Lactides and Caprolactones: examples poly-DL-Lactide, polylactide-co-glycolactide; polylactide-co-polycaprolactone, poly(L-lactide-co-trimethylene carbonate), polylactide-co-caprolactone, polytrimethylene carbonate and copolymers; polyhydroxybutyrate and copolymers; polyhydroxyvalerate and copolymers, poly orthoesters and copolymers, poly anhydrides and copolymers, polyiminocarbonates and copolymers and the like. A particularly preferred polymer comprises a copolymer of L-lactide and glycolide, preferably with a weight ratio of 85% L-lactide to 15% glycolide.

In some embodiments, the biodegradable copolymer is selected from the group consisting of poly(L-lactide-co-D-lactide), poly(L-lactide-co-D,L-lactide), poly(D-lactide-co-D,L-lactide), poly(lactide-co-glycolide), poly(lactide-co-ε-caprolactone), poly(glycolide-co-ε-caprolactone), poly(lactide-co-dioxanone), poly(glycolide-co-dioxanone), poly(lactide-co-trimethylene carbonate), poly(glycolide-co-trimethylene carbonate), poly(lactide-co-ethylene carbonate), poly(glycolide-co-ethylene carbonate), poly(lactide-co-propylene carbonate), poly(glycolide-co-propylene carbonate), poly(lactide-co-2-methyl-2-carboxyl-propylene carbonate), poly(glycolide-co-2-methyl-2-carboxyl-propylene carbonate), poly(3-hydroxybutyrate-co-4-hydroxybutyrate), poly(hydroxybutyrate-co-hydroxyvalerate), poly(3-hydroxybutyrate-co-3-hydroxyvalerate), poly(4-hydroxybutyrate-co-3-hydroxyvalerate), poly(ε-caprolactone-co-fumarate), poly(ε-caprolactone-co-propylene fumarate), poly(lactide-co-ethylene glycol), poly(glycolide-co-ethylene glycol), poly(ε-caprolactone-co-ethylene glycol), poly(DETOSU-1,6-HD-co-DETOSU-t-CDM), poly(lactide-co-glycolide-co-ε-caprolactone), poly(lactide-co-glycolide-co-trimethylene carbonate), poly(lactide-co-ε-caprolactone-co-trimethylene carbonate), poly(glycolide-co-ε-caprolactone-co-trimethylene carbonate), and poly(3-hydroxybutyrate-co-3-hydroxyvalerate-co-4-hydroxybutyrate), wherein lactide includes L-lactide, D-lactide and D,L-lactide.

In some embodiments, the biodegradable copolymer is a block or random copolymer of D-Lactide, DL-Lactide or L-lactide and ε-caprolactone in a weight or molar ratio of about 70:30 to about 99.9:0.1. In an embodiment, the biodegradable copolymer is a random copolymer of D-Lactide, DL-Lactide or L-lactide and ε-caprolactone in a weight or molar ratio of about 90:10, or of about 95:5, or of about 85:15. In an embodiment, the biodegradable copolymer is a random copolymer of D-Lactide, DL-Lactide or L-lactide and glycolic acid in a weight or molar ratio of about 70:30 to about 99.9:0.1. In an embodiment, the biodegradable copolymer is a random copolymer of D-Lactide, DL-Lactide or L-lactide and glycolic acid in a weight or molar ratio of about 90:10, or of about 95:5, or of about 85:15.

In some embodiments, the biodegradable copolymer is a block or random copolymer of glycolic acid and ε-caprolactone in a weight or molar ratio of about 70:30 to about 99.9:0.1. In an embodiment, the biodegradable copolymer is a random copolymer of glycolic acid and ε-caprolactone in a weight or molar ratio of about 95:5, or of about 90:10, or of about 85:15. In some embodiments, the biodegradable copolymer is a block or random copolymer of D-Lactide, DL-Lactide or L-lactide and ε-caprolactone and glycolic acid in a weight or molar ratio of about 70% poly lactide:30% (glycolic acid and ε-caprolactone) to about 99% Poly Lactide: 0.1% (glycolic acid and ε-caprolactone). In an embodiment, the biodegradable copolymer is a random copolymer of D-Lactide, DL-Lactide or L-Lactide and glycolic acid and ε-caprolactone in a weight or molar ratio of about 70:5:25, or of about 85:5:10, or of about 75:20:5.

In yet another embodiment, the stent or the body of the device can comprise one or more additional biodegradable polymers or co-polymers, and/or one or more additional non-degradable polymers. In yet another embodiment, the stent or the body of the device can comprise one or more biodegradable monomers. These monomers can be same or different type from polymer incorporated in the body or stent. Moreover, the stent or body of the device can comprise one or more biologically active agents, and/or one or more additives such as carbon nano fibers or tubes. The additives can serve any of a variety of functions, including controlling degradation, increasing the strength, increasing elongation, controlling Tg, or/and increasing toughness of the material (e.g., polymeric material) comprising the body of the device (or the material comprising a coating on the body), and/or increasing crystallinity.

In further embodiments, the body of the device comprises a layer containing the biodegradable copolymer, and one or more additional layers containing a biodegradable polymer or a corrodible metal or metal alloy, wherein the layers can be in any order. The layer containing the biodegradable copolymer and any additional layer(s) containing a biodegradable polymer can contain one or more additional biodegradable polymers and/or one or more non-degradable polymers, and can also contain one or more biologically active agents and/or one or more additives. In further embodiments, the body of the device comprises one or more layers of the biodegradable copolymer, and optionally one or more additional layers of a biodegradable polymer same or different or a corrodible metal or metal alloy, wherein the layers can be in any order. The one or more layers of the biodegradable copolymer and optionally the one or more additional layers of a biodegradable polymer (same or different polymer, degradable or non degradable polymer) or a corrodible metal or metal alloy optionally may contain one or more biologically active agents and/or one or more additives in one or more of the layers.

In some embodiments, the polylactide copolymer is formed from two or more different monomers selected from the group consisting of α-hydroxyacids, L-lactic acid/L-lactide, D-lactic acid/D-lactide, D,L-lactic acid/D,L-lactide, glycolic acid/glycolide, hydroxyalkanoates, hydroxybutyrates, 3-hydroxybutyrate, 4-hydroxybutyrate, hydroxyvalerates, 3-hydroxyvalerate, lactones, ε-caprolactone, δ-valerolactone, β-butyrolactone, β-propiolactone, 1,4-dioxanone (dioxanone), 1,3-dioxanone, carbonates, trimethylene carbonate, ethylene carbonate, propylene carbonate, 2-methyl-2-carboxylpropylene carbonate, fumarates, propylene fumarate, oxides, ethylene oxide, propylene oxide, anhydrides, orthoesters, DETOSU-1,6HD, DETOSU-t-CDM, ketals and acetals, wherein at least one monomer is L-lactic acid/L-lactide, D-lactic acid/D-lactide or D,L-lactic acid/D,L-lactide. In an embodiment, one of the monomers of the polylactide copolymer is L-lactic acid/L-lactide.

In certain embodiments, the polylactide copolymer is selected from the group consisting of poly(L-lactide-co-D-lactide), poly(L-lactide-co-D,L-lactide), poly(D-lactide-co-D,L-lactide), poly(lactide-co-glycolide), poly(lactide-co-ε- caprolactone), poly(lactide-co-dioxanone), poly(lactide-co-trimethylene carbonate), poly(lactide-co-ethylene carbonate), poly(lactide-co-propylene carbonate), poly(lactide-co-2-methyl-2-carboxyl-propylene carbonate), poly(lactide-co-ethylene glycol), poly(lactide-co-glycolide-co-ε-caprolactone), poly(lactide-co-glycolide-co-trimethylene carbonate), and poly(lactide-co-ε-caprolactone-co-trimethylene carbonate), wherein lactide includes L-lactide, D-lactide and D,L-lactide. In an embodiment, the polylactide copolymer is poly(lactide-co-ε-caprolactone). In another embodiment, the polylactide copolymer is poly(lactide-co-glycolide).

The biodegradable implantable device comprising a body comprised of a biodegradable polylactide copolymer can have any features of a biodegradable implantable device comprising a polymeric material or body comprised of a biodegradable polymer (including homopolymer or copolymer) described herein.

In certain embodiments, the biodegradable polymer is selected from the group consisting of polyesters, poly(α-hydroxyacids), polylactide, polyglycolide, poly(ε-caprolactone), polydioxanone, poly(hydroxyalkanoates), poly(hydroxypropionates), poly(3-hydroxypropionate), poly(hydroxybutyrates), poly(3-hydroxybutyrate), poly(4-hydroxybutyrate), poly(hydroxypentanoates), poly(3-hydroxypentanoate), poly(hydroxyvalerates), poly(3-hydroxyvalerate), poly(4-hydroxyvalerate), poly(hydroxyoctanoates), poly(3-hydroxyoctanoate), polysalicylate/polysalicylic acid, polycarbonates, poly(trimethylene carbonate), poly(ethylene carbonate), poly(propylene carbonate), tyrosine-derived polycarbonates, L-tyrosine-derived polycarbonates, polyiminocarbonates, poly(DTH iminocarbonate), poly(bisphenol A iminocarbonate), poly(amino acids), poly(ethyl glutamate), poly(propylene fumarate), polyanhydrides, polyorthoesters, poly(DETOSU-1,6HD), poly(DETOSU-t-CDM), polyurethanes, polyphosphazenes, polyamides, nylons, nylon 12, polyoxyethylated castor oil, poly(ethylene glycol), polyvinylpyrrolidone, poly(L-lactide-co-D-lactide), poly(L-lactide-co-D,L-lactide), poly(D-lactide-co-D,L-lactide), poly(lactide-co-glycolide), poly(lactide-co-ε-caprolactone), poly(glycolide-co-ε-caprolactone), poly(lactide-co-dioxanone), poly(glycolide-co-dioxanone), poly(lactide-co-trimethylene carbonate), poly(glycolide-co-trimethylene carbonate), poly(lactide-co-ethylene carbonate), poly(glycolide-co-ethylene carbonate), poly(lactide-co-propylene carbonate), poly(glycolide-co-propylene carbonate), poly(lactide-co-2-methyl-2-carboxyl-propylene carbonate), poly(glycolide-co-2-methyl-2-carboxyl-propylene carbonate), poly(lactide-co-hydroxybutyrate), poly(lactide-co-3-hydroxybutyrate), poly(lactide-co-4-hydroxybutyrate), poly(glycolide-co-hydroxybutyrate), poly(glycolide-co-3-hydroxybutyrate), poly(glycolide-co-4-hydroxybutyrate), poly(lactide-co-hydroxyvalerate), poly(lactide-co-3-hydroxyvalerate), poly(lactide-co-4-hydroxyvalerate), poly(glycolide-co-hydroxyvalerate), poly(glycolide-co-3-hydroxyvalerate), poly(glycolide-co-4-hydroxyvalerate), poly(3-hydroxybutyrate-co-4-hydroxybutyrate), poly(hydroxybutyrate-co-hydroxyvalerate), poly(3-hydroxybutyrate-co-3-hydroxyvalerate), poly(3-hydroxybutyrate-co-4-hydroxyvalerate), poly(4-hydroxybutyrate-co-3-hydroxyvalerate), poly(4-hydroxybutyrate-co-4-hydroxyvalerate), poly(ε-caprolactone-co-fumarate), poly(ε-caprolactone-co-propylene fumarate), poly(ester-co-ether), poly(lactide-co-ethylene glycol), poly(glycolide-co-ethylene glycol), poly(ε-caprolactone-co-ethylene glycol), poly(ester-co-amide), poly(DETOSU-1,6HD-co-DETOSU-t-CDM), poly(lactide-co-cellulose ester), poly(lactide-co-cellulose acetate), poly(lactide-co-cellulose butyrate), poly(lactide-co-cellulose acetate butyrate), poly(lactide-co-cellulose propionate), poly(glycolide-co-cellulose ester), poly(glycolide-co-cellulose acetate), poly(glycolide-co-cellulose butyrate), poly(glycolide-co-cellulose acetate butyrate), poly(glycolide-co-cellulose propionate), poly(lactide-co-glycolide-co-ε-caprolactone), poly(lactide-co-glycolide-co-trimethylene carbonate), poly(lactide-co-ε-caprolactone-co-trimethylene carbonate), poly(glycolide-co-ε-caprolactone-co-trimethylene carbonate), poly(3-hydroxybutyrate-co-3-hydroxyvalerate-co-4-hydroxybutyrate), poly(3-hydroxybutyrate-co-4-hydroxyvalerate-co-4-hydroxybutyrate), collagen, casein, polysaccharides, cellulose, cellulose esters, cellulose acetate, cellulose butyrate, cellulose acetate butyrate, cellulose propionate, chitin, chitosan, dextran, starch, modified starch, and combination thereof, and copolymers thereof, and wherein lactide includes L-lactide, D-lactide and D,L-lactide. In an embodiment, the biodegradable polymer is poly(lactide-co-ε-caprolactone). In another embodiment, the biodegradable polymer is poly(lactide-co-glycolide). In another embodiment, the biodegradable polymer is poly(lactide-co-ε-caprolactone), copolymerized or blended/mixed with poly-glycolide. In another embodiment, the biodegradable polymer is poly(lactide-co-ε-caprolactone), copolymerized or blended/mixed with poly-glycolide, and/or carbon nano tubes or fibers. In another embodiment, the biodegradable polymer is poly(lactide-co-ε-caprolactone-co-glycolide) blended, or mixed, with carbon nano fibers or nanotubes. In yet another embodiment, the polymer is at least one of poly lactide, poly glycolide, and poly ε-caprolactone, co-polymerized or mixed with one or more of the other two, and/or blended with carbon nano tubes or fibers. One skilled in the art can appreciate that one or more of the embodiments above or part of the embodiments above can be combined.

The partially self-expandable biodegradable stent comprising a body comprised of a biodegradable polymer can have any features of a biodegradable stent comprising a body comprised of or comprising a biodegradable polymer (including homopolymer or copolymer) described herein.

Additional embodiments of the disclosure relate to a biodegradable stent comprising a body comprised of a material, wherein the material comprises a biodegradable copolymer of L-lactide and ε-caprolactone in a weight or molar ratio of about 70:30 to about 99.9:0.1. In certain embodiments, the biodegradable copolymer comprises L-lactide and ε-caprolactone in a weight or molar ratio of about 90:10. In certain embodiments, the biodegradable copolymer comprises L-lactide and ε-caprolactone in a weight or molar ratio of about 99.9:0.1 to about 70:30, or about 99:1 to about 80:20, or about 95:5 to about 90:10, or about 95:5, or about 90:10, or about 85:15, or about 80:20, or about 75:25, or about 70:30. In certain embodiments, the biodegradable copolymer comprises L-lactide and ε-caprolactone in a weight or molar ratio of about 99.9:0.1 to about 70:30, or about 99:1 to about 80:20, or about 95:5 to about 90:10, or about 95:5, or about 90:10, or about 85:15, or about 80:20, or about 75:25, or about 70:30 wherein the polymer (copolymer (or three polymer or more) are substantially amorphous, or semicrystalline, or has orientation, or does not have orientation, or is randomly oriented, or has reduced internal stresses, or has low or no phase separation, or has porosity. In some embodiments, the PLLA/polycaprolactone (PCL) has at least one or more additional polymer or copolymer selected from polyglycolic acid (PGA), or/and carbon nanotube or fibers. This additional agent can enhance strength, ductility, or reduce recoil. The biodegradable stent comprising a body comprised of a biodegradable poly(L-lactide-co-ε-caprolactone) copolymer or polymer blend or mixture can have any features of a biodegradable stent comprising a body comprised of a biodegradable polymer (including homopolymer or copolymer) described herein.

Non-limiting examples of a biodegradable polymer that can be used to form a biodegradable endoprosthesis or a tubular body thereof, or a polymeric article from which the endoprosthesis or tubular body is formed, include polylactide and copolymers thereof, poly(D,L-lactide), poly(lactide-co-glycolide), poly(lactide-co-ε-caprolactone), poly(lactide-co-trimethylene carbonate), poly(L-lactide-co-trimethylene carbonate), polytrimethylene carbonate and copolymers thereof, polyhydroxybutyrates and copolymers thereof, polyhydroxyvalerates and copolymers thereof, polyorthoesters and copolymers thereof, polyanhydrides and copolymers thereof, and polyiminocarbonates and copolymers thereof, wherein lactide includes L-lactide, D-lactide and D,L-lactide.

In certain embodiments, the biodegradable endoprosthesis, tubular body or polymeric article is formed from a poly(L-lactide-co-glycolide) copolymer comprising about 80% to about 90% L-lactide and about 10% to about 20% glycolide by weight or molarity. In one embodiment, the poly(L-lactide-co-glycolide) copolymer comprises about 85% L-lactide and about 15% glycolide by weight or molarity. In further embodiments, the biodegradable endoprosthesis, tubular body or polymeric article is formed from a poly(L-lactide-co-ε-caprolactone) copolymer comprising about 85% to about 95% L-lactide and about 5% to about 15% ε-caprolactone by weight or molarity. In one embodiment, the poly(L-lactide-co-ε-caprolactone) copolymer comprises about 90% L-lactide and about 10% ε-caprolactone by weight or molarity.

In some embodiments, the biodegradable copolymer or polymer comprising the body of the device is derived or formed from, or is comprised of, one, two or more different monomers or polymers selected from the group consisting of α-hydroxyacids, L-lactic acid/L-lactide, D-lactic acid/D-lactide, D,L-lactic acid/D,L-lactide, glycolic acid/glycolide, hydroxyalkanoates, hydroxybutyrates, 3-hydroxybutyrate, 4-hydroxybutyrate, hydroxyvalerates, 3-hydroxyvalerate, 4-hydroxyvalerate, hydroxybenzoic acids, salicylic acid, lactones, ε-caprolactone, δ-valerolactone, β-butyrolactone, β-propiolactone, 1,4-dioxanone (dioxanone), 1,3-dioxanone, carbonates, trimethylene carbonate, ethylene carbonate, propylene carbonate, 2-methyl-2-carboxylpropylene carbonate, tyrosine carbonates, L-tyrosine carbonate, fumarates, propylene fumarate, cellulose esters, cellulose acetate, cellulose butyrate, cellulose acetate butyrate, cellulose propionate, oxides, ethylene oxide, propylene oxide, anhydrides, orthoesters, DETOSU-1,6HD, DETOSU-t-CDM, ketals, and acetals. In certain embodiments, one of the monomers or polymers of the biodegradable copolymer or polymer is L-lactic acid/L-lactide. Poly(DETOSU-1,6HD) and poly(DETOSU-t-CDM) are polyorthoesters based on the diketene acetal 3,9-diethylidene-2,4,8,10-tetraoxaspiro[5.5]undecane (DETOSU) and 1,6-hexanediol (1,6-HD) or trans-cyclohexanedimethanol (t-CDM).

In certain embodiments, the biodegradable copolymer or polymer is selected from the group consisting of poly(L-lactide-co-D-lactide), poly(L-lactide-co-D,L-lactide), poly(D-lactide-co-D,L-lactide), poly(lactide-co-glycolide), poly(lactide-co-ε-caprolactone), poly(glycolide-co-ε-caprolactone), poly(lactide-co-dioxanone), poly(glycolide-co-dioxanone), poly(lactide-co-trimethylene carbonate), poly(glycolide-co-trimethylene carbonate), poly(lactide-co-ethylene carbonate), poly(glycolide-co-ethylene carbonate), poly(lactide-co-propylene carbonate), poly(glycolide-co-propylene carbonate), poly(lactide-co-2-methyl-2-carboxylpropylene carbonate), poly(glycolide-co-2-methyl-2-carboxyl-propylene carbonate), poly(lactide-co-hydroxybutyrate), poly(lactide-co-3-hydroxybutyrate), poly(lactide-co-4-hydroxybutyrate), poly(glycolide-co-hydroxybutyrate), poly(glycolide-co-3-hydroxybutyrate), poly(glycolide-co-4-hydroxybutyrate), poly(lactide-co-hydroxyvalerate), poly(lactide-co-3-hydroxyvalerate), poly(lactide-co-4-hydroxyvalerate), poly(glycolide-co-hydroxyvalerate), poly(glycolide-co-3-hydroxyvalerate), poly(glycolide-co-4-hydroxyvalerate), poly(3-hydroxybutyrate-co-4-hydroxybutyrate), poly(hydroxybutyrate-co-hydroxyvalerate), poly(3-hydroxybutyrate-co-3-hydroxyvalerate), poly(3-hydroxybutyrate-co-4-hydroxyvalerate), poly(4-hydroxybutyrate-co-3-hydroxyvalerate), poly(4-hydroxybutyrate-co-4-hydroxyvalerate), poly(ε-caprolactone-co-fumarate), poly(ε-caprolactone-co-propylene fumarate), poly(lactide-co-ethylene glycol), poly(glycolide-co-ethylene glycol), poly(ε-caprolactone-co-ethylene glycol), poly(DETOSU-1,6-HD-co-DETOSU-t-CDM), poly(lactide-co-cellulose ester), poly(lactide-co-cellulose acetate), poly(lactide-co-cellulose butyrate), poly(lactide-co-cellulose acetate butyrate), poly(lactide-co-cellulose propionate), poly(glycolide-co-cellulose ester), poly(glycolide-co-cellulose acetate), poly(glycolide-co-cellulose butyrate), poly(glycolide-co-cellulose acetate butyrate), poly(glycolide-co-cellulose propionate), poly(lactide-co-glycolide-co-ε-caprolactone), poly(lactide-co-glycolide-co-trimethylene carbonate), poly(lactide-co-ε-caprolactone-co-trimethylene carbonate), poly(glycolide-co-ε-caprolactone-co-trimethylene carbonate), poly(3-hydroxybutyrate-co-3-hydroxyvalerate-co-4-hydroxybutyrate), and poly(3-hydroxybutyrate-co-4-hydroxyvalerate-co-4-hydroxybutyrate), wherein lactide includes L-lactide, D-lactide and D,L-lactide.

In some embodiments, the biodegradable copolymer is a polylactide copolymer, wherein lactide includes L-lactide, D-lactide and D,L-lactide. In certain embodiments, the biodegradable copolymer is a poly(L-lactide) copolymer. The poly(L-lactide) copolymer can comprise L-lactide and one or more other monomers selected from any of the monomers described herein. In certain embodiments, the biodegradable copolymer is selected from the group consisting of poly(L-lactide-co-D-lactide), poly(L-lactide-co-D,L-lactide), poly(L-lactide-co-glycolide), poly(L-lactide-co-ε-caprolactone), poly(L-lactide-co-dioxanone), poly(L-lactide-co-3-hydroxybutyrate), poly(L-lactide-co-4-hydroxybutyrate), poly(L-lactide-co-4-hydroxyvalerate), poly(L-lactide-co-ethylene carbonate), poly(L-lactide-co-propylene carbonate), poly(L-lactide-co-trimethylene carbonate), and poly(L-lactide-co-cellulose acetate butyrate).

In some embodiments, the biodegradable poly(L-lactide) copolymer or polymer comprises L-lactide or D-Lactide or DL-Lactide in at least about 70%, 75%, 80%, 85%, 90%, 95%, 96%, 97%, 98%, 99%, 99.5% or 99.9% by weight or molarity, and each of the one or more other monomers or polymers in no more than about 0.1%, 0.5%, 1%, 1.5%, 2%, 2.5%, 3%, 3.5%, 4%, 4.5%, 5%, 6%, 7%, 8%, 9%, 10%, 15%, 20%, 25% or 30% by weight or molarity. In certain embodiments, the biodegradable poly(L-lactide) copolymer or polymer comprises L-lactide or D-Lactide or DL-Lactide in at least about 90%, 95% or 99% by weight or molarity, and each of the one or more other monomers or polymers in no more than about 1%, 5% or 10% by weight or molarity.

In further embodiments, the biodegradable copolymer is poly(lactide-co-ε-caprolactone). In certain embodiments, the biodegradable copolymer is a block or random copolymer of L-Lactide or D-Lactide or DL-Lactide and ε-caprolactone in a weight or molar ratio of about 70:30 to about 99.9:0.1, or about 80:20 to about 99:1, or about 85:15 to about 99:1, or about 85:15 to about 95:5, or about 87:13 to about 93:7, or about 90:10. In an embodiment, the biodegradable copolymer is a random copolymer of L-lactide or D-Lactide or DL-Lactide and ε-caprolactone in a weight or molar ratio of about 90:10. In an embodiment, the biodegradable polymer is a blend or mixture of L-lactide or D-Lactide or DL-Lactide and ε-caprolactone in a weight or molar ratio of about 70:30 to about 99.9:0.1.

In other embodiments, the biodegradable copolymer is poly(lactide-co-glycolide). In certain embodiments, the biodegradable copolymer is a block or random copolymer of L-Lactide or D-Lactide or DL-Lactide and glycolide in a weight or molar ratio of about 70:30 to about 99:1, or about 75:25 to about 95:5, or about 80:20 to about 90:10, or about 82:18 to about 88:12, or about 85:15. In an embodiment, the biodegradable copolymer is a random copolymer of L-lactide or D-Lactide or DL-Lactide and glycolide in a weight or molar ratio of about 85:15.

In additional embodiments, the body of the device, or the material comprising or comprising the body of the device, comprises the biodegradable polymer or copolymer, and a second biodegradable polymer or a non-degradable polymer or both. The non-degradable polymer can be any non-degradable polymer described herein. The amount of the non-degradable polymer used can be selected to provide the device with desired characteristics while not extending the degradation time of the device beyond the desired time period. In certain embodiments, the non degradable polymer is selected from the group consisting of polyacrylates, polymethacrylates, poly(n-butyl methacrylate), poly(hydroxyethylmethacrylate), polyamides, nylons, nylon 12, poly(ethylene glycol), polydimethylsiloxane, polyvinylpyrrolidone, phosphorylcholine-containing polymers, poly(2-methacryloyloxyethylphosphorylcholine), poly(2-methacryloyloxyethylphosphorylcholine-co-butyl methacrylate), and polymers or copolymers thereof.

The second biodegradable polymer can be any biodegradable polymer or copolymer described herein. In some embodiments, the second biodegradable polymer is selected from the group consisting of polyesters, poly(α-hydroxyacids), polylactide including L-Lactides, D-Lactide, and DL-Lactide, polyglycolide, poly(ε-caprolactone), polydioxanone, poly(hydroxyalkanoates), poly(hydroxypropionates), poly(3-hydroxypropionate), poly(hydroxybutyrates), poly(3-hydroxybutyrate), poly(4-hydroxybutyrate), poly(hydroxypentanoates), poly(3-hydroxypentanoate), poly(hydroxyvalerates), poly(3-hydroxyvalerate), poly(4-hydroxyvalerate), poly(hydroxyoctanoates), poly(3-hydroxyoctanoate), polysalicylate/polysalicylic acid, polycarbonates, poly(trimethylene carbonate), poly(ethylene carbonate), poly(propylene carbonate), tyrosine-derived polycarbonates, L-tyrosine-derived polycarbonates, polyiminocarbonates, poly(DTH iminocarbonate), poly(bisphenol A iminocarbonate), poly(amino acids), poly(ethyl glutamate), poly(propylene fumarate), polyanhydrides, polyorthoesters, poly(DETOSU-1,6HD), poly(DETOSU-t-CDM), polyurethanes, polyphosphazenes, polyamides, nylons, nylon 12, polyoxyethylated castor oil, poly(ethylene glycol), polyvinylpyrrolidone, poly(L-lactide-co-D-lactide), poly(L-lactide-co-D,L-lactide), poly(D-lactide-co-D,L-lactide), poly(lactide-co-glycolide), poly(lactide-co-ε-caprolactone), poly(glycolide-co-ε-caprolactone), poly(lactide-co-dioxanone), poly(glycolide-co-dioxanone), poly(lactide-co-trimethylene carbonate), poly(glycolide-co-trimethylene carbonate), poly(lactide-co-ethylene carbonate), poly(glycolide-co-ethylene carbonate), poly(lactide-co-propylene carbonate), poly(glycolide-co-propylene carbonate), poly(lactide-co-2-methyl-2-carboxyl-propylene carbonate), poly(glycolide-co-2-methyl-2-carboxyl-propylene carbonate), poly(lactide-co-hydroxybutyrate), poly(lactide-co-3-hydroxybutyrate), poly(lactide-co-4-hydroxybutyrate), poly(glycolide-co-hydroxybutyrate), poly(glycolide-co-3-hydroxybutyrate), poly(glycolide-co-4-hydroxybutyrate), poly(lactide-co-hydroxyvalerate), poly(lactide-co-3-hydroxyvalerate), poly(lactide-co-4-hydroxyvalerate), poly(glycolide-co-hydroxyvalerate), poly(glycolide-co-3-hydroxyvalerate), poly(glycolide-co-4-hydroxyvalerate), poly(3-hydroxybutyrate-co-4-hydroxybutyrate), poly(hydroxybutyrate-co-hydroxyvalerate), poly(3-hydroxybutyrate-co-3-hydroxyvalerate), poly(3-hydroxybutyrate-co-4-hydroxyvalerate), poly(4-hydroxybutyrate-co-3-hydroxyvalerate), poly(4-hydroxybutyrate-co-4-hydroxyvalerate), poly(ε-caprolactone-co-fumarate), poly(ε-caprolactone-co-propylene fumarate), poly(ester-co-ether), poly(lactide-co-ethylene glycol), poly(glycolide-co-ethylene glycol), poly(ε-caprolactone-co-ethylene glycol), poly(ester-co-amide), poly(DETOSU-1,6HD-co-DETOSU-t-CDM), poly(lactide-co-cellulose ester), poly(lactide-co-cellulose acetate), poly(lactide-co-cellulose butyrate), poly(lactide-co-cellulose acetate butyrate), poly(lactide-co-cellulose propionate), poly(glycolide-co-cellulose ester), poly(glycolide-co-cellulose acetate), poly(glycolide-co-cellulose butyrate), poly(glycolide-co-cellulose acetate butyrate), poly(glycolide-co-cellulose propionate), poly(lactide-co-glycolide-co-ε-caprolactone), poly(lactide-co-glycolide-co-trimethylene carbonate), poly(lactide-co-ε-caprolactone-co-trimethylene carbonate), poly(glycolide-co-ε-caprolactone-co-trimethylene carbonate), poly(3-hydroxybutyrate-co-3-hydroxyvalerate-co-4-hydroxybutyrate), poly(3-hydroxybutyrate-co-4-hydroxyvalerate-co-4-hydroxybutyrate), collagen, casein, polysaccharides, cellulose, cellulose esters, cellulose acetate, cellulose butyrate, cellulose acetate butyrate, cellulose propionate, chitin, chitosan, dextran, starch, modified starch, and copolymers thereof, wherein lactide includes L-lactide, D-lactide and D,L-lactide. Poly(DTH iminocarbonate) is a polymer of the desaminotyrosyl-tyrosine hexyl ester (DTH) iminocarbonate. In some embodiments, the second biodegradable polymer is a polylactide homopolymer or copolymer, wherein lactide includes L-lactide, D-lactide and D,L-lactide. In certain embodiments, the second biodegradable polymer is a poly(L-lactide) homopolymer or copolymer.

In certain embodiments, the second biodegradable polymer is selected from the group consisting of poly(L-lactide), poly(D-lactide), poly(D,L-lactide), polyglycolide, poly(ε-caprolactone), polydioxanone, poly(L-lactide-co-glycolide), poly(D-lactide-co-glycolide), poly(D,L-lactide-co-glycolide), poly(L-lactide-co-ε-caprolactone), poly(D-lactide-co-ε-caprolactone), poly(D,L-lactide-co-ε-caprolactone), poly(glycolide-co-ε-caprolactone), poly(L-lactide-co-trimethylene carbonate), poly(D-lactide-co-trimethylene carbonate), poly(D,L-lactide-co-trimethylene carbonate), poly(glycolide-co-trimethylene carbonate), poly(DTH iminocarbonate), poly(bisphenol A iminocarbonate), poly(DETOSU-1,6HD-co-DETOSU-t-CDM), and a combination thereof.

In some embodiments, the body of the device, or the material comprising the body of the device, comprises a blend of the biodegradable copolymer, and a second biodegradable polymer or a non-degradable polymer or both. In certain embodiments, the body of the device, or the material comprising the body of the device, comprises a blend of a block or random copolymer of L-lactide or D-Lactide or DL-Lactide and ε-caprolactone in a weight or molar ratio of about 70:30 to about 99.9:0.1 and a different block or random copolymer of L-lactide or D-Lactide or DL-Lactide and ε-caprolactone in a weight or molar ratio of about 70:30 to about 99.9:0.1; or a blend of a block or random copolymer of L-lactide or D-Lactide or DL-Lactide and ε-caprolactone in a weight or molar ratio of about 85:15 to about 99.9:0.1 and a different block or random copolymer of L-lactide or D-Lactide or DL-Lactide and ε-caprolactone in a weight or molar ratio of about 85:15 to about 99.9:0.1; or a blend of a block or random copolymer of L-lactide or D-Lactide or DL-Lactide and ε-caprolactone in a weight or molar ratio of about 70:30 to about 90:10 and a different block or random copolymer of L-lactide or D-Lactide or DL-Lactide and ε-caprolactone in a weight or molar ratio of about 90:10 to about 99:1; or a blend of a block or random copolymer of L-lactide or D-Lactide or DL-Lactide and ε-caprolactone in a weight or molar ratio of 85:15 to about 90:10 and a different block or random copolymer of L-lactide or D-Lactide or DL-Lactide and ε-caprolactone in a weight or molar ratio of about 90:10 to about 95:5; or a blend of about 85:15 block or random poly(lactide-co-ε-caprolactone) such as poly(L-lactide-co-ε-caprolactone) and about 95:5 block or random poly(lactide-co-ε-caprolactone) such as poly(L-lactide-co-ε-caprolactone); or a blend of a block or random copolymer of L-lactide or D-Lactide or DL-Lactide and ε-caprolactone in a weight or molar ratio of about 85:15 to about 99:1, with about 85:15 block or random poly(lactide-co-ε-caprolactone) such as poly(L-lactide-co-ε-caprolactone), or about 90:10 block or random poly(lactide-co-ε-caprolactone) such as poly(L-lactide-co-ε-caprolactone), or about 95:5 block or random poly(lactide-co-ε-caprolactone) such as poly(L-lactide-co-ε-caprolactone), or poly(ε-caprolactone), or polylactide, or polyglycolide, or polydioxanone, or poly(hydroxybutyrate), or poly(hydroxyvalerate), or poly(trimethylene carbonate), or poly(ethylene carbonate), or poly(propylene carbonate), or poly(DTH iminocarbonate), or poly(bisphenol A iminocarbonate), or poly(lactide-co-glycolide), or poly(lactide-co-trimethylene carbonate), or poly(glycolide-co-trimethylene carbonate), or poly(glycolide-co-ε-caprolactone), or poly(DETOSU-1,6HD-co-DETOSU-t-CDM), or a combination thereof, wherein lactide includes L-lactide, D-lactide and D,L-lactide.

In further embodiments, the body of the device comprises a first layer containing the biodegradable copolymer or polymer, and one, two, three, four or more additional layers, wherein each additional layer contains a biodegradable polymer or a corrodible metal or metal alloy, and wherein the first layer and the additional layer(s) can be in any order. The biodegradable polymer that can compose any additional layer(s) can independently be any biodegradable polymer described herein. The first layer containing the biodegradable copolymer and any additional layer(s) containing a biodegradable polymer can each optionally and independently contain an additional biodegradable polymer or a non-degradable polymer or both. The additional biodegradable polymer that can optionally compose the first layer and any additional layer(s) can independently be any biodegradable polymer described herein, and the non-degradable polymer that can optionally compose the first layer and any additional layer(s) can independently be any non-degradable polymer described herein.

Non-limiting examples of corrodible metals and metal alloys that can independently comprise any additional layer(s) of the body of the device include cast ductile irons (e.g., 80-55-06 grade cast ductile iron), corrodible steels (e.g., AISI 1010 steel, AISI 1015 steel, AISI 1430 steel, AISI 5140 steel and AISI 8620 steel), melt-fusible metal alloys, bismuth-tin alloys (e.g., 40% bismuth-60% tin and 58% bismuth-42% tin), bismuth-tin-indium alloys, magnesium alloys, tungsten alloys, zinc alloys, shape-memory metal alloys, and superelastic metal alloys.

If the body of the device contains multiple layers, each layer can be selected to have certain characteristics based on its composition so that the device has desired overall characteristics. For example, the material comprising a particular layer can be selected to have certain characteristics (e.g., strength, toughness, ductility, degradation rate, etc.) by containing certain biodegradable polymer(s), and optionally certain nondegradable polymer(s) and certain additive(s), and certain amount thereof, where the characteristics of that material can be substantially similar to or different from the characteristics of the material comprising each of the other layer(s). As a non-limiting example, the body of the device can comprise a middle one or more layer(s) containing a high-strength material, e.g., a high-strength polymer, such as poly(L-lactide) or a copolymer thereof] and inner and outer layer(s) containing a ductile material, e.g., a ductile polymer, such as poly(ε-caprolactone), such that the device possesses sufficient strength, flexibility and toughness.

In some embodiments, the biodegradable copolymer, optional second biodegradable polymer, optional additional biodegradable polymer(s), or optional non-degradable polymer(s), or any combination thereof, comprising the body of the device are crosslinked. In certain embodiments, the polymer(s) are crosslinked by exposure to radiation (e.g., ultraviolet (UV) light, or ionizing radiation, such as e-beam or gamma radiation), exposure to heat, use of a degradable or non-degradable crosslinker, or use of a crosslinking agent and an initiator.

In certain embodiments, the degradable or non-degradable crosslinker is selected from the group consisting of diisocyanates, methylene diphenyl diisocyanates, tetramethylenediisocyanate, pentamethylenediisocyanate, hexamethylenediisocyanate, disuccinimidyl glutarate, disuccinimidyl suberate, bis(succinimidoxycarbonyl)poly(ethylene glycol), bis(2-[succinimidoxycarbonyloxy]ethyl)sulfone, tris(2-succinimidoxycarbonylethyl)-amine, multi-armed poly(ethylene glycol), dipentaerythritol, tripentaerythritol, pentaerythritol ethoxylate, pentaerythritol propoxylate, methyl silyl ether crosslinkers, ethyl silyl ether crosslinkers, propyl silyl ether crosslinkers, isopropyl silyl ether crosslinkers, butyl silyl ether crosslinkers, and tert-butyl silyl ether crosslinkers.

In some embodiments, the crosslinking agent is selected from the group consisting of maleic anhydride, 1,2-bis(maleimido)ethane, 1,4-bis(maleimido)butane, 1,6-bis(maleimido)hexane, 1,8-bis(maleimido)diethylene glycol, and tris(2-maleimidoethyl)amine. In certain embodiments, the initiator is selected from the group consisting of organic peroxides, di-tert-butyl peroxide, dicumyl peroxide, benzoyl peroxide, methyl ethyl ketone peroxide, azo compounds, 1,1'-azobis(cyclohexanecarbonitrile), and 1,1'-azobis(isobutyronitrile).

Further embodiments of the disclosure relate to a biodegradable implantable device comprising a body comprising a material which comprises a blend of polymers, wherein the blend includes a biodegradable polymer, and an additional biodegradable polymer or a non-degradable polymer or both. The biodegradable polymer and the additional biodegradable polymer can be any biodegradable polymer described herein, and the non-degradable polymer can be any non-degradable polymer described herein. The amount of any non-degradable polymer utilized can be selected to impart desired characteristics (e.g., strength) to the material or the device without prolonging the degradation time of the device over a certain length of time. Embodiments herein relating to a biodegradable implantable device comprising a polymeric material or body comprised of a material which comprises a biodegradable copolymer also relate to a biodegradable implantable device comprising a body comprised of a material which comprises a blend of polymers, where a blend of polymers can substitute for a biodegradable copolymer in such embodiments.

In some embodiments, the biodegradable implantable device comprises polymeric material or a body comprising a material which comprises Poly(Lactide) such as poly(L-lactide) or a poly(L-lactide) copolymer, and an additional biodegradable polymer or a non-degradable polymer or both. The poly(L-lactide) copolymer can be any poly(L-lactide) copolymer described herein. In certain embodiments, the material comprising the body of the device comprises poly(L-lactide) and poly(ε-caprolactone). In some embodiments, the weight percent of poly(L-lactide) or the poly(L-lactide) copolymer in the material comprising the body of the device is at least about 70%, 75%, 80%, 85%, 90%, 95%, 96%, 97%, 98%, 99%, 99.5% or 99.9%, and the weight percent of each of the additional biodegradable polymer and/or the non-degradable polymer is no more than about 0.1%, 0.5%, 1%, 1.5%, 2%, 2.5%, 3%, 3.5%, 4%, 4.5%, 5%, 6%, 7%, 8%, 9%, 10%, 15%, 20%, 25% or 30%. In certain embodiments, the weight percent of poly(L-lactide) or the poly(L-lactide) copolymer in the material comprising the body of the device is at least about 90%, 95% or 99%, and the weight percent of each of the additional biodegradable polymer and/or the non-degradable polymer is no more than about 1%, 5% or 10%.

Examples of biodegradable polymers that can be used to form biodegradable endoprostheses (e.g., stents) include without limitation polylactide, poly(trimethylene carbonate), poly(lactide-co-glycolide), poly(lactide-co-ε-caprolactone), poly(lactide-co-trimethylene carbonate), polyhydroxybutyrates, polyhydroxyvalerates, polyorthoesters, polyanhydrides, polyiminocarbonates, and copolymers, blends and combinations thereof, wherein lactide includes L-lactide, D-lactide and D,L-lactide. In some embodiments, the polymeric material or the body of a biodegradable endoprosthesis is comprises a polylactide homopolymer or copolymer, wherein lactide includes L-lactide, D-lactide and D,L-lactide. In certain embodiments, the body of the biodegradable endoprosthesis comprises a poly(L-lactide) homopolymer or copolymer.

In some embodiments, a biodegradable endoprosthesis comprises poly(L-lactide-co-glycolide) copolymer or polymer comprising about 80% to about 90% L-lactide and about 10% to about 20% glycolide by weight or molarity. In an embodiment, the poly(L-lactide-co-glycolide) copolymer or polymer comprises about 85% L-lactide and about 15% glycolide by weight or molarity. In further embodiments, a biodegradable endoprosthesis is formed from a poly(L-lactide-co-ε-caprolactone) copolymer or polymer comprising about 85% to about 95% L-lactide and about 5% to about 15% ε-caprolactone by weight or molarity. In an embodiment, the poly(L-lactide-co-ε-caprolactone) copolymer or polymer comprises about 90% L-lactide and about 10% ε-caprolactone by weight or molarity.

Additional examples of biodegradable polymers that can be used to form biodegradable endoprostheses (e.g., stents) include without limitation polyesters, polyanhydrides, polyalkylene carbonates, polyiminocarbonates, polyorthoesters, poly(ether esters), polyamides, poly(ester amides), polyamines, poly(ester amines), polyurethanes, poly(ester urethanes), polyureas, poly(ethylene imines), polyphosphazenes, polyphosphates, polyphosphonates, polysulfonates, polysulfonamides, polyethers, polyacrylic acids, polycyanoacrylates, polyvinylacetate, polylactide, polyglycolide, poly(malic acid), poly(L-lactic acid-co-D,L-lactic acid), poly(lactide-co-glycolide), poly(ε-caprolactone), polydioxanone, poly(trimethylene carbonate), poly(ethylene carbonate), poly(propylene carbonate), poly(ethylene carbonate-co-trimethylene carbonate), poly(lactic acid-co-trimethylene carbonate), poly(L-lactic acid-co-trimethylene carbonate-co-D,L-lactic acid), poly(glycolic acid-co-trimethylene carbonate), poly(ε-caprolactone-co-trimethylene carbonate), poly(glycolic acid-co-trimethylene carbonate-co-dioxanone), polyhydroxybutyrates, polyhydroxyvalerates, poly(3-hydroxybutyrate-co-hydroxyvalerate), poly(ethyl glutamate), modified poly(ethylene terephthalate), poly(butylene succinate), poly(butylene succinate adipate), poly(butylene succinate terephthalate), poly(butylene adipate-co-terephthalate), starch-based polymers, hyaluronic acid, regenerated cellulose, oxidized and non-oxidized regenerated cellulose copolymers, and copolymers, blends and combinations thereof, wherein lactic acid/lactide includes L-lactic acid/L-lactide, D-lactic acid/D-lactide and D,L-lactic acid/D,L-lactide.

The biodegradable polymers can be homopolymers, block copolymers, random copolymers, graft copolymers, polymers having functional groups (e.g., acidic, basic, hydrophilic, amino, hydroxyl, thiol, and/or carboxyl groups) along the backbone and/or at the ends, or a blend of two or more homopolymers and/or copolymers. In certain embodiments, the body of a biodegradable endoprosthesis is comprised of a random copolymer. In certain embodiments, the body of a biodegradable endoprosthesis is comprised of a biodegradable blend or mixture of polymers. In yet another embodiment, the biodegradable polymer comprises one or more polymers.

The polymeric material/article and/or the tubular body and/or the prosthesis or device can undergo any of a variety of modification or treatments (e.g., longitudinal extension, radial expansion, heating, cooling, quenching, pressurizing, vacuuming, exposure/incorporation of solvents, incorporation of additive, removal of additives or impurities, or exposure to radiation or carbon dioxide, or a combination thereof) designed to control or enhance characteristics (e.g., crystallinity, strength, toughness and degradation, Tg, recoil, shortening, expansion) of the article, the tubular body, and/or the prosthesis or device. The biodegradable implantable device comprising a polymeric polymer (including homopolymer or copolymer) described herein.

In certain embodiments, the modification comprises annealing/heating the biodegradable polymer (e.g., tubular body), wherein the biodegradable polymer or co-polymer or tubular body or stent is heated to a temperature at about Tg, or below Tg from about 1° C. to about 50° C. below Tg, or from about 5° C. to about 25° C. below Tg, or from about 10° C. to about 15° C. below Tg, or above the glass transition temperature ($T_g$) of the polymeric material and below the melting point ($T_m$) of the polymeric material for a period of time (e.g., about one minute to about three hours, at one temperature, or more than one temperature in controlled increments), or to a temperature to melt the material, or to a temperature that is of about 1° C.-70° C. above Tg, or about 5° C.-50° C. above Tg, or about 10° C.-40° C. above Tg, or about 15-30° C. above Tg; and then is slowly or quickly cooled or quenched to a lower temperature, e.g., to ambient temperature or lower, or to about −80° C. to about 30° C. or about −20° C. to about 25° C., or about 0° C. to about 25° C., in about 5 seconds to 2 hours or about a fraction of a second to 5 hours. Either before or after being annealed, the biodegradable polymer (tube) can be patterned into an endoprosthesis structure (e.g., a structure capable of radial contraction and expansion, such as a stent) by laser cutting or other method known in the art. Exemplary stent patterns are described in U.S. patent application Ser. No. 12/016,077, whose entire disclosure is incorporated herein by reference. Alternatively, the tubular body can be annealed both before and after being patterned into an endoprosthesis structure, or additional annealing steps can be performed so that the biodegradable polymer tube can be subjected to two, three, four or more annealing steps during the fabrication process. In other embodiments, the annealing temperature is about 50° C. below Tg to about Tg, or 35° C. below Tg to about Tg, or about 20° C. below Tg to about Tg, or about 10° C. below Tg to about Tg, Or about 20° C. to about 45° C. In a third embodiment, an annealing of the tubular body or the stent is performed post radiation or sterilization at a temperature ranging from about 20° C. to about 80° C., or from about 25° C. to about 50° C., or from about 25° C. to about 35° C.; for about 1 minute to about 7 days, or for about 10 minutes to about 3 days, or for about 1 hour to about 1 day.

A polymeric material can be made into an article (e.g., a tube) by spraying, dipping, extrusion, molding, injection molding, compression molding, 3-D printing or other process. The polymeric article or tube can be placed under vacuum (e.g., about −25 in. Hg or lower) and/or heated to remove any residual solvents and monomers, and then can be annealed and quenched to increase crystallinity (e.g., degree of crystallinity) of the polymeric material and/or reduce residual or internal stress in the polymeric article or tube. In some embodiments, the polymeric article or tube is placed under vacuum (e.g., at about 1 torr or below) and/or is heated at temperature ranging from below Tg, about Tg, or above Tg, or at elevated temperature (e.g., at about 40° C. or above) to remove any residual water, solvents and monomers, and is then annealed by being heated to a temperature below Tg, about Tg, or above the glass transition temperature ($T_g$) and below the melting temperature ($T_m$) of the polymeric material. In certain embodiments, the annealing temperature is at least about 1° C., 5° C., 10° C., 20° C., 30° C., 40° C. or 50° C. higher than the $T_g$, and is at least about 1° C., 5° C., 10° C., 20° C., 30° C., 40° C., 50° C., 75° C. or 100° C. lower than the $T_m$ of the polymeric material. In an embodiment, the annealing temperature is at least about 10° C. above the $T_g$ and is at least about 20° C. below the $T_m$ of the polymeric material. In certain embodiments, the annealing time is about 1 minute to about 10 days, or about 5 or 30 minutes to about 1 day, or about 15 or 30 minutes to about 12 hours, or about 15 or 30 minutes to about 6 hours, or about 15 or 30 minutes to about 3 hours, or about 1 hour to about 6 hours, or about 1 hour to about 3 hours, or about 1.5 hours to about 2.5 hours. In an embodiment, the annealing time is about 30 minutes to about 6 hours.

In some embodiments, the polymeric article undergoes one or more cycles of annealing involving heating and cooling, which can, e.g., increase the strength of the material (e.g., polymeric material), reduce residual or internal stress in the polymeric article, and/or control its crystallinity, including its degree of crystallinity and the size, number and distribution of crystals or crystalline regions in the material (e.g., polymeric material). In certain embodiments, the polymeric article is heated at a temperature equal to or greater than the glass transition temperature ($T_g$) of the first biodegradable polymer or the material (e.g., polymeric material) comprising the polymeric article for a period of time (e.g., at least about 0.1, 0.25, 0.5, 1, 4, 8, 12 or 24 hours), and then quickly or slowly cooled to a lower temperature (e.g., at least about 10° C., 20° C., 30° C., 40° C. or 50° C. below the $T_g$, or to ambient temperature or below) over a period of time (e.g., about 10 sec, 30 sec, 1 min, 10 min, 30 min, 1 hr, 4 hr, 8 hr or 12 hr). In further embodiments, the polymeric article is heated at a temperature above the $T_g$ and below the melting temperature ($T_m$) of the first biodegradable polymer or the material (e.g., polymeric material) comprising the polymeric article for a period of time (e.g., at least about 0.1, 0.25, 0.5, 1, 4, 8, 12 or 24 hours), and then cooled to a lower temperature (e.g., at least about 10° C., 20° C., 30° C., 40° C. or 50° C. below the $T_g$, or to ambient temperature or below) over a period of time (e.g., about 10 sec, 30 sec, 1 min, 10 min, 30 min, 1 hr, 4 hr, 8 hr or 12 hr). In certain embodiments, the polymeric article is heated at a temperature within the cold crystallization temperature range of the first biodegradable polymer or the material (e.g., polymeric material) comprising the polymeric article for a period of time (e.g., at least about 0.1, 0.25, 0.5, 1, 4, 8, 12 or 24 hours), and then cooled to a lower temperature (e.g., at least about 10° C., 20° C., 30° C., 40° C. or 50° C. below the $T_g$, or to ambient temperature or below) over a period of time (e.g., about 10 sec, 30 sec, 1 min, 10 min, 30 min, 1 hr, 4 hr, 8 hr or 12 hr). In still further embodiments, the polymeric article is heated at a temperature equal to or greater than the $T_m$ of the first biodegradable polymer or the material (e.g., polymeric material) comprising the polymeric article for a period of time (e.g., at least about 0.1, 0.25, 0.5, 1, 4, 8, 12 or 24 hours) to melt crystalline regions of the first biodegradable polymer or the material (e.g., polymeric material), and then cooled to a lower temperature (e.g., at least about 10° C., 20° C., 30° C., 40° C. or 50° C. below the $T_g$, or to ambient temperature or below) over a period of time (e.g., about 10 sec, 30 sec, 1 min, 10 min, 30 min, 1 hr, 4 hr, 8 hr or 12 hr).

In one preferred embodiment, the polymeric material is treated wherein the treatment comprises inducing or incorporation of monomers or polymers including co-polymers wherein the one or more monomers or polymers amounts in the polymeric material or the stent after treatment ranges from 0.001% to 10% by weight, preferably ranges from 0.1% to 5% by weight, more preferably ranges from 0.1% to 3% by weight. In one preferred embodiment, the polymeric material is treated wherein the treatment comprises inducing or incorporation of monomers or polymers wherein the one or more monomers or polymers amounts in the polymeric material or the stent after treatment ranges from 0.001% to 10% by weight, preferably ranges from 0.1% to 5% by weight, more preferably ranges from 0.1% to 3% by weight and wherein the stent at body temperature is capable to expand from a crimped configuration to a deployed diameter without fracture and have sufficient strength to support a body lumen. In one preferred embodiment, the polymeric material is treated wherein the treatment comprises inducing or incorporation of monomers or polymers wherein the one or more monomers or polymers amounts in the polymeric material or the stent after treatment ranges from 0.001% to 10% by weight, preferably ranges from 0.1% to 5% by weight, more preferably ranges from 0.1% to 3% by weight and wherein the one or more monomers or polymers substantially does not affect degradation of the stent (preferably does not affect degradation the stent. In other embodiments the monomer opr polymer accelerates degradation of the stent) and wherein the stent at body temperature is capable to expand from a crimped configuration to a deployed diameter without fracture and have sufficient strength to support a body lumen. In one preferred embodiment, the polymeric material is treated wherein the treatment comprises inducing or incorporation of monomer or polymer wherein the one or more monomer or polymer amounts in the polymeric material or the stent after treatment ranges from 0.001% to 10% by weight, preferably ranges from 0.1% to 5% by weight, more preferably ranges from 0.1% to 3% by weight and wherein the one or more monomer or polymer preferably substantially does not affect the stent degradation (preferably accelerates the stent degradation) and wherein the one or more monomer or polymer substantially remains in the stent in the ranges described above before deployment of the stent) wherein the stent at body temperature is capable to expand from a crimped configuration to a deployed diameter without fracture and have sufficient strength to support a body lumen. In another preferred embodiment, the one or more monomer or polymer amounts are greater than 0.1%, preferably greater than 1%, more preferably greater than 3%, more preferably greater than 5% by weight of the polymeric material. Examples of monomers or polymers include lactides, glycolides, caprolactones, lactides and glycolides, lactides and caprolactones to name a few. Incorporation of monomers can take place, for example by spraying as described herein, or inducing by radiation. Preferred Tg ranges from 20° C. to 50° C., more preferred from greater than 37° C. to less than 50° C. Preferred crystallinity ranges from 1% to 60%, preferably from 1% to 55%, more preferably from 1% to 45%, most preferably from 1% to 35%. The polymeric material preferably has an initial diameter, preferably 1-1.5 times the deployment diameter of the stent. In a preferred embodiment, the stent is capable of being crimped from an expanded diameter to a crimped diameter, and at body temperature is capable to expand from a crimped configuration to a deployed diameter without fracture and have sufficient strength to support a body lumen. Examples of polymeric material are materials comprising lactide, lactide and glycolide, or lactides and caprolactones, or a combination thereof.

In some embodiments, the diameter of the tubular body or the polymeric material or the stent may, at the time of treatment (e.g., treatment diameter), be optionally smaller or optionally greater than the deployment diameter, where the deployment diameter may include, for example, the diameter of the tubular body or the stent within a lumen. In some embodiments, the treatment diameter may be 1-2 times the deployment diameter, or 1-1.9 times the deployment diameter, or 1-1.8 times the deployment diameter, or 1-1.7 times the deployment diameter, or 1-1.6 times the deployment diameter, or 1-1.5 times the deployment diameter, or 1-1.4 times the deployment diameter, or 1-1.3 times the deployment diameter, or 1-1.2 times the deployment diameter, or 1-1.05 times the deployment diameter. In other embodiments, the treatment diameter may be 0.95-1 times the deployment diameter. In other embodiments, the treatment diameter may be 0.9-1 times the deployment diameter, or 0.8-1 times the deployment diameter, or 0.7-1 times the deployment diameter, or 0.6-1 times the deployment diameter, or 0.5-1 times the deployment diameter, or 0.4-1 times the deployment diameter, or 0.3-1 times the deployment diameter, or 0.2-1 times the deployment diameter. The stent expanded/deployed diameter typically is 2 mm and higher, 2.5 mm and higher, 3 mm and higher, 3.5 mm and higher, 4 mm and higher, 4.5 mm and higher, 5 mm and higher, 5.5 mm and higher. In other embodiments, the stent deployed diameter ranges from 2 mm-25 mm, preferably ranges from 2.5 mm to 15 mm, more preferably from 3 mm to 10 mm. The stent length ranges from 1 mm to 200 cm, preferably from 5 mm to 60 cm, more preferably from 5 mm to 6 cm.

In some embodiments, an annealed polymeric article or tube is quenched by being cooled fast from the annealing temperature to a lower temperature (e.g., at least about 10° C., 20° C., 30° C., 40° C. or 50° C. below the $T_g$, or to ambient temperature or below) over a period of about 1 second to about 1 hour, or about 10 seconds to about 1 hour, or about 30 seconds to about 30 minutes, or about 1 minute to about 30 minutes, or about 1 minute to about 15 minutes, or about 1 minute to about 5 minutes, or about 5 minutes to about 15 minutes, or about 10 seconds to about 1 minute. In other embodiments, an annealed article or tube is quenched by being cooled slowly from the annealing temperature to a lower temperature (e.g., at least about 10° C., 20° C., 30° C., 40° C. or 50° C. below the $T_g$, or to ambient temperature or below) over a period of about 1 hour to about 24 hours, or about 1 hour to about 12 hours, or about 1 hour to about 6 hours, or about 2 hours to about 12 hours, or about 4 hours to 12 hours, or about 4 hours to about 8 hours, or about 6 hours to 10 about hours. In some embodiments, a heat-treated article or tube is cooled to a temperature below ambient temperature for a period of about 1 minute to about 96 hours, or about 24 hours to about 72 hours, or about 30 minutes to about 48 hours, or about 1 hour to about 48 hours, or about 1 hour to about 36 hours, or about 1 hour to about 24 hours, or about 1 hour to about 12 hours, or about 4 hours to about 12 hours, to stabilize the crystals and/or terminate crystallization in the polymeric material. Annealing and quenching of the polymeric article or tube can initiate and promote nucleation of crystals in the polymeric material, increase the mechanical strength of the material (e.g., polymeric material) comprising the polymeric article or tube, and/or reduce residual/internal stress in the polymeric article or tube. The annealing temperature and duration and the cooling temperature and rate of cooling can be controlled to optimize the size, number and distribution of the crystals and crystalline regions in the material (e.g., polymeric material) and the strength thereof.

In further embodiments, an unannealed or annealed polymeric article or tube is exposed to ionizing radiation (e.g., e-beam or gamma radiation) at, above or below ambient temperature, with a single dose or multiple doses of radiation totaling about 1 kGray (kGy) to about 100 kGy, or about 10 kGy to about 50 kGy, or about 10 kGy to about 30 kGy, or about 20 kGy to about 60 kGy, or about 20 kGy to about 40 kGy. In certain embodiments, an unannealed or annealed article or tube is cooled to reduced temperature (e.g., below 0° C.) and then is exposed to a single dose or multiple doses of ionizing radiation (e.g., e-beam or gamma radiation) totaling about 10 kGy to about 50 kGy.

In a preferred embodiment, there is a desire to minimize the amount of heat and/or duration the tubular body or the stent or the biodegradable material sees after forming. Examples include treating the tubular body by heating the tubular body after forming to temperature at about Tg or lower than Tg or within 10° C. higher than Tg, of the biodegradable polymeric material Tg, for duration ranging from a fraction of a second to 7 days, or 5 seconds to 7 days, preferably from 15 seconds to 1 day, more preferably from 30 seconds to 5 hours, and optionally cooling or quenching after heating to above ambient, ambient temperatures or below ambient. The heating can take place once or more than once at various stages of the tubular body or stent prosthesis fabrication. In one embodiment, the biodegradable stent prosthesis comprising a tubular body comprising a biodegradable polymeric material, wherein the tubular body has been formed using extrusion, molding, dipping, or spraying and has been treated by heating the tubular body at about Tg or lower of the biodegradable polymeric material Tg, said biodegradable polymeric material is substantially amorphous after said treatment and has a Tg greater than 37° C., and the stent prosthesis at body temperature is radially expandable and has sufficient strength to support a body lumen. In another embodiment, the biodegradable stent prosthesis comprising a tubular body comprising a biodegradable polymeric material, wherein the tubular body has been formed using extrusion, molding, dipping, or spraying and has been treated by heating the tubular body at about Tg or lower of the biodegradable polymeric material Tg, said biodegradable polymeric material has crystallinity of 10%-60% (or 10%-50% or 10%-40% or 10% to 30% or 10%-20% or 0%-10% or 0% to 30%) after said treatment and has a Tg greater than 37° C., and the stent prosthesis at body temperature is radially expandable and has sufficient strength to support a body lumen. In one embodiment, the Tg is greater than 37° C. and less than 60° C., preferably greater than 37° C. and less than 55° C., more preferably greater than 37° C. and less than 45° C., more preferably greater than 35° C. and less than 45° C.

In another preferred embodiment, there is a desire to minimize the amount of heat and/or duration the tubular body or the stent or the biodegradable material sees after forming Examples include treating the tubular body by heating the tubular body after forming to temperature at about Tg or lower than Tg or within 10° C. higher than Tg, or having one (or more than one) heat treatment above Tg, of the biodegradable polymeric material Tg, for duration ranging from a fraction of a second to 7 days, preferably from 15 seconds to 1 day, more preferably from 30 seconds to 5 hours, and optionally cooling or quenching, after heating, to above ambient, ambient temperatures or below ambient. The heating can take place once or more than once at various stages of the tubular body or stent prosthesis fabrication. In one embodiment, the biodegradable stent prosthesis comprising a tubular body comprising a biodegradable polymeric material, wherein the tubular body has been formed using extrusion, molding, dipping, or spraying and has been treated by heating the tubular body at about Tg or lower of the biodegradable polymeric material Tg and one heat treatment above Tg, said biodegradable polymeric material is substantially amorphous after said treatments and has a Tg greater than 37° C., and the stent prosthesis at body temperature is radially expandable and has sufficient strength to support a body lumen. In another embodiment, the biodegradable stent prosthesis comprising a tubular body comprising a biodegradable polymeric material, wherein the tubular body has been formed using extrusion, molding, dipping, or spraying and has been treated by heating the tubular body at about Tg or lower of the biodegradable polymeric material Tg and one heat treatment above Tg, said biodegradable polymeric material has crystallinity of 10%-60% (or 10%-50% or 10%-40% or 10% to 30% or 10%-20% or 0%-10% or 0% to 30%) after said treatment and has a Tg greater than 37° C., and the stent prosthesis at body temperature is radially expandable and has sufficient strength to support a body lumen. In one embodiment, the Tg is greater than 37° C. and less than 60° C., preferably greater than 37° C. and less than 55° C., more preferably greater than 37° C. and less than 45° C., more preferably greater than 35° C. and less than 45° C.

In a preferred embodiment, there is a desire to minimize the amount of heat and/or duration the tubular body or the stent or the biodegradable material sees after forming. Examples include treating the tubular body by heating the tubular body after forming to temperature at about Tg or lower than Tg or within 10° C. higher than Tg, of the biodegradable polymeric material Tg, for duration ranging from a fraction of a second to 7 days, or 5 seconds to 7 days, preferably from 15 seconds to 1 day, more preferably from 30 seconds to 5 hours, and optionally cooling or quenching after heating to above ambient, ambient temperatures or below ambient. The heating can take place once or more than once at various stages of the tubular body or stent prosthesis fabrication. In one embodiment, the biodegradable stent prosthesis comprising a tubular body comprising a biodegradable polymeric material, wherein the tubular body has been formed using extrusion, molding, dipping, or spraying and has been treated by heating the tubular body at about Tg or lower of the biodegradable polymeric material Tg, said biodegradable polymeric material is substantially amorphous after said treatment and has a Tg greater than 37° C., and the stent prosthesis at body temperature is radially expandable and has sufficient strength to support a body lumen. In another embodiment, the biodegradable stent prosthesis comprising a tubular body comprising a biodegradable polymeric material, wherein the tubular body has been formed using extrusion, molding, dipping, or spraying and has been treated by heating the tubular body at about Tg or lower of the biodegradable polymeric material Tg, said biodegradable polymeric material has crystallinity of 10%-60% (or 10%-50% or 10%-40% or 10% to 30% or 10%-20% or 0%-10% or 0% to 30%) after said treatment and has a Tg greater than 37° C., and the stent prosthesis at body temperature is radially expandable and has sufficient strength to support a body lumen. In one embodiment, the Tg is greater than 37° C. and less than 60° C., preferably greater than 37° C. and less than 55° C., more preferably greater than 37° C. and less than 45° C., more preferably greater than 35° C. and less than 45° C.

In some embodiments, the endoprosthesis (e.g., a stent) or the polymeric article (e.g., a polymeric tube) from which it is formed, with or without at least one surface being positioned against a non-deformable surface (e.g., the stent or the polymeric tube optionally being placed inside a non-deformable tube having a larger diameter), is pressurized to at least about 100 psi, 200 psi, 300 psi, 400 psi, 500 psi, 600 psi or 700 psi, with or without added heat, and in the presence or absence of carbon dioxide gas or liquid.

In further embodiments, the material (e.g., polymeric material) comprising the body of an endoprosthesis (e.g., a stent) has increased strength and/or crystallinity (e.g., through induced or increased orientation of crystals, crystalline regions or polymer chains), and/or has reduced residual or internal stress, by at least heating the endoprosthesis and/or the polymeric article (e.g., a polymeric tube) from which it is formed at a temperature equal to the $T_g$, or above the $T_g$ and below the $T_m$, or equal to or above the $T_m$, of the material (e.g., polymeric material), or below Tg, for a period of time (e.g., at least about 0.01, 1, 4, 8, 12, 24, 36 or 48 hours), and quickly or slowly cooling the endoprosthesis and/or the polymeric article to a lower temperature (e.g., at least about 10° C., 20° C., 25° C., 30° C., 40° C. or 50° C. below the $T_g$, or to ambient temperature or below); or by at least minimizing heating conditions of the tubular body or stent during processing such that % crystallinity does not increase by more than 20% or between 1% to about 20%. In some embodiments, the material (e.g., polymeric material) comprising the body of an endoprosthesis (e.g., a stent) has increased strength and/or crystallinity, and/or has reduced residual or internal stress, by heating the endoprosthesis and/or the polymeric article (e.g., a polymeric tube) from which it is formed at a temperature at least about 1° C., 5° C., 10° C., 20° C., 30° C., 40° C. to about 50° C. (e.g., polymeric material) for a period of time (e.g., at least about 0.1, 4, 8, 12, 24, 36 or 48 hours), and quickly or slowly cooling the endoprosthesis and/or the polymeric article to lower temperature (e.g., at least about 10° C., 20° C., 25° C., 30° C., 40° C. or 50° C. below the $T_g$, or to ambient temperature or below). In certain embodiments, the endoprosthesis and/or the polymeric article are heated at a temperature equal to or no more than about 1° C., 5° C., 10° C., 15° C., 20° C., 25° C. or 30° C. below the temperature used to induce or increase orientation of crystals, crystalline regions or polymer chains of the material (e.g., polymeric material) comprising the endoprosthesis or the polymeric article.

Another modification treatment that a polymeric article (e.g., a polymeric tube) and/or an endoprosthesis (e.g., a stent) can undergo is crosslinking. A polymeric material comprising the body of the endoprosthesis and/or a polymeric material comprising any coating on the endoprosthesis can be crosslinked by exposure to radiation (e.g., UV radiation or ionizing radiation, such as e-beam or gamma radiation), exposure to heat, use of a crosslinker, or use of a crosslinking agent and an initiator, as described herein. In certain embodiments, the polymeric material(s) are crosslinked by exposure to e-beam or gamma radiation having a cumulative dose of about 1 kGy to about 1000 KGy, or about 5 kGy to about 100 kGy, or about 10 kGy to about 50 kGy, or about 10 kGy to about 30 kGy, or about 20 kGy to about 60 kGy, or about 20 kGy to about 40 kGy. Crosslinking of the polymeric material(s) can be performed, e.g., to increase their crystallinity and/or reduce recoil of an endoprosthesis (e.g., a stent) comprised of the polymeric material(s).

In another embodiment, the biodegradable stent material has increased crystallinity by increasing orientation of polymer chains with in the biodegradable stent material in radial and/or longitudinal direction by drawing, pressurizing and/or heating the stent material. In another embodiment, the drawing, pressurizing and/or heating the stent material occurs simultaneously or sequentially.

In one embodiment, the biodegradable stent material is placed with at least one surface against a non deformable surface and is pressurized to at least 200 psi, preferably to at least 300 psi, more preferably to at least 500 psi. In another embodiment, the biodegradable stent material is pressurized to at least 200 psi, preferably to at least 300 psi, more preferably to at least 500 psi.

In one embodiment, the biodegradable stent material tube is placed with in a larger diameter non deformable tube and is pressurized to at least 200 psi, preferably to at least 300 psi, more preferably to at least 500 psi. In another embodiment, the biodegradable stent material tube is pressurized to at least 200 psi, preferably to at least 300 psi, more preferably to at least 500 psi.

In one embodiment, the biodegradable stent material has increased crystallinity by increasing the orientation of the polymer chains by at least heating the biodegradable stent material above its glass transition temperature (Tg) and below its melting temperature.

In one embodiment, the biodegradable stent material has increased crystallinity by heating the material to a temperature at least 10° C. higher than its Tg, preferably at least 20° C. higher, more preferably at least 30° C. higher than the Tg of the biodegradable stent material.

In one embodiment, biodegradable stent material has increased crystallinity after drawing, heat and/or pressurizing and annealing at elevated temperature with or without vacuum. In one embodiment, the annealing temperature is below the temperature used for orientation of the polymer chains of the biodegradable stent material. In another embodiment, the annealing temperature is at most 20° C. below, preferably at most 15° C. below, more preferably at most 10° C. below the temperature for orientation of the polymer chains of the biodegradable stent material.

In one embodiment, the biodegradable stent material after annealing is quenched below Tg of the biodegradable stent material, preferably at least 25° C. below Tg, more preferably at least 50° C. below Tg of the biodegradable stent material.

The polymeric material or the tubular body formed there from can be modified to control crystallinity (e.g., degree of crystallinity) of the polymeric material. In certain embodiments, the substantially amorphous or semi-crystalline polymeric material or the tubular body formed therefrom undergoes a modification treatment to introduce a desired degree of crystallinity into the polymeric material to increase the strength of the polymeric material without substantially lengthening its degradation time. In another embodiment, tubular body comprising the polymer or copolymer comprised of at least one of PLLA, PLLA-PCL, or PLGA, wherein the tubular body or stent is substantially amorphous or semi crystalline after modification. In another embodiment, the tubular body comprising the polymer or copolymer is comprised of at least one of PLLA, PLLA-PCL, or PLGA, wherein the tubular body or stent is substantially amorphous or semi crystalline after modification, and wherein the crystallinity ranges from about 5% to about 40%. In another embodiment, the tubular body comprising the polymer or copolymer is comprised of at least one of PLLA, PLLA-PCL, PLGA, wherein the tubular body or stent is substantially amorphous or semi crystalline after modification, and wherein the crystallinity ranges from about 5% to about 30%. In another embodiment, the tubular body comprising the polymer or copolymer is comprised of at least one of PLLA, PLLA-PCL, PLGA, wherein the tubular body or stent is substantially amorphous or semi crystalline after modification and wherein the crystallinity ranges from about 5% to about 25%.

The treated stent or other endoprosthesis can be crimped onto a delivery balloon using mechanical crimpers comprising of wedges such as crimpers from Machine Solutions, Fortimedix, or others. The stent can also be crimped by placing the stent in a shrink tube and stretching the shrink tube slowly at a rate of 0.1 to 2 inches/minutes, more preferably 0.2 to 0.5 inches/minutes until the stent is crimped to the desired crimped diameter. During crimping, the stent is heated to a temperature of 20° C. below the Tg to 10° C. above the Tg for 30 minutes, more preferably to 10° C. below the Tg to Tg, and most preferably at the Tg of the stent material. This process facilitates or enables the stent to maintain the final crimped diameter. After crimping, the ability for the stent to remain the crimped diameter can further be improved by fixing the stent in the crimped diameter while exposing it to a temperature of 20° C. below the Tg to 10° C. above the Tg for 30 minutes, more preferably to 10° C. below the Tg to Tg, and most preferably at the Tg of the stent material, for 1 minute to 24 hours, more preferably 15 minutes to 1 hour. After holding at this crimping temperature, it is preferred to fix the stent in the crimped diameter while at or below ambient temperatures until further processing (i.e., sterilization). The stent can either be crimped while it is on the balloon of the stent delivery catheter or first crimped alone and then slipped onto the balloon of the catheter. In a further embodiment, the crimped stent is cooled below ambient temperature to lock in the crystals or terminate crystallization for 1 minute to 96 hours, more preferably 24 hours to 72 hours.

In a preferred embodiment, the final crimped stent on the catheter is sterilized by 25 to 30 kGy dose of ebeam, typically with a single dose of 30 kGy or with multiple smaller doses (e.g., 3×10 kGy). The stent system is usually kept below ambient temperature before, during and/or after multiple smaller doses of sterilization. The stent that has been packaged and sterilized can also be exposed to heat treatment like that described above. In one embodiment, the biodegradable polymer stent is heated at about the Tg of the biodegradable stent material during expansion of the stent. The temperature during expansion can range from 10° C. above Tg to 10° C. below Tg.

Upon deployment of such stent, the processes provide means to minimize stent recoil to less than 10% after expansion from the crimped state to an expanded state.

A stent can be crimped to a smaller diameter using a mechanical crimper. A stent can also be crimped by placing the stent in a shrink tube and stretching the shrink tube slowly at a rate of about 0.1 to about 2 inches/minute, or about 0.1 to about 1 inch/minute, or about 0.2 to about 0.5 inch/minute, until the stent is crimped to the desired diameter. A stent can be crimped onto the balloon of a delivery catheter, or can be crimped and then mounted onto the balloon of a catheter to provide a stent delivery system.

In certain embodiments, a stent is crimped at ambient temperature, or is crimped at a temperature (crimping temperature) of at least about 30° C., 35° C., 40° C., 45° C. or 50° C., and then the stent crimped at elevated temperature is cooled to a lower temperature (e.g., at least about 5° C., 10° C., 15° C., 20° C., 25° C. or 30° C. below the crimping temperature, or to ambient temperature or below). In an embodiment, the stent is crimped at about 35° C. or above, and then the crimped stent is cooled to a temperature at least about 5° C. below the crimping temperature. In further embodiments, the crimping temperature is at or below the $T_g$ of the material (e.g., polymeric material) of which the stent body is composed, or at least about 1° C., 5° C., 10° C., 15° C., 20° C., 25° C., 30° C., 35° C., 40° C., 45° C. or 50° C. below the $T_g$. In an embodiment, the crimping temperature is at least about 5° C. below the $T_g$ of the material (e.g., polymeric material) comprising the stent body.

In some embodiments, a stent is exposed to the crimping temperature for at least about 0.5, 1, 3, 5 or 10 minutes and allowed to reach the crimping temperature prior to being crimped. The stent can be exposed to the crimping temperature using a heated crimper. The crimped stent can be stabilized in the crimped state as described herein. In additional embodiments, the crimped stent is cooled below ambient temperature for a period of about 1 minute to about 96 hours, or about 24 hours to about 72 hours, or about 30 minutes to about 48 hours, or about 1 hour to about 48 hours, or about 1 hour to about 36 hours, or about 1 hour to about 24 hours, or about 1 hour to about 12 hours, or about 4 hours to about 12 hours, to stabilize the stent, and/or stabilize the crystals and/or terminate crystallization in the stent polymeric material.

In some embodiments, a stent is exposed to carbon dioxide gas at elevated pressure (e.g., at least about 100, 150, 200, 250, 300, 350, 400, 450 or 500 psi) for a period of time (e.g., at least about 10, 20 or 30 minutes, or at least about 1, 2 or 3 hours), e.g., to soften the material (e.g., polymeric material) comprising the body of the stent and/or a coating on the stent. After exposure to carbon dioxide, the stent can be crimped at or below the $T_g$ of the material (e.g., polymeric material) comprising the body of the stent (e.g., at least about 1° C., 5° C., 10° C., 15° C., 20° C., 25° C., 30° C., 35° C., 40° C., 45° C. or 50° C. below the $T_g$), or at about ambient temperature to about 50° C.

An endoprosthesis (e.g., a stent or a stent delivery system) and/or the polymeric article (e.g., a polymeric tube) from which it is formed can be exposed to ionizing radiation such as electron beam or gamma radiation or to ethylene oxide gas (e.g., for purposes of sterilization) as described herein. In addition to serving as a sterilization treatment, such exposure can serve as a modification or treatment in that it can, e.g., control crystallinity (e.g., degree of crystallinity) and/or enhance the strength of the material (e.g., polymeric material) comprising the polymeric article or the endoprosthesis. In some embodiments, the polymeric article and/or the endoprosthesis are exposed to a single dose or multiple doses of e-beam or gamma radiation totaling about 5 or 10 kGy to about 50 kGy, or about 20 kGy to about 40 kGy of radiation, e.g., a single dose of 30 kGy or multiple smaller doses (e.g., 3×10 kGy doses), where the polymeric article and/or the endoprosthesis are cooled to low temperature (e.g., about −10° C. to about −30° C., or about −20° C.) for a period of time (e.g., at least about 20, 30 or 40 minutes) prior to exposure to the single dose or to each of the multiple doses of radiation. In certain embodiments, the polymeric article and/or the endoprosthesis are exposed to a single dose or multiple doses of e-beam or gamma radiation totaling about 10 kGy to about 50 kGy, or about 30 kGy. A polymeric article and/or an endoprosthesis that have been exposed to ionizing radiation or ethylene oxide gas can also undergo one or more other modification treatments (e.g., heating or annealing) described herein.

In certain embodiments, an endoprosthesis (e.g., a stent) is patterned by laser cutting or other method from a polymeric tube that has a (e.g., inner or outer) diameter substantially equal to or smaller than an intended deployed (e.g., inner or outer) diameter of the endoprosthesis. In other embodiments, an endoprosthesis (e.g., a stent) is patterned from a polymeric tube that has a (e.g., inner or outer) diameter, either when the tube is formed or after the tube is radially expanded to a second larger diameter, larger than an intended deployed (e.g., inner or outer) diameter of the endoprosthesis. Patterning a stent from a polymeric tube having a (e.g., inner or outer) diameter larger than an intended deployed (e.g., inner or outer) diameter of the stent can impart advantageous characteristics to the stent, such as reducing radially inward recoil of the stent after deployment. In certain embodiments, a stent is patterned from a polymeric tube having a (e.g., inner or outer) diameter about 0.85, 0.90, 1.0, 1.05 to about 1.5 times, or about 1.1 to about 1.5 times, or about 1.1 to about 1.3 times, or about 1.15 to about 1.25 times, smaller, same, or larger than an intended deployed (e.g., inner or outer) diameter of the stent. In an embodiment, the stent is patterned from a polymeric tube having a (e.g., inner or outer) diameter about 1.1 to about 1.3 times larger than an intended deployed (e.g., inner) diameter of the stent. For example, a stent having a deployed (e.g., inner or outer) diameter of about 2.5, 3 or 3.5 mm can be patterned from a tube having a (e.g., inner or outer) diameter of about 2.75, 3.3 or 3.85 mm (1.1 times larger), or about 3.25, 3.9 or 4.55 mm (1.3 times larger), or some other (e.g., inner or outer) diameter larger than the deployed (e.g., inner or outer) diameter of the stent. In other embodiments, the initial diameter of the formed tube is larger than the crimped diameter (e.g., crimped diameter on a delivery system) of the stent prosthesis wherein the tubular body is expanded to a second larger diameter than the initial diameter before patterning or before crimping to the crimped diameter; or wherein the tubular body remains substantially the same diameter before patterning or before crimping to a crimped diameter; or wherein the tubular body is crimped to a smaller diameter than the initial formed diameter before patterning or after patterning. In another embodiment, the initial diameter of the formed tube is smaller than the crimped diameter of the stent prosthesis wherein the tubular body is expanded to a second larger diameter than the initial diameter before patterning or before crimping; or wherein the tubular body remains substantially the same diameter before patterning or before crimping; or wherein the tubular body is crimped to a smaller diameter than the crimped diameter of the stent prosthesis before patterning or after patterning. In another embodiment, the initial diameter of the formed tubular body is greater than 0.015 inches, or greater than 0.050 inches, or greater than 0.092 inches, or greater than 0.120 inches, or greater than 0.150 inches. Stent prosthesis intended deployment diameter is the diameter of the labeled delivery system or balloon catheter. For example when a stent prosthesis is crimped onto a balloon labeled 3.0 mm diameter, the stent prosthesis' intended deployment diameter is 3.0 mm. Similarly, self expandable stent crimped onto a delivery system is labeled a certain deployment diameter.

The stent cut from a polymeric tube can be any kind of stent and can have any pattern and design suitable for its intended use, including any kind of stent and any pattern and design described herein. Further, the stent can be a fully self-expandable stent, a balloon-expandable stent, or a stent capable of radially self-expanding prior to balloon expansion to an intended deployed diameter.

The stent material may lose some crystallinity during stent cutting. In such cases, the stent annealed after cutting and/or a second time to re-crystallize the polymer to a higher crystallinity. Thus, the cut stent may be annealed a second time as generally described above. Annealing/heating followed by cooling as described above can be repeated one or more times to further increase crystallinity. In a further embodiment, the heat treated stent is cooled below ambient temperature to lock in the crystals or terminate crystallization for 1 minute to 96 hours, more preferably 24 hours to 72 hours.

In certain embodiments, the polymeric article is a polymeric tube and the structure is a substantially cylindrical structure. In an embodiment, the substantially cylindrical structure is a mandrel.

In further embodiments, the polymeric tube is substantially concentric. In certain embodiments, the polymeric tube has a concentricity of about 0.0025 inch (about 64 microns) or less, or about 0.002 inch (about 51 microns) or less, or about 0.0015 inch (about 38 microns) or less, or about 0.001 inch (about 25 microns) or less, or about 0.0005 inch (about 13 microns) or less, or about 0.00025 inch (about 6 microns) or less. In an embodiment, concentricity is two times the distance between the centers of the inner and outer diameters of the tube. In some embodiments, the polymeric tube has a percent concentricity of at least about 75%, 80%, 85%, 90%, 91%, 92%, 93%, 94%, 95%, 96%, 97%, 98% or 99%. In an embodiment, percent concentricity is calculated as follows: % concentricity=(minimum wall thickness/maximum wall thickness)×100. In certain embodiments, the polymeric tube has a concentricity of about 0.001 inch (about 25 microns) or less, or a percent concentricity of at least about 90%.

When the biodegradable device is a stent, in some embodiments the stent is patterned from a polymeric tube that has a (e.g., inner) diameter substantially equal to an intended deployment (e.g., inner) diameter or the maximum allowable expansion (e.g., inner) diameter of the stent. In other embodiments, the stent is patterned from a polymeric tube that has a (e.g., inner) diameter greater than (e.g., at least about 5%, 10%, 15%, 20%, 25%, 30%, 35%, 40%, 45% or 50% greater than) an intended deployment (e.g., inner) diameter or the maximum allowable expansion (e.g., inner) diameter of the stent. In an embodiment, the stent is patterned from a polymeric tube that has a (e.g., inner) diameter at least about 10% greater than an intended deployment (e.g., inner) diameter or the maximum allowable expansion (e.g., inner) diameter of the stent. In some embodiments, the stent is patterned from a polymeric tube that has a (e.g., inner) diameter of about 2.5 mm to about 4.5 mm, or about 2.75 mm to about 4.5 mm, or about 3 mm to about 4.5 mm, or about 2.75 mm to about 4 mm, or about 3 mm to about 4 mm, or about 3.3 mm to about 3.8 mm. In certain embodiments, the stent is patterned from a polymeric tube that has a (e.g., inner) diameter of about 2.75 mm to about 4.5 mm, or about 2.75 mm to about 4 mm.

In one embodiment, the tubular body or stent prosthesis diameter ranges from about 0.25 mm to about 25 mm, preferably from about 2 mm to about 15 mm, more preferably from about 2.5 mm to about 10 mm, and most preferably from about 3 mm to about 7 mm.

The stent or other endoprosthesis is patterned from a tube of the stent material in an expanded diameter and subsequently crimped to a smaller diameter and fitted onto a balloon of a delivery catheter. The stent is patterned, typically by laser cutting, with the tubing diameter about 1 to 1.3 times, preferably 1.1 to 1.5 times, more preferably 1.15 to 1.25 times, larger the intended deployed diameter. For example, a stent cut at a 3.5 mm×18 mm outer diameter is crimped on a 3.0 mm×18 mm stent delivery catheter. In a further embodiment, the unannealed and/or annealed stent is exposed to ebeam or gamma radiation, with single or multiple doses of radiation ranging from 5 kGy to 100 kGy, more preferably from 10 kGy to 50 kGy.

An intended deployment diameter is one or more of the following: the labeled deployment diameter of the stent prosthesis. An example is a stent prostheiss IFU or box or label with a certain labeled diameter such as a nominal deployment diameter, for example 3.0 mm. It can also be the deployed diameter of the stent prosthesis. It can also be a diameter between a nominal deployment diameter and the rated burst diameter or higher. It can also be the diameter (where in the case of a balloon or mechanical expansion) where the balloon is expanded to at least 90% of the nominal diameter of the balloon. The most preferred embodiment of an intended deployment diameter is the labeled deployment diameter or the nominal deployment diameter.

In a preferred embodiment, when the stent is expanded to at least 1 times or at least 1.1 times or at least 1.15 times or at least 1.2 times or at least 1.25 time or at least 1.3 times, or at least 1.4, or at least 1.5 times deployed diameter or an intended deployment diameter at 37° C., wherein the stent prosthesis is capable of expansion to at least said diameters without breakage/fracture in one or more of the stent prosthesis struts, crowns, or links.

In another embodiment, when the stent is expanded to at least 1 times or at least 1.1 times or at least 1.15 times or at least 1.2 times or at least 1.25 time or at least 1.3 times a deployed diameter or an intended deployment diameter in a body lumen or in water at 37° C., wherein the stent prosthesis is capable of expansion to at least said diameters without breakage/fracture in two or more of the stent prosthesis struts, crowns, or links.

In one embodiment, when the stent is expanded to at least 1 times or at least 1.1 times or at least 1.15 times or at least 1.2 times or at least 1.25 time or at least 1.3 times an intended deployment diameter in a body lumen or in water at 37° C., wherein the stent prosthesis is capable of expansion to at least said diameters without breakage/fracture in three or more of the stent prosthesis struts, crowns, or links.

In a preferred embodiment, the biodegradable stent prosthesis comprising a biodegradable polymeric material, wherein the polymeric material has been formed using extrusion, molding, dipping, 3D printing, or spraying, said biodegradable polymeric material has been treated at a diameter of 1-1.5 times an intended deployment diameter (deployed diameter) of the stent prosthesis, and the stent prosthesis at body temperature is radially expandable and has sufficient strength to support a body lumen and without fracture.

In a preferred embodiment, the biodegradable stent prosthesis comprising a biodegradable polymeric material, wherein the polymeric material has been formed using extrusion, molding, dipping, 3D printing, or spraying, said biodegradable polymeric material has been treated at a diameter of 1-1.5 times an intended deployment diameter (deployed diameter) of the stent prosthesis, wherein the treatment comprises heating the polymeric material to between Tg and Tm (melting temperature of the material), and the stent prosthesis at body temperature is radially expandable and has sufficient strength to support a body lumen and without fracture.

In a preferred embodiment, the biodegradable stent prosthesis comprising a biodegradable polymeric material, wherein the polymeric material has been formed using extrusion, molding, dipping, 3D printing, or spraying, said biodegradable polymeric material has been treated at a diameter of 1-1.5 times an intended deployment diameter of the stent prosthesis, wherein the treatment comprises heating the polymeric material to about Tg or less, and the stent prosthesis at body temperature is radially expandable and has sufficient strength to support a body lumen and without fracture.

In a preferred embodiment, the biodegradable stent prosthesis comprising a biodegradable polymeric material, wherein the polymeric material has been formed using extrusion, molding, dipping, 3D printing, or spraying, said biodegradable polymeric material has been treated at a diameter of 1-1.5 times an intended deployment diameter of the stent prosthesis, wherein the treatment comprises heating the polymeric material to about Tg or less or/and about Tg or more from at least a fraction of a second to about 7 days, and the stent prosthesis at body temperature is radially expandable and has sufficient strength to support a body lumen and without fracture.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated at a diameter of 1-1.5 times an intended deployment diameter of the stent prosthesis, wherein the treatment comprises heating the polymeric material from about Tg or higher, and the stent prosthesis at body temperature is radially expandable and has sufficient strength to support a body lumen.

In a preferred embodiment, the biodegradable stent prosthesis comprising biodegradable polymeric material, wherein the polymeric material has been formed using extrusion, molding, dipping, 3D printing, or spraying, said biodegradable polymeric material has been treated at a diameter of 1-1.5 times an intended deployment diameter of the stent prosthesis, wherein the treatment comprises heating the polymeric material from about Tg or higher and wherein the polymeric material has crystallinity after treatment between 0% to 60%, and the stent prosthesis at body temperature is radially expandable and has sufficient strength to support a body lumen and without fracture.

In a preferred embodiment, the biodegradable stent prosthesis comprising a biodegradable polymeric material, wherein the polymeric material has been formed using extrusion, molding, dipping, 3D printing, or spraying, said biodegradable polymeric material has been treated at a diameter of 1-1.5 times an intended deployment diameter of the stent prosthesis, wherein the treatment comprises heating the polymeric material from about Tg or higher and wherein the polymeric material has crystallinity after treatment between 0% to 60%, and the stent prosthesis at body temperature is radially expandable and has sufficient strength to support a body lumen and without fracture.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated at a diameter of 0.75-1.5 times an intended deployment diameter of the stent prosthesis, wherein the treatment comprises heating the polymeric material from about Tg or less to about Tg or higher and wherein the polymeric material has crystallinity after treatment between 0% to 60%, and the stent prosthesis at body temperature is radially expandable and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated at a diameter of 0.85-1.5 times an intended deployment diameter of the stent prosthesis, wherein the treatment comprises heating the polymeric material from about Tg or less to about Tg or higher and wherein the polymeric material has crystallinity after treatment between 0% to 60%, and the stent prosthesis at body temperature is radially expandable and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated at a diameter of 0.9-1.5 times an intended deployment diameter of the stent prosthesis, wherein the treatment comprises heating the polymeric material from about Tg or less to about Tg or higher and wherein the polymeric material has crystallinity after treatment between 0% to 60%, and the stent prosthesis at body temperature is radially expandable and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated at a diameter of 0.75-1.5 times an intended deployment diameter of the stent prosthesis, wherein the treatment comprises heating the polymeric material from about Tg or less to about Tg or higher and wherein the polymeric material has crystallinity after treatment between 0% to 60%, and the stent prosthesis is radially expandable to an intended deployment diameter at a temperature ranging from greater than 37° C. to 50° C. and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated at a diameter of 0.75-1.5 times an intended deployment diameter of the stent prosthesis, wherein the treatment comprises heating the polymeric material from about Tg or less to about Tg or higher and wherein the polymeric material has crystallinity after treatment between 0% to 60%, and the stent prosthesis at body temperature is radially expandable to an intended deployment diameter and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated at a diameter of 0.75-1.5 times an intended deployment diameter of the stent prosthesis, wherein the treatment comprises heating the polymeric material from about Tg or less to about Tg or higher and wherein the polymeric material has crystallinity after treatment between 0% to 60%, and the stent prosthesis at body temperature is radially expandable to at least 1.0 times an intended deployment diameter and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated at a diameter of 0.75-1.5 times an intended deployment diameter of the stent prosthesis, wherein the treatment comprises heating the polymeric material from about Tg or less to about Tg or higher and wherein the polymeric material has crystallinity after treatment between 0% to 60%, and the stent prosthesis at body temperature is radially expandable to at least 1.1 times an intended deployment diameter and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated at a diameter of 0.75-1.5 times an intended deployment diameter of the stent prosthesis, wherein the treatment comprises heating the polymeric material from about Tg or less to about Tg or higher and wherein the polymeric material has crystallinity after treatment between 0% to 60%, and the stent prosthesis at body temperature is radially expandable to at least 1.15 times an intended deployment diameter and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated at a diameter of 0.75-1.5 times an intended deployment diameter of the stent prosthesis, wherein the treatment comprises heating the polymeric material from about Tg or less to about Tg or higher and wherein the polymeric material has crystallinity after treatment between 0% to 60%, and the stent prosthesis at body temperature is radially expandable to at least 1.2 times an intended deployment diameter and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated at a diameter of 0.75-1.5 times an intended deployment diameter of the stent prosthesis, wherein the treatment comprises heating the polymeric material from about Tg or less to about Tg or higher and wherein the polymeric material has crystallinity after treatment between 0% to 60%, and the stent prosthesis is radially expandable to an intended deployment diameter at a temperature ranging from 30° C. to less than 37° C. and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.0 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.1 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.11 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.12 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.13 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.14 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.15 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.16 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.17 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.18 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.18 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.19 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.2 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.21 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.22 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.23 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.24 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.25 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.26 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.27 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.28 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.29 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to at least 1.3 times an intended deployment diameter of the stent prosthesis and has sufficient strength to support a body lumen.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated and said polymeric material has crystallinity between 0% to 60%, and the stent prosthesis at body temperature is radially expandable to greater than 1.1 times an intended deployment diameter of the stent prosthesis and has sufficient strength to support a body lumen and has recoil of less than 10% from an expanded diameter.

In a preferred embodiment, the biodegradable stent prosthesis comprising a tubular body comprising a biodegradable polymeric material, wherein the tubular body has been formed using extrusion, molding, dipping, 3D printing, or spraying, said biodegradable polymeric material has been treated at a diameter of 0.9-1.5 times an intended deployment diameter and said polymeric material after treatment has crystallinity between 0% to 60% and Tg between 37° C. and 50° C., and the stent prosthesis at body temperature is radially expandable to greater than 1.1 times an intended deployment diameter of the stent prosthesis and has sufficient strength to support a body lumen and has recoil of less than 10% from an expanded diameter.

In another embodiment, the tubular body is formed at a diameter of 0.75 to 1.5 times an intended deployment diameter of the stent prosthesis. In yet another embodiment, the tubular body is formed at a diameter less than an intended deployment diameter and expanded to a diameter of 0.75 to 1.5 times an intended deployment diameter before patterning or before crimping the stent prosthesis. In a further embodiment, the tubular body is formed at a diameter less than an intended deployment diameter.

Yet further embodiments of the disclosure relate to a biodegradable stent comprising a body comprising or comprised of a material which comprises a biodegradable polymer or copolymer or polymer blend, wherein prior to being balloon-expanded, the stent is capable of radially self-expanding by about 0.025 inch (about 635 microns) or less, or by about 25% or less of an initial crimped diameter of the stent, after being in aqueous condition at about 37° C. in vitro or in vivo for about 5 minutes or less. In some embodiments, prior to being balloon-expanded, the stent radially self-expands by about 0.025 inch (about 635 microns) or less, or by about 25% or less of the initial crimped diameter of the stent, after being in aqueous condition at about 37° C. in vitro or in vivo for about 5 minutes or less.

Yet further embodiments of the disclosure relate to a biodegradable stent comprising a body which comprises a biodegradable polymer or copolymer, wherein prior to being balloon-expanded, the stent is capable of radially self-expanding by about 0.001-0.025 inches, or about 0.003-0.015 inches, or about 0.005-0.10 inches, or about 0.001 inches or more, or about 0.003 inches or more, or about 0.005 inches or more, or about 0.010 inches or more, or about 0.025 inch or more, or by about 0.25% or more of an initial crimped diameter of the stent, after being in aqueous condition at about 37° C. in vitro or in vivo for about 1 minute or less, or about 5 minutes or less, or about 15 minutes or less. In some embodiments, prior to being balloon-expanded, the stent radially self-expands by about 0.025 inch or less, or by about 25% or less of the crimped diameter of the stent, after being in aqueous condition at about 37° C. in vitro or in vivo for about 1 minute or less, or about 5 minutes or less, or about 15 minutes or less. In some embodiments, the stent is secured in place at least in part from moving at least in one longitudinal direction by about 0.5 mm or less, or about 1 mm or less, or about 2 mm or less, or about 5 mm or less, by various means. Such means include at least one of configuring an expandable member proximal and/or distal to the stent, configuring a non expandable member or stops proximal and/or distal to the stent, configuring an attachment or adhesive means adjacent to the stent that does not prevent the stent from being balloon expandable, or configuring a sleeve that ends proximal to the stent, on top of the sent or distal to the stent.

In a further embodiment, the biodegradable stent comprising a body which comprises a biodegradable polymer, or copolymer, polymer blends, polymer blocks, polymer mixture wherein the polymer material is configured to be capable of being balloon expandable and self expanding, wherein prior to being balloon-expanded, the stent self-expands by about 0.001-0.025 inches, or about 0.003-0.015 inches, or about 0.005-0.10 inches, or about 0.001 inches or more, or 0.003 inches or more, or 0.005 inches or more, or 0.010 inches or more, or 0.025 inch or more, or by about 0.25% or more of an initial crimped diameter of the stent, after being in aqueous condition at about 37° C. in vitro or in vivo for about 1 minute, or about 5 minutes or less, or about 15 minutes or less.

In a further embodiment, the biodegradable stent comprising a body which comprises a biodegradable copolymer or polymer, or mixture of 2-3 polymers, or blend of polymers, or wherein the copolymer or polymer is configured to be capable of balloon expandable and self expanding, wherein prior to being balloon-expanded, the stent radially self-expands by about 0.001-0.025 inches, or about 0.003-0.015 inches, or 0.005-0.10 inches, or about 0.001 inches or more, or about 0.003 inches or more, or about 0.005 inches or more, or about 0.010 inches or more, or about 0.025 inch or more, or by about 0.25% or more of an initial crimped diameter of the stent, after being in aqueous condition at about 37° C. in vitro or in vivo for about 1 minute or less, or about 5 minutes or less, or about 15 minutes or less, and wherein the stent or the stent body has one or more of the following properties: radial strength of about 5 psi to about 20 psi, or about 5 psi or greater, or about 10 psi or greater, or about 15 psi or greater, recoil of about 3%-10% or about 10% or less, or % elongation at break >50%, or about 100%-about 600%, or about 50% to about 300%, or Tg of about 37° C.-60° C. or Tg of about 45° C.-55° C., after being in aqueous condition at about 37° C. in vitro or in vivo for about 1 minute or less, or about 5 minutes or less, or about 15 minutes or less.

In a further embodiment, the biodegradable stent comprising a body which comprises a biodegradable copolymer or polymer, wherein the copolymer or polymer is configured to be balloon expandable and self expanding, wherein prior to being balloon-expanded, the stent radially self-expands by about 0.025-0.25 inches, or about 0.50-0.15 inches, or about 0.025 inches or more, or about 0.050 inches or more, or about 0.1 inches or more, or by about 0.25% or more of an initial crimped diameter of the stent, after being in aqueous condition at about 37° C. in vitro or in vivo for about 1 minute or less, or about 5 minutes or less, or about 15 minutes or less. Optionally, the stent is constrained from self expanding using a sheath or other means and then such constraining means is removed, disengaged, or withdrawn, or released after the stent is positioned for deployment, allowing the stent to self deploy.

In a further embodiment, the biodegradable stent comprising a body which comprises a biodegradable copolymer or polymer, wherein the copolymer or polymer is configured to be self expanding, wherein prior to being balloon-expanded, the stent radially self-expanded by about 0.025-0.25 inches, or about 0.50-0.15 inches, or about 0.025 inches or more, or about 0.050 inches or more, or about 0.1 inches or more, or about 0.2 inches or more, or by about 0.25% or more of an initial crimped diameter of the stent, after being in aqueous condition at about 37° C. in vitro or in vivo for about 1 minute or less, or about 5 minutes or less, or about 15 minutes or less. The stent can/may be constrained from self expanding using a sheath or other means until the stent is positioned for deployment and is released from such means for deployment.

In further embodiments, the stent self expands to a diameter that is less than the final intended deployment diameter of the stent prior to being balloon expanded to the final intended deployment diameter after being in aqueous condition at about 37° C. in vitro or in vivo for about 1 minute or less, or about 5 minutes or less, or about 15 minutes or less.

In some embodiments, the biodegradable stent is a partially or fully self-expandable stent. In other embodiments, the stent is a balloon-expandable stent. In yet other embodiments, the stent is capable of radially self-expanding initially without a balloon assisting expansion and is then radially expanded to an intended deployment diameter with balloon assistance. In addition, in some embodiments, the implantable device, prosthesis, and/or articles are configured for uniform expansion (uniformly expanded) during or after either types of expansion from a crimped condition to an expanded condition. In some embodiments the stent prosthesis is substantially uniformly expanded from a crimped condition. In some embodiments, the stent prosthesis is uniformly expanded from a crimped state to an expanded state wherein the struts remain intact (or wherein the struts are not broken) after expansion from the crimped state. In other embodiments, the stent prosthesis is uniformly expanded at an intended deployment diameter wherein 70% or more of the crowns connecting two struts expand (or open) at an angle (between the struts connected by the crown excluding a link if present) greater than 75 degrees. In other embodiments, the stent prosthesis is uniformly expanded at an intended deployment diameter wherein 70% or more of the crowns connecting two struts expand (or open) at an angle (between the struts connected by the crown excluding a link if present) greater than 90 degrees. In other embodiments, the stent prosthesis is uniformly expanded at an intended deployment diameter wherein 70% or more of the crowns connecting two struts expand (or open) at an angle (between the struts connected by the crown excluding a link if present) greater than 100 degrees. In other embodiments, the stent prosthesis is uniformly expanded at an intended deployment diameter wherein 70% or more of the crowns connecting two struts expand (or open) at an angle (between the struts connected by the crown excluding a link if present) greater than 120 degrees. In other embodiments, the stent prosthesis is uniformly expanded at an intended deployment diameter wherein 60% or more of the crowns connecting two struts expand (or open) at an angle (between the struts connected by the crown excluding a link if present) greater than 75 degrees or greater than 90 degrees or greater than 120 degrees. In some cases a link that joins adjacent rings is connected to crowns. In such cases, these links are not considered struts but are links connecting adjacent rings. Angles for such crowns exclude the presence of links.

In certain embodiments, prior to being balloon-expanded (e.g., to an intended deployment diameter), the biodegradable stent is capable of radially self-expanding, or radially self-expands, by about 0.015 inch (about 381 microns) or less, or by about 0.01 inch (about 254 microns) or less, or by about 0.007 inch (about 178 microns) or less, or by about 0.005 inch (about 127 microns) or less, after being in aqueous condition (e.g., in aqueous solution, water, saline solution or physiological conditions) at about 37° C. in vitro or in vivo for about 3 minutes or less, or by about 0.025 inch (about 635 microns) or less, or by about 0.02 inch (about 508 microns) or less, or by about 0.015 inch (about 381 microns) or less, or by about 0.01 inch (about 254 microns) or less, after being in aqueous condition (e.g., in aqueous solution, water, saline solution or physiological conditions) at about 37° C. in vitro or in vivo for about 5 minutes or less.

In some embodiments, prior to being balloon-expanded (e.g., to an intended deployment diameter), the stent is capable of radially self-expanding, or radially self-expands, by about 15% or less, or by about 10% or less, or by about 5% or less, of the initial crimped diameter of the stent after being in aqueous condition (e.g., in aqueous solution, water, saline solution or physiological conditions) at about 37° C. in vitro or in vivo for about 3 minutes or less, or by about 25% or less, or by about 20% or less, or by about 15% or less, or by about 10% or less, of the initial crimped diameter after being in aqueous condition (e.g., in aqueous solution, water, saline solution or physiological conditions) at about 37° C. in vitro or in vivo for about 5 minutes or less.

In certain embodiments, prior to being balloon-expanded (e.g., to an intended deployment diameter), the biodegradable stent is capable of radially self-expanding, or radially self-expands, by about 0.025 inch (about 635 microns) or less, or by about 25% or less of the initial crimped diameter, after being in aqueous condition (e.g., in aqueous solution, water, saline solution or physiological conditions) at about 37° C. in vitro or in vivo for about 5 minutes or less.

In other embodiments, prior to being balloon-expanded (e.g., to an intended deployment diameter), the biodegradable stent is capable of radially self-expanding, or radially self-expands, by more than about 0.025 inch (about 635 microns), or by more than about 25% of the initial crimped diameter, after being in aqueous condition (e.g., in aqueous solution, water, saline solution or physiological conditions) at about 37° C. in vitro or in vivo for about 15 minutes or less, or about 10 minutes or less, or about 5 minutes or less.

Further embodiments of the disclosure relate to a biodegradable stent comprising a body which comprises a biodegradable polymer, wherein prior to being balloon-expanded, the stent is capable of radially self-expanding by about 0.001-0.025 inches, or about 0.003-0.015 inches, or about 0.005-0.10 inches, or about 0.001 inches or more, or about 0.003 inches or more, or about 0.005 inches or more, or about 0.010 inches or more, or about 0.025 inch (about 635 microns) or more, or by about 0.25% or more of an initial crimped diameter of the stent, after being in aqueous condition at about 37° C. in vitro or in vivo for about 1 minute or less, or about 5 minutes or less, or about 15 minutes or less.

In some embodiments, prior to being balloon-expanded, the stent radially self-expands by about 0.001-0.025 inches, or about 0.003-0.015 inches, or about 0.005-0.10 inches, or about 0.001 inches or more, or about 0.003 inches or more, or about 0.005 inches or more, or about 0.010 inches or more, or about 0.025 inch (about 635 microns) or more, or by about 0.25% or more of the crimped diameter of the stent, after being in aqueous condition at about 37° C. in vitro or in vivo for about 1 minute or less, or about 5 minutes or less, or about 15 minutes or less.

In some embodiments, the stent is secured in place at least in part from moving at least in one longitudinal direction by about 0.5 mm or less, or about 1 mm or less, or about 2 mm or less, or about 5 mm or less, by various means. Such means include at least one of configuring an expandable member proximal and/or distal to the stent, configuring a non expandable member or stops proximal and/or distal to the stent, configuring an attachment or adhesive means adjacent to the stent that does not prevent the stent from being balloon expandable, or configuring a sleeve that ends proximal to the stent, on top of the sent or distal to the stent. In an embodiment wherein the stent constraining means are expandable member proximal and/or distal to the stent and wherein the expandable means is deflated or collapsed at least partially prior to removing the delivery system into the guide.

In a further embodiment, the biodegradable stent comprising a body which comprises a biodegradable copolymer, polymer blends, polymer blocks, polymeric mixtures (with a combination of two or more polymers) wherein suitable copolymers, including the ones described herein, but not limited to the disclosed copolymers, are configured to be capable of being balloon expandable and self expanding, wherein prior to being balloon-expanded, the stent self-expands by about 0.001-0.025 inches, or about 0.003-0.015 inches, or about 0.005-0.10 inches, or about 0.001 inches or more, or about 0.003 inches or more, or about 0.005 inches or more, or about 0.010 inches or more, or about 0.025 inch (about 635 microns) or more, or by about 0.25% or more of an initial crimped diameter of the stent, after being in aqueous condition at about 37° C. in vitro or in vivo for about 1 minute, or about 5 minutes or less, or about 15 minutes or less.

In some embodiments, the biodegradable implantable devices (e.g., a stent) comprising a polymeric material or body (e.g., a tubular body), wherein the material has a wet or dry glass transition temperature ($T_g$) of about 10° C. to about 70° C., or about 35° C. to about 70° C., or about 40° C. to about 60° C., or about 45° C. to about 55° C., or about 45° C. to about 50° C., or about 37° C. to about 70° C., or about 37° C. to about 60° C., or about 37° C. to about 55° C., or about 37° C. to about 50° C., or about 37° C. to about 45° C., or greater than 37° C. to about 70° C., or greater than 37° C. to about 60° C., or greater than 37° C. to about 55° C., or greater than 37° C. to about 50° C., or greater than 37° C. to about 45° C., or greater than 37° C. to less than 45° C., or greater than 36° C. to less than 45° C., or greater than 36° C. to less than 40° C., or about 30° C. to about 70° C., or about 30° C. to about 60° C., or about 30° C. to about 50° C., or about 30° C. to about 45° C. In another embodiment the biodegradable stent comprises a tubular body which comprises a biodegradable polymer material; having crystallinity and glass transition temperatures as described in this application.

In further embodiments, the one or more materials comprising the body, or the stent, or the stent material, or the tubular body or the polymeric material may have a wet or dry glass transition temperature ($T_g$) greater than 20° C., or greater than 30° C., or greater than 31° C., or greater than 32° C., or greater than 33° C., or greater than about 34° C., or greater than 35° C., or greater than 36° C., or greater than 37° C. In some embodiments, the one or more materials comprising the body, or the stent, or the tubular body have a $T_g$ less than 45° C., or less than 44° C., or less than 43° C., or less than 42° C., or less than 41° C., or less than 40° C., or less than 39° C., or less than 38° C., or less than 37° C., or less than 36° C. In some embodiments, the one or more materials comprising the body, or the stent, or the tubular body have a $T_g$ of about 20° C. to about 55° C., or about 20° C. to about 50° C., or about 31° C. to about 45° C., or about 32° C. to about 45° C., or about 33° C. to about 45° C., or about 34° C. to about 45° C., or about 35° C. to about 45° C., or about 36° C. to about 45° C., or about 37° C. to about 45° C., or about 38° C. to about 45° C., or about 39° C. to about 45° C., or about 40° C. to about 45° C. In some embodiments, the one or more materials comprising the body, or the stent, or the tubular body have a $T_g$ of about 20° C. to about 45° C., or about 30° C. to about 44° C., or about 30° C. to about 43° C., or about 30° C. to about 42° C., or about 30° C. to about 41° C., or about 30° C. to about 40° C., or about 30° C. to about 39° C., or about 30° C. to about 38° C., or about 30° C. to about 37° C. In some embodiments, the one or more materials comprising the body, or the stent, or the tubular body has a $T_g$ greater than 37° C. and less than 45° C., or greater than 37° C. and less than 40° C., or greater than 37° C. to less than 50° C., or greater than 37° C. to less than 55° C.

In certain embodiments, the material comprising the body of the device or the biodegradable copolymer or the stent, has a degree of crystallinity of about 0% to about 40% and a $T_g$ of about or greater than 37° C. to about 60° C. In certain embodiments, the material comprising the body of the device or the biodegradable copolymer or the stent has a degree of crystallinity of about 0% to about 30% and a $T_g$ of about or greater than 37° C. to about 55° C. In certain embodiments, the material comprising the body of the device or the biodegradable copolymer or the stent has a degree of crystallinity of about 0% to about 30% and a $T_g$ of about or greater than 37° C. to about 45° C. In certain embodiments, the material comprising the body of the device or the biodegradable copolymer or the stent has a degree of crystallinity of about 0% to about 30% and a $T_g$ of about or greater than 10° C. to about 35° C.

The biodegradable stent prosthesis comprising a tubular body comprising a biodegradable polymeric material, wherein the tubular body has been formed using extrusion, molding, dipping, or spraying, said biodegradable polymeric material has an initial crystallinity and has a Tg greater than 37° C. and the stent prosthesis has a crystallinity (biodegradable stent material) lower than the initial crystallinity and at body temperature is radially expandable and has sufficient strength to support a body lumen.

In another embodiment of any of the above embodiments, the Tg is greater than 30° C. and less than 60° C., preferably greater than 30° C. and less than 55° C., preferably greater than 30° C. and less than 45° C., more preferably greater than 30° C. and less than 40° C., or more preferably greater than 30° C. and less than 37° C.

In still further embodiments, the material (e.g., polymeric material) comprising the body of the device or the biodegradable copolymer or polymer has a glass transition temperature ($T_g$) of at least about 10° C., 15° C., 20° C., 25° C., 30° C., 35° C., 37° C., 38° C., 40° C., 45° C., 50° C., 55° C., 60° C., 65° C. or 70° C. In some embodiments, the material (e.g., polymeric material) comprising the body of the device or the biodegradable copolymer has a $T_g$ of about 10° C., 35° C., 37° C. or 38° C. to about 70° C.; or about 10° C., 35° C., 37° C. or 38° C. to about 65° C.; or about 10° C., 35° C., 37° C. or 38° C. to about 60° C.; or about 10° C., 35° C., 37° C. or 38° C. to about 55° C.; or about 10° C., 35° C., 37° C. or 38° C. to about 50° C. In certain embodiments, the material (e.g., polymeric material) comprising the body of the device or the biodegradable copolymer has a $T_g$ of about 35° C. to about 70° C., or about 45° C. to about 60° C., or about 45° C. to about 55° C. In further embodiments, the material (e.g., polymeric material) comprising the body of the device or the biodegradable copolymer has a $T_g$ of about 10° C. to about 37° C., or about 40° C. to about 60° C.

In some embodiments, the Tg refers to the Tg of the tubular body or the polymeric material in a pellet form or after forming the tubular body or before treatment(s) or after treatment(s) or prior to implantation.

In some embodiments, when the treatment or modification is by heating, said heating can be at about Tg or below Tg, and the treatment(s) is prior to patterning or after patterning.

In other embodiments, the heat treatment or modification can be during patterning, such as during laser patterning.

In some embodiments, the Tg refers to the Tg of the tubular body or the polymeric material as a pellet or after forming the tube, or the Tg is measured prior to the treatment or modification, or the Tg is measured after the treatment or modification, or the Tg is measured prior to implantation.

In other embodiments, it is desired to control Tg to a desired range from 30° C. to 60° C., preferably 35° C. to 55° C., more preferably from 37° C. to 50° C., more preferably greater than 37° C. to 50° C. This allows for fabrication of a stent prosthesis capable of radial expansion at body temperature, or above body temperature, or below body temperature. Examples of controlling Tg (e.g., lowering it) can be accomplished through additives such as plasticizers and monomers, presence or addition of solvents (such water, DCM, ethanol), and radiation. Controlling Tg (e.g., increasing it) can be accomplished by heating the material (below Tg, Tg, or above Tg), pressurizing the material, removing additives or platicizers or solvents, and sometimes (depending on the material) through radiation. Control of radiation, increase or decrease or maintaining it, from substantially maintaining it the same from after forming to prior to implant, or increasing it from forming to prior to implant, or decreasing it from forming to prior to implant. In some embodiments Tg changes ranging from 0% change in Tg to 100% change in Tg, preferably from 5% to 50%, and more preferably 10% to 25%. In other embodiment, Tg changes by at least 0% from initial Tg, or by at least 10% of the initial or original Tg, and more preferably Tg changes by at least 25% of the original Tg.

In one embodiment, the biodegradable stent prosthesis comprising a tubular body comprising a biodegradable polymeric material, wherein the tubular body has been formed using extrusion, molding, dipping, or spraying, said biodegradable polymeric material has been treated to control Tg to between 35° C. to 55° C., and the stent prosthesis at body temperature is radially expandable and has sufficient strength to support a body lumen.

In additional embodiments, the material (e.g., polymeric material) comprising the body of the device or the biodegradable polymer or copolymer has a melting enthalpy ($\Delta H_m$) of about 7 J/g to about 50 J/g, or about 7 J/g to about 45 J/g, or about 7 J/g to about 40 J/g, or about 20 J/g to about 45 J/g, or about 20 J/g to about 40 J/g, or about 20 J/g to about 35 J/g, or about 25 J/g to about 35 J/g. In an embodiment, the material (e.g., polymeric material) comprising the body of the device or the biodegradable copolymer or polymer has a $\Delta H_m$ of about 7 J/g to about 50 J/g.

In further embodiments, the material (e.g., polymeric material) comprising the body of the device or the biodegradable copolymer or polymer has a crystallization enthalpy ($\Delta H_c$) less than about 5 J/g, or less than about 3 J/g, or less than about 1 J/g, or of about 0 J/g, during first heating. In yet further embodiments, the material (e.g., polymeric material) comprising the body of the device or the biodegradable copolymer or polymer has a crystallization enthalpy less than about 5 J/g, or less than about 3 J/g, or less than about 1 J/g, or of about 0 J/g, during first cooling. In certain embodiments, the material (e.g., polymeric material) comprising the body of the device or the biodegradable copolymer or polymer has a $\Delta H_c$ less than about 5 J/g during first heating and a $\Delta\Delta H_c$ less than about 5 J/g during first cooling.

In another embodiment, it is desired to control crystallinity in a manner to preserve the material properties after forming. For example it is desirable to treat the tubular body or the biodegradable polymeric material wherein the crystallinity of the tubular body after forming is substantially unchanged from the crystallinity of the stent prosthesis material prior to implant. In such cases, the treatment(s) of the biodegradable polymeric material controls maintaining crystallinity to be substantially the same.

In another embodiment, it is desired to control crystallinity in a manner to lower crystallinity after forming. For example it is desirable to treat the tubular body or the biodegradable polymeric material wherein the crystallinity of the stent prosthesis material prior to implant is lower than the crystallinity of the tubular body after forming.

The biodegradable stent prosthesis comprising a tubular body comprising a biodegradable polymeric material, wherein the tubular body has been formed using extrusion, molding, dipping, or spraying, said biodegradable polymeric material has an initial crystallinity and has a Tg greater than 37° C., and the stent prosthesis has a crystallinity (biodegradable stent material) that is substantially the same as the initial crystallinity and at body temperature is radially expandable and has sufficient strength to support a body lumen.

The biodegradable stent prosthesis comprising a tubular body comprising a biodegradable polymeric material, wherein the tubular body has been formed using extrusion, molding, dipping, or spraying, said biodegradable polymeric material has an initial crystallinity and has a Tg greater than 37° C., and the stent prosthesis has a crystallinity (biodegradable stent material) lower than the initial crystallinity and at body temperature is radially expandable and has sufficient strength to support a body lumen.

In another embodiment of any of the above embodiments, the Tg is greater than 30° C. and less than 60° C., preferably greater than 30° C. and less than 55° C., preferably, greater than 30° C. and less than 45° C., more preferably greater than 30° C. and less than 40° C., or more preferrably greater than 30° C. and less than 37° C.

A measure of residual/internal stress in a polymeric article or a device is shrinkage of the polymeric article or the device in a direction (e.g., longitudinal direction and/or radial direction) over a period of time when the polymeric article or the device is heated over that period of time at about the $T_g$ or above the $T_g$ or below the $T_g$ of the material comprising the polymeric article or the body of the device. In some embodiments, a tube comprised of a biodegradable polymeric material or a stent formed from such a tube exhibits shrinkage in length of no more than about 25%, 20%, 15%, 10% or 5%, and/or shrinkage in diameter of no more than about 25%, 20%, 15%, 10% or 5%, over a period of time (e.g., about 0.1, 12, 24, 48 to about 72 hours) when the tube or the stent is heated over that period of time at about the $T_g$, or above $T_g$, or below $T_g$ (e.g., about 5° C., 10° C., 20° C. or 30° C. above) the $T_g$ of the polymeric material comprising the tube or the stent body, or (e.g., about 5° C., 10° C., 20° C., or 30° C.) below the $T_g$ of the polymeric material comprising the tube or the stent body. In certain embodiments, a tube comprised of a biodegradable polymeric material or a stent formed from such a tube exhibits shrinkage in length of no more than about 10% or 5%, and/or shrinkage in diameter of no more than about 10% or 5%, over a period of time (e.g., about 1, 12, or 24 hours) when the tube or the stent is heated over that period of time at about the $T_g$ or above (e.g., about 10° C. or 20° C. to about 30° C. above) the $T_g$, or below Tg (e.g., about 5° C., 10° C., to about 30° C. below $T_g$ of the polymeric material comprising the tube or the stent body.

In a further embodiment, the biodegradable stent comprising a body which comprises a biodegradable copolymer, polymer blends, polymer blocks, polymeric mixtures (with a combination of two or more polymers) wherein suitable copolymers, including the ones described herein, but not limited to the disclosed copolymers, are configured to be capable of balloon expandable and self expanding, wherein prior to being balloon-expanded, the stent radially self-expands by about 0.001-0.025 inches, or about 0.003-0.015 inches, or 0.005-0.10 inches, or about 0.001 inches or more, or about 0.003 inches or more, or about 0.005 inches or more, or about 0.010 inches or more, or about 0.025 inch (about 635 microns) or more, or by about 0.25% or more of an initial crimped diameter of the stent, after being in aqueous condition at about 37° C. in vitro or in vivo for about 1 minute or less, or about 5 minutes or less, or about 15 minutes or less, and wherein the stent or the stent body has one or more of the following properties and retains one or more such properties during a period of use: radial strength of about 5 psi to about 20 psi, or about 5 psi or greater, or about 10 psi or greater, or about 15 psi or greater; recoil of about 3%-10% or about 10% or less; % elongation at break of about 50%, or about 100%-about 600%, or about 50% to about 300%; Tg of about 37° C.-60° C. or Tg of about 45° C.-55° C., after being in aqueous condition at about 37° C. in vitro or in vivo for about 1 minute or less, or about 5 minutes or less, or about 15 minutes or less. Other applicable properties are described in the disclosure herein.

In further embodiments, the stent self expands to a diameter that is less than the final intended deployment diameter of the stent prior to being balloon expanded to the final intended deployment diameter after being in aqueous condition at about 37° C. in vitro or in vivo for about 1 minute or less, or about 5 minutes or less, or about 15 minutes or less.

In some embodiments, the properties described herein with respect to the material (e.g., polymeric material) such as inherent viscosity, tensile strength, percent elongation at break or yield, and ductility are in the ranges stated prior to deployment of the stent, or after deployment of the stent.

A partially self-expandable stent can be retained on a balloon-catheter by any suitable means, including any means described herein. Such a stent can be restrained from prematurely self-expanding by partially or fully covering the stent with a sheath or other constraining means. After the stent is delivered to an intended site of deployment, the sheath or other constraining means can be withdrawn or removed to allow the stent to radially self-expand prior to balloon-expansion to an intended deployment diameter.

Partial self-expansion of a stent can be promoted or controlled by any of a variety of ways. For example, the body of the stent can be comprised of a polymeric material that has a $T_g$ closer to but above body temperature. The stent polymeric material having a $T_g$ closer to but above body temperature can control self-expansion of the stent. Having some differentiation between the $T_g$ of the stent polymeric material and body temperature can prevent self-expansion of a crimped stent that has some memory of the larger diameter of the polymeric tube from which it was patterned, as soon as the stent reaches body temperature. Water permeability of the polymeric material comprising the stent body can promote self-expansion of the stent, as water absorption into the stent body can cause the stent to swell and self-expand. Coating the stent with a material that is more crystalline or reduces water absorption, or incorporating an additive in the coating of the stent which reduces water absorption or reacts with water, can control self-expansion of the stent. Moreover, exposing the crimped stent to low heat (e.g., about 20° C. to about 35° C. for at least about 5, 12, 24, 36, 48 or 72 hours, or about 30° C. for at least about 2, 8, 16 or 24 hours) can control self-expansion of the stent when in aqueous condition at about 37° C. in vitro or in vivo.

In some embodiments, the biodegradable stent is capable of being crimped to, e.g., inner (luminal)] diameter of about 0.5 mm to about 4 mm, or about 1 mm to about 2 mm, or about 1.2 mm to about 1.6 mm, or about 1.3 mm to about 1.5 mm, and is capable of being radially expanded, e.g., in aqueous condition (e.g., in aqueous solution, water, saline solution or physiological conditions) at about 37° C. in vitro or in vivo, to a (e.g., inner) diameter of about 2 mm to about 8 mm, or about 2 mm to about 6 mm, or about 2 mm to about 4 mm, or about 2.5 mm to about 4 mm, or about 2.7 mm to about 3.8 mm, or about 3 mm to about 3.6 mm, without substantial damage to struts, crowns or links of the stent, or without breakage/fracture to struts, crowns or links of the stent, or without substantial recoil, or all three. In certain embodiments, the stent is capable of being crimped to a (e.g., inner) diameter of about 1.2 mm to about 1.6 mm and is capable of being radially expanded, e.g., in aqueous condition (e.g., in aqueous solution, water, saline solution or physiological conditions) at about 37° C. in vitro or in vivo, to a (e.g., inner) diameter of about 2.5 mm to about 4 mm without substantial damage to struts, crowns or links or without substantial recoil, or both.

In further embodiments, the biodegradable stent is capable of being radially expanded, e.g., in aqueous condition (e.g., in aqueous solution, water, saline solution or physiological conditions) at about 37° C. in vitro or in vivo, to an initial deployment diameter and then to a second deployment diameter that is about 1% to about 300%, or about 10% to about 300%, or about 10% to about 100%, or to a greater than the initial deployment diameter, wherein the stent is uniformly expanded; or without substantial damage and/or without fracture/breakage to struts, crowns or links of the stent or/and without substantial recoil; or at least some.

In additional embodiments, the biodegradable stent is capable of being radially expanded to an intended deployment diameter. e.g., in aqueous condition (e.g., in aqueous solution, water, saline solution or physiological conditions) at about 37° C. in vitro or in vivo with about 50% or less of crowns of the stent having a crack length of about 50% of the local crown width or shorter, or about 40% or less of the crowns having a crack length of about 40% of the local crown width or shorter, or about 30% or less of the crowns having a crack length of about 30% of the local crown width or shorter, or about 25% or less of the crowns having a crack length of about 25% of the local crown width or shorter, or about 20% or less of the crowns having a crack length of about 20% of the local crown width or shorter, or about 10% or less of the crowns having a crack length of about 10% of the local crown width or shorter, or about 5% or less of the crowns having a crack length of about 5% of the local crown width or shorter. In certain embodiments, the stent is capable of being radially expanded to an intended deployment diameter, e.g., in aqueous condition (e.g., in aqueous solution, water, saline solution or physiological conditions) at about 37° C. in vitro or in vivo, with about 25% or less of the crowns having a crack length of about 25% of the local crown width or shorter. In certain embodiment, the stent is capable of being deployed to an expanded diameter ranging from about 2 mm to about 4 mm in aqueous environment at 37° C. without breakage (fracture) in any of the struts, crowns, or links. In yet another embodiment, the stent prosthesis is capable of uniform radial expansion to an intended diameter from a crimped state without cracks, or without fracture/breakage in any of the links, struts, or crowns.

Cracking or fracture of a structure (e.g., a stent) can be analyzed by any suitable method known in the art, including without limitation by visualization using a microscope, optical comparator or scanning electron microscope.

Cracking or fracture of a biodegradable polymeric stent can be reduced by any of a variety of ways. For example, treatment of the polymeric material, control of one of Tg, crystallinity, and molecular weight. Additional treatment, design, or control of material properties include: making the body of the stent from a polymeric material that is ductile and tough under physiological conditions can reduce cracking of the stent. Water permeability of the stent polymeric material can also reduce cracking (and improve radial strength) of the stent. When water permeates into the stent body, it can swell the polymeric material of the body, which can reduce the brittleness of the polymeric material. Further, designing the stent to have a longer radius of curvature can reduce cracking or fracture/breakage. Moreover, minimizing exposure of the crimped stent to heat (in terms of, e.g., temperature and exposure time), as described herein with respect to reducing recoil, can decrease cracking of the stent. In some embodiment, the stent is at least partially configured to radially self expand to decrease cracking or breakage of struts, crowns, or links upon deployment of the stent.

The conditions and manner in which the stent is radially expanded can also affect cracking (and radial strength and recoil) of the stent. Other means of reducing cracking include without limitation allowing the stent to reach approximately body temperature, or within about 2° C. to about 25° C. of body temperature, prior to balloon radial expansion, and/or allowing time (e.g., at least about 0.1, 0.25, 0.5, 1, 2, 3, 4 or 5 minutes) for the stent to heat or/and absorb water into the stent prior to balloon radial expansion. Moreover, cracking or fracture can be decreased by radially expanding the stent substantially uniformly such that crowns of the stent open at a substantially similar angle, or within 50 degrees of one another. Furthermore, cracking or fracture can be reduced by maintaining a balloon-expanded stent at the radially expanded state with the balloon inflated for a longer time (e.g., at least about 0.1, 0.25, 0.5, 1, 2, 3, 4 or 5 minutes), and/or using a stent-delivery catheter (e.g., Lifestream™ catheter from Abbott) that allows blood to flow through while the balloon is inflated for a longer time (e.g., about 1, 3 or 5 or more minutes).

If the stent is a balloon-expandable stent (whether partially self-expandable or not), a slow rate of inflation of the balloon in the beginning of balloon-assisted expansion can reduce cracking. For example, a 3 mm stent can be deployed (radially expanded to the intended deployment diameter) by inflation of the balloon to about 6 to 16 atmospheres of pressure. During the first about 2 to 3 atmospheres of pressure, the rate of inflation of the balloon can be about 2 or 5 to about 20 seconds per atmosphere, or about 7 to about 15 seconds per atmosphere. Thereafter the balloon can be inflated at a faster rate (e.g., about 0.1 to about 5 seconds per atmosphere). After the stent is radially expanded to the intended deployment diameter, the pressure of the balloon can be maintained for a period of time, e.g., for at least about 0.1, 0.25, 0.5, 1, 2 or 3 minutes. A stent-delivery catheter (e.g., Lifestream™ catheter) that allows blood to flow through while the balloon is inflated can be employed.

Exposure of the stent to a temperature substantially equal to or above body temperature prior to and/or during radial expansion can also decrease cracking or fracture of the stent. In certain embodiments, prior to and/or during radial expansion the stent is exposed to a temperature at least about 1° C., 4° C., 8° C., 12° C. or 16° C. above body temperature, or to a temperature within about 20° C., 15° C., 10° C. or 5° C. of the $T_g$ (below or above the $T_g$), or equal to or above the $T_g$, of the material (e.g., polymeric material) comprising the body of the stent. Exposure of the stent to a temperature substantially equal to or above body temperature can be accomplished by any of a variety of means, such as use of a heating coil or element(s) in the balloon, use of heating element(s) on the surface of the balloon or the proximal shaft of the delivery catheter, heating of a liquid inside the balloon, introduction of a heated liquid into the balloon, or introduction of a heated aqueous (e.g., saline) solution into the bodily fluid (e.g., blood stream) at the site of stent deployment.

In some embodiments, fatigue of a stent is measured by the appearance of a certain number of pieces (e.g., one piece) missing from the stent, or the appearance of a certain number of fractures (e.g., two fractures), or the appearance of a certain number of cracks (e.g., three cracks), optionally under certain conditions, e.g., in dry condition or in aqueous condition (e.g., aqueous solution, water, saline solution or physiological conditions) at a certain temperature (e.g., ambient temperature or about 37° C.) in vitro or in vivo, and optionally over a certain period of time (e.g., about 1 minute to about 1, 2 or 3 weeks, or about 1, 2, 3, 4, 5 or 6 months). In certain embodiments, a crack is cracking that does not extend through the whole width of a crown, and a fracture is cracking that extends through the whole width or depth of a crown, strut, or a link, thereby breaking the crown, strut, or link.

In further embodiments, fatigue of a stent is measured based on the number of cycles (or the number of months of fatigue) before the appearance of a certain number of pieces (e.g., one piece) missing from the stent. Fatigue testing can be conducted under real-time or accelerated condition. In a real-time test, the stent can be subjected to a cyclic loading of, e.g., about 1 to 2 Hz (about 60 to 120 cycles per minute, substantially similar to a human heart beat). The test can be conducted for about 1, 2 or 3 months or longer to simulate the time period of implantation in a subject. The stent can be tested in vitro in a tube that has a radial compliance of, e.g., about 3% to 5% (the tube could radially expand by about 3% to 5%), which is substantially similar to the compliance of an artery. Under accelerated condition, the stent can be subjected to a cyclic loading greater than about 2 Hz (e.g., about 30 Hz). At 30 Hz, it would take about 6 days of continuous cycling, compared to about 90 days at 2 Hz, to attain about 3 months of fatigue. In some embodiments, the stent does not exhibit missing pieces or complete fracture of a link, a strut, or a crown after fatigue testing at one of the above conditions from about 1 day to about 6 months, or from about one week to about one month or from about 2 weeks to about 3 months.

Resistance of a stent to fatigue (or fatigue strength) can be enhanced by any of a variety of ways. For example, fatigue resistance/strength can be increased by making the stent from a polymeric material that is ductile and tough under physiological conditions, and/or by configuring the stent to be capable of radially self-expanding prior to balloon expansion to an intended deployment diameter. As another example, fatigue resistance/strength can be enhanced by the pattern or design of the stent, by decreasing the sharpness (or increasing the smoothness) of edges of crowns of the stent, and/or by increasing the uniformity of the cross-section of the crowns. As a further example, fatigue resistance/strength can be increased by minimizing exposure of the stent to extremely high temperature or extremely low temperature, and/or by minimizing bending and other stresses on the stent (e.g., when the stent is at, below or above body temperature).

In some embodiments, the biodegradable stent has a radial strength of at least about 5, 7, 10, 12, 14, 15, 16, 18, 20, 22, 24, 25 or 30 psi in aqueous condition (e.g., in aqueous solution, water, saline solution or physiological conditions) at about 37° C. in vitro or in vivo. In certain embodiments, the stent has a radial strength of about 5 psi to about 30 psi, or about 5 psi to about 25 psi, or about 10 psi to about 25 psi, or about 12 psi to about 23 psi, or about 10 psi to about 20 psi, or about 15 psi to about 20 psi, or about 16 psi to about 22 psi, in aqueous condition (e.g., in aqueous solution, water, saline solution or physiological conditions) at about 37° C. in vitro or in vivo. In certain embodiments, the stent has a radial strength of about 5 psi to about 30 psi, or about 10 psi to about 25 psi, in aqueous condition (e.g., in aqueous solution, water, saline solution or physiological conditions) at about 37° C. in vitro or in vivo.

Radial strength of a biodegradable polymeric stent can be improved in any of a variety of ways. As an example, making the stent body from a polymeric material that is ductile and tough under physiological conditions can enhance the radial strength of the stent. Further, radial strength can be increased by orienting the stent polymeric material, or the crystals, crystalline regions or chains of the polymeric material, substantially in the circumferential direction. For example, prior to patterning the stent from a polymeric tube, the tube can be radially expanded, optionally while the tube is heated at elevated temperature (e.g., at or above the $T_g$ of the tube polymeric material) and optionally with cooling of the radially expanded tube to a lower temperature (e.g., below $T_g$), to impart substantially circumferential orientation or biaxial (neither preferentially circumferential nor preferentially longitudinal) orientation to the polymeric material, or its crystals, crystalline regions or polymer chains. Crimping the stent to a smaller diameter under certain conditions can minimize radial strength loss upon expansion of the stent. In one embodiment, the stent is crimped gradually at a temperature ranging from about 25° C. to about 50° C. in 10 seconds to about 10 minutes.

The conditions and manner in which the stent is radially expanded can also affect the radial strength of the stent. Non-limiting conditions and ways in which the stent can be radially expanded to improve radial strength are described with respect to reducing cracking or improving stent expanded uniformity.

In further embodiments, the biodegradable stent exhibits a percentage radially inward recoil of about 15% or less, or about 12% or less, or about 10% or less, or about 8% or less, or about 6% or less, or about 5% or less, or about 4% or less, or about 3% or less, after a period of time (e.g., about 1, 3 or 5 days, or about 1, 2 or 3 weeks, or about 1, 2 or 3 months) after being radially expanded to an intended deployment diameter in aqueous condition (e.g., in aqueous solution, water, saline solution or physiological conditions) at about 37° C. in vitro or in vivo. In certain embodiments, the stent exhibits a percentage radially inward recoil of about 10% or less, or about 8% or less, about one week to about one month after being radially expanded to an intended deployment diameter in aqueous condition (e.g., in aqueous solution, water, saline solution or physiological conditions) at about 37° C. in vitro or in vivo.

Recoil of the stent can be reduced by any of a variety of ways. For example, the body of the stent can be comprised of a polymeric material that is ductile and tough under physiological conditions, has a $T_g$ that is not too high (e.g., about 60° C., 55° C., 50° C. or lower), and/or has a molecular weight of at least a certain value (e.g., a weight-average molecular weight of at least about 120 kDa, 150 kDa, 180 kDa, 210 kDa, 240 kDa, 500 kDa, or 900 kDa). In some embodiments, recoil of a stent comprised of a polymeric material having molecular weight in the range of about 120 kDa to about 1200 kDa is less than 10% as a result of greater entanglement of longer polymer chains. In some embodiments, the recoil of a stent comprised of a polymeric material having molecular weight in the range of about 120 kDa to about 1200 kDa is less than 10% as a result of greater entanglement of longer polymer chains. Greater entanglement of polymer chains can further reduce recoil of the polymeric tubular body having higher molecular weight.

In some embodiments, a stent is designed to have reduced recoil by being configured to be fully self-expandable or be capable of radially self-expanding (e.g., by at least about 0.01 inch or 0.025 inch, or by at least about 10% or 25% of the initial crimped diameter) prior to balloon expansion to an intended deployment diameter. In certain embodiments, the body of a partially self-expandable stent is comprised of a polymeric material that has a $T_g$ of about 35° C. to about 55 or 60° C., or about 37° C. to about 55 or 60° C., or about 40° C. to about 50 or 55° C., or about 45° C. to about 50 or 55° C. In some embodiments, during the initial partial self-expansion of the stent (e.g., by at least about 0.01 inch or 0.025 inch, or by at least about 10% or 25% of the initial crimped diameter), and/or during balloon expansion of the stent to an intended deployment diameter, the stent is exposed to a temperature within about 15° C., 10° C., 5° C. or 3° C. of the $T_g$ (below or above the $T_g$), or at or above the $T_g$. In further embodiments, the body of a fully self-expandable stent or a partially self-expandable stent is comprised of a polymeric material that has a $T_g$ of about 10° C. to about 35 or 37° C., or about 15° C. to about 35 or 37° C., or about 20° C. to about 30 or 35° C., or about 25° C. to about 30 or 35° C. In certain embodiments, a partially or fully self-expandable stent is patterned from a polymeric tube having a diameter greater than an intended deployment diameter or the maximum allowable expansion diameter of the stent, as described herein.

Recoil of a biodegradable stent can also be reduced by patterning the stent from a polymeric tube having a diameter (e.g., inner diameter) that is slightly smaller, same, or greater than (e.g., at least about −10%, −5%, 0%, 5%, 10%, 20%, 30%, 40% or 50%) the intended deployment (e.g., inner) diameter or the maximum allowable expansion (e.g., inner) diameter of the stent. After deployment in aqueous condition at about 37° C., the stent can have a tendency or ability to self-expand over time to the larger diameter of the tube from which the stent was cut if the stent is exposed to a temperature equal to or above the $T_g$ of the polymeric material comprising the stent body. The $T_g$ of a polymeric material in aqueous condition (wet $T_g$) can be lower (e.g., about 1-5° C. lower, or about 1-10° C. lower, or about 1-15° C. lower, or about 5° C., 10° C. or 15° C. lower) than its dry $T_g$. The stent's tendency or ability to self-expand to the larger tube diameter can minimize or prevent radially inward recoil of the stent after deployment.

The conditions in which the stent is crimped, and the crimped stent is treated and handled, can affect recoil of the stent. For example, recoil can be reduced by crimping the stent at a temperature at about the $T_g$ or below the $T_g$ (e.g., at least about 1° C., 5° C., 10° C., 15° C., 20° C., 25° C., 30° C., or 35° C. below the $T_g$) of the material (e.g., polymeric material) comprising the stent body. Minimizing exposure of the crimped stent to heat (in terms of, e.g., temperature and exposure time), as described herein, can also reduce recoil (and reduce cracking and improve radial strength). Heat may promote generation of a crimped-state memory and may promote erasure of some amount of the as-cut tube memory (the diameter of the tube used to pattern the stent). For example, recoil can be decreased by exposing the crimped stent to a temperature not exceeding the $T_g$, or at least about 1° C., 5° C., 10° C., 15° C., 20° C., 25° C. or 30° C. below the $T_g$, of the material (e.g., polymeric material) comprising the stent body during, e.g., stabilization of the stent in the crimped state, mounting of the crimped stent onto a balloon-catheter, sterilization of the stent delivery system (e.g., with e-beam), and storage.

The conditions and manner in which the stent is radially expanded can also affect recoil of the stent. Non-limiting conditions and ways in which the stent can be radially expanded to reduce recoil are described with respect to reducing cracking.

In additional embodiments, the biodegradable stent exhibits reduction in length of no more than about 25%, 20%, 15%, 10% or 5% after a period of time (e.g., about 1, 3 or 5 days, or about 1, 2 or 3 weeks, or about 1, 2 or 3 months) after being radially expanded to an intended deployment diameter in aqueous condition (e.g., in aqueous solution, water, saline solution or physiological conditions) at about 37° C. in vitro or in vivo. In certain embodiments, the biodegradable stent exhibits reduction in length of no more than about 10% about one week to about one month after being radially expanded to an intended deployment diameter in aqueous condition (e.g., in aqueous solution, water, saline solution or physiological conditions) at about 37° C. in vitro or in vivo. In a further embodiment, the biodegradable stent comprising a body which comprises a biodegradable polymer, or copolymer, polymer blends, polymer blocks, polymer mixture wherein the polymer material is configured to be capable of being balloon expandable and self expanding, wherein prior to being balloon-expanded, the stent self-expands by about 0.001-0.025 inches, or about 0.003-0.015 inches, or about 0.005-0.10 inches, or about 0.001 inches or more, or 0.003 inches or more, or 0.005 inches or more, or 0.010 inches or more, or 0.025 inch or more, or by about 0.25% or more of an initial crimped diameter of the stent, after being in aqueous condition at about 37° C. in vitro or in vivo for about 1 minute, or about 5 minutes or less, or about 15 minutes or less.

In a further embodiment, the biodegradable stent comprising a body which comprises a biodegradable copolymer or polymer, or mixture of 2-3 polymers, or blend of polymers, or wherein the copolymer or polymer is configured to be capable of balloon expandable and self expanding, wherein prior to being balloon-expanded, the stent radially self-expands by about 0.001-0.025 inches, or about 0.003-0.015 inches, or 0.005-0.10 inches, or about 0.001 inches or more, or about 0.003 inches or more, or about 0.005 inches or more, or about 0.010 inches or more, or about 0.025 inch or more, or by about 0.25% or more of an initial crimped diameter of the stent, after being in aqueous condition at about 37° C. in vitro or in vivo for about 1 minute or less, or about 5 minutes or less, or about 15 minutes or less, and wherein the stent or the stent body has one or more of the following properties: radial strength of about 5 psi to about 20 psi, or about 5 psi or greater, or about 10 psi or greater, or about 15 psi or greater, recoil of about 3%-10% or about 10% or less, or % elongation at break >50%, or about 100%-about 600%, or about 50% to about 300%, or Tg of about 37° C.-60° C. or Tg of about 45° C.-55° C., after being in aqueous condition at about 37° C. in vitro or in vivo for about 1 minute or less, or about 5 minutes or less, or about 15 minutes or less.

In further embodiments, the biodegradable stent comprising a body which comprises a biodegradable copolymer or polymer, wherein the copolymer or polymer is configured to be balloon expandable and self expanding, wherein prior to being balloon-expanded, the stent radially self-expands by about 0.025-0.25 inches, or about 0.50-0.15 inches, or about 0.025 inches or more, or about 0.050 inches or more, or about 0.1 inches or more, or by about 0.25% or more of an initial crimped diameter of the stent, after being in aqueous condition at about 37° C. in vitro or in vivo for about 1 minute or less, or about 5 minutes or less, or about 15 minutes or less. Optionally, the stent is constrained from self expanding using a sheath or other means and then such constraining means is removed, disengaged, or withdrawn, or released after the stent is positioned for deployment, allowing the stent to self deploy.

In further embodiments, the material comprising the body of the device or the biodegradable polymer, copolymer or polymer blend, or the tubular body comprising the biodegradable polymer, or the stent; is, or has crystals, crystalline regions, or polymer chains that are: substantially not uniaxially oriented, or circumferentially oriented, or longitudinally oriented, or biaxially oriented. In other embodiments, the biodegradable copolymer has crystals, crystalline regions, molecular architecture, structural order, orientation, or polymer chains that are: substantially not uniform, or has low degree of order, or has varying degree of order, or is not substantially oriented as a result of not performing at least one of pressurizing and stretching of the tubular body, or is at least partially oriented as a result of spraying or dipping or crystallization or recrystallization, or radiation, or is at least partially oriented as a result of solvent evaporation or annealing or radiation, or is substantially not oriented, or not uniformly oriented, or low order oriented, or varying degree oriented, or randomly oriented, as a result of spraying or dipping, or solvent evaporation, or annealing, or radiation, or crystallization or recrystallization. In yet another embodiment, the biodegradable copolymer has crystals, crystalline regions, molecular architecture, structural order, orientation, or polymer chains that are: substantially oriented, or oriented, or biaxially oriented, or uniaxially oriented, or oriented in a direction that is longitudinal, or oriented in a direction that is circumferential, or oriented in a direction that is not longitudinal or circumferential, or oriented as a result of at least one of pressurizing the copolymer tube or stretching or drawing the tube, or oriented as a result of modification or treatment. In yet further embodiments, the material comprising the body of the device or the biodegradable polymer, or copolymer or polymer blend, or the tubular body comprising the biodegradable polymer; has a tensile strength of at least about 2000 psi, or at least about 2500 psi, or at least about 3000 psi, or at least about 4000 psi, or 5000 psi. In yet further embodiments, the biodegradable polymeric material or the tubular body or the stent; has stiffness of at least 1000 MPa, or at least 1500 MPa, or at least 2000 MPa, or at least 2500 MPa, or at least 3000 MPa, or at most 5000 MPa, or at most 4000 MPa; when measured at ambient or body temperature. In yet further embodiments, the biodegradable polymeric material or the tubular body or the stent; has elastic modulus of at least 250 MPa, or at least 350 MPa, or at least 400 MPa, or at least 450 MPa, or at least 500 MPa; when measured at ambient or body temperature. In yet another embodiment, the material comprising the body or the biodegradable polymer or copolymer or polymer blend, or the tubular body comprising the biodegradable polymer, or the stent; has a percent elongation at break of about 20% to about 600%, or of about 20% to about 300%, or of about 20% to about 200%, or of about 20% to about 100%, or of about 20% to about 50%, or of about 10% to about 600%, or of about 10% to about 300%, or of about 5% to about 600%, or of about 5% to about 300%, or of about 1% to about 600%, or of about 1% to about 300%, or of about 1% to about 200%, or of about 1% to about 150%; when measured wet or dry at ambient temperature, or body temperature. In other embodiments, the biodegradable polymer, copolymer or polymer blend or tubular body comprising the biodegradable polymer material or prosthesis has stiffness dry or wet at about 37° C. of about 0.4 N/mm2 to about 2 N/mm2, or of about 0.5 N/mm2 to about 1.5 N/mm2, or of about 0.7 N/mm2 to about 1.4 N/mm2, or of about 0.8 N/mm2 to about 1.3 N/mm2. In other embodiments, the biodegradable polymer or copolymer or polymer blend or tubular body comprising the biodegradable polymer material or prosthesis; has elastic modulus dry or wet at about body temperature, of about 0.2 Pa to about 20 Pa, or of about 0.3 Pa to about 5 Pa, or of about 0.4 to about 2.5 Pa, or of about 0.5 Pa to about 1 Pa, or at least 0.2 Pa, or at least 0.3 Pa, or at least 0.4 Pa, or at least 0.5 Pa. In other embodiments, the biodegradable polymer or copolymer or polymer blend or tubular body comprising the biodegradable polymer material or prosthesis; has yield strain of at most 15%, preferably at most 10%, more preferably at most 5%, in water at 37° C. In yet another embodiment, the prosthesis has radial strength sufficient to support a body lumen. In yet another embodiment, the biodegradable polymer or copolymer or tubular body or prosthesis; has a radial strength in an aqueous environment at about 37° C. of about 3 psi to about 25 psi, or of about 5 psi to about 22 psi, or of about 7 psi to about 20 psi, or of about 9 psi to about 18 psi. In yet another embodiment, the biodegradable polymer or copolymer or tubular body or prosthesis; has a radial strength in an aqueous environment at body temperature of, greater than 3 psi, or greater than 8 psi, or greater than 10 psi, or greater than 15 psi. Radial strength can be measured in a variety of methods known in the art. For example the flat plate method or iris method or other known methods. Radial force can be measured with several methods known in the art. For example when the stent radial strength is not sufficient to support a body lumen, or the expanded diameter is reduced by a substantial amount, or reduced by at least 15%, or reduced by at least 20%, or reduced by at least 25%, or reduced by at least 50%. In other embodiments, the biodegradable copolymer, or polymer blend, or polymer, or tubular body comprising the biodegradable polymer, or prosthesis has a % recoil in an aqueous environment at 37° C. of about −20% to about 20%, or of about −15% to about 15%, or of about −10% to about 10%, or of about −10% to about 0%, or of about 0% to about 10%, or of about 3% to about 10%, or of about 4% to about 9%, or less than 25%, or less than 20%, or less than 15%, or less than 10%, or less than 5%; after expansion from a crimped state. % recoil is measured in a variety of ways in-vitro or in-vivo with methods known in the art. For example in-vitro % recoil can be measured by expanding the stent in an aqueous environment at about 37° C. inside a tube or unconstrained and measuring % recoil after expansion using laser micrometer. For an example for in-vivo % recoil measurement using QCA see, e.g., Catheterization and Cardiovascular Interventions, 70:515-523 (2007). In yet another embodiment, the biodegradable polymer or copolymer or tubular body or prosthesis, has a radial strength (in an aqueous environment at 37° C. for about 1 minute to about 1 day) of about 3 psi to about 25 psi; wherein the radial strength increases by about 1 psi to about 20 psi, or by about 2 psi to about 15 psi, or by about 3 psi to about 10 psi, or by about 4 psi to about 8 psi, after being in such an aqueous environment for about 1 day to about 60 days. In other embodiments, the biodegradable, polymer, or copolymer, or polymer blend, or tubular body, or stent; is substantially amorphous, or substantially semi crystalline, or substantially crystalline; after modification, or before modification, or after radiation, or before implantation into a mammalian body. In other embodiments, the biodegradable polymer, or copolymer or polymer blend, or tubular body, or stent; is substantially amorphous before and after modification, or substantially amorphous before a modification and substantially semi crystalline after modification, or substantially amorphous before a modification and substantially crystalline after modification, or substantially semi crystalline before a modification and substantially amorphous after modification, or substantially semi crystalline before a modification and substantially semi crystalline after modification, or substantially semi crystalline before a modification and crystalline after modification, or substantially crystalline before modification and substantially semi crystalline after a modification, or substantially crystalline before a modification and substantially amorphous after a modification, or substantially crystalline before a modification and after modification. In other embodiments, the biodegradable polymer or copolymer or polymer blend or tubular body or implant has longitudinal shrinkage of about 0% to about 30%, or of about 5% to about 25%, or of about 7% to about 20%, or of about 10% to about 15%; when heated (e.g. in an oven) at temperatures ranging from about 30° C. to about 150° C. (with or without a mandrel inserted into the copolymer or tubular body or prosthesis for a time ranging from about 30 minutes to about 24 hours), or upon expansion of the stent from a crimped state to an expanded state. In yet another embodiment, the longitudinal shrinkage is less than 30%, or less than 25%, or less than 20%, or less than 15%, or less than 10%, of the original length. In yet another embodiment, the stent or polymer material or polymer tube has longitudinal shrinkage of less than about 25% or less, or about 15% or less, or about 10% or less, or about 5% or less, or about 1-25%, or about 5-15%, after being in aqueous condition at about 37° C. in vitro or in vivo for about 1 minute or less, or about 5 minutes or less, or about 15 minutes or less, or after expansion from the crimped state. In other embodiments the stent or polymer material or polymer tube has longitudinal shrinkage of less than about 25% or less, or about 15% or less, or about 10% or less, or about 5% or less, or about 1-25%, or about 5-15%, after being in aqueous condition at about 37° C.

in vitro or in vivo for about 1 minute or less, or about 5 minutes or less, or about 15 minutes or less, or after expansion from the crimped state by configuring the polymer to be; more amorphous, or substantially amorphous, or reducing internal stresses, or reducing or minimizing orientation of the polymer, and/or optimizing design of the stent, or a combination thereof. In yet another embodiment, the amorphous, or semi-crystalline, or crystalline polymer has internal stresses, or longitudinal shrinkage of no more than 15% from before a modification to after modification. In yet another embodiment, the polymer comprises a polymer, or a co-polymer, or a blend of polymers, or a mixture of polymers, or a blend of polymer and at least one monomer, or a blend of co-polymer and at least one monomer, or a combination thereof. In yet another embodiment, the polymer blend, copolymer, or mixture of polymers, substantially does not exhibit phase separation. In yet another embodiment, the polymer or tubular body or prosthesis, is porous; such that it will grow in the radial direction by about 0.025 mm to about 1 mm when soaked in an aqueous environment at 37° C. from about 1 minute to about 15 minutes. In another embodiment, the copolymer material, or tubular body, or prosthesis, has a textured surface, or non uniform surface, or surface with ridges, or bumpy surface, or surface with grooves, or wavy surface. The distance between the peak and trough of the surface texture ranges from about 0.01 micron to about 30 micron, or from about 0.1 micron to about 20 micron, or from about 1 micron to about 15 micron.

In certain embodiments, the yield strength of the material (e.g., polymeric material) comprising the body of an endoprosthesis (e.g., a stent) is at least about 50%, 60%, 70%, 75%, 80%, 90% or 95% of ultimate strength in aqueous condition (e.g., in aqueous solution, water, saline solution or physiological conditions) at about 37° C. in vitro or in vivo. In an embodiment, the yield strength of the material (e.g., polymeric material) comprising the body of the endoprosthesis (e.g., stent) is at least about 75% of ultimate strength in aqueous condition (e.g., in aqueous solution, water, saline solution or physiological conditions) at about 37° C. in vitro or in vivo.

In some embodiments, the elastic modulus of the material (e.g., polymeric material) comprising the body of an endoprosthesis (e.g., a stent) is at least about 0.1, 0.25, 0.5, 0.75, 1, 1.5, 2, 3, 4, 5, 6, 7, 8, 9 or 10 GPa in aqueous condition (e.g., in aqueous solution, water, saline solution or physiological conditions) at about 37° C. in vitro or in vivo. In certain embodiments, the elastic modulus of the material (e.g., polymeric material) comprising the body of the endoprosthesis (e.g., stent) is at least about 0.5 or 0.75 GPa in aqueous condition (e.g., in aqueous solution, water, saline solution or physiological conditions) at about 37° C. in vitro or in vivo.

In further embodiments, the elastic recovery of a strained material (e.g., polymeric material) comprising the body of an endoprosthesis (e.g., a stent) is at most about 20%, 18%, 16%, 15%, 14%, 12%, 10%, 8%, 6%, 5%, 4% or 2% in aqueous condition (e.g., in aqueous solution, water, saline solution or physiological conditions) at about 37° C. in vitro or in vivo. In certain embodiments, the elastic recovery of a strained material (e.g., polymeric material) comprising the body of the endoprosthesis (e.g., stent) is at most about 15% or 10% in aqueous condition (e.g., in aqueous solution, water, saline solution or physiological conditions) at about 37° C. in vitro or in vivo.

In yet further embodiments, the yield strain of the material (e.g., polymeric material) comprising the body of an endoprosthesis (e.g., a stent) is at most about 15%, 14%, 12%, 10%, 8%, 6%, 5%, 4%, 3% or 2% in aqueous condition (e.g., in aqueous solution, water, saline solution or physiological conditions) at about 37° C. in vitro or in vivo. In an embodiment, the yield strain of the material (e.g., polymeric material) comprising the body of the endoprosthesis (e.g., stent) is at most about 10% in aqueous condition (e.g., in aqueous solution, water, saline solution or physiological conditions) at about 37° C. in vitro or in vivo.

In additional embodiments, the plastic strain of the material (e.g., polymeric material) comprising the body of an endoprosthesis (e.g., a stent) is at least about 10%, 20%, 30%, 40%, 50% or 60% in aqueous condition (e.g., in aqueous solution, water, saline solution or physiological conditions) at about 37° C. in vitro or in vivo. In an embodiment, the plastic strain of the material (e.g., polymeric material) comprising the body of the endoprosthesis (e.g., stent) is at least about 30% in aqueous condition (e.g., in aqueous solution, water, saline solution or physiological conditions) at about 37° C. in vitro or in vivo.

In some embodiments, the radial strength of an endoprosthesis (e.g., a stent) comprised of a biodegradable polymeric material is at least about 5, 7, 10, 12, 14, 15, 16, 18, 20, 22, 24, 25 or 30 psi in aqueous condition (e.g., in aqueous solution, water, saline solution or physiological conditions) at about 37° C. in vitro or in vivo. In certain embodiments, the radial strength of the endoprosthesis (e.g., stent) is at least about 10 or 15 psi in aqueous condition (e.g., in aqueous solution, water, saline solution or physiological conditions) at about 37° C. in vitro or in vivo.

In further embodiments, after being radially expanded to an intended deployed diameter in aqueous condition (e.g., in aqueous solution, water, saline solution or physiological conditions) at about 37° C. in vitro or in vivo, an endoprosthesis (e.g., a stent) comprised of a biodegradable polymeric material retains at least about 25%, 30%, 40%, 50%, 60%, 70%, 80%, 90% or 95% of its strength (e.g., radial strength) after a period of time (e.g., about 1, 3 or 5 days, or about 1, 2 or 3 weeks, or about 1, 2 or 3 months). In an embodiment, the endoprosthesis (e.g., stent) retains at least about 50% of its strength (e.g., radial strength) about one month after being radially expanded to an intended deployed diameter in aqueous condition (e.g., in aqueous solution, water, saline solution or physiological conditions) at about 37° C. in vitro or in vivo.

In still further embodiments, after being radially expanded to an intended deployed diameter in aqueous condition (e.g., in aqueous solution, water, saline solution or physiological conditions) at about 37° C. in vitro or in vivo, an endoprosthesis (e.g., a stent) comprised of a biodegradable polymeric material increases by at least about 5%, 10%, 20%, 25%, 30%, 40% or 50% in strength (e.g., radial strength) after a period of time (e.g., about 1, 2, 3, 4, 5 or 6 weeks). In an embodiment, the endoprosthesis (e.g., stent) increases by at least about 10% in strength (e.g., radial strength) about one day to about two weeks after being radially expanded to an intended deployed diameter in aqueous condition (e.g., in aqueous solution, water, saline solution or physiological conditions) at about 37° C. in vitro or in vivo.

In additional embodiments, an endoprosthesis (e.g., a stent) comprised of a biodegradable polymeric material exhibits a percentage radially inward recoil of about 15%, 12%, 10%, 8%, 6%, 5%, 4% or 3% or less after a period of time (e.g., about 1, 3 or 5 days, or about 1, 2 or 3 weeks, or about 1, 2 or 3 months) after being radially expanded to an intended deployed diameter in aqueous condition (e.g., in aqueous solution, water, saline solution or physiological conditions) at about 37° C. in vitro or in vivo. In certain embodiments, the endoprosthesis (e.g., stent) exhibits a percentage radially inward recoil of about 10% or less, or about 8% or less, upon deployment, or after deployment, or about one week to about one month after being radially expanded to an intended deployed diameter in aqueous condition (e.g., in aqueous solution, water, saline solution or physiological conditions) at about 37° C. in vitro or in vivo.

When the device is a stent, the stent can have any pattern and design suitable for its intended use. The stent can be implanted in a subject for treatment of a wide variety of conditions, including obstruction or narrowing of a vessel (e.g., blood vessel) or other tubular tissue or organ in the body. In certain embodiments, the biodegradable stent exhibits a percentage radially inward recoil of about 20% or less, or of about 15% or less, or of about 10% or less, or of about 8% or less, or of about 6% or less, upon deployment or after deployment of the stent, or at any time ranging from about day 0 to about day 30 after deployment in aqueous condition at about 37° C. in vitro or in vivo. In an embodiment, the stent exhibits percent recoil of about 10% or less after deployment, or after radial expansion in aqueous condition at about 37° C. in vitro or in vivo.

In one embodiment, the biodegradable stent prosthesis comprising a tubular body comprising a biodegradable polymeric material, wherein the tubular body has been formed using extrusion, molding, dipping, or spraying, said biodegradable polymeric material has been treated to control Tg to between 35° C. to 55° C., and the stent prosthesis at body temperature is radially expandable and has sufficient strength to support a body lumen and has a percent recoil lower than 15% from an expanded state.

In further embodiments, the material (e.g., polymeric material) comprising the body of the device or the biodegradable copolymer or polymer is ductile and tough. In yet further embodiments, the material (e.g., polymeric material) comprising the body of the device or the biodegradable copolymer or polymer has high tensile strength or high elongation, or both. In some embodiments, the material (e.g., polymeric material) comprising the body of the device or the biodegradable copolymer or polymer has a tensile strength of at least about 1000 psi (about 6.9 MPa), 2000 psi (about 13.8 MPa), 3000 psi (about 20.7 MPa), 4000 psi (about 27.6 MPa), 5000 psi (about 34.5 MPa), 6000 psi (about 41.4 MPa), 7000 psi (about 48.3 MPa), 8000 psi (about 55.2 MPa), 9000 psi (about 62.1 MPa) or 10,000 psi (about 68.9 MPa). In certain embodiments, the material (e.g., polymeric material) comprising the body of the device or the biodegradable copolymer or polymer has a tensile strength of at least about 3000 psi or 5000 psi. In additional embodiments, the material (e.g., polymeric material) comprising the body of the device or the biodegradable copolymer or polymer has a tensile strength of about 1000 psi to about 3000 psi, or about 3000 psi to about 5000 psi, or about 5000 psi to about 10,000 psi.

In certain embodiments, the material (e.g., polymeric material) comprising the body of the device or the biodegradable copolymer or polymer has a weight-average molecular weight ($M_W$) of at least about 60,000 daltons (60 kDa), 90 kDa, 120 kDa, 150 kDa, 180 kDa, 210 kDa, or 240 kDa, or 500 kDa, or 750 kDa, or 1000 kDa. In an embodiment, the material (e.g., polymeric material) comprising the body of the device or the biodegradable copolymer or polymer has an $M_W$ of at least about 120 kDa. In further embodiments, the material (e.g., polymeric material) comprising the body of the device or the biodegradable copolymer or polymer has an $M_W$ of about 60 kDa to about 900 kDa, or about 90 kDa to about 600 kDa, or about 120 kDa to about 400 kDa, or about 150 kDa to about 250 kDa, or about 80 kDa to about 250 kDa. In an embodiment, the material (e.g., polymeric material) comprising the body of the device or the biodegradable copolymer or polymer has a $M_W$ of about 120 kDa to about 250 kDa; before treatment, or after treatment, or the stent prosthesis In some embodiments, the material (e.g., polymeric material) comprising the body of the device or the biodegradable copolymer has a percent elongation at break, or at yield, or at failure of at least about 20%, 50%, 70%, 100%, 150%, 200%, 250%, 300%, 400%, 500% or 600%. In certain embodiments, the material (e.g., polymeric material) comprising the body of the device or the biodegradable copolymer or polymer has a % elongation at yield or break or failure of about 20% to about 600%, or about 20% to about 300%, or about 50% to about 500%, or about 50% to about 400%, or about 50% to about 300%, or about 100% to about 400%, or about 100% to about 300%, or about 70% to about 250%, or about 100% to about 250%, or about 100% to about 200%. In an embodiment, the material (e.g., polymeric material) comprising the body of the device or the biodegradable copolymer or polymer has a % elongation at break or yield or failure of about 20% to about 300%. In a further embodiment, the material (e.g., polymeric material) comprising the body of the device or the biodegradable copolymer has a tensile strength of at least about 3000 psi or 5000 psi, and a % elongation at break or failure or yield of about 20% to about 300%.

Ductility of a polymeric material can be increased by increasing the molecular weight and decreasing the % crystallinity of the polymeric material. A polymeric material of higher molecular weight can also have increased strength (e.g., tensile strength and/or radial strength).

In one embodiment, yield strength for the biodegradable polymeric stent material is at least 50% of ultimate strength, preferably at least 75% of ultimate strength, more preferably at least 90% of ultimate strength, in water at 37° C.

In one embodiment, the elastic modulus for the biodegradable metallic stent material is at least 50 GPa, preferably at least 100 GPa, more preferably at least 150 GPa.

In another embodiment, the elastic modulus for the biodegradable polymeric stent material is at least 0.5 GPa, preferably at least 0.75 GPa, more preferably at least 1 GPa, in water at 37° C.

In one embodiment, the yield strain for the biodegradable polymeric stent material is at most 10%, preferably at most 5%, more preferably at most 3%, in water at 37° C.

In one embodiment, the plastic strain for the biodegradable polymeric stent material is at least 20%, preferably at least 30%, more preferably at least 40%, in water at 37° C.

In one embodiment, the elastic recovery of the strained biodegradable polymeric stent material is at most 15%, preferably at most 10%, more preferably at most 5%, in water at 37° C.

In one embodiment, the expanded biodegradable stent in physiological conditions at least after 1 month retains at least 25%, preferably at least 40%, more preferably at least 70% of the strength or recoil.

The strength and/or crystallinity (e.g., degree of crystallinity) of the material (e.g., polymeric material) comprising the body of an endoprosthesis (e.g., a stent) can be increased by inducing or increasing orientation of crystals, crystalline regions or polymer chains of the polymeric material substantially in the radial (circumferential) direction and/or the longitudinal direction. Strength and/or crystallinity in the longitudinal direction can be increased by orienting crystals, crystalline regions or polymer chains substantially in the longitudinal direction, and strength and/or crystallinity in the circumferential direction can be increased by orienting crystals, crystalline regions or polymer chains substantially in the circumferential direction or substantially in a biaxial direction (neither preferentially circumferential nor preferentially longitudinal). Orientation of crystals, crystalline regions or polymer chains substantially in the longitudinal direction, the circumferential direction or a biaxial direction can be induced or increased by any of various methods, such as longitudinally extending, drawing, radially expanding, blow molding, pressurizing, heating or a combination thereof (performed simultaneously or sequentially), any of which can optionally be performed under vacuum. Such method(s) can be performed at any suitable stage of the process for fabricating the endoprosthesis, e.g., before the polymeric article or tube is formed (e.g., heating and/or drawing of the polymeric material by extrusion), when the polymeric article or tube is being formed, after the polymeric article or tube is formed (e.g., heating, pressurizing, longitudinally extending and/or radially expanding the tube), and/or after the endoprosthesis is formed (e.g., heating, pressurizing, longitudinally extending and/or radially expanding the endoprosthesis). In certain embodiments, orientation of crystals, crystalline regions or polymer chains is induced or increased substantially in a direction (e.g., longitudinal, circumferential or other direction) by expanding the polymeric article and/or the endoprosthesis in that direction while the polymeric article and/or the endoprosthesis is heated at elevated temperature, e.g., at or above the $T_g$ of the material (e.g., polymeric material) comprising the polymeric article and/or the endoprosthesis, and cooling the expanded polymeric article and/or endoprosthesis to a lower temperature (e.g., below $T_g$).

In further embodiments, the first biodegradable polymer or material (e.g., polymeric material) comprising the polymeric article or the body of the device is, or has crystals, crystalline regions or polymer chains that are, substantially uniaxially oriented, circumferentially oriented or longitudinally oriented. In yet further embodiments, the first biodegradable polymer or the material (e.g., polymeric material) comprising the polymeric article or the body of the device is, or has crystals, crystalline regions or polymer chains that are, substantially biaxially oriented (neither preferentially circumferentially oriented nor preferentially longitudinally oriented). In other embodiments, the first biodegradable polymer or the material (e.g., polymeric material) comprising the polymeric article or the body of the device is, or has crystals, crystalline regions or polymer chains that are, substantially not uniaxially oriented, circumferentially oriented, longitudinally oriented or biaxially oriented. In certain embodiments, the first biodegradable polymer or the material (e.g., polymeric material) comprising the polymeric article or the body of the device is, or has crystals, crystalline regions or polymer chains that are, substantially randomly oriented.

In some embodiments, the biodegradable polymeric stent material can have varying molecular architecture such as linear, branched, crosslinked, hyperbranched or dendritic.

In some embodiments, the biodegradable polymeric stent material in the invention can range from 10 kDa to 10,000 kDa in molecular weight, preferably from 100 kDa to 1000 kDa, more preferably 300 kDa to 600 kDa.

Further embodiments of the disclosure relate to a biodegradable implantable device comprising a body comprised of a material which comprises a biodegradable polylactide copolymer, wherein the material comprising the body or the polylactide copolymer is, or has crystals, crystalline regions or polymer chains that are, substantially not uniaxially oriented, circumferentially oriented, longitudinally oriented or biaxially oriented. In certain embodiments, the material comprising the body of the device or the polylactide copolymer is, or has crystals, crystalline regions or polymer chains that are, substantially randomly oriented.

In some embodiments, the material (e.g., polymeric material) comprising the body of the device or the biodegradable polymer or copolymer has small-size or relatively small-size crystals or crystalline regions, or a large number or a relatively large number of small-size or relatively small-size crystals or crystalline regions. In certain embodiments, the material (e.g., polymeric material) comprising the body of the device or the biodegradable copolymer or polymer is substantially randomly crystalline, or has substantially randomly distributed crystals or crystalline regions.

In further embodiments, the material (e.g., polymeric material) comprising the body of the device or the biodegradable copolymer or polymer is, or has crystals, crystalline regions or polymer chains that are, substantially not uniaxially oriented, circumferentially oriented, longitudinally oriented or biaxially oriented. In certain embodiments, the material (e.g., polymeric material) comprising the body of the device or the biodegradable copolymer is, or has crystals, crystalline regions or polymer chains that are, substantially randomly oriented. In still further embodiments, the material (e.g., polymeric material) comprising the body of the device or the biodegradable copolymer or polymer has substantially no preferred orientation or substantially no internal texture, or has crystals, crystalline regions or polymer chains that have substantially no preferred orientation or substantially no internal texture. In additional embodiments, the material (e.g., polymeric material) comprising the body of the device or the biodegradable copolymer or polymer is, or has crystals, crystalline regions, molecular architecture, structural order or polymer chains that are, substantially not oriented in a particular direction, uniaxially oriented, circumferentially oriented, longitudinally oriented or biaxially oriented, in certain embodiments as a result of pressurizing or expanding in a direction a polymeric article or the device comprised of the material or the biodegradable copolymer or polymer.

In additional embodiments, the material (e.g., polymeric material) comprising the body of the device or the biodegradable copolymer or polymer has a number-average molecular weight ($M_N$) of at least about 20 kDa, 30 kDa, 40 kDa, 50 kDa, 60 kDa, 70 kDa or 80 kDa. In an embodiment, the material (e.g., polymeric material) comprising the body of the device or the biodegradable copolymer or polymer has an $M_N$ of at least about 40 kDa.

In further embodiments, the material (e.g., polymeric material) comprising the body of the device or the biodegradable copolymer or polymer has an $M_W$ of at least about 60 kDa, 90 kDa, 120 kDa, 150 kDa, 180 kDa, 210 kDa or 240 kDa, and/or an $M_N$ of at least about 20 kDa, 30 kDa, 40 kDa, 50 kDa, 60 kDa, 70 kDa or 80 kDa, after the implantable device is exposed to radiation (e.g., ionizing radiation, such as e-beam or gamma radiation), or after exposure to heat and/or humidity treatment. In certain embodiments, the material (e.g., polymeric material) comprising the body of the device or the biodegradable copolymer or polymer has an $M_W$ of at least about 120 kDa or an $M_N$ of at least about 40 kDa, or both, after the device is exposed to radiation, or after exposure to heat/and or humidity treatment. In some embodiments, the material (e.g., polymeric material) comprising the body of the device or the biodegradable copolymer or polymer has an $M_W$ of about 120 kDa to about 250 kDa after the device is exposed to radiation, or after the device is exposed to heat and/or humidity treatment.

In some embodiments, the material (e.g., polymeric material) comprising the body of the device or the biodegradable copolymer or polymer has a polydispersity of about 5 or less, or about 4 or less, or about 3 or less, or about 2.5 or less, or about 2 or less, or about 1.5 or less, or about 1. In an embodiment, the material (e.g., polymeric material) comprising the body of the device or the biodegradable copolymer has a polydispersity of about 3 or less. A polymeric material of substantially low polydispersity can be prepared by any of various methods, such as ionic polymerization, living polymerization, column separation, column chromatography, size separation or gel-permeation chromatography, or a combination thereof.

In some embodiments, the material (e.g., polymeric material) comprising the body of the device or the biodegradable copolymer or polymer has an intrinsic viscosity of at least about 0.1 dl/g, or about 0.5 dl/g, or at least about 1 dl/g, or at least about 1.5 dl/g, or at least about 2 dl/g, or at least about 2.5 dl/g, or at least about 3 dl/g; optionally after the device is exposed to radiation (e.g., ionizing radiation, such as electron beam (e-beam) radiation or gamma radiation). In certain embodiments, the material (e.g., polymeric material) comprising the body of the device or the biodegradable copolymer or polymer has an inherent viscosity or an intrinsic viscosity of at least about 0.5 or at least 1 dl/g; optionally after the device is exposed to radiation. In additional embodiments, the material (e.g., polymeric material) comprising the body of the device or the biodegradable copolymer or polymer has a relative viscosity of at least about 0.2 dl/g, or at least about 0.5 dl/g, or at least about 1 dl/g, optionally after the device is exposed to radiation.

The biodegradable polymeric material comprising the body of an endoprosthesis (e.g., a stent), and the biodegradable polymeric material comprising any coating on the endoprosthesis, can have any suitable molecular architecture, such as linear, branched, hyperbranched, dendritic or crosslinked. The molecular weight (e.g., weight-average molecular weight or number-average molecular weight) of the polymeric material(s) can be about 10 kDa to about 10,000 kDa, or about 50 kDa to about 5000 kDa, or about 100 kDa to about 1000 kDa, or about 100 kDa to about 500 kDa, or about 100 kDa to about 300 kDa, or about 300 kDa to about 600 kDa. In certain embodiments, the weight-average molecular weight of the polymeric material comprising the body of the endoprosthesis (e.g., stent), or the polymeric material comprising a coating on the endoprosthesis, is about 100 kDa to about 500 kDa.

In one embodiment, controlling the orientation of the polymeric material achieves the desired crystallinity, or Tg. In another embodiment, the polymeric material orientation is controlled such that the stent is capable to be crimped from an expanded condition to a crimped condition. In another embodiment, the polymeric material orientation is controlled such that the stent is capable to be expanded to a deployed diameter from a crimped configuration. In another embodiment, the polymeric material orientation is controlled such that the stent is capable to be expanded from a crimped configuration to a deployed configuration without fracture. In another embodiment, the polymeric material orientation is controlled such that the material has sufficient strength to support a body lumen. In a preferred embodiment, the polymeric material orientation is controlled by pressurizing the polymeric material with a medium such as gas such as $CO_2$ wherein the orientation control affects crystallinity to a range from 1% to 35%, or 1% to 45%, or 1% to 55%.

Orientation of a material (e.g., polymeric material), or crystals, crystalline regions or polymer chains in the material, can be determined, measured or analyzed by any technique known in the art, including without limitation X-ray diffraction, see, e.g., D. Breiby and E. Samuelsen, *J. Polymer Science Part B: Polymer Physics,* 41:2375-2393 (2003), X-ray diffraction using a texture goniometer, see, e.g., O. Engler and V. Randle, Introduction to Texture Analysis Macrotexture, Microtexture, and Orientation Mapping, 2nd Ed., CRC Press, Boca Raton, Fla. (2010), near edge X-ray absorption fine structure (NEXAFS) spectroscopy, see, e.g., J. Stöhr, NEXAFS Spectroscopy, Springer-Verlag, Berlin (1992), scanning transmission λ-ray microscopy (STXM), see, e.g., D. Cruz et al., *Biomacromolecules,* 7:836-843 (2006), electron backscatter diffraction (EBSD) using a scanning electron microscope (see, e.g., Engler and Randle, supra), transmission electron microscopy (TEM), see, e.g., A. Donald and A. Windle, *J. Materials Science,* 18:1143-1150 (1983), and Fourier transform-infrared (FT-IR) transmission spectroscopy and IR dichroism, see, e.g., G. Lamberti and V. Brucato, *J. Polymer Science Part B: Polymer Physics,* 41:998-1008 (2003).

In addition to a biodegradable polymeric material, the polymeric article (e.g., tubular body) can comprise or be comprised of a non-degradable polymeric material, a metallic material, other material described herein, or a combination thereof. The polymeric article can be made by any suitable method, such as spraying, dipping, extrusion, molding, injection molding, compression molding or 3-D printing, or a combination thereof. In some embodiments, the polymeric article (e.g., a polymeric tube) is made by spraying a solution or mixture of a biodegradable polymer dissolved or dispersed in a solvent onto a structure (e.g., a cylindrical structure such as a mandrel). An additional biodegradable polymer, a non-degradable polymer, a drug or an additive (e.g., a strength-enhancing material), or a combination thereof, can optionally be mixed with the polymer in the solvent so that the additional material(s) are incorporated in the polymeric article. Before or after the endoprosthesis is formed from the polymeric article, one or more coatings containing a biodegradable polymer, a non-degradable polymer, a drug or an additive, or a combination thereof, can be applied to a surface of the polymeric article or to a surface of the endoprosthesis.

Additives can be added to the endoprosthesis to affect strength, recoil, or degradation rate, or combinations thereof. Additives can also affect processing of biodegradable stent material, radiopacity or surface roughness or others. Additives can be biodegradable or non-biodegradable. The additives can be incorporated in to the biodegradable stent or polymer material by blending, extrusion, injection molding, coating, surface treatment, chemical treatment, mechanical treatment, stamping, or others or combinations thereof. The additives can be chemically modified prior to incorporation in to the biodegradable stent material.

In one embodiment, the percentage in weight of the additives can range from 0.01% to 25%, preferably 0.1% to 10%, more preferably 1% to 5%.

In one embodiment, the additive includes at least nanoclay, nanotubes, nanoparticles, exfoliates, fibers, whiskers, platelets, nanopowders, fullerenes, nanosperes, zeolites, polymers or others or combination thereof.

Examples of nanoclay includes Montmorillonite, Smectites, Talc, or platelet-shaped particles, modified clay or others or combination thereof. Clays can be intercalated or exfoliated. Example of clays include Cloisite NA, 93A, 30B, 25A, 15A, 10A or others or combination thereof.

Examples of fibers include cellulose fibers such as Linen, cotton, rayon, acetate; proteins fibers such as wool or silk; plant fiber; glass fiber; carbon fiber; metallic fibers; ceramic fibers; absorbable fibers such as polyglycolic acid, polylactic acid, polyglyconate or others.

Examples of whiskers include hydroxyapatite whiskers, tricalcium phosphate whiskers or others.

In another embodiment, the additives includes at least modified starch, soybean, hyaluronic acid, hydroxyapatite, tricarbonate phosphate, anionic and cationic surfactants such as sodium docecyl sulphate, triethylene benzylammonium chloride, pro-degradant such as D2W (from Symphony Plastic Technologies), photodegradative additives such as UV-H (from Willow Ridge Plastics), oxidative additives such as PDQ (from Willow Ridge Plastics), TDPA, family of polylactic acid and its random or block copolymers or others.

In another embodiment, the additives include electroactive or electrolyte polymers, hydroscopic polymers, dessicants, or others.

In one embodiment, the additive is an oxidizer such an acids, perchlorates, nitrates, permanganates, salts or other or combination thereof.

In one embodiment, the additive is a monomer of the biodegradable polymeric stent material. For example glycolic acid is an additive to polyglycolic acid or its copolymer stent material.

In one embodiment, the additive can be water repellent monomers, oligomers or polymers such as bees wax, low MW polyethylene or others.

In another embodiment, the additive can be water attractant monomers, oligomers or polymers such as polyvinyl alcohol, polyethylene oxide, glycerol, caffeine, lidocaine or other.

In one embodiment, the additive can affect crystallinity of the biodegradable polymeric stent material. Example of additive of nanoclay to PLLA affects its crystallinity.

In further embodiments, the body of the device, or the material comprising the body of the device, or the material comprising one or more layers of the body of the device, comprises one or more additives. The additive(s) can serve any of a variety of functions, including without limitation facilitating processing of the material comprising the body (or the material comprising any coating on the body), imparting surface roughness to a surface of a polymer layer in the body or on the body (e.g., to improve adhesion of a metal layer to the polymer layer in the body or on the body of the device), imparting radiopacity to the device, and controlling physical characteristics of the material comprising the body (or the material comprising any coating on the body), such as controlling (e.g., promoting or slowing down) its degradation and/or controlling its crystallinity, enhancing its strength, and enhancing its toughness. The additive(s) can be biodegradable or non-degradable. The additive(s) can be incorporated in and/or on the body (and in and/or on any coating on the body of the device) by any suitable method, such as mixing, blending, spraying, dipping, extrusion, injection molding, coating, printing, surface treatment, chemical treatment, mechanical treatment, stamping, or a combination thereof.

In some embodiments, the weight percent of an additive in the material (e.g., polymeric material) comprising the body of the device, or the material (e.g., polymeric material) comprising a particular layer in the body, or the material (e.g., polymeric material) comprising a particular coating on the body, is about 0.01% or 0.1% to about 50%, or about 0.01% or 0.1% to about 40%, or about 0.01% or 0.1% to about 30%, or about 0.01% or 0.1% to about 25%, or about 0.05% or 0.1% to about 20%, or about 0.05% or 0.1% to about 15%, or about 0.1% to about 10% or 20%, or about 0.5% to about 10% or 20%, or about 1% to about 10% or 20%, or about 0.5% or 1% to about 5%. In certain embodiments, the weight percent of an additive in the material (e.g., polymeric material) comprising the body of the device, or the material (e.g., polymeric material) comprising a particular layer in the body, or the material (e.g., polymeric material) comprising a particular coating on the body, is about 0.1% to about 25%.

Non-limiting examples of additives include nanotubes, carbon nanotubes, carbon nano fibers, boron nanotubes, fullerenes, nanoparticles, nanospheres, nanopowders, nanoclays, zeolites, exfoliates, fibers, whiskers, platelets, polymers, monomers, oxidizers, stabilizers, antioxidants, butylated hydroxytoluene (BHT), degradation-controlling agents, buffers, conjugate bases, weak bases, getters, ionic surfactants, salts, barium salts, barium sulfate, calcium salts, calcium carbonate, calcium chloride, calcium hydroxyapatite, tricalcium phosphate, magnesium salts, sodium salts, sodium chloride, blowing agents, gases, carbon dioxide, solvents, methanol, ethanol, isopropanol, dichloromethane, dimethylsulfoxide, metals, metal alloys, semi-metals, ceramics, radiopaque agents, and contrast agents.

Examples of nanoclays include, but are not limited to, montmorillonites, smectites, bentonites, talc, particles have any desired shape (e.g., platelet-shaped particles), and modified clays. Additional examples of nanoclays include Cloisite® NA, 10A, 15A, 25A, 30B and 93A. Nanoclays can be, e.g., intercalated or exfoliated, and can serve any of a variety of functions, such as controlling crystallinity of the material (e.g., polymeric material) comprising the body of the device or a coating on the body, e.g., a nanoclay as an additive can affect crystallinity of poly(L-lactide).

Examples of fibers include without limitation plant fibers and cellulose fibers (e.g., linen, cotton, rayon and cellulose acetate), proteins fibers (e.g., wool and silk), glass fibers, carbon fibers, metallic fibers, ceramic fibers, and absorbable polymeric fibers (e.g., polyglycolic acid/polyglycolide, polylactic acid/polylactide, poly(lactide-co-ϵ-caprolactone), and polyglyconate). Examples of whiskers include, but are not limited to, hydroxyapatite whiskers and tricalcium phosphate whiskers.

The additives can be a blowing agent, which is a substance capable of producing a cellular structure in a variety of materials that undergo hardening or phase transition, such as polymers, plastics and metals. The blowing agent can be applied when the material is in a liquid stage or in a liquid solution or mixture. Blowing agents include without limitation gases (e.g., compressed gases) that expand when pressure is released, solids (e.g., soluble solids) that form pores when they leach out from the material, liquids that develop a cellular structure (e.g., cells) when they change to gases, and chemical agents that decompose or react under the influence of heat or radiation to form, e.g., a gas or a solid that can form pores when it leaches out. Chemical blowing agents include, but are not limited to, salts (e.g., ammonium and sodium salts, such as ammonium and sodium bicarbonate) and nitrogen-releasing agents.

Examples of radiopaque agents and material that can be additives include without limitation barium sulfate, gold, magnesium, platinum, platinum-iridium alloys (e.g., those containing at least about 1%, 5%, 10%, 20% or 30% iridium), tantalum, tungsten, and alloys thereof. The radiopaque agent or material can be in any suitable form (e.g., nanoparticle or microparticle), and in amounts ranging from about 0.1% to about 10%.

Contrast agents include without limitation radiocontrast agents and MRI contrast agents. Non-limiting examples of radiocontrast agents include iodine-based agents, ionic iodine-based agents, diatrizoate, ioxaglate, metrizoate, non-ionic (organic) iodine-based agents, iodixanol, iohexyl, iopamidol, iopromide, ioversol, ioxilan, barium-based agents, and barium sulfate. Non-limiting examples of MRI contrast agents include gadolinium-based agents, gadobenic acid, gadobutrol, gadocoletic acid, gadodenterate, gadodiamide, gadofosveset, gadomelitol, gadopenamide, gadopentetic acid, gadoteric acid, gadoteridol, gadoversetamide, gadoxetic acid, iron oxide-based agents, Cliavist, Combidex®, Endorem (Feridex), Resovist®, Sinerem, manganese-based agents, and mangafodipir (Mn(II)-dipyridoxyl diphosphate).

The additives can also be selected from modified starch, soybean, hyaluronic acid, hydroxyapatite, tricarbonate phosphate, Totally Degradable Plastic Additive (TDPA™), desiccants (e.g., calcium sulfate, calcium chloride, activated alumina, silica gel, montmorillonites, zeolites and molecular sieves), anionic and cationic surfactants (e.g., sodium dodecyl sulphate and triethylene benzylammonium chloride), pro-degradant additives (e.g., D2W from Symphony Plastic Technologies), photodegradative additives (e.g., UV-H from Willow Ridge Plastics), oxidative additives (e.g., PDQ from Willow Ridge Plastics), and oxidizers (e.g., acids, salts, perchlorates, nitrates and permanganates).

Furthermore, the additives can be selected from electroactive polymers, electrolyte polymers, hygroscopic polymers, and hydrophilic polymers (e.g., polylactic acid/polylactide and polyglycolic acid/polyglycolide and copolymers thereof). The additives can also be monomers of the polymeric material comprising the body of the device (or the polymeric material comprising a coating on the body). For example, glycolic acid or glycolide is an additive for a polymer containing glycolic acid/glycolide, e.g., polyglycolic acid/polyglycolide or a copolymer thereof, such as poly(lactide-co-glycolide), lactic acid or lactide is an additive for a polymer containing lactic acid/lactide, e.g., polylactic acid/polylactide or a copolymer thereof, such as poly(lactide-co-glycolide), and ε-caprolactone is an additive for a polymer containing ε-caprolactone, e.g., poly(ε-caprolactone) or a copolymer thereof, such as poly(lactide-co-ε-caprolactone). Additives that are monomers can serve any of a variety of functions, such as controlling degradation of the material (e.g., polymeric material) comprising the body of the device or a coating on the body (e.g., acidic monomers such as glycolic acid and lactic acid can promote degradation of the polymeric material), or plasticizing or softening the polymeric material, which can, e.g., reduce its crystallinity or brittleness and enhance its toughness. In other embodiments, monomers of a different type than copolymers or polymers can be used.

In some embodiments, the additives are degradation-controlling agents that control degradation of the material (e.g., polymeric material) comprising the body of the device or a coating on the body, or that control degradation of any portion of the device. Non-limiting examples of degradation-controlling agents include salts (e.g., aluminum chloride, calcium chloride, ferric chloride, magnesium chloride, sodium chloride and zinc chloride), acids (e.g., ammonium chloride, aminosulfonic acid, hydrochloric acid, hydrofluoric acid, nitric acid, phosphoric acid, sulfuric acid, hexafluorosilicic acid, sodium bisulfite, acetic acid, adipic acid, hydroxyadipic acids, citric acid, formic acid, lactic acid and oxalic acid), bases (e.g., potassium hydroxide, sodium hydroxide, calcium carbonate, potassium carbonate, sodium carbonate, potassium bicarbonate, sodium bicarbonate, phosphates, potassium phosphate, sodium phosphate, hydroxyapatites and calcium hydroxyapatite), natural and unnatural amino acids (e.g., the 20 natural amino acids in the human body), polymers with acidic or basic byproduct (e.g., polylactide and copolymers thereof, and polyglycolide and copolymers thereof), blowing agents (e.g., bromine, chlorine, nitrogen, oxygen, carbon dioxide, nitrogen-releasing agents, and ammonium and sodium salts, such as ammonium and sodium bicarbonate), and metals and metal alloys (e.g., metals and metal alloys that comprise calcium, chromium, lithium, magnesium, potassium, silicon, a silicate or sodium, or a combination thereof). Additional examples of degradation-controlling agents are described herein and in U.S. patent application Ser. No. 11/398,363, the full disclosure of which is incorporated herein by reference.

In certain embodiments, the additives are degradation-controlling agents that promote degradation of a non-degradable polymer. For example, pro-degradant additives such as D2W, photodegradative additives such as UV-H, oxidative additives such as PDQ, and Totally Degradable Plastic Additive (TDPA™) can promote degradation of non-degradable polymers such as polyethylene, polypropylene and poly(ethylene terephthalate).

In other embodiments, the additives are degradation-controlling agents that help to resist degradation of a material (e.g., a polymer, a metal or metal alloy, a biologically active agent, or another additive), such as oxidative degradation, photodegradation, high energy-exposure degradation, thermal degradation, hydrolytic degradation, acid-catalyzed degradation, or other kinds of degradation. Non-limiting examples of additives that can help to resist degradation of a material include antioxidants, e.g., vitamin C and butylated hydroxy toluene (BHT), stabilizers (e.g., xanthum gum, succinoglycan, carrageenan and propylene glycol alginate), getters (e.g., titanium-containing beads and aluminium oxide), salts (e.g., calcium chloride), and bases (e.g., potassium carbonate, sodium carbonate, potassium bicarbonate, sodium bicarbonate, sodium sulfate and magnesium sulfate).

In addition, the additives can be water-attractant substances such as glycerol, caffeine, lidocaine, monomers, oligomers or polymers (e.g., polyvinyl alcohol or polyethylene oxide). The additives can also be water-repellent substances such as monomers, oligomers, polymers (e.g., low molecular weight polyethylene) or waxy substances (e.g., beeswax). Water-attractant additives can serve any of a variety of functions, including promoting degradation of the material (e.g., polymeric material) comprising the body of the device or a coating on the body and permeation of water into the polymeric material, which can swell the polymeric material, reduce its brittleness and increase its toughness. Water-repellent additives can serve any of a variety of functions, including slowing down degradation of the material (e.g., polymeric material) comprising the body of the device or a coating on the body.

In certain embodiments, the additives are additives that reduce water absorption, act as a water barrier or react with water (designed, e.g., to control degradation of the device, control elasticity or ductility of a polymeric material comprising the device, or control self-expansion of a self-expandable device in aqueous condition at about 37° C.). For example, the additives can be metals or metal alloys that react with water, such as magnesium, magnesium alloys, iron or iron alloys. As another non-limiting example, the additives can be salts that react with water, such as calcium salts, magnesium salts or sodium salts.

Additives that might be non-degradable can be removed by a variety of means, such as by cells (e.g., macrophages and monocytes) or by excretion (e.g., when they are not used in a large amount).

In certain embodiments, the material (e.g., polymeric material) comprising the body of the device, or the material (e.g., polymeric material) comprising a particular layer of the body, comprises novolimus and an antioxidant. In an embodiment, the antioxidant is butylated hydroxytoluene (BHT). In some embodiments, the weight percent of the antioxidant in the novolimus-containing material is about 0.1% to about 2%, or about 0.1% to about 1%, or about 0.5% to about 1%. In certain embodiments, the material (e.g., polymeric material) comprising the body of the device or any particular layer or all layers of the body comprises novolimus and BHT, wherein the weight percent of the BHT in the material is about 0.1% to about 1%.

In some embodiments, the biodegradable implantable devices described herein comprise one or more reinforcement additives. The reinforcement additives can improve properties of the devices, such as strength (e.g., tensile strength, radial strength) and modulus (e.g., elastic modulus, tensile modulus). Further, the additives can increase retention or control release of a biologically active agent, e.g., as a result of physical interaction, non-covalent interaction (e.g., van der Waals interaction or hydrogen bonding), and/or covalent interaction (e.g., if the additives are functionalized) between the additive and the bioactive agent.

Non-limiting examples of reinforcement additives include nanotubes (including carbon nanotubes/nanofibers and boron nanotubes/nanofibers), fullerenes (including buckyballs), nanoparticles, nanospheres, nanopowders, nanoclays, zeolites, exfoliates, fibers (including nanofibers), whiskers, platelets and polymers. Nanoclays can be added to one or more polymers comprising the body of the device or a coating on the device by any suitable method, such as in situ polymerization intercalation, melt intercalation and solution intercalation. In certain embodiments, the reinforcement additives incorporated in the body of the device, a layer of the body or a coating on the device include carbon nanotubes. In further embodiments, the device comprising one or more reinforcement additives is a stent.

In some embodiments, the weight percent of a reinforcement additive in the material (e.g., polymeric material) comprising the body of the device, or the material (e.g., polymeric material) comprising a layer of the body, or the material (e.g., polymeric material) comprising a coating on the device, is about 0.01% or 0.1% to about 25%, or about 0.1% to about 15% or 20%, or about 0.1% or 0.25% to about 10%, or about 0.25% or 0.5% to about 5%, or about 1% to about 5%. In certain embodiments, the weight percent of a reinforcement additive is about 0.5% to about 5%, or about 1% to about 3%. In further embodiments, the volume fraction or volume percent of a reinforcement additive in the body of the device, a layer of the body or a coating on the device is about 0.05% or 0.1% to about 25%, or about 0.25% or 0.5% to about 10%, or about 0.75% or 1% to about 5%. In certain embodiments, the volume fraction or volume percent of a reinforcement additive is about 0.75% to about 5%, or about 1% to about 3%.

In certain embodiments, the material (e.g., polymeric material) comprising the body of the device, or the material (e.g., polymeric material) comprising a particular layer of the body, comprises nanotubes (e.g., carbon nanotubes, boron nanotubes) or one or more other reinforcement additives having a larger feature (e.g., length) and a smaller feature (e.g., diameter or width) such that the ratio of these two features results in a relatively high aspect ratio. In some embodiments, the average aspect ratio (e.g., length divided by diameter or width) of a reinforcement additive is about 2 to about 40,000, or about 10 or 30 to about 25,000, or about 100 to about 1000, 5000 or 10,000, or about 50 or 100 to about 500.

Incorporation of one or more reinforcement additives having a relatively high aspect ratio in the material comprising the body of the device or a layer of the body (e.g., by mixing or dispersing the additives in one or more polymers comprising the body or a layer of the body) can improve properties of the device. For example, use of such reinforcement additives can increase the strength (e.g., tensile strength, radial strength), stiffness, modulus (e.g., tensile modulus, elastic modulus), toughness, crack resistance, fatigue resistance, work to failure, and/or thermal conductivity of the device (e.g., a stent), and can decrease cracking, fatigue, creep and/or recoil of the device.

In some embodiments, the material (e.g., polymeric material) comprising the body of the device, or the material (e.g., polymeric material) comprising a particular layer of the body, comprises carbon nanotubes. Carbon nanotubes can be strong and flexible, and can enhance properties of the material, such as increasing its strength (e.g., tensile strength, radial strength) and/or modulus (e.g., elastic modulus, tensile modulus) without substantially decreasing its ductility. In certain embodiments, the device comprising carbon nanotubes is a stent.

The carbon nanotubes (CNTs) can be single-walled carbon nanotubes (SWCNTs), double-walled carbon nanotubes (DWCNTs), and/or multi-walled carbon nanotubes (MWCNTs). In certain embodiments, the number of walls of MWCNTs is about 2 to about 5, 10, 15 or 20. In an embodiment, the number of walls of MWCNTs is about 2 to about 4. MWCNTs can potentially be straighter and/or more crystalline than SWCNTs, and can potentially provide higher mechanical properties than SWCNTs. SWCNTs can comprise a graphene sheet rolled into a cylinder, and MWCNTs can comprise multiple concentric graphene cylinders. Carbon nanotubes can be produced by any suitable method, such as high-temperature evaporation using arc discharge, laser ablation, chemical vapor deposition, high-pressure carbon monoxide, or a catalytic growth process.

In some embodiments, the average length of the carbon nanotubes is about 100 nm to about 50 or 100 mm, or about 500 nm to about 0.5 or 1 mm, or about 500 nm to about 50 or 100 μm, or about 1 or 5 μm to about 50 μm, or about 10 μm to about 20 μm. In certain embodiments, the average diameter of the carbon nanotubes is about 0.4 nm to about 1 μm, or about 1 nm to about 100 or 500 nm, or about 10 or 30 nm to about 50 nm. In some embodiments, the average aspect ratio (length divided by diameter) of the carbon nanotubes is about 2 to about 40,000, or about 10 or 30 to about 25,000, or about 100 to about 1000, 5000 or 10,000. In further embodiments, the average surface area of the carbon nanotubes is about 10 to about 1000 $m^2/g$, or about 25 to about 750 $m^2/g$, or about 50 or 100 to about 500 $m^2/g$.

In additional embodiments, the purity of the carbon nanotubes is at least about 50%, 60%, 70%, 75%, 80%, 90%, 95%, 96%, 97%, 98% or 99%. In an embodiment, the purity of the carbon nanotubes is at least about 95%. In certain embodiments, impurities of carbon nanotubes include amorphous carbon, heavy metals and/or chemicals.

In certain embodiments, the material (e.g., polymeric material) comprising the body of the device or a particular layer of the body comprises carbon nanotubes in a weight percent of about 0.1% or 0.5% to about 10%, or about 0.1% or 0.5% to about 5%, or about 0.1%, 0.5%, 1%, 1.5%, 2%, 2.5%, 3%, 3.5%, 4%, 4.5%, 5%, 6%, 7%, 8%, 9% or 10%. In some embodiments, the material (e.g., polymeric material) comprising the body of the device or a particular layer of the body comprises carbon nanotubes in a weight percent of about 0.1% or 0.5% to about 3%, or about 0.1%, 0.5%, 1%, 1.5%, 2%, 2.5% or 3%. In further embodiments, the carbon nanotube-containing material comprises a polylactide homopolymer or copolymer, wherein lactide includes L-lactide, D-lactide and D,L-lactide. In certain embodiments, the material comprising the body of the device or a particular layer of the body comprises a poly(L-lactide) copolymer, e.g., poly(L-lactide-co-ε-caprolactone) or any other poly(L-lactide) copolymer described herein, and carbon nanotubes in a weight percent of about 0.1% or 0.5% to about 3%, or about 0.1%, 0.5%, 1%, 1.5%, 2%, 2.5% or 3% (e.g., about 2%).

One or more reinforcement additives can be incorporated in the body of the device or a coating on the device in any of a variety of ways. In some embodiments, one or more additives are mixed or dispersed in one or more polymers comprising the body of the device, a layer of the body or a coating on the device when the polymer(s) are untangled or lack form or crystalline structure, which can promote interaction or incorporation of the additive(s) with the polymer molecules. Substantially amorphous polymers or semi crystalline polymers or polymers of lower crystallinity can have higher loading of additives, which can result in greater increase in strength and/or toughness and/or lower creep.

In some embodiments, one or more reinforcement additives are mixed or dispersed in one or more polymers comprising the body of the device, a layer of the body or a coating on the device such that the polymer(s) contact or wet the surface of the additive(s), which can help to transfer stress from the polymer(s) to the additive(s) and increase the strength of the polymeric material. In certain embodiments, the additive(s) are substantially completely or substantially uniformly dispersed in the polymer(s), which can prevent or minimize aggregation of the additive(s) and disperse stress.

Chemical modification of additives can prevent the additives from aggregating, improve dispersion of the additives in solvents (e.g., water, organic solvents), improve dispersion of the additives in polymers, and improve interaction between the additives and polymers. For example, modification of additives can create stronger interaction between the additives and polymers, which can increase the strength and toughness of the resulting material. Non-limiting examples of modifications of additives include acid treatment, base treatment, plasma treatment, oxidation (e.g., with oxygen), functionalization of a functional group (e.g., an amino, hydroxyl or carboxyl group), and conjugation to a polymer, e.g., polyethylene glycol, poly(propionylethylenimine-co-ethylenimine). As an example, the surface of carbon nanotubes can be functionalized with carboxyl, hydroxyl, amino, amide, fluoro, alkyl, and/or other groups. Further, the surface of carbon nanotubes can be conjugated to poly(m-phenylenevinylene) having octyloxy chains, polyethylene glycol, poly(propionylethylenimine-co-ethyleneimine), polyethyleneimine, and/or other polymers, which can prevent aggregation of the nanotubes and improve dispersion of the nanotubes in a solvent or a polymeric material comprising the body of the device or a coating on the device.

The manner in which an additive is mixed with a polymer in a solvent (which can be a mixture of solvents) can influence how uniformly dispersed in the polymer the additive is. Non-limiting examples of solvents that can be used to dissolve, suspend or disperse additives include amide-containing solvents, dimethylformamide, N-methylpyrrolidone, ketones, acetone, ethers, tetrahydrofuran, halogenated solvents, dichloromethane, chloroform, Freon, Freon substitutes, monochlorobenzene, alcohols, ethanol, and methanol. In certain embodiments, an additive is slowly added (e.g., in increments or dropwise) to a solvent that may or may not contain a polymer. To aid dissolution, suspension or dispersion of the additive in the solvent, the mixture can be stirred, shaken or vortexed. The mixture can also be subjected to a relatively high RPM mixer or centrifuge, and/or exposed to ultrasound energy (homogenizer or bath). In certain embodiments, the mixture is exposed to ultrasound having a frequency no more than about 45 kHz, 35 kHz, 25 KHz or 15 kHz.

An anionic, cationic or non-ionic surfactant can be used to aid dissolution, suspension or dispersion of an additive in a solvent. Non-limiting examples of such surfactants include polyvinylpyrrolidone, polystyrenesulfonate and polyallylamine hydrochloride, sodium dodecylbenzenesulfonate, sodium lauryl sulfate, ethoxylated castor oil, polyethylene glycol, polyvinyl butyral, poly(oxy-1,2-ethanediyl), Tween surfactants (e.g., Tween 20, Tween 60), Pluronic surfactants (e.g., Pluronic F127, Pluronic L61, Pluronic L92), Triton surfactants (e.g., Triton X-100, Triton X-405), Igepal surfactants (e.g., Igepal CO-720, Igepal CO-890), and derivatives and adducts thereof. In certain embodiments, the amount of a surfactant relative to the weight of an additive is about 0.1% or 0.5% to about 20%, or about 0.1% or 0.5% to about 10%, or about 0.5% or 1% to about 7.5%, or about 0.5% or 1% to about 5%.

A solution or mixture containing one or more reinforcement additives and one or more polymers can be applied to a structure (e.g., a substantially cylindrical structure, such as a mandrel) by spraying or dipping to form a polymeric article (e.g., a polymeric tube) or a layer of the polymeric article, or can be applied by spraying or dipping to form a coating on a device (e.g., a stent). Alternatively, such a solution or mixture can optionally be filtered and then can be concentrated (e.g., by evaporation or in vacuo) to provide a material that can be used to form a polymeric article (e.g., a polymeric tube) by extrusion, 3-D printing or molding (e.g., injection molding or compression molding). The polymeric article can undergo any treatments described herein (e.g., longitudinal extension, radial expansion, heating, pressurizing, vacuuming, or exposure to radiation or carbon dioxide, or a combination thereof), which can control or improve characteristics (e.g., crystallinity, strength, toughness, residual/internal stress, and/or degradation) of the material comprising the polymeric article. A device (e.g., a stent) can be formed from the polymeric article (e.g., polymeric tube) by any suitable method (e.g., laser cutting).

In some embodiments, one or more reinforcement additives are mixed with or dispersed in one or more polymers having an adjustable or controllable $T_g$ in the body of the device, a layer of the body or a coating on the device. In certain embodiments, the $T_g$ of a polymer mixed with a reinforcement additive is substantially similar to the $T_g$ of the polymer not mixed with the additive (e.g., as a result of a lack of chemical interaction between the polymer and the additive). Physical interaction between a polymer and an additive can be maximized, without chemical interaction between the polymer and the additive, e.g., by having the polymer wrap around (e.g., helically) the additive. In other embodiments, the $T_g$ of a polymer mixed with a reinforcement additive is higher than the $T_g$ of the polymer not mixed with the additive, which can be a result of chemical interaction (e.g., non-covalent interaction, such as van der Waals interaction or hydrogen boding) between the polymer and the additive. In yet other embodiments, the $T_g$ of a polymer mixed with a reinforcement additive is lower than the $T_g$ of the polymer not mixed with the additive, which can be a result of a lack of chemical interaction between the polymer and the additive and/or a lack of void or free surface between the polymer and the additive.

In additional embodiments, one or more reinforcement additives incorporated in the body of the device, a layer of the body or a coating on the device are oriented in a substantially similar direction. In certain embodiments, the additive(s) are oriented in a direction of stress (e.g., radial direction), which can enhance the tensile modulus, stiffness and/or yield strength of the material (e.g., polymeric material) comprising the body of the device or a coating on the device. Orientation of the additive(s) can be promoted by electric or magnetic field before the material becomes hardened, and can be controlled by temperature and shear stress (e.g., longitudinal or radial). Orientation of the additive(s) can also be promoted by spinning a substantially cylindrical structure (e.g., a mandrel) in the direction of desired orientation while applying a solution or mixture of polymer(s) and the additive(s) onto the mandrel by spraying or dipping.

The biodegradable implantable device can be any of a wide variety of implantable devices, and can be implanted in a subject for treatment of a wide variety of diseases, disorders and conditions. In some embodiments, the device substantially completely degrades within about 4 years, or within about 3 years, or within about 2 years, or within about 1 year, or within about 6 months in aqueous condition at about 37° C. in vitro or in vivo. In an embodiment, the device substantially completely degrades within about 2 years in aqueous condition at about 37° C. in vitro or in vivo.

In one embodiment, the biodegradable stent material degrades substantially within 2 years, preferably within 1 year, more preferably within 9 months.

In one embodiment, the biodegradable polymeric stent materials degrades by at least bulk erosion, surface erosion, or combination thereof.

In one embodiment, the biodegradable polymeric stent material degrades by at least hydrolytic degradation, enzymatic degradation, oxidative degradation, photo degradation, degradation under physiological environment or combination thereof.

In some embodiments, the biodegradable device described herein substantially completely degrades within about 48 months, or within about 42 months, or within about 36 months, or within about 30 months, or within about 24 months, or within about 18 months, or within about 12 months, or within about 9 months, or within about 6 months, or within about 3 months in aqueous condition (e.g., in aqueous solution, water, saline solution or physiological conditions) at about 37° C. in vitro or in vivo. In an embodiment, the device substantially completely degrades within about two years in aqueous condition (e.g., in aqueous solution, water, saline solution or physiological conditions) at about 37° C. in vitro or in vivo.

In certain embodiments, the device substantially completely degrades within about 24 months, 18 months, 12 months, 9 months or 6 months, and the body of the device is comprised of the biodegradable copolymer and an additional biodegradable polymer and/or a non-degradable polymer, wherein degradation of at least one of the polymers (homopolymer or copolymer) is promoted in the presence of the other polymers. For example, degradation of at least one of the polymers (e.g., a lactide-, glycolide- or caprolactone-containing homopolymer or copolymer) can provide an acidic or basic by-product (e.g., lactic acid, glycolic acid or caproic acid) that promotes degradation of at least one of the other polymers.

Without limiting to any mechanisms of action, it is believed that certain levels of inflammation are related to the pH of the degradation by products of the biodegradable devices and biodegradable polymers described herein. In some embodiments, the pH of lactic acid produced from lactide based polymers is about 3 to about 5 and the pH of glycolic acid produced from glycolide based polymers is from about 2 to about 5. In some preferred embodiments, the pH of the by products produced from the degradation of the biodegradable devices and biodegradable polymers is about 2 to about pH 7 and in certain other embodiments the pH is acidic and is higher than about 5. Following in vivo implantation of the implantable device, prosthesis, and articles described herein, the following semi-quantitative scores may be obtained to determine the effect of the device, prosthesis, or article—injury score, inflammation score, fibrin score, endothelialization score, and neointimal immaturity score. Such scores are obtained following examination of suitable tissue samples under a light microscope. Such scores may be related to the acid degradation by products of the material (e.g., polymeric material). The injury score is related to the laceration of the internal elastic lamina, the inflammation score is related to the amount of inflammatory cells at the implant location, fibrin score is related to the amount of fibrin, endothelialization score is related to the % of artery circumference covered by endothelium, and the neointimal immaturity score is related to the neointimal containing hypocellular areas. In preferred embodiments, following implantation the implantable device, prosthesis, and articles described herein provide low or medium scores for the injury score, inflammation score, fibrin score, endothelialization score, and neointimal immaturity score. For example, if the scoring scheme is 0 for no inflammation and 3 for high inflammation, it is preferred to have a mean score or 0, 1, or 2, or 2.5. Such inflammation scores, in some embodiments, are maintained for the entire period of use. Also, in some embodiments, the inflammation scores are maintained at 7 day or less, or 28 day or less, or about 60 day or less, or about 90 day or less.

In some embodiments, the device decreases in mass by about 50% or more within about 24 months, or within about 18 months, or within about 12 months, or within about 9 months, or within about 6 months, or within about 3 months in aqueous condition (e.g., in aqueous solution, water, saline solution or physiological conditions) at about 37° C. in vitro or in vivo. In an embodiment, the device decreases in mass by about 50% or more within about one year in aqueous condition (e.g., in aqueous solution, water, saline solution or physiological conditions) at about 37° C. in vitro or in vivo.

In additional embodiments, the average mass loss of the device, or the average mass loss of the material comprising the body of the device, or the average mass loss of the material comprising a coating on the device, is about 0.05% per day to about 3% per day, or about 0.075% per day to about 2% per day, or about 0.1% per day to about 1% per day, or about 0.14% per day to about 1.1% per day, or about 0.1% per day to about 0.75% per day, or about 0.15% per day to about 0.8% per day, or about 0.14% per day to about 0.6% per day, or about 0.2% per day to about 0.6% per day, or about 0.25% per day to about 0.5% per day. In an embodiment, the average mass loss of the device is about 0.14% per day to about 0.6% per day.

Degradation of the body of the device and/or a coating on the device may occur in multiple phases, such as a slower degradation rate in one phase and a faster degradation rate in another phase. In some embodiments, the body of the device and/or a coating on the device degrade at a slower rate in an initial phase and at a faster rate in a later phase. In other embodiments, the body of the device and/or a coating on the device degrade at a faster rate in an initial phase and at a slower rate in a later phase. Degradation may be uniform along or throughout the body of the device and/or a coating on the device, or may be variable along or throughout the body of the device and/or a coating on the device.

Degradation of the device can be controlled by any of a variety of ways. As an example, the body of the device can be comprised of a polymer that has a weight-average molecular weight of a certain value or in a certain range of values. For example, using a polymer of lower weight-average molecular weight can result in shorter degradation time. As another example, the body of the device can comprise a polymer, e.g., poly(L-lactide-co-ε-caprolactone), and/or a coating on the device can comprise a polymer, e.g., poly(L-lactide-co-glycolide)], that is amorphous, hydrophilic or water-permeable to promote degradation of the body and/or the coating. As a further example, the body of the device and/or a coating on the device can comprise a more crystalline polymer, e.g., poly(L-lactide), that absorbs less water over time to slow down degradation of the body and/or the coating.

As yet another example, the body of the device and/or a coating on the device can comprise one or more additives that promote absorption of water, react with water or promote hydrolysis of the material(s), e.g., polymeric material(s), comprising the body and/or the coating, which can promote degradation of the body and/or the coating. As a further example, the body of the device and/or a coating on the device can comprise one or more additives that reduce water absorption or act as a water barrier, which can slow down degradation of the body and/or the coating.

Furthermore, the body of the device can comprise features in and/or on the body, and/or a coating on the device can comprise features in and/or on the coating, which promote degradation of the body and/or the coating. Examples of degradation-promoting features include without limitation openings, pores (including partial pores and through pores), holes (including partial holes and through holes), voids, recesses, pits, cavities, trenches, reservoirs and channels. Such features can allow water to penetrate into the body and/or the coating, and/or can collect water and any degradation by-product(s), e.g., acidic or basic by-product(s) of degradation of polymer(s), to promote degradation of the polymer(s) and any metal(s) or metal alloy(s) comprising the body and/or the coating. Additional examples of degradation-promoting features include corrosion-inducing features described in U.S. patent application Ser. No. 11/398,363.

In some embodiments, the material (e.g., polymeric material) comprising the body of an endoprosthesis (e.g., a stent) substantially degrades within about 2 years, or within about 1.5 years, or within about 1 year, or within 9 months, or within about 6 months, or within about 3 months in aqueous condition (e.g., in aqueous solution, water, saline solution or physiological conditions) at about 37° C. in vitro or in vivo.

In additional embodiments, an endoprosthesis (e.g., a stent) comprised of a biodegradable polymeric material substantially completely degrades within about 4 years, or within about 3.5 years, or within about 3 years, or within about 2.5 years, or within about 2 years, or within about 1.5 years, or within about 1 year, or within about 9 months, or within about 6 months, or within about 3 months in aqueous condition (e.g., in aqueous solution, water, saline solution or physiological conditions) at about 37° C. in vitro or in vivo. In an embodiment, the endoprosthesis (e.g., stent) substantially completely degrades within about two years in aqueous condition (e.g., in aqueous solution, water, saline solution or physiological conditions) at about 37° C. in vitro or in vivo.

The material (e.g., polymeric material) comprising the body of an endoprosthesis (e.g., a stent), and the material (e.g., polymeric material) comprising any coating on the endoprosthesis, can degrade by bulk erosion and/or surface erosion. The material(s), e.g., polymeric material(s), can degrade by any mechanism, such as degradation under physiological conditions, hydrolytic degradation, enzymatic degradation, oxidative degradation, photo-degradation, or a combination thereof.

The body of the device can be formed from a polymeric material made by any suitable method, such as spraying, dipping, extrusion, molding, injection molding, compression molding, or three-dimensional (3-D) printing, or a combination thereof. In certain embodiments, the body of the device is formed from a polymeric article made by spraying a solution or mixture containing at least the biodegradable copolymer or polymer and at least one solvent onto a structure. When the device is a stent, a stent can be laser-cut from a polymeric tube made by spraying the polymer solution or mixture onto a mandrel. In another embodiment, the tubular body comprising the biodegradable polymer is patterned into a stent using (3-D) printing or laser cut. In another embodiment, the tubular body comprising the biodegradable polymer is formed using extrusion or spraying or dipping, or molding, and is patterned into a stent. In certain embodiments, the stent or body of the device comprises one or more additional polymer layers, and/or one or more metal or metal alloy layers, the additional polymer layer(s) of the polymeric material can be formed by spraying additional solution(s) or mixture(s) containing a biodegradable polymer, and/or the metal layer(s) can be formed by applying metal film(s), foil(s) or tube(s). In some embodiments, a polymer solution or mixture can contain one or more additional biodegradable polymers and/or one or more non-degradable polymers, and can also contain one or more biologically active agents and/or one or more additives. In another embodiment, the stent or tubular body comprises radiopaque markers. Radiopaque markers can be metallic such as gold, platinum, iridium, bismuth, or combination thereof, or alloys thereof. Radiopaque markers can also be polymeric material. Radiopaque markers can be incorporated in the stent or tubular body when it is being formed or incorporated into the stent or the tubular body after forming.

In some embodiments, the body of the biodegradable material or implant or the body comprising the biodegradable polymer or co-polymer or polymer blend, is substantially a tube. In other embodiments, it is substantially oval, or has the shape of substantially the anatomy in which the implant is to be deployed into, or substantially the shape in which the anatomy is desired to be shaped into. The shape of the body may depend on the structure used to form the body shape.

One or more coatings can be applied onto the body of the device. Each of the coatings can contain one or more biodegradable polymers, one or more non-degradable polymers, one or more metals or metal alloys, one or more biologically active agents, or one or more additives, or a combination thereof. The coating(s) can serve any of a variety of functions, including controlling degradation of the body of the device, improving or controlling physical characteristics (e.g., strength, recoil, toughness) of the device, and delivering one or more biologically active agents to a site of treatment.

In additional embodiments, the biodegradable implantable device comprises a first coating disposed over or adjacent to at least a portion of the body of the device, wherein the first coating comprises a biodegradable polymer or a non-degradable polymer or both. The biodegradable polymer of the first coating can be any biodegradable polymer described herein, and the non-degradable polymer of the first coating can be any non-degradable polymer described herein. In certain embodiments, the biodegradable polymer of the first coating is a polylactide homopolymer or copolymer, wherein lactide includes L-lactide, D-lactide and D,L-lactide. In some embodiments, the biodegradable polymer of the first coating is a copolymer of L-lactide and glycolide in a weight or molar ratio of about 70:30 to about 99.9:0.1, or about 75:25 to about 95:5, or about 80:20 to about 90:10, or about 82:18 to about 88:12. In an embodiment, the biodegradable polymer of the first coating is a copolymer of lactide such as L-lactide and glycolide in a weight or molar ratio of about 85:15. In other embodiments, the biodegradable polymer of the first coating is lactide such as poly(L-lactide).

In further embodiments, the first coating comprises one or more biologically active agents. The biologically active agent(s) of the first coating can be any biologically active agent described herein.

In still further embodiments, the first coating comprises one or more additives. The additive(s) of the first coating can be any additive described herein. In some embodiments, the additive(s) of the coating are additive(s) that reduce water absorption, act as a water barrier or react with water (designed, e.g., to control degradation of the device or self-expansion of a self-expandable device). The additive(s) can form a thin layer, or be incorporated in a coating, on any surface of the device (e.g., the luminal surface and/or the abluminal surface of a stent). As a non-limiting example, the additive(s) can be waxy substances, such as beeswax. As another example, the additive(s) of the coating can be salts that react with water, such as calcium salts, magnesium salts or sodium salts. As a further example, the additive(s) can be metals or metal alloys that react with water, such as magnesium, magnesium alloys, iron or iron alloys. The metals or metal alloys can be in any suitable form, such as nanoparticles, microparticles or colloids.

In additional embodiments, the biodegradable implantable device comprises a second coating disposed over or adjacent to at least a portion of the first coating, wherein the second coating comprises a biodegradable polymer or a non-degradable polymer or both. The biodegradable polymer of the second coating can be any biodegradable polymer described herein, and the non-degradable polymer of the second coating can be any non-degradable polymer described herein.

In further embodiments, the second coating comprises one or more biologically active agents. The biologically active agent(s) of the second coating can be any biologically active agent described herein. In yet further embodiments, the second coating comprises one or more additives. The additive(s) of the second coating can be any additive described herein.

The biodegradable implantable device can comprise a third, fourth or additional coating, as generally described for the first coating and the second coating.

In some embodiments, at least one coating (e.g., the first coating) comprises myolimus or novolimus. In further embodiments, at least one coating (e.g., the first coating) comprises novolimus and an antioxidant. In an embodiment, the antioxidant is butylated hydroxytoluene (BHT). In certain embodiments, the weight percent of the antioxidant in the novolimus-containing coating is about 0.1% to about 2%, or about 0.1% to about 1%, or about 0.5% to about 1%. In some embodiments, at least one coating (e.g., the first coating) comprises novolimus and BHT, wherein the weight percent of the BHT in the coating is about 0.1% to about 1%.

In further embodiments, at least one coating comprises an antioxidant. In an embodiment, the antioxidant is butylated hydroxytoluene (BHT). In certain embodiments, the weight percent of the antioxidant in the coating is about 0.1% to about 10%, or about 0.1% to about 5%, or about 0.5% to about 3%, of the percent weight of coating. In another embodiment, the at least one coating comprising an antioxidant is a top coating.

In certain embodiments, at least one coating of the device comprises an anti-proliferative agent, anti-mitotic agent, cytostatic agent, anti-migratory agent or anti-inflammatory agent. In additional embodiments, at least one coating of the device comprises an anti-proliferative agent, anti-mitotic agent, cytostatic agent, anti-migratory agent or anti-inflammatory agent, and at least one coating (whether the same or different coating) comprises an anticoagulant, anti-thrombotic agent, thrombolytic agent, anti-thrombin agent, anti-fibrin agent or anti-platelet agent. In further embodiments, the body of the device comprises an anti-proliferative agent, anti-mitotic agent, cytostatic agent, anti-migratory agent or anti-inflammatory agent, and at least one coating of the device comprises an anticoagulant, anti-thrombotic agent, thrombolytic agent, anti-thrombin agent, anti-fibrin agent or anti-platelet agent. In yet further embodiments, the body of the device comprises an anticoagulant, anti-thrombotic agent, thrombolytic agent, anti-thrombin agent, anti-fibrin agent or anti-platelet agent, and at least one coating of the device comprises an anti-proliferative agent, anti-mitotic agent, cytostatic agent, anti-migratory agent or anti-inflammatory agent.

In additional embodiments, the body of a substantially tubular device (e.g., a stent) has an outer (abluminal) layer that contains an anti-proliferative agent, anti-mitotic agent, cytostatic agent, anti-migratory agent or anti-inflammatory agent for preventing or reducing, e.g., any proliferative or inflammatory response at the treated tissue, and has an inner (luminal) layer that contains an anticoagulant, anti-thrombotic agent, thrombolytic agent, anti-thrombin agent, anti-fibrin agent or anti-platelet agent for preventing or reducing, e.g., any coagulation or thrombosis formation of blood flowing through the device. In further embodiments, the outer (abluminal) surface of a substantially tubular device (e.g., a stent) has a coating that contains an anti-proliferative agent, anti-mitotic agent, cytostatic agent, anti-migratory agent or anti-inflammatory agent, and the inner (luminal) surface of the device has a coating that contains an anticoagulant, anti-thrombotic agent, thrombolytic agent, anti-thrombin agent, anti-fibrin agent or anti-platelet agent.

In some embodiments, the thickness (e.g., average thickness) of each of the first coating and any additional coating(s) independently is about 20 microns or less, or about 15 microns or less, or about 10 microns or less, or about 5 microns or less, or about 4 microns or less, or about 3 microns or less, or about 2 microns or less, or about 1 micron or less, or about 0.1 micron or less, or about 0.1 micron or less. In certain embodiments, the thickness (e.g., average thickness) of the first coating is about 5 microns or less, or about 3 microns or less.

In further embodiments, the biodegradable copolymer or polymers and any additional biodegradable polymer(s), and optionally any non-degradable polymer(s), comprising the body of the device, a layer of the body or a coating on the body are sufficiently biocompatible and at least some degrade into by-products (e.g., acidic, basic or neutral substances corresponding to monomers of the polymers) that are at least some naturally present in the body of a subject or do not cause significant harmful effect to (e.g., significant injury or toxicity to or significant immunological reaction in) the body of the subject. In additional embodiments, any corrodible metal(s) or metal alloy(s), and optionally any non-corrodible metal(s) or metal alloy(s), comprising the body of the device, a layer of the body or a coating on the body are biocompatible and degrade into by-products that are naturally present in the body of a subject or do not cause significant harmful effect to (e.g., significant injury or toxicity to or significant immunological reaction in) the body of the subject.

In certain embodiments, the body of the device, a particular layer of the body or a coating on the device, or the material (e.g., polymeric material) comprising the body of the device, a particular layer of the body or a coating on the body, is substantially non-porous. In other embodiments, the body of the device, a particular layer of the body or a coating on the device, or the material (e.g., polymeric material) comprising the body of the device, a particular layer of the body or a coating on the device, is substantially porous.

In another embodiment, the biodegradable polymeric material is treated at least by heat at a temperature above Tg, preferably between Tg-50 C above Tg, before patterning for a time period ranging from 10 seconds to 5 hours (at a diameter that is substantially the same as the formed diameter, or at a diameter that is substantially the same as the patterned diameter, or at a diameter that is greater than the nominal deployment diameter of the stent), and then crimping the stent (to a smaller diameter than patterned diameter, or to a smaller diameter than formed diameter, or to a smaller diameter than nominal deployed diameter of the stent) onto a delivery system at a temperature below Tg for a time period ranging from ten seconds to 60 minutes. The stent at body temperature is capable to expand from a crimped configuration to a deployed configuration with sufficient strength to support a body lumen. Optionally, the biodegradable polymeric material is treated at least by heat at a temperature above Tg, preferably between Tg-50° C. above Tg, after patterning for a time period ranging from 10 seconds to 5 hours (at a diameter that is substantially the same as the formed diameter, or at a diameter that is substantially the same as the patterned diameter, or at a diameter that is greater than the nominal deployment diameter of the stent), before crimping to a smaller diameter as described above.

An example is a biodegradable stent comprising a polymeric material formed optionally into a tubular body wherein the polymeric material comprises lactide-co-caprolactone (or a blend of lactide and caprolactone). The tubular body is formed optionally by spraying the polymeric material onto a mandrel. DCM (or other suitable solvent capable of dissolving completely the polymeric material) is incorporated into the solution such that the amount of DCM after treatment is less than 1.5% by weight of the polymeric material. The tubular body is treated by heating at a temperature above Tg of the polymeric material for a time period ranging from 10 seconds to 5 hours, and/or cooling at a temperature below Tg of the polymeric material, is patterned at substantially the same diameter as the formed diameter, and is crimped onto a delivery system at a temperature below Tg of the polymeric material. The stent at body temperature (about 37° C.) is expandable from the crimped configuration to an expanded diameter that is 1.2 times the nominal deployment diameter (labeled diameter) of the stent without fracture and having sufficient strength to support a body lumen.

In another embodiment, the tubular polymeric material is treated substantially without increasing the outer diameter of the tubular material or without substantially changing the diameter of the tube; before patterning or after patterning. In another embodiment, the polymeric tube is treated to increase the inner diameter of the tubular polymeric material without substantially increasing the outer diameter of the polymeric tube or without increasing the outer diameter of the tubular body. Examples include treatment of stent or tubular body at substantially the same diameter of the formed polymeric tube outer diameter, by pressure, and/or heat at a temperature above Tg, and/or stretching; before patterning; and then patterning the tubular body before crimping the stent to a smaller diameter onto a delivery system at a temperature below Tg. The stent at body temperature is capable to expand from a crimped configuration to an expanded configuration and have sufficient strength to support a body lumen. For example, a 4.00 mm outer diameter and 3.70 mm inner diameter polymeric tube comprising 85:15 poly(L-lactide-co-glycolide) formed by extrusion, spraying, dipping, or the like. This tube is placed inside a metal (or glass) mold with approximately 4.0 mm diameter cylindrical hole (inner diameter of the mold), (or optionally 4.0 mm inner diameter mold, or optionally less than 4.0 mm ID mold, or optionally 4.1 mm ID mold, or optionally a mold ID with 0.9-1.15 times the formed OD of the polymeric material, or optionally a mold ID with 0.9-1.1, times the formed OD of the polymeric material). The mold optionally could be composed of two halves for ease of tube placement and removal. The mold and/or the polymeric material is heated to above the polymeric material Tg. The ID of the polymeric material is pressurized at pressure(s) ranging from 100 psi to 5000 psi in a fraction of a second to 5 minutes, and the polymeric material is optionally stretched by an amount ranging from 10% to 500% of the polymeric material length in a time ranging from a fraction of a second to 5 minutes. The polymeric material is optionally cooled at a temperature below Tg in a time ranging from a fraction of a second to 50 minutes. The compressed polymeric tubing with approximately 4.00 mm outer diameter (+/−0.1 mm) and an inner diameter ranging from 3.8 to approximately 3.6 mm inner diameter is then removed. The wall of the polymeric tube in this example is compressed approximately 0.0005". The modified tube is patterned at substantially the same diameter, and subsequently coated with a drug or drug-polymer and subsequently crimped onto a delivery system at a temperature below Tg of the polymeric material and then sterilized. The stent at body temperature (about 37° C.) is expandable from the crimped configuration to an expanded diameter having sufficient strength to support a body lumen.

In another embodiment, the stent at body temperature is expandable from a crimped configuration to an expanded configuration and have sufficient strength to support a body lumen wherein the stent expands further in the body lumen to a diameter larger than the deployed diameter of the stent.

In another embodiment, the stent at body temperature is expandable from a crimped configuration to an expanded configuration and have sufficient strength to support a body lumen after an inward recoil of less than 15% (or between 1% and 15% inward recoil, or between 2%-10%) from the expanded configuration wherein the stent further expands in the body to a diameter larger than the deployed diameter (or expanded configuration) of the stent. The further expansion of the stent diameter or area or volume by at least 5%, by at least 10%, or by at least 15% larger than the deployed diameter. The further expansion of the scaffold in the body lumen occurs after deployment in the body, within 7 days, within 30 days, within 6 months, within 1 year, or within 2 years of the deployment of the stent in the body.

In another embodiment, the stent at body temperature is expandable from a crimped configuration to an expanded configuration and have sufficient strength to support a body lumen after an inward recoil of less than 15% (or between 1% and 15% inward recoil, or between 2%-10%) from the expanded configuration wherein the stent further expands in the body to a diameter larger than the deployed diameter (or expanded configuration) of the stent and wherein the lumen further expands to a diameter (or area or volume) larger than lumen diameter (or area or volume) at deployment. The further expansion of the lumen diameter or area or volume is by at least 5%, by at least 10%, or by at least 15% larger than the lumen diameter or area or volume at deployment. The further expansion of the body lumen occurs after deployment of the stent in the body, within 7 days, within 30 days, within 6 months, within 1 year, or within 2 years after the deployment of the stent in the body. The stent and body lumen diameter or area or volume can be measured by QCA, IVUS, OCT, or MSCT.

In further embodiments, the body of the device, or the stent, or the material comprising the body of the device, or the material comprising one or more layers of the body of the device, comprises one or more biologically active agents. In some embodiments, the biologically active agent(s) are selected from the group consisting of anti-proliferative agents, anti-mitotic agents, cytostatic agents, anti-migratory agents, immunomodulators, immunosuppressants, anti-inflammatory agents, anticoagulants, anti-thrombotic agents, thrombolytic agents, anti-thrombin agents, anti-fibrin agents, anti-platelet agents, anti-ischemia agents, anti-hypertensive agents, anti-hyperlipidemia agents, anti-diabetic agents, anti-cancer agents, anti-tumor agents, anti-angiogenic agents, angiogenic agents, anti-bacterial agents, anti-fungal agents, anti-chemokine agents, and healing-promoting agents. In certain embodiments, the body of the device comprises an anti-proliferative agent, anti-mitotic agent, cytostatic agent or anti-migratory agent. In further embodiments, the body of the device comprises an anticoagulant, anti-thrombotic agent, thrombolytic agent, anti-thrombin agent, anti-fibrin agent or anti-platelet agent in addition to an anti-proliferative agent, anti-mitotic agent, cytostatic agent or anti-migratory agent. It is appreciated that specific examples of biologically active agents disclosed herein may exert more than one biological effect.

Examples of anti-proliferative agents, anti-mitotic agents, cytostatic agents and anti-migratory agents include without limitation inhibitors of mammalian target of rapamycin (mTOR), rapamycin (also called sirolimus), deuterated rapamycin, TAFA93, 40-O-alkyl-rapamycin derivatives, 40-O-hydroxyalkyl-rapamycin derivatives, everolimus {40-O-(2-hydroxyethyl)-rapamycin}, 40-O-(3-hydroxy)propyl-rapamycin, 40-O-[2-(2-hydroxy)ethoxy]ethyl-rapamycin, 40-O-alkoxyalkyl-rapamycin derivatives, biolimus {-40-O-(2-ethoxyethyl)-rapamycin}, 40-O-acyl-rapamycin derivatives, temsirolimus {-40-(3-hydroxy-2-hydroxymethyl-2-methylpropanoate)-rapamycin, or CCI-779}, 40-O-phospho-containing rapamycin derivatives, ridaforolimus (40-dimethylphosphinate-rapamycin, or AP23573), 40(R or S)-heterocyclyl- or heteroaryl-containing rapamycin derivatives, zotarolimus {-40-epi-(N1-tetrazolyl)-rapamycin, or ABT-578}, 40-epi-(N2-tetrazolyl)-rapamycin, 32(R or S)-hydroxy-rapamycin, myolimus (32-deoxo-rapamycin), novolimus (16-O-desmethyl-rapamycin), AP20840, AP23464, AP23675, AP23841, taxanes, paclitaxel, docetaxel, cytochalasins, cytochalasins A through J, latrunculins, and salts, isomers, analogs, derivatives, metabolites, prodrugs and fragments thereof. The IUPAC numbering system for rapamycin is used herein. In certain embodiments, the body of the device comprises myolimus or novolimus.

Table 1 provides non-limiting examples of derivatives of each of rapamycin, everolimus, biolimus, temsirolimus, ridaforolimus, zotarolimus, myolimus and novolimus.

TABLE 1

Derivatives of rapamycin-type compounds
Derivatives of Each of Rapamycin, Everolimus, Biolimus,
Temsirolimus, Ridaforolimus, Zotarolimus, Myolimus and Novolimus N7-oxide
2-hydroxy
3-hydroxy
4-hydroxy
5-hydroxy
6-hydroxy
11-hydroxy
12-hydroxy TABLE 1-continued Derivatives of rapamycin-type compounds
Derivatives of Each of Rapamycin, Everolimus, Biolimus,
Temsirolimus, Ridaforolimus, Zotarolimus, Myolimus and Novolimus 13-hydroxy
14-hydroxy
23-hydroxy
24-hydroxy
25-hydroxy
31-hydroxy
35-hydroxy
43-hydroxy (11-hydroxymethyl)
44-hydroxy (17-hydroxymethyl)
45-hydroxy (23-hydroxymethyl)
46-hydroxy (25-hydroxymethyl)
47-hydroxy (29-hydroxymethyl)
48-hydroxy (31-hydroxymethyl)
49-hydroxy (35-hydroxymethyl)
17,18-dihydroxy
19,20-dihydroxy
21,22-dihydroxy
29,30-dihydroxy
10-phosphate
28-phosphate
40-phosphate
16-O-desmethyl
27-O-desmethyl
39-O-desmethyl
16,27-bis(O-desmethyl)
16,39-bis(O-desmethyl)
27,39-bis(O-desmethyl)
16,27,39-tris(O-desmethyl)
16-desmethoxy
27-desmethoxy
39-O-desmethyl-14-hydroxy
17,18-epoxide
19,20-epoxide
21,22-epoxide
29,30-epoxide
17,18-29,30-bis-epoxide
17,18-19,20-21,22-tris-epoxide
19,20-21,22-29,30-tris-epoxide
16-O-desmethyl-17,18-19,20-bis-epoxide
16-O-desmethyl-17,18-29,30-bis-epoxide
16-O-desmethyl-17,18-19,20-21,22-tris-epoxide
16-O-desmethyl-19,20-21,22-29,30-tris-epoxide
27-O-desmethyl-17,18-19,20-21,22-tris-epoxide
39-O-desmethyl-17,18-19,20-21,22-tris-epoxide
16,27-bis(O-desmethyl)-17,18-19,20-21,22-tris-epoxide
16-O-desmethyl-24-hydroxy-17,18-19,20-bis-epoxide
16-O-desmethyl-24-hydroxy-17,18-29,30-bis-epoxide
12-hydroxy and opened hemiketal ring Examples of immunomodulators and immunosuppressants include, but are not limited to, tacrolimus (also called FK-506), ascomycin, pimecrolimus, TKB662, cyclosporins, cyclosporine (also called cyclosporin A), cyclosporin G, vocyclosporin, myriocin, and salts, isomers, analogs, derivatives, metabolites, prodrugs and fragments thereof. In certain embodiments, the body of the device (or a coating on the device) comprises tacrolimus.

Non-limiting examples of anti-inflammatory agents include non-steroidal anti-inflammatory drugs (NSAIDs); salicylates, aspirin, diflunisal, salsalate; propionic acid derivatives, ibuprofen, naproxen, fenoprofen, flurbiprofen, ketoprofen, oxaprozin; acetic acid derivatives, diclofenac, etodolac, indomethacin, ketorolac, nabumetone, sulindac, tetradecylthioacetic acid, tolmetin; enolic acid derivatives, droxicam, isoxicam, lornoxicam, meloxicam, piroxicam, tenoxicam; fenamic acid derivatives, flufenamic acid, meclofenamic acid, mefenamic acid, tolfenamic acid; cyclooxygenase-2 (COX-2) inhibitors, celecoxib, etoricoxib, lumiracoxib, parecoxib, parecoxib sodium, rofecoxib, valdecoxib, sulfonanilides, nimesulide, flosulide, acetaminophen, o-(acetoxyphenyl)hept-2-ynyl-2-sulfide (APHS), DuP-697, JTE-522, L-745337, L-748780, L-761066, N-[2-(cyclohexyloxy)-4-nitrophenyl]-methanesulfonamide (NS-398), RS-57067, S-2474, SC-57666, SC-58125; lipooxygenase (LOX)/cyclooxygenase (COX) inhibitors, licofelone; glucocorticoids, beclometasone, betamethasone, cortisol (hydrocortisone), cortisone, cortisone acetate, dexamethasone, dexamethasone acetate, dexamethasone phosphate, fluprednisolone, fluticasone, fluticasone propionate, meprednisone, methylprednisone, methylprednisolone, paramethasone, prednisolone, prednisone, triamcinolone; pseudopterosins; and salts, isomers, analogs, derivatives, metabolites, prodrugs and fragments thereof. In certain embodiments, the body of the device (or a coating on the device) comprises dexamethasone.

Examples of anticoagulants, anti-thrombotic agents, thrombolytic agents, anti-thrombin agents, anti-fibrin agents, and anti-platelet agents include without limitation catechins, including (+)-catechin and (−)-catechin, epicatechins, including (+)-epicatechin and (−)-epicatechin, epigallocatechin-3-O-gallate, vitamin K antagonists, 4-hydroxycoumarins, warfarin, acenocoumarol, brodifacoum, coumatetralyl, dicoumarol, phenprocoumon, tioclomarol, 1,3-indandiones, clorindione, diphenadione, fluindione, phenindione, factor Xa inhibitors, apixaban, betrixaban, rivaroxaban, DU-176b, LY-517717, YM-150, heparin, low molecular weight heparin, nadroparin (Fraxiparine®), heparin analogs, fondaparinux (Arixtra®), idraparinux, thrombin/factor IIa inhibitors, argatroban, dabigatran, ximelagatran, melagatran, AZD-0837, hirudin, hirudin analogs, bivalirudin, desirudin, lepirudin, COX inhibitors, aspirin, adenosine diphosphate (ADP) receptor inhibitors, clopidogrel (Plavix®), prasugrel, ticlopidine, phosphodiesterase (PDE) inhibitors, cilostazol, glycoprotein IIb/IIIA inhibitors, abciximab, eptifibatide, tirofiban, adenosine reuptake inhibitors, dipyridamole, cytochalasins, cytochalasin B, cytochalasin D, epoprostenol, anistreplase, streptokinase, urokinase, tissue plasminogen activators (t-PAs), alteplase, reteplase, tenecteplase, and salts, isomers, analogs, derivatives, metabolites, prodrugs and fragments thereof. In certain embodiments, the body of the device (or a coating on the device) comprises argatroban, dabigatran, rivaroxaban, low molecular weight heparin, warfarin, aspirin or clopidogrel, or a combination thereof.

Examples of anti-ischemia agents include, but are not limited to, isosorbide dinitrate, ranolazine, and salts, isomers, analogs, derivatives, metabolites, prodrugs and fragments thereof.

Non-limiting examples of anti-hypertensive agents include angiotensin-converting enzyme (ACE) inhibitors, captopril, cilazapril, lisinopril, calcium channel blockers, amlodipine, nifedipine, adalat, atenolol, candesartan, diovan, diltiazem, and salts, isomers, analogs, derivatives, metabolites, prodrugs and fragments thereof.

Examples of anti-hyperlipidemia agents include without limitation HMG-CoA reductase inhibitors; statins, atorvastatin, cerivastatin, fluvastatin, lovastatin, mevastatin, pitavastatin, pravastatin, rosuvastatin, simvastatin; fibrates, bezafibrate, ciprofibrate, clofibrate, aluminium clofibrate, etofibrate, fenofibrate, gemfibrozil; bile acid sequestrants, cholestyramine, colesevelam, colestipol; ezetimibe, niacin; and salts, isomers, analogs, derivatives, metabolites, prodrugs and fragments thereof.

Non-limiting examples of anti-diabetic agents include biguanides, buformin, metformin, phenformin; meglitinides, nateglinide, repaglinide; sulfonylureas, acetohexamide, chlorpropamide, glibenclamide (also called glyburide), gliclazide, glimepiride, glipizide, gliquidone, glyclopyramide, tolazamide, tolbutamide; agonists of peroxisome proliferator-activated receptors γ (PPARγ), thiazolidinediones, ciglitazone, MCC-555, pioglitazone, rivoglitazone, rosiglitazone, troglitazone; dipeptidyl peptidase-4 inhibitors, alogliptin, berberine, dutogliptin, gemigliptin, linagliptin, saxagliptin, sitagliptin, vildagliptin; and salts, isomers, analogs, derivatives, metabolites, prodrugs and fragments thereof.

Examples of anti-cancer agents and anti-tumor agents include without limitation ABJ879, acivicin, aclarubicin, acodazole, acronycine, actinomycins, actinomycin D (dactinomycin), adozelesin, alanosine, aldesleukin, allopurinol, allopurinol sodium, altretamine, aminoglutethimide, amonafide, ampligen, amsacrine, androgens, anguidine, antiopeptin, aphidicolin, aphidicolin glycinate, asaley, asparaginase, 5-azacitidine, azathioprine, *Bacillus* Calmette-Guerin (BCG), methanol extraction residue of *Bacillus* Calmette-Guerin, Baker's Antifol (soluble), beta-2'-deoxythioguanosine, bisantrene, bisantrene HCL, bleomycin, bleomycin sulfate, BMS-247550, busulfan, buthionine sulfoximine, BWA 773U82, BW 502U83, BW 502U83HCl, BW 7U85, BW 7U85 mesylate, ceracemide, carbetimer, carboplatin, carmustine, chlorambucil, 2-chlorodeoxyadenosine, chloroquinoxaline sulfonamide, chlorozotocin, chromomycins, chromomycin A3 (toyomycin), cisplatin, cladribine, corticosteroids, *Corynebacterium parvum*, CPT-11, crisnatol, cyclocytidine, cyclophosphamide, cytarabine, cytembena, dabis maleate {(1,4-bis(2'-chloroethyl)-1,4-diaza-bicyclo[2.2.1]heptane dihydrogen dimaleate}, dacarbazine, daunorubicin, daunorubicin HCl, deazauridine, denibulin (MN-029), dexrazoxane, dianhydrogalactitol, diaziquone, dibromodulcitol, didemnins, didemnin B, diethyldithiocarbamate, diglycoaldehyde, dihydro-5-azacytidine, doxorubicin, echinomycin, ecteinascidins, edatrexate, edelfosine, eflornithine, Elliott's solution, elsamitrucin, epirubicin, epothilones, epothilone B, epothilone C, epothilone D, esorubicin, estramustine, estramustine phosphate, estrogens, ET-743, etanidazole, ethiofos, etoposide, fadrazole, fazarabine, fenretinide, filgrastim, finasteride, flavones, flavone acetic acid, floxuridine, fludarabine phosphate, 5-fluorouracil, Fluosol®, flutamide, gallium nitrate, gemcitabine, goserelin, goserelin acetate, hepsulfam, hexamethylene bisacetamide, homoharringtonine, hydrazine, hydrazine sulfate, 4-hydroxyandrostenedione, hydroxyurea, idarubicin, idarubicin HCl, ifosfamide, interferons, interferon-α, interferon-β, interferon-γ, interleukins, interleukin-1 alpha and beta, interleukin-3, interleukin-4, interleukin-6, 4-ipomeanol, iproplatin, irinotecan, isotretinoin, leucovorin, leucovorin calcium, leuprolide, leuprolide acetate, levamisole, liposomal daunorubicin, liposome-encapsulated doxorubicin, lomustine, lonidamine, maytansine, mechlorethamine, mechlorethamine hydrochloride, melphalan, menogaril, merbarone, 6-mercaptopurine, mesna, methotrexate, N-methylformamide, mifepristone, mitoguazone, mitomycins, mitomycin C, mitotane, mitoxantrone, mitoxantrone hydrochloride, monocyte/macrophage colony-stimulating factor, nabilone, nafoxidine, neocarzinostatin, octreotide, octreotide acetate, ormaplatin, oxaliplatin, patupilone, N-phosphonacetyl-L-aspartate (PALA), pentostatin, piperazinedione, pipobroman, pirarubicin, pirfenidone, piritrexim, piroxantrone, piroxantrone HCl, PIXY-321, plicamycin, porfimer sodium, prednimustine, procarbazine, progestins, pyrazofurin, QP-2, razoxane, sargramostim, semustine, sirolimus, spirogermanium, spiromustine, streptonigrin, streptozocin, sulofenur, suramin, suramin sodium, tamoxifen, taxanes, docetaxel (Taxotere®), paclitaxel (Taxol®), tegafur, teniposide, terephthalamidine, teroxirone, tetrahydroisoquinoline alkaloids, thioguanine, thiotepa, thymidine, tiazofurin, topotecan, toremifene, tretinoin, trifluoperazine, trifluoperazine HCl, trifluridine, trimetrexate, tumor necrosis factor, uracil mustard, vinca alkaloids, vinblastine, vinblastine sulfate, vincristine, vincristine sulfate, vindesine, vinorelbine, vinzolidine, Yoshi 864, zorubicin, and salts, isomers, analogs, derivatives, metabolites, prodrugs and fragments thereof. In certain embodiments, the body of the device (or a coating on the device) comprises docetaxel or paclitaxel.

Non-limiting examples of anti-angiogenic agents include angioarrestin, angiostatin, antithrombin III fragment, calreticulin, canstatin, endostatin, thrombospondin 1 (TSP-1), TSP-2, tumistatin, vasculostatin, vasostatin, vascular endothelial growth factor (VEGF) inhibitors, bevacizumab, prolactin, matrix metalloproteinase inhibitors, batimastat, marimastat, prinomastat, angiostatic steroids, 2-methoxyestradiol, carboxyamidotriazole, cytochalasins, cytochalasin E, linomide, retinoids, suramin, tecogalan, thalidomide, TNP-470, and salts, isomers, analogs, derivatives, metabolites, prodrugs and fragments thereof.

Examples of angiogenic agents include, but are not limited to, angiogenin, angiopoietin-1, becaplermin, follistatin, leptin, midkine, and salts, isomers, analogs, derivatives, metabolites, prodrugs and fragments thereof.

Anti-bacterial agents include chelators, antibiotics, bacteriostatic agents, bacteriocidal agents, and anti-septic agents. Non-limiting examples of anti-bacterial agents include aminoglycosides, amikacin, gentamicin, kanamycin, neomycin, netilmicin, tobramycin, paromomycin; ansamycins, geldanamycin, herbimycin; carbacephems, loracarbef; carbapenems, ertapenem, doripenem, imipenem (cilastatin), meropenem; first-generation cephalosporins, cefadroxil, cefazolin, cefalotin (cefalothin), cefalexin; second-generation cephalosporins, cefaclor, cefamandole, cefoxitin, cefprozil, cefuroxime; third-generation cephalosporins, cefixime, cefdinir, cefditoren, cefoperazone, cefotaxime, cefpodoxime, ceftazidime, ceftibuten, ceftizoxime, ceftriaxone; fourth-generation cephalosporins, cefepime; fifth-generation cephalosporins, ceftobiprole; glycopeptides, teicoplanin, vancomycin, telavancin; lincosamides, clindamycin, lincomycin; lipopeptides, daptomycin; macrolides, azithromycin, clarithromycin, dirithromycin, erythromycin, roxithromycin, troleandomycin, telithromycin, spectinomycin; monobactams, aztreonam; nitrofurans, furazolidone, nitrofurantoin; penicillins, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin; penicillin-containing combinations, amoxicillin/clavulanate, ampicillin/sulbactam, piperacillin/tazobactam, ticarcillin/clavulanate; polypeptides, bacitracin, colistin, polymyxin B; quinolones, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin; sulfonamides, mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, trimethoprim-sulfamethoxazole (co-trimoxazole); tetracyclines, demeclocycline, doxycycline, minocycline, oxytetracycline, tetracycline; anti-mycobacteria agents, clofazimine, dapsone, capreomycin, cycloserine, ethambutol, ethionamide, isoniazid, pyrazinamide, rifampicin (rifampin), rifabutin, rifapentine, streptomycin; arsphenamine, chloramphenicol, fosfomycin, fusidic acid, linezolid, metronidazole, mupirocin, platensimycin, quinupristin/dalfopristin, rifaximin, thiamphenicol, timidazole; and salts, isomers, analogs, derivatives, metabolites, prodrugs and fragments thereof.

Examples of anti-fungal agents include without limitation polyene antifungals, amphotericins, amphotericin B, candicin, filipin, hamycin, natamycin, nystatin, rimocidin; inhibitors of lanosterol 14 α-demethylase; imidazole antifungals, bifonazole, butoconazole, clotrimazole, econazole, fenticonazole, isoconazole, ketoconazole, miconazole, omoconazole, oxiconazole, sertaconazole, sulconazole, tioconazole; triazole antifungals, fluconazole, isavuconazole, itraconazole, posaconazole, ravuconazole, terconazole, voriconazole; thiazole antifungals, abafungin; squalene epoxidase inhibitors; allylamine antifungals, butenafine, naftifine, terbinafine; inhibitors of 1,3-β glucan synthase; echinocandins, anidulafungin, caspofungin, micafungin; allicin, ciclopirox, ECO-4601, farnesylated dibenzodiazepinone, 5-fluorocytosine, griseofulvin, haloprogin, polygodial, tolnaftate, undecylenic acid; and salts, isomers, analogs, derivatives, metabolites, prodrugs and fragments thereof.

Examples of anti-chemokine agents include, but are not limited to, 3-acylaminolactams, acylaminocaprolactams, 3-acylaminoglutarimides, FX125L, and salts, isomers, analogs, derivatives, metabolites, prodrugs and fragments thereof.

For a vessel-contacting device (e.g., a stent), in some embodiments a healing-promoting agent can promote re-endothelialization of a damaged vessel (e.g., blood vessel) to promote healing of the damaged tissue. The portion(s) of the device containing a healing-promoting agent can attract, bind and become encapsulated by endothelial cells (e.g., endothelial progenitor cells, which help repair damage blood vessels), which can reduce or prevent formation of emboli or thrombi. In certain embodiments, healing-promoting agents are endothelial cell-binding agents (including endothelial progenitor cell-binding agents), including without limitation an active fragment of osteopontin (Asp-Val-Asp-Val-Pro-Asp-Gly-Asp-Ser-Leu-Ala-Try-Gly), RGD-containing peptide sequences, RGD mimetics, collagen type 1, single chain Fv fragment (scFv A5), junction membrane protein vascular endothelial-cadherin, epithelial cell antibodies, CD-34, CD-133, vascular endothelial growth factor (VEGF) type 2 receptor, and fragments thereof.

In certain embodiments, the body of the device (and/or one or more coatings on the device) comprises one or more biologically active agents selected from the group consisting of mTOR inhibitors, rapamycin, TAFA93, rapamycin derivatives, 40-O-alkyl-rapamycin derivatives, 40-O-hydroxyalkyl-rapamycin derivatives, everolimus, 40-O-(3-hydroxy)propyl-rapamycin, 40-O-[2-(2-hydroxy)ethoxy]ethyl-rapamycin, 40-O-alkoxyalkyl-rapamycin derivatives, biolimus, 40-O-acyl-rapamycin derivatives, temsirolimus, 40-O-phospho-containing rapamycin derivatives, ridaforolimus, 40(R or S)-heterocyclyl- or heteroaryl-containing rapamycin derivatives, zotarolimus, 40-epi-(N2-tetrazolyl)-rapamycin, 32(R or S)-hydroxy-rapamycin, myolimus, novolimus, AP20840, AP23464, AP23675, AP23841, taxanes, paclitaxel, docetaxel, cytochalasins, latrunculins, tacrolimus, ascomycin, pimecrolimus, TKB662, cyclosporins, cyclosporine, cyclosporin G, vocyclosporin, myriocin, non-steroidal anti-inflammatory drugs, salicylates, propionic acid derivatives, acetic acid derivatives, enolic acid derivatives, fenamic acid derivatives, COX-2 inhibitors, LOX/COX inhibitors, glucocorticoids, betamethasone, dexamethasone, methylprednisolone, pseudopterosins, catechins, epicatechins, epigallocatechin-3-O-gallate, vitamin K antagonists, 4-hydroxycoumarins, warfarin, acenocoumarol, brodifacoum, coumatetralyl, dicoumarol, phenprocoumon, tioclomarol, 1,3-indandiones, clorindione, diphenadione, fluindione, phenindione, factor Xa inhibitors, apixaban, betrixaban, rivaroxaban, DU-176b, LY-517717, YM-150, heparin, low molecular weight heparin, nadroparin (Fraxiparine®), heparin analogs, fondaparinux (Arixtra®), idraparinux, thrombin/factor IIa inhibitors, argatroban, dabigatran, ximelagatran, melagatran, AZD-0837, hirudin, hirudin analogs, bivalirudin, desirudin, lepirudin, COX inhibitors, aspirin, adenosine diphosphate (ADP) receptor inhibitors, clopidogrel (Plavix®), prasugrel, ticlopidine, phosphodiesterase (PDE) inhibitors, cilostazol, glycoprotein IIb/IIIA inhibitors, abciximab, eptifibatide, tirofiban, adenosine reuptake inhibitors, dipyridamole, cytochalasin B, cytochalasin D, epoprostenol, anistreplase, streptokinase, urokinase, tissue plasminogen activators (t-PAs), alteplase, reteplase, tenecteplase, isosorbide dinitrate, ranolazine, angiotensin-converting enzyme inhibitors, captopril, cilazapril, lisinopril, calcium channel blockers, amlodipine, nifedipine, adalat, atenolol, candesartan, diovan, diltiazem, HMG-CoA reductase inhibitors, statins, fibrates, bile acid sequestrants, ezetimibe, niacin sulfonylurea anti-diabetics, biguanides, meglitinides, PPARγ agonists, thiazolidinediones, dipeptidyl peptidase-4 inhibitors, actinomycins, actinomycin D, azathioprine, bleomycin, busulfan, chlorambucil, cyclophosphamide, daunorubicin, didemnins, didemnin B, doxorubicin, epothilones, epothilone B, etoposide, 5-fluorouracil, gemcitabine, irinotecan, methotrexate, mitomycin, mitoxantrone, pirfenidone, plicamycin, procarbazine, tamoxifen, topotecan, vinca alkaloids, vinblastine, vincristine, angioarrestin, angiostatin, antithrombin III fragment, calreticulin, canstatin, endostatin, thrombospondin 1 (TSP-1), TSP-2, tumistatin, vasculostatin, vasostatin, VEGF inhibitors, bevacizumab, prolactin, matrix metalloproteinase inhibitors, batimastat, marimastat, prinomastat, angiostatic steroids, 2-methoxyestradiol, carboxyamidotriazole, cytochalasin E, linomide, retinoids, suramin, tecogalan, thalidomide, TNP-470, angiogenin, angiopoietin-1, becaplermin, follistatin, leptin, midkine, β-lactam antibiotics, cephalosporins, penicillins, monobactam antibiotics, aminoglycoside antibiotics, glycopeptide antibiotics, lipopeptide antibiotics, polypeptide antibiotics, ansamycins, carbacephems, carbapenems, lincosamides, macrolide antibiotics, nitrofuran antibiotics, quinolone antibiotics, sulfonamide antibiotics, tetracyclines, anti-mycobacteria agents, chloramphenicol, linezolid, thiamphenicol, allylamine antifungals, echinocandins, polyene antifungals, imidazole antifungals, triazole antifungals, thiazole antifungals, ECO-4601, farnesylated dibenzodiazepinone, griseofulvin, 3-acylaminolactams, acylaminocaprolactams, 3-acylaminoglutarimides, FX125L, endothelial cell-binding agents, and salts, isomers, analogs, derivatives, prodrugs, metabolites and fragments thereof.

Depending in part on the type of device it is, the biodegradable implantable device described herein can be used to treat or prevent a wide variety of diseases, disorders and conditions, or promote a wide variety of therapeutic effects. In some embodiments, the biodegradable device is implanted in a subject for treatment or prevention of a disorder or condition, or promotion of a therapeutic effect, selected from the group consisting of wound healing, hyper-proliferative disease, cancer, tumor, vascular disease, cardiovascular disease, coronary artery disease, peripheral arterial disease, atherosclerosis, thrombosis, vulnerable plaque, stenosis, restenosis, ischemia, myocardial ischemia, peripheral ischemia, limb ischemia, hyper-calcemia, vascular obstruction, vascular dissection, vascular perforation, aneurysm, vascular aneurysm, aortic aneurysm, abdominal aortic aneurysm, cerebral aneurysm, chronic total occlusion, patent foramen ovale, hemorrhage, claudication, diabetic disease, pancreas obstruction, kidney obstruction, bile duct obstruction, intestine obstruction, duodenum obstruction, colon obstruction, ureter obstruction, urethra obstruction, sphincter obstruction, airway obstruction, anastomosis, anastomotic proliferation of artery, vein or artificial graft, bone injury, bone crack, bone fracture, osteoporosis, skeletal defect, bone defect, weak bone, bone thinning, improper bone union or healing, fusing bone, fusion of adjacent vertebrae, osteochondral defect, chondral defect, cranial defect, scalp defect, calvarial defect, craniofacial defect, craniomaxillofacial defect, segmental bone loss, thoracic cage defect, cartilage defect, cartilage repair, cartilage regeneration, bone-cartilage bridging, bone-tendon bridging, spinal disorder, scoliosis, nerve damage, nerve injury, nerve defect, nerve repair, nerve reconstruction, nerve regeneration, herniation, abdominal herniation, disc herniation, acute or chronic low back pain, discogenic pain, trauma, abdominal wall defect, septal repair, burn injury, facial reconstruction, facial regeneration, aging, and contraception. The biodegradable device can also be used outside the body, e.g., in tissue engineering to generate tissue.

When the biodegradable device is a stent, the stent can also be used to treat or prevent a wide variety of diseases, disorders and conditions. In some embodiments, the biodegradable stent is implanted in a subject for treatment or prevention of obstruction, occlusion, constriction, stricture, narrowing, stenosis, restenosis, intimal hyperplasia, collapse, dissection, thinning, perforation, kinking, aneurysm, failed access graft, cancer or tumor of a vessel, passage, conduit, tubular tissue or tubular organ, such as an artery, vein, peripheral artery, peripheral vein, subclavian artery, superior caval vein, inferior caval vein, popliteal artery, popliteal vein, arterial duct, coronary artery, carotid artery, brain artery, aorta, ductus arteriosus, right ventricular outflow tract conduit, transitional atrioventricular canal, interatrial septum, iliac artery, common iliac artery, external iliac artery, internal iliac artery, iliac vein, internal pudendal artery, mammary artery, femoral artery, superficial femoral artery, femoral vein, pancreatic artery, pancreatic duct, renal artery, hepatic artery, splenic artery, biliary artery, bile duct, stomach, small intestine, duodenum, jejunum, ileum, large intestine, cecum, colon, rectosigmoid colon, sphincter, rectum, colorectum, ureter, urethra, prostatic duct, pulmonary artery, aortopulmonary collateral artery, aortopulmonary collateral vessel, airway, nasal passage, nostril, throat, pharynx, larynx, esophagus, epiglottis, glottis, trachea, carina, bronchus, bilateral main bronchus, intermediate branch bronchus, transbronchial passage, or tracheobronchus.

Obstruction, occlusion, constriction, stricture, narrowing, stenosis, restenosis, intimal hyperplasia, collapse, dissection, thinning, perforation, kinking, aneurysm, failed access graft, cancer or tumor of a vessel, passage, conduit, tubular tissue or tubular organ can be associated with any of a variety of diseases, disorders and conditions, such as atherosclerosis, hardening of the artery (e.g., with fatty acid, cholesterol or calcium), thrombosis, vulnerable plaque, hypertension, diabetes mellitus, brain aneurysm, amyloidosis, congenital heart disease, chronic stable angina, unstable angina, myocardial infarction, acute myocardial infarction, aortic aneurysm, abdominal aortic aneurysm, thoracic aortic aneurysm, aortic tearing, aortic recoarctation, patent ductus arteriosus, atrial septal defect, ventricular septal defect, right ventricular hypoplasia, pulmonary atresia, vascular anomaly, vascular malformation, dextro-transposition of the great arteries, pancreatitis, pancreatic divisum, chronic renal disease, acute renal failure, primary sclerosing cholangitis, inflammatory bowel disease, Crohn's disease, mucous colitis, ulcerative colitis, diverticulitis, colonic fistula, detrusor external sphincter dyssynergia, enlarged prostate, benign prostatic hyperplasia, lower urinary tract symptom, recurrent bulbar urethral stricture, erectile dysfunction, deviated septum, kyphoscoliosis, sarcoidosis, diphtheria, lung disease, tuberculosis, Wegener's granulomatosis, emphysema, cystic fibrosis, respiratory distress, asthma, respiratory infection, respiratory papillomatosis, chronic obstructive pulmonary disease, bronchitis, intrinsic airway obstruction, apnea, dyspnea, blunt or sharp laryngeal trauma, laryngotracheal disorder, laryngotracheal reconstruction, tracheal trauma or rupture, tracheobronchial disease, tracheal tear, tracheoesophageal fistula, tracheomalacia, bronchomalacia, tracheobronchomalacia, vocal fold paralysis, bilateral vocal fold mobility impairment, epiglottitis, idiopathic progressive subglottic stenosis, dysphagia, intrinsic compression, extrinsic compression, or thyroid goiter.

In some embodiments, the biodegradable stent is implanted in a subject for treatment or prevention of wound healing, hyper-proliferative disease, vascular disease, cardiovascular disease, coronary artery disease, peripheral arterial disease, atherosclerosis, thrombosis, vulnerable plaque, stenosis, restenosis, ischemia, myocardial ischemia, peripheral ischemia, limb ischemia, hyper-calcemia, vascular obstruction, vascular dissection, vascular perforation, vascular aneurysm, aortic aneurysm, abdominal aortic aneurysm, cerebral aneurysm, chronic total occlusion, patent foramen ovale, hemorrhage, claudication, pancreas obstruction, kidney obstruction, bile duct obstruction, intestine obstruction, duodenum obstruction, colon obstruction, ureter obstruction, urethra obstruction, sphincter obstruction, airway obstruction, anastomosis, or anastomotic proliferation of artery, vein or artificial graft. In certain embodiments, the stent is implanted in a subject for treatment or prevention of a hyper-proliferative disease, a vascular disease or restenosis.

The biodegradable implantable device described herein can be any of a wide variety of devices and can have any shape, configuration or form suitable for its intended function or site of implantation. For example, the body of the device can have a shape suitable for the anatomy in which the device is intended to be implanted. In certain embodiments, the body of the device is substantially tubular. The device can serve any of a variety of functions, such as supporting a bodily tissue or structure (e.g., a vessel), holding together bodily tissues or structures (e.g., bones), plugging or closing an opening (e.g., a wound), containing a synthetic or natural material useful for exerting a therapeutic effect (e.g., endothelial progenitor cells), delivering a drug or a biologic (e.g., an anti-proliferative agent) to a site of treatment, or a combination thereof.

In some embodiments, the biodegradable device is selected from the group consisting of drug-delivery devices, parenteral drug-delivery devices, biologic-delivery devices, vascular implants, luminal implants, stents, stent-grafts, graft implants, grafts, catheters, abdominal aortic aneurysm coils, cerebral aneurysm coils, wound closure implants, sutures, urinary tract implants, organ implants, orthopedic implants, bone implants, dental implants, defect scaffolds, fixation plates, fusion spacers, internal fixators for long bone shafts, spinal correctors, spine stabilizers, spine restrictors, spinal fixators, spinal fusion implants, spinal disks, vertebral spacers, intervertebral spacers, bone fusers, bone replacement implants, bone-loss replacements, bone fillers, bone plugs, bone plates, bone fixation devices, bone screws, bridges, spacers, defect fillers, craniomaxillofacial surgery patches, craniofacial scaffolds, nerve regeneration implants, nerve guide tubes, nerve conduits, nerve protectors, tendon protectors, staples, staple line reinforcements, osteotomy staples, anastomosis staples, anastomosis fasteners, septal repair implants, skin patches, skin substitutes, intrauterine implants, and contraceptive devices.

In certain embodiments, the biodegradable device is a stent. Non-limiting examples of stents include vascular stents, coronary stents, coronary heart disease (CHD) stents, carotid stents, brain aneurysm stents, peripheral stents, peripheral vascular stents, venous stents, femoral stents, superficial femoral artery (SFA) stents, pancreatic stents, renal stents, biliary stents, intestinal stents, duodenal stents, colonic stents, ureteral stents, urethral stents, prostatic stents, sphincter stents, airway stents, tracheobronchial stents, tracheal stents, laryngeal stents, esophageal stents, single stents, segmented stents, joined stents, overlap stents, tapered stents, and bifurcated stents. In certain embodiments, the biodegradable device is a vascular or coronary stent.

Biodegradable implantable devices described herein can be stents. Non-limiting examples of stents include vascular stents, coronary stents, coronary heart disease (CHD) stents, carotid stents, brain aneurysm stents, peripheral stents, peripheral vascular stents, venous stents, femoral stents, superficial femoral artery (SFA) stents, pancreatic stents, renal stents, biliary stents, duodenal stents, colonic stents, ureteral stents, urethral stents, prostatic stents, sphincter stents, airway stents, tracheobronchial stents, tracheal stents, laryngeal stents, esophageal stents, single stents, segmented stents, joined stents, overlap stents, tapered stents, and bifurcated stents.

When the device is a stent, the stent can have any pattern and design suitable for its intended use. The stent can be implanted in a subject for treatment of a wide variety of conditions, including obstruction or narrowing of a vessel (e.g., blood vessel) or other tubular tissue or organ in the body. In certain embodiments, the biodegradable stent exhibits a percentage radially inward recoil of about 20% or less, or of about 15% or less, or of about 10% or less, or of about 8% or less, or of about 6% or less, upon deployment or after deployment of the stent, or at any time ranging from about day 0 to about day 30 after deployment in aqueous condition at about 37° C. in vitro or in vivo. In an embodiment, the stent exhibits percent recoil of about 10% or less after deployment, or after radial expansion in aqueous condition at about 37° C. in vitro or in vivo.

The stents can have any pattern and design suitable for their intended use. For example, the stents can comprise serpentine rings connected to one another directly or via links, have open cells or closed cells, comprise helical ring(s), comprise coil(s), comprise corrugated rings, have a slide-and-lock design, be a slotted tube, be a rolled sheet, or a combination thereof. Furthermore, the stents can have supporting features, as described in U.S. patent application Ser. No. 12/016,077 and U.S. Provisional Patent Application No. 60/885,700, the full disclosure of each of which is incorporated herein by reference. Moreover, the stents can have openings in the struts, crowns and/or links, as described in U.S. 60/885,700.

To help determine the position of a stent in the body of a subject, the stent can have a radiopaque marker at any suitable position, e.g., at the proximal end and the distal end of the stent, and optionally in an intermediate portion of the stent. Alternatively or in addition, the body of the stent or a layer of the body, and/or a coating on the stent, can contain a radiopaque agent or material.

In some embodiments, biodegradable implantable devices have substantially W-shaped cells. In certain embodiments, stents having substantially W-shaped cells have the stent pattern shown in FIG. 1 or a substantially similar pattern. The stent pattern in FIG. 1 is in an "as cut" state.

Figure 1:
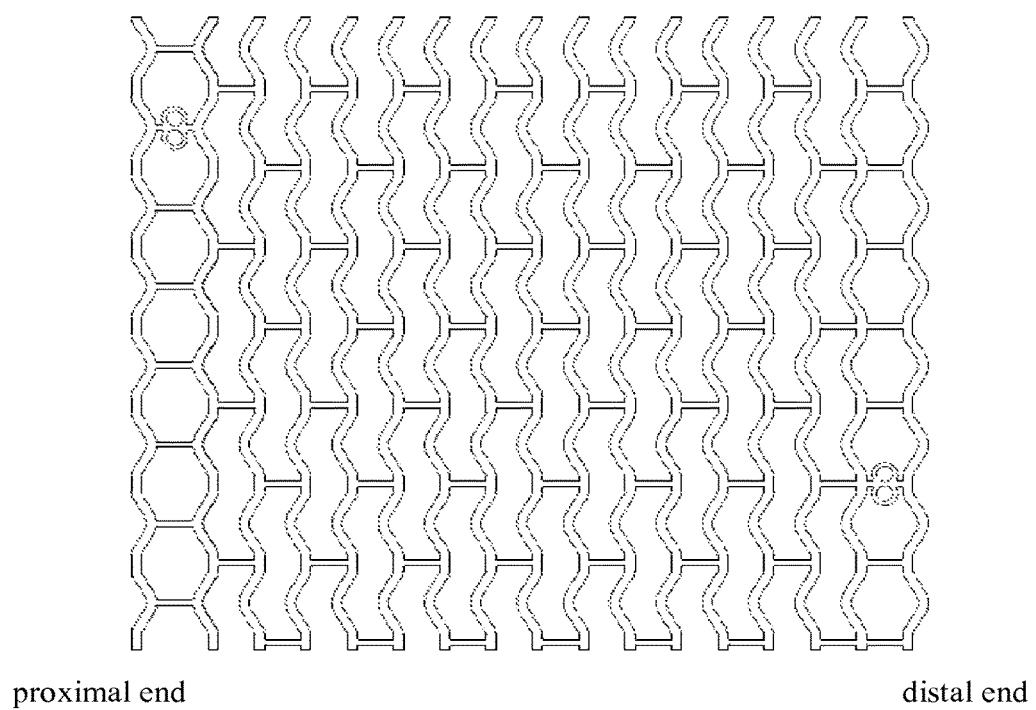
FIG. 1 depicts an example of stent pattern having substantially W and/or V-shaped cells.

The stent pattern in FIG. 1 comprises a plurality of intermediate cylindrical rings between the cylindrical ring at the proximal end and the cylindrical ring at the distal end of the stent, each cylindrical ring comprising a plurality of struts and a plurality of crowns connecting immediately adjacent struts which form a substantially sinusoidal pattern of alternating peaks and troughs, wherein immediately adjacent intermediate cylindrical rings are connected to one another at crowns via a plurality of links, and wherein:

immediately adjacent intermediate cylindrical rings and links define a plurality of substantially W-shaped cells;

each substantially W-shaped cell not immediately adjacent to the cylindrical ring at the proximal or distal end abuts six other substantially W-shaped cells; and the perimeter of each substantially W-shaped cell includes 8 struts, 10 crowns and 2 links.

In some embodiments, each substantially W-shaped cell immediately adjacent to the cylindrical ring at the proximal end of the stent, and/or each substantially W-shaped cell immediately adjacent to the cylindrical ring at the distal end, does not abut six other substantially W-shaped cells. In certain embodiments, none of the substantially W-shaped cells immediately adjacent to the cylindrical ring at the proximal end of the stent, and/or none of the substantially W-shaped cells immediately adjacent to the cylindrical ring at the distal end, abuts six other substantially W-shaped cells.

In the stent pattern of FIG. 1, the links connecting immediately adjacent intermediate cylindrical rings are substantially parallel to the longitudinal axis of the stent. In other embodiments, the links are oriented at an angle (e.g., about 1 degree to about 45 degrees, or about 5 degrees to about 35 degrees, or about 10 degrees to about 25 degrees) relative to the longitudinal axis of the stent.

In FIG. 1, crowns of an intermediate cylindrical ring which are not connected to a crown of an immediately adjacent intermediate cylindrical ring via a link are substantially curved, except that certain crowns of the intermediate cylindrical ring immediately adjacent to the proximal end and certain crowns of the intermediate cylindrical ring immediately adjacent to the distal end which are not connected to a crown of the respective immediately adjacent intermediate cylindrical ring via a link are substantially flat. Crowns of an intermediate cylindrical ring which are connected to a crown of an immediately adjacent intermediate cylindrical ring via a link are substantially flat. In other embodiments, crowns of an intermediate cylindrical ring which are not connected to a crown of an immediately adjacent intermediate cylindrical ring via a link are substantially flat, and crowns of an intermediate cylindrical ring which are connected to a crown of an immediately adjacent intermediate cylindrical ring via a link are substantially curved. In yet other embodiments, all crowns of intermediate cylindrical rings are substantially curved. In still other embodiments, all crowns of intermediate cylindrical rings are substantially flat.

In certain embodiments, immediately adjacent struts of intermediate cylindrical rings are oriented relative to one another at an interior angle of about 90 degrees to about 150 degrees, or about 100 degrees to about 140 degrees, or about 110 degrees to about 130 degrees, when the stent is in a non-deformed configuration (e.g., the as cut state). In an embodiment, immediately adjacent struts of intermediate cylindrical rings are oriented relative to one another at an interior angle of about 120 degrees when the stent is in a non-deformed configuration (e.g., the as cut state). In some embodiments, the interior angle of immediately adjacent struts connected by a substantially curved crown is substantially similar to the interior angle of immediately adjacent struts connected by a substantially flat crown when the stent is in a non-deformed configuration (e.g., the as cut state) or in a deformed configuration (e.g., crimped or radially expanded).

In the stent pattern of FIG. 1, immediately adjacent intermediate cylindrical rings are substantially in-phase of one another. In other embodiments, opposing peaks of immediately adjacent intermediate cylindrical rings are circumferentially offset from one another, opposing troughs of immediately adjacent intermediate cylindrical rings are circumferentially offset from one another, and opposing peaks and troughs of immediately adjacent intermediate cylindrical rings are circumferentially offset from one another. In certain embodiments, immediately adjacent intermediate cylindrical rings are substantially completely out-of-phase of one another, where opposing peaks and troughs of immediately adjacent intermediate cylindrical rings are substantially circumferentially aligned.

In FIG. 1, immediately adjacent intermediate cylindrical rings are connected to one another via a plurality of peak-to-peak links. In other embodiments, immediately adjacent intermediate cylindrical rings are connected to one another via a plurality of trough-to-trough links. In yet other embodiments, immediately adjacent intermediate cylindrical rings are connected to one another via a plurality of peak-to-trough links, or via a plurality of trough-to-peak links.

In the stent pattern of FIG. 1, links connecting a pair of immediately adjacent intermediate cylindrical rings are circumferentially offset by two crowns from circumferentially adjacent links connecting an immediately adjacent pair of immediately adjacent intermediate cylindrical rings. In other embodiments, links connecting a pair of immediately adjacent intermediate cylindrical rings are circumferentially offset by one crown, or three crowns, or four crowns, or more crowns from circumferentially adjacent links connecting an immediately adjacent pair of immediately adjacent intermediate cylindrical rings. In still other embodiments, links connecting a pair of immediately adjacent intermediate cylindrical rings are substantially not circumferentially offset from circumferentially adjacent links connecting an immediately adjacent pair of immediately adjacent intermediate cylindrical rings.

In FIG. 1, immediately adjacent intermediate cylindrical rings have 16 crowns (8 peaks and 8 troughs) and are connected to one another via 4 links to form 4 substantially W-shaped cells. In other embodiments, immediately adjacent intermediate cylindrical rings have 8 crowns (4 peaks and 4 troughs) and are connected to one another via 2 links to form 2 substantially W-shaped cells. In yet other embodiments, immediately adjacent intermediate cylindrical rings have 12 crowns (6 peaks and 6 troughs) and are connected to one another via 3 links to form 3 substantially W-shaped cells. In further embodiments, immediately adjacent intermediate cylindrical rings have 20 crowns (10 peaks and 10 troughs) and are connected to one another via 5 links to form 5 substantially W-shaped cells. In still further embodiments, immediately adjacent intermediate cylindrical rings have 24 crowns (12 peaks and 12 troughs) and are connected to one another via 6 links to form 6 substantially W-shaped cells. The present disclosure also encompasses embodiments where immediately adjacent intermediate cylindrical rings having, e.g., 16 crowns (8 peaks and 8 troughs) are connected to one another via a plurality of links other than 4 links (e.g., via 2, 3, 5, 6, 7, 8, 9, 10, 11, 12, 13, 14, 15 or 16 links), in which case the rings and links connecting them may form or may not form substantially W-shaped cells.

The cylindrical ring at the proximal end of the stent is connected to the intermediate cylindrical ring immediately adjacent thereto at crowns via a plurality of links, and the cylindrical ring at the distal end is connected to the intermediate cylindrical ring immediately adjacent thereto at crowns via a plurality of links.

In the stent pattern of FIG. 1, the links connecting the cylindrical ring at the proximal end to the intermediate cylindrical ring immediately adjacent thereto are substantially parallel to the longitudinal axis of the stent, and the links connecting the cylindrical ring at the distal end to the intermediate cylindrical ring immediately adjacent thereto are substantially parallel to the longitudinal axis of the stent. In other embodiments, the links connecting the cylindrical ring at the proximal end to the intermediate cylindrical ring immediately adjacent thereto are oriented at an angle (e.g., about 1 degree to about 45 degrees, or about 5 degrees to about 35 degrees, or about 10 degrees to about 25 degrees) relative to the longitudinal axis of the stent, and/or the links connecting the cylindrical ring at the distal end to the intermediate cylindrical ring immediately adjacent thereto are oriented at an angle (e.g., about 1 degree to about 45 degrees, or about 5 degrees to about 35 degrees, or about 10 degrees to about 25 degrees) relative to the longitudinal axis of the stent.

In FIG. 1, crowns of the cylindrical ring at the proximal end which are not connected to a crown of the intermediate cylindrical ring immediately adjacent thereto via a link are substantially flat, and crowns of the cylindrical ring at the proximal end which are connected to a crown of the intermediate cylindrical ring immediately adjacent thereto via a link are substantially curved. In other embodiments, crowns of the cylindrical ring at the proximal end which are not connected to a crown of the intermediate cylindrical ring immediately adjacent thereto via a link are substantially curved, and crowns of the cylindrical ring at the proximal end which are connected to a crown of the intermediate cylindrical ring immediately adjacent thereto via a link are substantially flat. In yet other embodiments, all crowns of the cylindrical ring at the proximal end are substantially curved. In still other embodiments, all crowns of the cylindrical ring at the proximal end are substantially flat.

Also in FIG. 1, crowns of the cylindrical ring at the distal end which are not connected to a crown of the intermediate cylindrical ring immediately adjacent thereto via a link are substantially curved, and crowns of the cylindrical ring at the distal end which are connected to a crown of the intermediate cylindrical ring immediately adjacent thereto via a link are substantially flat. In other embodiments, crowns of the cylindrical ring at the distal end which are not connected to a crown of the intermediate cylindrical ring immediately adjacent thereto via a link are substantially flat, and crowns of the cylindrical ring at the distal end which are connected to a crown of the intermediate cylindrical ring immediately adjacent thereto via a link are substantially curved. In yet other embodiments, all crowns of the cylindrical ring at the distal end are substantially curved. In still other embodiments, all crowns of the cylindrical ring at the distal end are substantially flat.

In certain embodiments, immediately adjacent struts of the cylindrical rings at the proximal and distal ends of the stent are oriented relative to one another at an interior angle of about 90 degrees to about 150 degrees, or about 100 degrees to about 140 degrees, or about 110 degrees to about 130 degrees, when the stent is in a non-deformed configuration (e.g., the as cut state). In an embodiment, immediately adjacent struts of the cylindrical rings at the proximal and distal ends are oriented relative to one another at an interior angle of about 120 degrees when the stent is in a non-deformed configuration (e.g., the as cut state). For the cylindrical rings at the proximal and distal ends, in some embodiments the interior angle of immediately adjacent struts connected by a substantially curved crown is substantially similar to the interior angle of immediately adjacent struts connected by a substantially flat crown when the stent is in a non-deformed configuration (e.g., the as cut state) or in a deformed configuration (e.g., crimped or radially expanded).

In the stent pattern of FIG. 1, the cylindrical rings at the proximal and distal ends and the respective immediately adjacent intermediate cylindrical ring are substantially completely out-of-phase of one another. In other embodiments, opposing peaks, opposing troughs, and opposing peaks and troughs of the cylindrical ring at the proximal end, and/or the cylindrical ring at the distal end, and the respective immediately adjacent intermediate cylindrical ring are circumferentially offset from one another. In still other embodiments, the cylindrical ring at the proximal end, and/or the cylindrical ring at the distal end, and the respective immediately adjacent intermediate cylindrical ring are substantially in-phase of one another.

In FIG. 1, the cylindrical rings at the proximal and distal ends of the stent and the respective immediately adjacent intermediate cylindrical ring are connected to one another via a plurality of peak-to-trough links. In other embodiments, the cylindrical ring at the proximal end, and/or the cylindrical ring at the distal end, and the respective immediately adjacent intermediate cylindrical ring are connected to one another via a plurality of trough-to-peak links, or peak-to-peak links, or trough-to-trough links.

Also in FIG. 1, links connecting the cylindrical ring at the proximal end and the intermediate cylindrical ring immediately adjacent thereto are circumferentially offset by one crown from circumferentially adjacent links connecting the cylindrical ring at the distal end and the intermediate cylindrical ring immediately adjacent thereto. In other embodiments, links connecting the cylindrical ring at the proximal end and the intermediate cylindrical ring immediately adjacent thereto are circumferentially offset by two crowns, or three crowns, or four crowns, or more crowns from circumferentially adjacent links connecting the cylindrical ring at the distal end and the intermediate cylindrical ring immediately adjacent thereto. In yet other embodiments, links connecting the cylindrical ring at the proximal end and the intermediate cylindrical ring immediately adjacent thereto are substantially not circumferentially offset from circumferentially adjacent links connecting the cylindrical ring at the distal end and the intermediate cylindrical ring immediately adjacent thereto.

In the stent pattern of FIG. 1, the cylindrical ring at the proximal end and the intermediate cylindrical ring immediately adjacent thereto are connected to one another via 8 links and form 8 non-W-shaped cells. In other embodiments, the cylindrical ring at the proximal end and the intermediate cylindrical ring immediately adjacent thereto are connected to one another via 2, 3, 4, 5, 6, 7, 9, 10 or more links and form one or more non-W-shaped cells and/or one or more substantially W-shaped cells. Also in FIG. 1, the cylindrical ring at the distal end and the intermediate cylindrical ring immediately adjacent thereto are connected to one another via 8 links and form 8 non-W-shaped cells. In other embodiments, the cylindrical ring at the distal end and the intermediate cylindrical ring immediately adjacent thereto are connected to one another via 2, 3, 4, 5, 6, 7, 9, 10 or more links and form one or more non-W-shaped cells and/or one or more substantially W-shaped cells.

In FIG. 1, the cylindrical rings at the proximal and distal ends of the stent have 16 crowns (8 peaks and 8 troughs). The cylindrical rings at the proximal and distal ends can also have any number of crowns ranging from 8 crowns (4 peaks and 4 troughs) to 24 crowns (12 peaks and 12 troughs), or from 12 crowns (6 peaks and 6 troughs) to 20 crowns (10 peaks and 10 troughs).

In some embodiments, at least one (e.g., one, two or more) of the links connecting the cylindrical ring at the proximal end and the intermediate cylindrical ring immediately adjacent thereto is a marker link comprising at least one opening for containing a radiopaque marker, and at least one (e.g., one, two or more) of the links connecting the cylindrical ring at the distal end and the intermediate cylindrical ring immediately adjacent thereto is a marker link comprising at least one opening for containing a radiopaque marker. In additional embodiments, at least one (e.g., one, two or more) of the links connecting immediately adjacent intermediate cylindrical rings is a marker link comprising at least one opening for containing a radiopaque marker.

The radiopaque marker can comprise any suitable radiopaque material. Examples of radiopaque material include without limitation gold, magnesium, platinum, platinum-iridium alloys (e.g., those containing at least about 1%, 5%, 10%, 20% or 30% iridium), tantalum, tungsten, and alloys thereof. The radiopaque marker can have any suitable form (e.g., particle or bead).

In certain embodiments, the at least one marker link at the proximal end, the at least one marker link at the distal end, and optionally at least one marker link connecting immediately adjacent intermediate cylindrical rings each comprise two openings for containing a radiopaque marker. In some embodiments, the two openings of the at least one marker link at the proximal end are substantially transverse to the axis of the link, the two openings of the at least one marker link at the distal end are substantially transverse to the axis of the link, and/or the two openings of the optional at least one marker link connecting immediately adjacent intermediate cylindrical rings are substantially transverse to the axis of the link. In other embodiments, the two openings of the at least one marker link at the proximal end are along the axis of the link, the two openings of the at least one marker link at the distal end are along the axis of the link, and/or the two openings of the optional at least one marker link connecting immediately adjacent intermediate cylindrical rings are along the axis of the link.

In some embodiments, the struts and crowns of the cylindrical rings have a substantially squarish, substantially rectangular, substantially circular or substantially oval cross-section. In certain embodiments, the struts and crowns of the cylindrical rings independently have a thickness (e.g., average thickness) of about 0.003 inch (about 76 microns) to about 0.01 inch (about 254 microns), or about 0.004 inch (about 102 microns) to about 0.008 inch (about 203 microns), or about 0.005 inch (about 127 microns) to about 0.007 inch (about 178 microns), and a width (e.g., average width) of about 0.003 inch (about 76 microns) to about 0.012 inch (about 305 microns), or about 0.005 inch (about 127 microns) to about 0.01 inch (about 254 microns), or about 0.004 inch (about 102 microns) to about 0.008 inch (about 203 microns). In some embodiments, the struts and crowns of the cylindrical rings independently have a thickness (e.g., average thickness) of about 0.004 inch (about 102 microns) to about 0.008 inch (about 203 microns), and a width (e.g., average width) of about 0.004 inch (about 102 microns) to about 0.008 inch (about 203 microns). In an embodiment, the struts and crowns of the cylindrical rings have an average thickness of about 0.006 inch (about 152 microns) and an average width of about 0.0065 inch (about 165 microns).

In other embodiments, the struts and crowns of the cylindrical rings have a substantially trapezoidal cross-section. In certain embodiments, the struts and crowns of the cylindrical rings independently have a thickness (e.g., average thickness) of about 0.003 inch (about 76 microns) to about 0.01 inch (about 254 microns), or about 0.004 inch (about 102 microns) to about 0.008 inch (about 203 microns), or about 0.005 inch (about 127 microns) to about 0.007 inch (about 178 microns), an outer (abluminal) width (e.g., average abluminal width) of about 0.003 inch (about 76 microns) to about 0.009 inch (about 229 microns), or about 0.004 inch (about 102 microns) to about 0.008 inch (about 203 microns), or about 0.005 inch (about 127 microns) to about 0.007 inch (about 178 microns), and an inner (luminal) width (e.g., average luminal width) of about 0.004 inch (about 102 microns) to about 0.012 inch (about 305 microns), or about 0.005 inch (about 127 microns) to about 0.01 inch (about 254 microns), or about 0.006 inch (about 152 microns) to about 0.009 inch (about 229 microns). In some embodiments, the struts and crowns of the cylindrical rings independently have a thickness (e.g., average thickness) of about 0.004 inch (about 102 microns) to about 0.008 inch (about 203 microns), an abluminal width (e.g., average abluminal width) of about 0.004 inch (about 102 microns) to about 0.008 inch (about 203 microns), and a luminal width (e.g., average luminal width) of about 0.005 inch (about 127 microns) to about 0.01 inch (about 254 microns). The outer (abluminal) width of the struts of the cylindrical rings can be greater or less than the inner (luminal) width of the struts, and the abluminal width of the crowns of the cylindrical rings can also be greater or less than the luminal width of the crowns. In some embodiments, the outer (abluminal) width of the struts and crowns of the cylindrical rings is less than the inner (luminal) width of the struts and crowns for better penetration of the struts and crowns into the wall of a treated vessel. In an embodiment, the struts and crowns of the cylindrical rings have an average thickness of about 0.006 inch (about 152 microns), an average outer (abluminal) width of about 0.006 inch (about 152 microns), and an average inner (luminal) width of about 0.0075 inch (about 190 microns).

In some embodiments, the struts of the cylindrical rings have a substantially similar cross-section, a substantially similar thickness and substantially similar width(s) as the crowns of the cylindrical rings. In other embodiments, the struts of the cylindrical rings have a different cross-section, a different thickness (greater or smaller), and/or different width(s) (greater or smaller) than the crowns of the cylindrical rings.

In further embodiments, the struts and crowns of the intermediate cylindrical rings have a substantially similar cross-section, a substantially similar thickness and substantially similar width(s) as the struts and crowns of the cylindrical rings at the proximal and distal ends of the stent. In other embodiments, the struts and crowns of the intermediate cylindrical rings have a different cross-section, a different thickness (greater or smaller), and/or different width(s) (greater or smaller) than the struts and crowns of the cylindrical rings at the proximal and distal ends.

In additional embodiments, the struts of the cylindrical rings have a length (e.g., average length) of about 0.005 inch (about 127 microns) to about 0.025 inch (about 635 microns), or about 0.01 inch (about 254 microns) to about 0.02 inch (about 508 microns). In an embodiment, the struts of the cylindrical rings have an average length of about 0.015 inch (about 381 microns). In certain embodiments, the struts of the intermediate cylindrical rings have a substantially similar length as the struts of the cylindrical rings at the proximal and distal ends of the stent. In other embodiments, the struts of the intermediate cylindrical rings have a different length (longer or shorter) than the struts of the cylindrical rings at the proximal and distal ends.

In further embodiments, the substantially flat crowns of the cylindrical rings have a length (e.g., average length) of about 0.002 inch (about 51 microns) to about 0.02 inch (about 508 microns), or about 0.006 inch (about 152 microns) to about 0.016 inch (about 406 microns). In an embodiment, the substantially flat crowns of the cylindrical rings have an average length of about 0.011 inch (about 279 microns). In some embodiments, the substantially flat crowns of the intermediate cylindrical rings have a substantially similar length as the substantially flat crowns of the cylindrical rings at the proximal and distal ends of the stent. In other embodiments, the substantially flat crowns of the intermediate cylindrical rings have a different length (longer or shorter) than the substantially flat crowns of the cylindrical rings at the proximal and distal ends.

In some embodiments, the links connecting immediately adjacent cylindrical rings have a substantially squarish, substantially rectangular, substantially circular or substantially oval cross-section. In certain embodiments, the links connecting immediately adjacent cylindrical rings have a thickness (e.g., average thickness) of about 0.003 inch (about 76 microns) to about 0.01 inch (about 254 microns), or about 0.004 inch (about 102 microns) to about 0.008 inch (about 203 microns), or about 0.005 inch (about 127 microns) to about 0.007 inch (about 178 microns), and a width (e.g., average width) of about 0.002 inch (about 51 microns) to about 0.008 inch (about 203 microns), or about 0.002 inch (about 51 microns) to about 0.006 inch (about 152 microns), or about 0.003 inch (about 76 microns) to about 0.005 inch (about 127 microns). In some embodiments, the links have a thickness (e.g., average thickness) of about 0.004 inch (about 102 microns) to about 0.008 inch (about 203 microns), and a width (e.g., average width) of about 0.002 inch (about 51 microns) to about 0.006 inch (about 152 microns). In an embodiment, the links have an average thickness of about 0.006 inch (about 152 microns) and an average width of about 0.004 inch (about 102 microns).

In other embodiments, the links connecting immediately adjacent cylindrical rings have a substantially trapezoidal cross-section. In certain embodiments, the links connecting immediately adjacent cylindrical rings have a thickness (e.g., average thickness) of about 0.003 inch (about 76 microns) to about 0.01 inch (about 254 microns), or about 0.004 inch (about 102 microns) to about 0.008 inch (about 203 microns), or about 0.005 inch (about 127 microns) to about 0.007 inch (about 178 microns), an outer (abluminal) width (e.g., average abluminal width) of about 0.002 inch (about 51 microns) to about 0.006 inch (about 152 microns), or about 0.002 inch (about 51 microns) to about 0.005 inch (about 127 microns), or about 0.003 inch (about 76 microns) to about 0.005 inch (about 127 microns), and an inner (luminal) width (e.g., average luminal width) of about 0.002 inch (about 51 microns) to about 0.008 inch (about 203 microns), or about 0.003 inch (about 76 microns) to about 0.006 inch (about 152 microns), or about 0.003 inch (about 76 microns) to about 0.005 inch (about 127 microns). In some embodiments, the links have a thickness (e.g., average thickness) of about 0.004 inch (about 102 microns) to about 0.008 inch (about 203 microns), an abluminal width (e.g., average abluminal width) of about 0.002 inch (about 51 microns) to about 0.005 inch (about 127 microns), and a luminal width (e.g., average luminal width) of about 0.003 inch (about 76 microns) to about 0.006 inch (about 152 microns). The outer (abluminal) width of the links can be greater or less than their inner (luminal) width. In some embodiments, the abluminal width of the links is less than their luminal width. In an embodiment, the links connecting immediately adjacent cylindrical rings have an average thickness of about 0.006 inch (about 152 microns), an average outer (abluminal) width of about 0.0035 inch (about 89 microns), and an average inner (luminal) width of about 0.0045 inch (about 114 microns).

In some embodiments, the links connecting immediately adjacent cylindrical rings have a substantially similar thickness as the struts and/or the crowns of the cylindrical rings. In other embodiments, the links have a thickness greater or less than the thickness of the struts and/or the crowns of the cylindrical rings. The links connecting immediately adjacent cylindrical rings can also have width(s) substantially similar to, or greater or less than, the width(s) of the struts and/or the crowns of the cylindrical rings. In certain embodiments, the links have width(s) less than the width(s) of the struts/or the crowns of the cylindrical rings.

In further embodiments, the links connecting the cylindrical ring at the proximal end and the intermediate cylindrical ring immediately adjacent thereto and the links connecting the cylindrical ring at the distal end and the intermediate cylindrical ring immediately adjacent thereto have a substantially similar cross-section, a substantially similar thickness and substantially similar width(s) as the links connecting immediately adjacent intermediate cylindrical rings. In other embodiments, the links connecting the cylindrical ring at the proximal end and the intermediate cylindrical ring immediately adjacent thereto and/or the links connecting the cylindrical ring at the distal end and the intermediate cylindrical ring immediately adjacent thereto have a different cross-section, a different thickness (greater or smaller), and/or different width(s) (greater or smaller) than the links connecting immediately adjacent intermediate cylindrical rings.

In additional embodiments, the marker links at the proximal and distal ends, and optional marker link(s) in intermediate portion(s) of the stent, have a substantially similar cross-section, a substantially similar thickness and substantially similar width(s) as the non-marker links at the proximal end, the distal end and intermediate portions. In other embodiments, the marker links at the proximal end, the distal end and/or intermediate portion(s) of the stent have a different cross-section, a different thickness (greater or smaller), and/or different width(s) (greater or smaller) than the non-marker links at the proximal end, the distal end and/or intermediate portions. In certain embodiments, the marker links at the proximal end, the distal end and/or intermediate portion(s) of the stent have a greater width than the non-marker links at the proximal end, the distal end and/or intermediate portions, e.g., when the marker links comprise one or more openings for containing radiopaque markers along the axis of the links.

In certain embodiments, the links connecting immediately adjacent cylindrical rings have a length (e.g., average length) of about 0.01 inch (about 254 microns) to about 0.035 inch (about 889 microns), or about 0.015 inch (about 381 microns)

to about 0.03 inch (about 762 microns). In an embodiment, the links have an average length of about 0.0225 inch (about 572 microns). In some embodiments, the links connecting the cylindrical ring at the proximal end and the intermediate cylindrical ring immediately adjacent thereto and the links connecting the cylindrical ring at the distal end and the intermediate cylindrical ring immediately adjacent thereto have a substantially similar length as the links connecting immediately adjacent intermediate cylindrical rings. In other embodiments, the links connecting the cylindrical ring at the proximal end and the intermediate cylindrical ring immediately adjacent thereto and the links connecting the cylindrical ring at the distal end and the intermediate cylindrical ring immediately adjacent thereto have a different length (longer or shorter) than the links connecting immediately adjacent intermediate cylindrical rings (e.g., the links at the proximal and distal ends may have a longer length when the marker links at the proximal and distal ends comprise one or more openings for containing radiopaque markers along the axis of the links).

The links connecting immediately adjacent cylindrical rings can have a length substantially similar to, or greater or less than, the length of the struts of the cylindrical rings. In certain embodiments, the length of the links is greater than the length of the struts.

In further embodiments, the curvilinear length (e.g., average curvilinear length) of a substantially W-shaped cell is about 0.02 inch (about 0.5 mm) to about 0.2 inch (about 5.1 mm), or about 0.05 inch (about 1.3 mm) to about 0.15 inch (about 3.8 mm) In an embodiment, the average curvilinear length of a substantially W-shaped cell is about 0.1 inch (about 2.5 mm) If the proximal end and/or the distal end of the stent have substantially W-shaped cells, the curvilinear length of a substantially W-shaped cell at the proximal end and/or the distal end can be substantially similar to, or greater or less than, the curvilinear length of a substantially W-shaped cell in an intermediate portion of the stent.

In additional embodiments, the curvilinear length (e.g., average curvilinear length) of a cylindrical ring is about 0.2 inch (about 5.1 mm) to about 0.6 inch (about 15.2 mm), or about 0.3 inch (about 7.6 mm) to about 0.5 inch (about 12.7 mm) In an embodiment, the average curvilinear length of a cylindrical ring is about 0.41 inch (about 10.4 mm) The cylindrical rings at the proximal and distal ends and the intermediate cylindrical rings can have a curvilinear length substantially similar to one another or different (greater or less) than one another. In certain embodiments, the curvilinear length of the cylindrical rings at the proximal and distal ends is substantially similar to the curvilinear length of the intermediate cylindrical rings.

A stent having the pattern of FIG. 1 or a substantially similar pattern can have any length suitable for its intended use. In some embodiments, the length of the stent is about 5 mm to about 40 mm, or about 10 mm to about 30 mm, or about 10 mm to about 20 mm, or about 10 mm to about 18 mm, or about 12 mm to about 16 mm, or about 13 mm to about 15 mm, or about 13 mm to about 14 mm, when the stent is in a non-deformed configuration (e.g., the as cut state) or in a deformed configuration (e.g., crimped or radially expanded). In certain embodiments, the length of the stent is about 10 mm to about 20 mm when the stent is in a non-deformed configuration (e.g., the as cut state) or in a deformed configuration (e.g., crimped or radially expanded). In certain embodiments, the length of the stent is about 13.3 or 13.5 mm when the stent is in a non-deformed configuration (e.g., the as cut state).

The number of cylindrical rings that a stent has may depend on various factors, including the length of the stent. In some embodiments, a stent having a length of about 10 mm to about 20 mm has about 10 to about 35 cylindrical rings, or about 12 to about 30 cylindrical rings, or about 13 to about 26 cylindrical rings, or about 15 to about 22 cylindrical rings. In certain embodiments, a stent having a length of about 10 mm to about 20 mm has about 13 to about 26 cylindrical rings. In further embodiments, a stent having a length of about 12 mm to about 16 mm has about 11 to about 28 cylindrical rings, or about 13 to about 25 cylindrical rings, or about 15 to about 21 cylindrical rings. In certain embodiments, a stent having a length of about 12 mm to about 16 mm has about 15 to about 21 cylindrical rings. In additional embodiments, a stent having a length of about 13.3 or 13.5 mm has about 17 cylindrical rings.

The following examples are provided merely to illustrate the present disclosure and are not intended to limit the scope of the disclosure.

Example 1

Stent Fabrication

A. Patterning and Coating a Stent

A 14 mm stent having a selected pattern (e.g., that of FIG. 1) was cut from a polymeric tube using a laser. The outer diameter (OD) of the stent was about 0.142 inch, and the thickness of the struts, crowns and links of the stent was about 0.006 inch. A solution containing a polymer, e.g., 85:15 poly (L-lactide-co-glycolide), and a drug (e.g., myolimus) in a weight ratio of about 3:2 and at a combined concentration of about 1.7 mg/mL in a solvent (e.g., dichloromethane) was sprayed onto the stent to form a coating on the stent containing a wet weight of the polymer and the drug of about 270 μg. The stent was put under vacuum at ambient temperature for at least 36 hours to remove, e.g., any residual solvent, yielding a dryer coating weight of about 130-150 μg. The coated stent was then heated at 70° C. for 15 minutes to stabilize the coating on the stent and remove any additional residual solvent, yielding a coating weight of about 125-135 μg. The average thickness of the coating was less than 5 microns.

B. Sterilizing the Stent

The stent delivery system (crimped stent mounted onto the balloon-catheter) was packaged in a pouch and sterilized by exposure to e-beam radiation (30 kGy total dose with the stent being exposed to an internal dose of about 22.5 kGy).

C. Physical Properties of the Stent

Physical properties of stents (having the pattern of FIG. 1) and polymeric tubes made of poly(L-lactide) (PLLA) homopolymer or one of various poly(L-lactide-co-ε-caprolactone) [poly(LLA-co-CL)] copolymers were measured. Radial strength, stiffness and % recoil of uncoated stents were measured after the stents were heated at 70° C. for 15 minutes and crimped without sterilization or after the stents were heated at 70° C. for 15 minutes, crimped and then sterilized. The % crystallinity, glass transition temperature ($T_g$), crystallization enthalpy ($\Delta H_c$) and melting enthalpy ($\Delta H_m$) of the polymeric material composing a tube having no coating were measured after the tube was heated at 70° C. for 15 minutes without sterilization or after the tube was heated at 70° C. for 15 minutes and then sterilized.

and stiffness. Without intending to be bound by theory, a possible reason for the low recoil of the stents made of 70:30 poly(LLA-co-CL) or 85:15 poly(LLA-co-CL) is that those stents may have a greater self-expandable character and hence may have an enhanced tendency to expand to the larger diameter of the polymeric tube from which the stent was cut.

TABLE 2

Properties of polymeric tubes and stents made of poly(L-lactide) or a poly(L-lactide-co-ε-caprolactone) copolymer

| Polymer (Molar Ratio of LLA:CL) | % Recoil at 37° C. | Radial Strength at 37° C. (psi) | Stiffness at 37° C. (N/mm²) | Percent Crystallinity (by wt) | g (° C.) (Dry) | $\Delta H_c$, 1$^{st}$ Heating (J/g) | $\Delta H_c$, 1$^{st}$ Cooling (J/g) | $H_m$ (J/g) | Sterilized with E-Beam? |
|---|---|---|---|---|---|---|---|---|---|
| 100% PLLA | 8.5% | 10.3 | 0.6 | 21.6% | 3.3 | 0.9 | 28.8 | 7.7 | Yes |
| 95:5 poly(LLA-co-CL) | 6.6% | 14.1 | 0.9 | 21.3% | 8.6 | 1.5 | 3.8 | 4.3 | Yes |
| 95:5 poly(LLA-co-CL) | 6.1% | 16.9 | 0.9 | 18.2% | 5.3 | 0.0 | 0.0 | 0.5 | No |
| 90:10 poly(LLA-co-CL) | 5.2% | 18.4 | 1.3 | 15.0% | 9.9 | 0.0 | 0.0 | 0.6 | Yes |
| 90:10 poly(LLA-co-CL) | 4.9% | 20.8 | 1.2 | 8.3% | 9.2 | 0.0 | 0.0 | 5.5 | No |
| 85:15 poly(LLA-co-CL) | 4.9% | 5.3 | 0.3 | 6.3% | 7.9 | 0.0 | | 2.0 | Yes |
| 70:30 poly(LLA-co-CL) | 5.1% | 6.5 | 0.4 | 5.8% | 9.8 | 1.4 | | 2.7 | Yes |

Percent recoil was measured according to the procedures described in the ASTM F 2079-09 document entitled "Standard Test Method for Measuring Intrinsic Elastic Recoil of Balloon-Expandable Stents". Radial strength and stiffness were measured according to the procedures described in the draft ASTM WK15227 document entitled "Standard Practice/Guide for Measuring Radial Strength of Balloon-Expandable and Self-Expandable Vascular Stents", adapted such that the stent was characterized under physiological conditions. The $T_g$, crystallization enthalpy and melting enthalpy were measured according to the procedures described in the ASTM D3418-08 document entitled "Standard Test Method for Transition Temperatures and Enthalpies of Fusion and Crystallization of Polymers by Differential Scanning calorimetry". H. Qin et al., *Macromolecules*, 37:5239-5249 (2004) also discuss crystallization enthalpies during first heating and first cooling.

Percent crystallinity by weight was measured by X-ray diffraction (XRD). Briefly, a sample was flattened in a die and hydraulic press prior to measurement and then was placed on a zero-background silicon sample holder. Scans were run on a Panalytical X'pert MPD Pro diffractometer using copper radiation at 45 KV/40 mA and covering the range of 5 degrees to 70 degrees with a step size of 0.02 degree and a counting time of 500 seconds per step.

Results of the measurements are shown in Table 2 below. Sterilization with e-beam had a greater effect on the % crystallinity of the polymeric material [90:10 poly(LLA-co-CL) or 95:5 poly(LLA-co-CL)] composing a polymeric tube than on its $T_g$. The stents made of 70:30 poly(LLA-co-CL) or 85:15 poly(LLA-co-CL) exhibited the lowest radial strength Physical properties of stents (having the pattern of FIG. 1) composed of a blend of poly(L-lactide-co-ε-caprolactone) [poly(LLA-co-CL)] copolymers having various L-lactide and caprolactone molar ratios (70:30, 85:15 or 95:5) were also measured. The stents were made using procedures substantially similar to those described in this Example. Radial strength, stiffness and % recoil of uncoated stents were measured after the stents were heated at 70° C. for 15 minutes (the step for stabilizing a coating on a stent in this Example), crimped and then sterilized with e-beam radiation. The results are shown in Table 3.

TABLE 3

Physical properties of stents composed of a blend of poly(LLA-co-CL) copolymers

| Composition of Stent | Radial Strength (psi) | Stiffness (N/mm²) | % Recoil |
|---|---|---|---|
| 40:60 (w/w) 95:5 poly(LLA-co-CL) + 85:15 poly(LLA-co-CL) | 15.9 | 1.1 | 4% |
| 50:50 (w/w) 95:5 poly(LLA-co-CL) + 85:15 poly(LLA-co-CL) | 17.0 | 1.1 | 6% |
| 75:25 (w/w) 95:5 poly(LLA-co-CL) + 70:30 poly(LLA-co-CL) | 14.1 | 0.8 | 6% |
| 90:10 (w/w) 95:5 poly(LLA-co-CL) + 70:30 poly(LLA-co-CL) | 15.8 | 1.0 | 5% |

D. Compositions of Polymeric Tubes and Coatings

Using procedures substantially similar to those described above in this Example, polymeric tubes having a variety of compositions (e.g., polymers, drugs and/or additives; see Table 4) were made and coatings containing various compositions (see Table 5) were applied to stents cut from polymeric tubes.

TABLE 4

| Compositions of polymeric tubes | | | | | |
|---|---|---|---|---|---|
| Polymer (P) | Additive (A) | Drug (D) | P:A or P:D Ratio (w/w) in Solvent | Spray Solvent | P + A or P + D Conc'n in Solvent (mg/mL) |
| 85:15 poly(LLA-co-GA) | none | none | | DCM | 7 |
| 90:10 poly(LLA-co-TMC) | none | none | | DCM | 10 |
| 95:5 poly(LLA-co-CL) | none | none | | | |
| 90:10 poly(LLA-co-CL) | none | none | | | |
| 85:15 poly(LLA-co-CL) | none | none | | | |
| 70:30 poly(LLA-co-CL) | none | none | | | |
| poly(L-lactide) | none | none | | DCM | 3 |
| polydioxanone | none | none | | DCM | |
| 95:5 poly(LLA-co-CL) + 85:15 poly(LLA-co-CL) (1:1 w/w) | none | none | | DCM | 4-5 |
| 95:5 poly(LLA-co-CL) + 70:30 poly(LLA-co-CL) (1:1 w/w) | none | none | | DCM | 4-5 |
| 95:5 poly(LLA-co-CL) + poly(ε-caprolactone) (90:10, 95:5 or 99:1 w/w) | none | none | | DCM | 4-5 |
| 85:15 poly(LLA-co-GA) + 85:15 poly(LLA-co-CL) (9:1 or 7:3 w/w) | none | none | | DCM | 4-5 |
| 85:15 poly(LLA-co-GA) + polyglycolide (3:7 w/w) | none | none | | DCM + HFP | 6 |
| 85:15 poly(LLA-co-GA) + polydioxanone (9:1 w/w) | none | none | | DCM | 7 |
| 85:15 poly(LLA-co-GA) + polypropylene carbonate (9:1 or 8:2 w/w) | none | none | | DCM | 7 |
| 85:15 poly(LLA-co-GA) + polyethylene carbonate (9:1 w/w) | none | none | | DCM | 7 |
| 85:15 poly(LLA-co-GA) + PEG (95:5 or 99:1 w/w) | none | none | | DCM | 7 |
| 85:15 poly(LLA-co-GA) + PVP (90:10, 95:5, 97.5:2.5 or 99:1 w/w) | none | none | | DCM | 7 |
| 85:15 poly(LLA-co-GA) + POECO (99:1, 99.5:0.5 or 99.9:0.1 w/w) | none | none | | DCM | 7 |
| 85:15 poly(LLA-co-GA) + polydimethylsiloxane (92.5:7.5, 95:5, 97:3 or 99:1 w/w) | none | none | | DCM | 7 |
| 85:15 poly(LLA-co-GA) + Nylon 12 (9:1 or 8:2 w/w) | none | none | | DCM | 7 |
| 85:15 poly(LLA-co-GA) | carbon nanotubes | none | 95:5, 99:1 or 99.9:0.1 | DCM | 10 |
| 90:10 poly(LLA-co-TMC) | carbon nanotubes | none | 95:5 or 99:1 | DCM | 10 |
| poly(L-lactide) | carbon nanotubes | none | 95:5, 97:3, or 99.5:0.5 | DCM | 3 |
| poly(L-lactide) | carbon nanotubes + NaCl | none | 96.5:0.5:3 or 98.5:0.5:1 | DCM + MeOH | 3 |
| 85:15 poly(LLA-co-GA) | BHT | none | 1:1, 100:1 or 500:1 | DCM | 7 |
| poly(L-lactide) | BHT | none | 500:1 | DCM | 3 |
| poly(L-lactide) | L-lactide | none | 93:7, 95:5, 99:1 or 99.5:0.5 | DCM | 3 |
| poly(L-lactide) | hydroxy-apatite whiskers | none | 97:3 | DCM | 3 |
| 85:15 poly(LLA-co-GA) | barium sulfate | none | 10:2.5 | DCM | 10 |
| 85:15 poly(LLA-co-GA) | calcium chloride | none | 90:10, 95:5 or 97.5:2.5 | DCM + MeOH | 6-7 |
| 85:15 poly(LLA-co-GA) | sodium chloride | none | 90:10 or 95:5 | DCM + MeOH | 6-7 |
| poly(L-lactide) | sodium chloride | none | 90:10, 93:7 or 99:1 | DCM + MeOH | 3 |
| 85:15 poly(LLA-co-GA) | DCM | none | 1 wt % DCM | | |
| poly(L-lactide) | DCM | none | 1.5 wt % DCM | | |
| poly(L-lactide) | DMSO | none | 8:2, 9:1, 95:5 or 99:1 | DCM | 3 |

TABLE 4-continued

Compositions of polymeric tubes

| Polymer (P) | Additive (A) | Drug (D) | P:A or P:D Ratio (w/w) in Solvent | Spray Solvent | P + A or P + D Conc'n in Solvent (mg/mL) |
|---|---|---|---|---|---|
| 85:15 poly(LLA-co-GA) | none | myolimus | 22:1, 44:1 or 66:1 | DCM | 7 |
| 85:15 poly(LLA-co-GA) | none | myolimus + dexamethasone acetate | 66:1:0.3 | DCM | 7 |
| poly(L-lactide) | none | novolimus | 93:7, 95:5, 99:1 or 99.5:0.5 | DCM | 3 |

CL = ε-caprolactone
GA = glycolide
LLA = L-lactide
TMC = trimethylene carbonate
PEG = polyethylene glycol
POECO = polyoxyethylated castor oil
PVP = polyvinylpyrrolidone
BHT = butylated hydroxytoluene
DCM = dichloromethane
DMSO = dimethylsulfoxide
HFP = 1,1,1,3,3,3-hexafluoro-2-propanol
MeOH = methanol

TABLE 5

Compositions of coatings on stents

| Polymer (P) | Drug (D) | P:D Ratio (w/w) in Solvent | Spray Solvent | P + D Conc'n in Solvent (mg/mL) | "Dry" Coating Weight (µg) |
|---|---|---|---|---|---|
| 85:15 poly(LLA-co-GA) | myolimus | 3:2 | DCM | 1.67 or 3 | 125 |
| 85:15 poly(LLA-co-GA) | novolimus | 3:2 | DCM | 1.67 | 260 |
| 85:15 poly(LLA-co-GA) | myolimus + dexamethasone acetate | 9:2:1.3 | DCM | 1.67 | |
| poly(L-lactide) | myolimus | 3:2 | DCM | 5 | 125 |
| 85:15 poly(LLA-co-GA) | none | | DCM | 1.67 | 260 |
| poly(ε-caprolactone) | none | | DCM | 1.67 | 250 |
| 90:10 poly(LLA-co-CL) (first coating) | novolimus | 3:2 | DCM | 1.67 | 235 |
| 90:10 poly(LLA-co-CL) (outer coating) | none | | DCM | 1.67 | 200 |
| poly(L-lactide) (first coating) | none | | DCM | 1.67 | 220 |
| poly(L-lactide) (outer coating) | novolimus | 3:2 | DCM | 1.67 | 200 |

CL = ε-caprolactone
GA = glycolide
LLA = L-lactide
DCM = dichloromethane

Example 2

Fabrication of Stents from Annealed Polymeric Tubes

Figure 4:
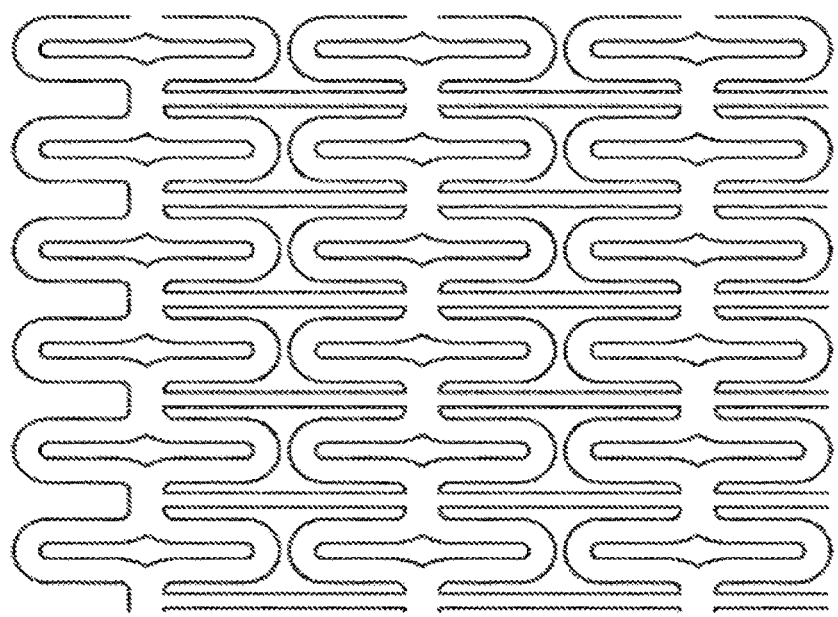
FIG. 4 depicts in a crimped state an example of pattern of a stent cut from a polymeric tube.
Figure 5A:
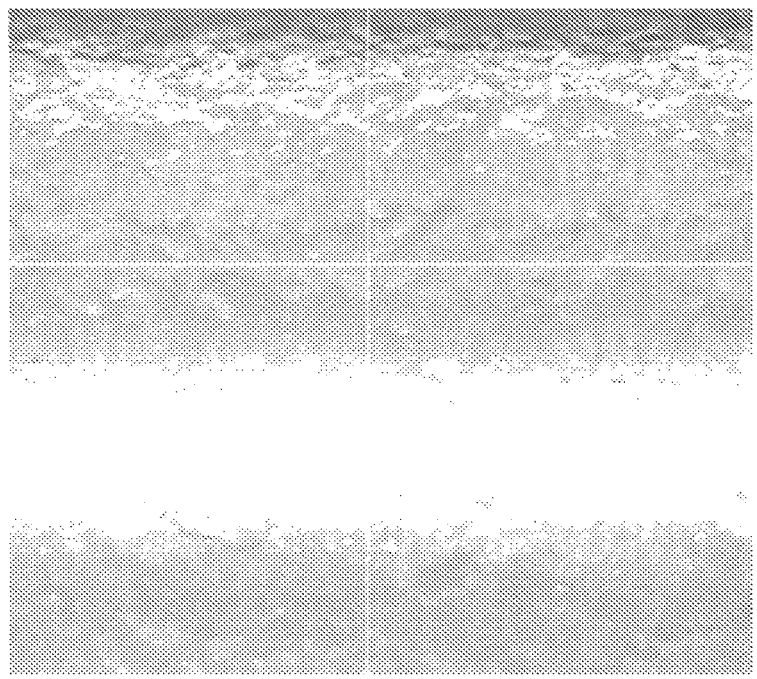
FIGS. 5A and 5B depict examples of the surface features of an embodiment of a device.
Figure 5B:
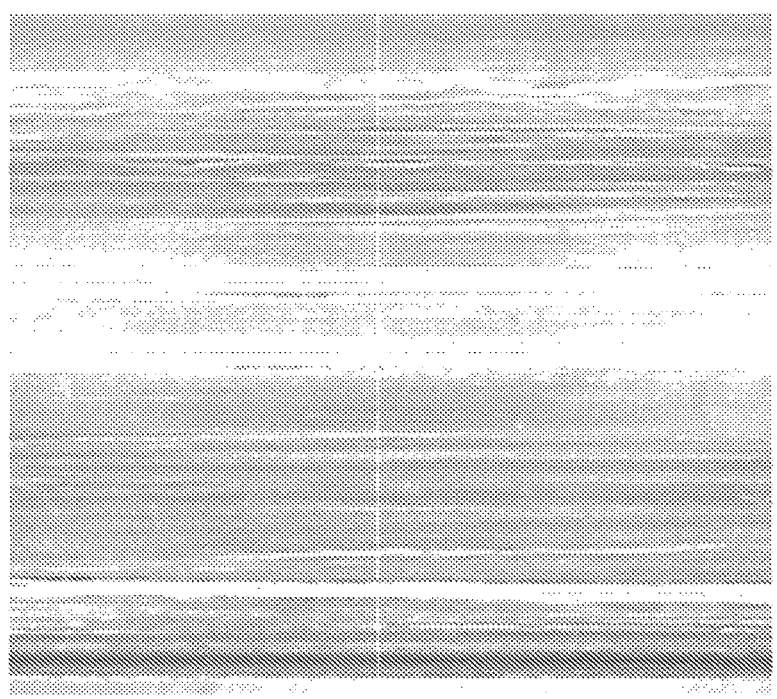

A solution containing a 1:22 weight ratio of myolimus and an amorphous poly(L-lactide-co-glycolide) copolymer comprising 85% L-lactide and 15% glycolide in dichloromethane was prepared. A polymeric tube was made by spraying the polymer and drug solution onto a mandrel rotating at 80 rpm and moving longitudinally at a rate of 0.050 inch/min. The resulting tube had a thickness of about 0.21 mm prior to heat and vacuum treatments. The tube was subjected to reduced pressure, heated under reduced pressure, annealed, and then cooled to ambient temperature. The thickness of the tube was about 0.18 mm after the heat and vacuum treatments. A stent having the pattern of FIG. 4 (shown in a crimped state) was cut from the annealed tube using a UV laser. The stent was crimped and mounted onto a balloon-catheter. The resulting stent delivery system was packaged in a pouch and sterilized by exposure to e-beam radiation (30 kGy total dose).

The radial strength of the stent after laser cutting, after crimping, after e-beam sterilization, or after radial expansion at the $T_g$ of the poly(L-lactide-co-glycolide) copolymer, with heat treatment (annealing) or without heat treatment of the polymeric tube from which the stent was cut, was tested at 37° C. in saline solution. The results are shown in Table 6 below. In each test scenario, the stent cut from an annealed tube ("heat-treated stent") exhibited higher radial strength than the stent cut from a non-annealed tube ("non-heat-treated stent").

TABLE 6

Comparison of radial strength of heat-treated and non-heat-treated stents

| State of the Stent | Not Heat-Treated | Heat-Treated |
|---|---|---|
| Radial strength after laser cutting stent | 7 Psi | 14 Psi |
| Radial strength after crimping stent | 6 Psi | 9 Psi |
| Radial strength after e-beam sterilization (30 kGy) | 3 Psi | 8 Psi |
| Radial strength after radial expansion at $T_g$ | n/a | 12.5 Psi |

TABLE 7

Physical properties of carbon nanotube-reinforced polymeric stents

| Composition of Stent | Radial Strength (psi) | Stiffness (N/mm$^2$) | % Recoil |
|---|---|---|---|
| 1 wt % MWCNTs, 90:10 poly(LLA-co-TMC) | 20.4 | 1.3 | 5.1% |
| 5 wt % MWCNTs, 90:10 poly(LLA-co-TMC) | 19.7 | 1.4 | 4.9% |
| 1 wt % MWCNTs, 85:15 poly(LLA-co-GA) | 7.8 | 1.1 | −1.6% |
| 5 wt % MWCNTs, 85:15 poly(LLA-co-GA) | 15.9 | 1.8 | 5.0% |
| 1 wt % MWCNTs, PLLA | 20.0 | NA | 6.5% |
| 2 wt % MWCNTs, PLLA | 19.5 | NA | 6.4% |
| 3 wt % MWCNTs, PLLA | 17.9 | NA | 5.5% |

GA = glycolide
LLA = L-lactide
TMC = trimethylene carbonate
MWCNTs = Multi-Walled Carbon Nanotubes
NA = not available Physical properties were also measured on stents having a body composed of poly(L-lactide) homopolymer and 3 wt % Multi-walled Carbon Nanotubes (MWCNTs) and a coating containing 3:2 (w/w) of 85:15 poly(L-lactide-co-glycolide) and myolimus. The MWCNTs had substantially similar physical dimensions as the MWCNTs described in this Example. The stents were made according to procedures substantially similar to those described in this Example and had the pattern of FIG. 1. Radial strength, stiffness and % recoil of the stents were measured after they were heated at 70° C., crimped, mounted on a balloon, and sterilized with e-beam. The stents exhibited a mean radial strength of 22.8 psi, mean stiffness of 1.3 N/mm$^2$, and a mean % recoil of 4.8%.

Example 3

Analysis of Residual/Internal Stress of Stents Cut from Polymeric Tubes Made by Spraying Stents having the pattern of FIG. 1 were laser cut from polymeric tubes made by spraying. To analyze residual/internal stress in the uncoated, as-cut stents, the stents were exposed in ambient environment to a temperature at about the $T_g$ or about 20° C. above the $T_g$ of the polymeric material composing the body of the stent. The amount of shrinkage of the stents as measured by % change in length and % change in outer diameter (OD) was measured over a period of 1 hour or 24 hours (Table 8). Without using any prior stabilization treatment (e.g., heating and pre-shrinkage), the stents exhibited reduction in length and/or OD of no more than 5%, which suggests that the stents cut from polymeric tubes made by spraying had minimal residual/internal stress.

TABLE 8

Reduction in length and outer diameter (OD) of heated stents

| Composition of Stent | Temp. (° C.) | Condition | 1 hr % Change in Length | 24 hr % Change in Length | 1 hr % Change in OD | 24 hr % Change in OD |
|---|---|---|---|---|---|---|
| 90:10 poly(LLA-co-CL) | 50 | at Tg | 2% | 3% | 2% | 2% |
| 90:10 poly(LLA-co-CL) | 50 | at Tg | 3% | 3% | 2% | 3% |
| 90:10 poly(LLA-co-CL) | 50 | at Tg | 2% | 3% | 1% | 2% |
| 90:10 poly(LLA-co-CL) | 70 | 20° C. above Tg | 4% | 4% | 2% | 3% |
| 90:10 poly(LLA-co-CL) | 70 | 20° C. above Tg | 4% | 4% | 3% | 3% |
| 90:10 poly(LLA-co-CL) | 70 | 20° C. above Tg | 3% | 3% | 3% | 3% |
| 95:5 (w/w) PLLA + PCL | 50 | at Tg | 0% | 0% | 1% | 2% |
| 95:5 (w/w) PLLA + PCL | 50 | at Tg | 0% | 0% | 1% | 1% |
| 95:5 (w/w) PLLA + PCL | 50 | at Tg | 0% | 0% | 1% | 1% |
| 95:5 (w/w) PLLA + PCL | 70 | 20° C. above Tg | 1% | 0% | 3% | 3% |
| 95:5 (w/w) PLLA + PCL | 70 | 20° C. above Tg | 1% | 2% | 4% | 4% |
| 95:5 (w/w) PLLA + PCL | 70 | 20° C. above Tg | 0% | 1% | 4% | 5% |
| 95:5 poly(LLA-co-CL) | 50 | at Tg | 1% | 1% | 1% | 1% |
| 95:5 poly(LLA-co-CL) | 50 | at Tg | 1% | 1% | 1% | 1% |
| 95:5 poly(LLA-co-CL) | 50 | at Tg | 1% | 2% | 0% | 2% |
| 95:5 poly(LLA-co-CL) | 70 | 20° C. above Tg | 4% | 5% | 3% | 3% |
| 95:5 poly(LLA-co-CL) | 70 | 20° C. above Tg | 4% | 5% | 3% | 3% |
| 95:5 poly(LLA-co-CL) | 70 | 20° C. above Tg | 4% | 4% | 3% | 3% |

PCL = poly(ε-caprolactone)
PLLA = poly(L-lactide)
poly(LLA-co-CL) = poly(L-lactide-co-ε-caprolactone) (molar ratio of monomers indicated)

Example 4

Myolimus Eluting Bioresorbable Coronary Stent System in the Porcine Model

Studies were performed in a porcine model with the Myolimus Eluting Bioresorbable Coronary Stent System which combines a polymer stent coated with a thin topcoat layer of polymer with Myolimus. The stents in the studies comprised PLLA, PLLAPGA, PLLAPCL, Poly(L lactide-co-Glycolide) and poly(L lactide-co-caprolactone). At least one of the studies is described below. The nominal drug dose in the coating on the 14 mm length stent is 40 μg of Myolimus and coating is poly(L-lactide-co-glycolide).

The purpose of the studies are to evaluate the efficacy and safety of the polymeric degradable drug eluting stent after a period of 28±2 days and open ended timepoint (OE). The vascular response, including the arterial minimal lumen diameter and percent stenosis, will be evaluated in all vessels using quantitative vessel angiography (QCA) at 28±2 days and at an OE endpoint with a follow up procedure at 90±3 days, 180±5 days and 270±14 days. Optical coherence tomography (OCT) will also be performed at these time points to assess stent apposition and recoil. Additionally, histopathologic analysis of the coronary arteries will be performed at 28±2 days and the OE timepoint to evaluate the cellular response to the stents. Another purpose of this study is to evaluate pharmacokinetics (PK) of the released drug at 3 days, 7 days, 28±2 days, and longer timepoints; drug release will be assessed by analysis of the drug remaining on the stents and uptake of the drug by the tissue. In addition, the polymer degradation is also evaluated by evaluating the molecular weight of the polymer remaining on the stent. The product size of 3.0×14 mm is used in the study.

A nonatherosclerotic swine model was chosen. Hybrid farm pigs (Landrance-Yorkshire) were selected for use in studies up to 90 days in length and Yucatan Mini Swine were selected for use in the 180 day and longer term studies due to starting size and growth expectations. When possible, stents are implanted in the 3 coronary arteries (left circumflex artery [LCx], left anterior descending artery [LAD] and right coronary artery [RCA]), and in the left and right internal mammary arteries (IMAs) per animal.

Upon assignment to the study and until sacrifice, animals will be monitored and observed at least twice a day. To prevent or reduce the occurrence of thrombotic events, animals are treated daily, with acetylsalicylic acid (325 mg, per os [PO]) and clopidogrel (300 mg on the first day and 75 mg daily afterwards, PO), beginning at least 3 days before intervention and continuing until sacrifice. The drugs will be crushed to powder and mixed with their food; therefore, treatment will not be administered when animals are fasted. Fasting (food, including any dietary supplements) will be conducted the morning prior to interventional procedures and scheduled sacrifice. Water will not be withheld. Animals will be tranquilized with ketamine, azaperone and atropine administered intramuscularly [IM]. Animal weight will be recorded. Anesthesia induction will be achieved with propofol injected intravenously [IV]. Upon induction of light anesthesia, the subject animal will be intubated and supported with mechanical ventilation. Isoflurane in oxygen will be administered to maintain a surgical plane of anesthesia. Intravenous fluid therapy will be initiated and maintained throughout the procedure. The rate may be increased to replace blood loss or to correct low systemic blood pressure. To prevent postoperative infection, animals will be given prophylactic antibiotic Draxxin® IM. Additional doses may be administered as deemed appropriate. In order to prevent pain sensitization and minimize postoperative pain, Torbugesic (butorphanol) will be administered IM as preemptive analgesia. After induction of anesthesia, the left or right femoral artery will be accessed through an incision made in the inguinal region. Bupivacain IM will be infiltrated into the femoral access site to achieve local anesthesia and manage pain after surgery. An arterial sheath will be introduced and advanced into the artery. An initial heparin bolus will be administered and ACT will be measured at least every 30 minutes and recorded. The device will not be introduced until ACT is confirmed to be >300 seconds. If ACT is <300 seconds, additional heparin will be administered. Under fluoroscopic guidance, a guiding catheter will be inserted through the sheath (6F) and advanced to the appropriate location. After placement of the guiding catheter, nitroglycerin will be delivered to achieve vasodilatation and angiographic images of the vessel will be obtained with contrast media to identify the proper location for the deployment site (designated pre-stent angiographies). A segment of coronary artery will be chosen and a guidewire will be inserted into the chosen artery. QCA will be performed at this time to document the reference diameter for stent placement. OCT will be performed before implantation to confirm vessel sizing at three locations per coronary vessel.

Stent Deployment Procedures: The stent will be introduced into the selected artery (diameter range of 2.6 to 3.0 mm if possible) by advancing the delivery system through the guiding catheter, over the guide wire to the deployment site. After the stent enters the guide catheter, there will be at least a one minute soak wait before deploying the stent. The stent will then be deployed. The balloon will be inflated at a slow rate: starting with 10 second intervals per atmosphere, bring the balloon to 2 atm. Further expansion completed at 3-5 second intervals for each subsequent atmosphere of pressure. This is approx. 40-50 seconds to nominal pressure. Final pressure is maintained for 20-30 seconds. An angiogram of the balloon at full inflation will be recorded (designated balloon angiography) and the inflation pressure will be noted. After the target stent to artery ratio has been achieved, vacuum will be slowly applied to the inflation device to deflate the balloon. Complete balloon deflation will be verified fluoroscopically. A second inflation may be conducted if a stent is not well apposed against arterial wall or if an animal is at risk. Injection of nitroglycerin will be repeated and a final angiogram of the treated vessel will be performed (designated post-stent angiography) to document device patency, and TIMI flow Implantation will be repeated in the other vessels.

OCT will be performed on all animals to assess stent recoil. OCT will be performed before implantation to confirm vessel sizing at three locations per coronary vessel. After all implants are completed, OCT will be performed again for the same (first) stent, followed by every other stent implanted in the coronaries (designated end of implant OCT).

Following the successful deployment of stents and completion of angiography, all catheters and the sheath will be removed from the animal and the femoral artery will be ligated. The incision will be closed in layers with appropriate suture materials. An antibiotic ointment will be applied to the wound.

The fluoroscopic output from the stent implantation (pre-stent, balloon inflation, post-stent, and end of implant) and at explanation (final) was recorded in digital format. From these images, QCA measurements were obtained for the 28 day and 180 day cohort animals. QCA was also performed at the 90 day follow-up for the 180 day cohort animals. OCT imaging was performed in each animal after the first stent was implanted and after all implants had been completed. OCT was also performed prior to sacrifice on the 28 day Cohort of animals. OCT was performed at a 90 day follow-up on the 180 day cohort. Analysis of each vessel may include: qualitative evaluation for evidence of lumen narrowing (in-stent and marginal), migration, presence of dissection, presence of aneurysms, presences of thrombosis and TIMI flow. Elastin stained sections were examined using light microscopy, image capture, and quantitative morphometric computer-assisted methods. Several semi-quantitative parameters were employed to assess the biological response of vascular tissue to the stents by light microscopy examination of stained sections. Other organ samples were observed for any abnormal findings. Scores to describe vessel injury, inflammation, fibrin deposition, calcification and endothelialization were performed.

Pharmacokinetics Analysis: The drug remaining on the stents was measured using an HPLC-UV analytical method for measuring the drug total content on stents. The drug tissue concentration in the explanted surrounding tissue (artery wall) as well as neointima containing some remaining stent struts (at later timepoints) were measured using a LC/MS bioanalytical method.

Analytical method for determination of polymer Stent Mass and Molecular Weight: Polymer Stent Mass and molecular weight (MW) determination were conducted using Gel Permeation Chromatography (GPC).

Figure 6:
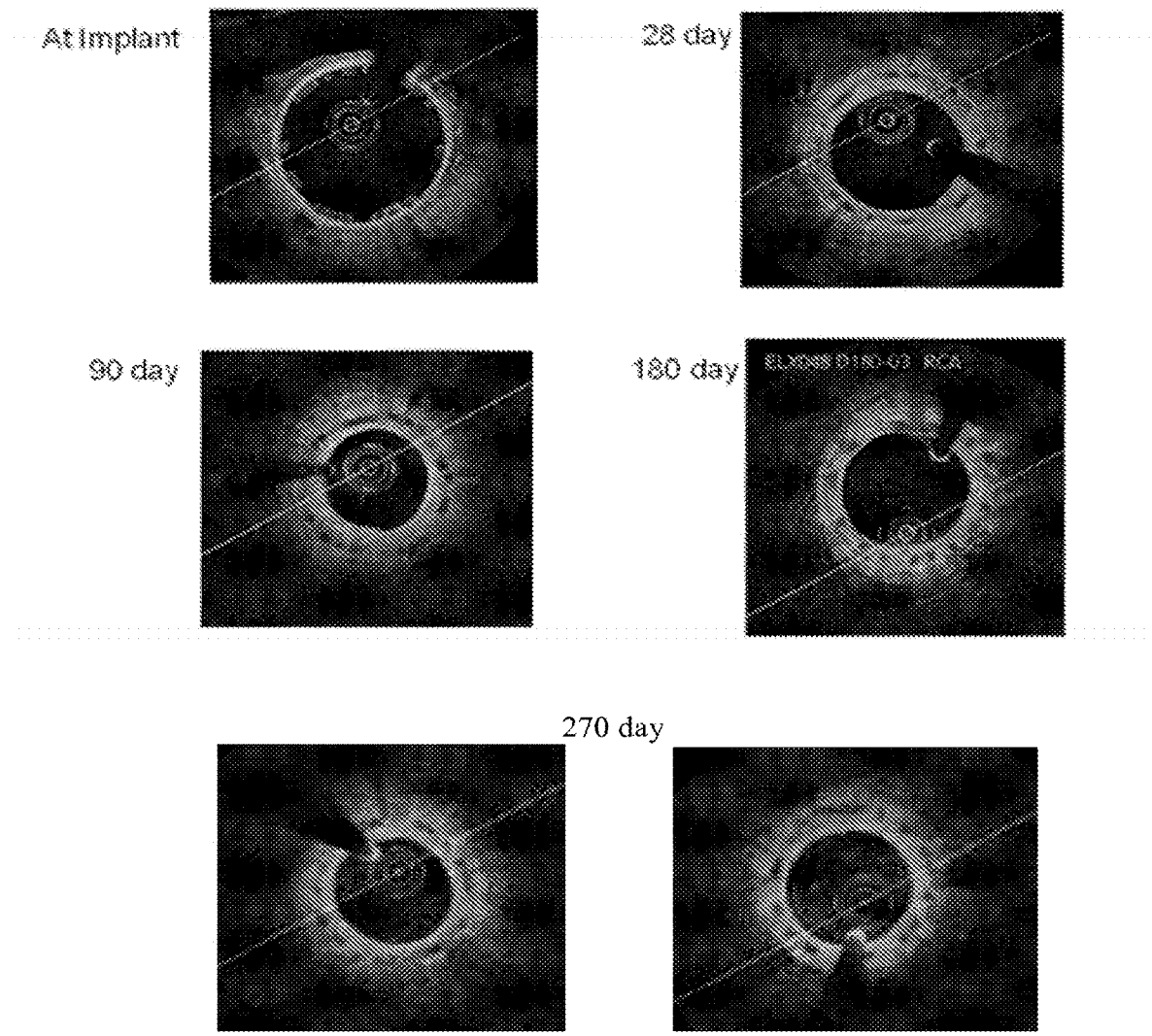
FIG. 6 shows a typical series of OCT images following implant of an embodiment of a device in a porcine model.
Figure 7:
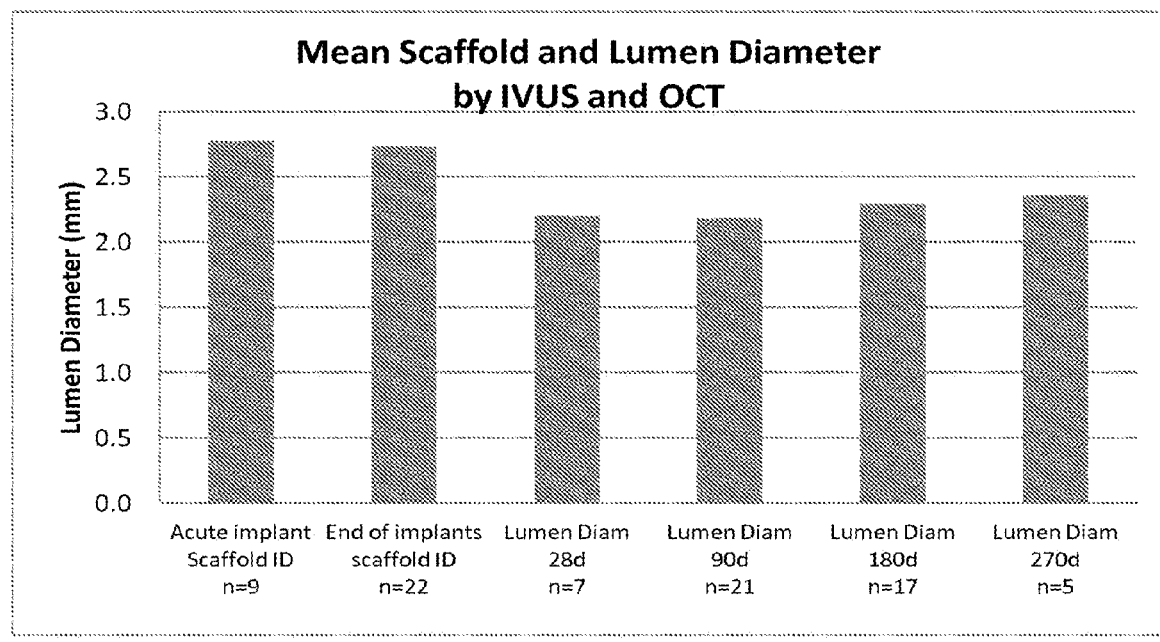
FIG. 7 shows the stent diameter at various time points following implant of an embodiment of a device in a porcine model.
Figure 8:
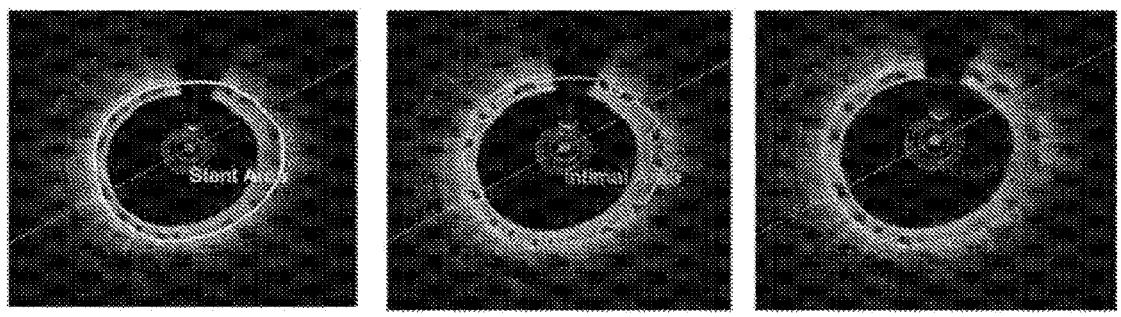
FIG. 8 depicts an example of a method used to calculate % stenosis following implant of an embodiment of a device in a porcine model.
Figure 9:
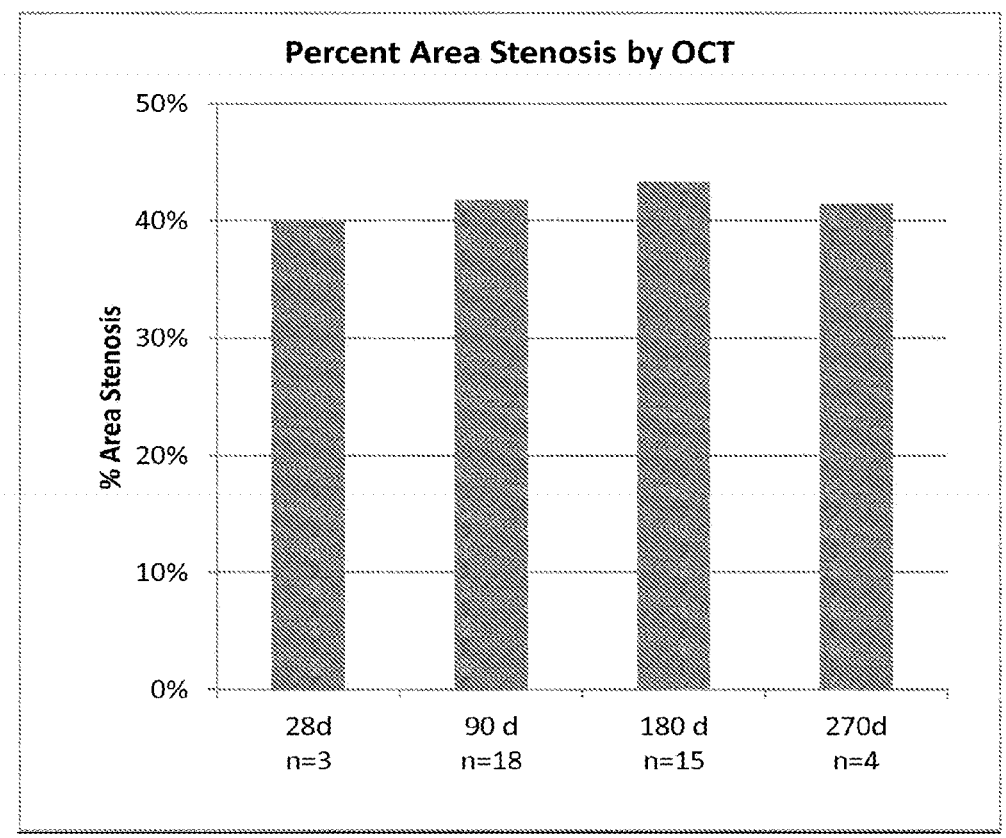
FIG. 9 shows the observed % stenosis following implant of an embodiment of a device in a porcine model.
Figure 10:
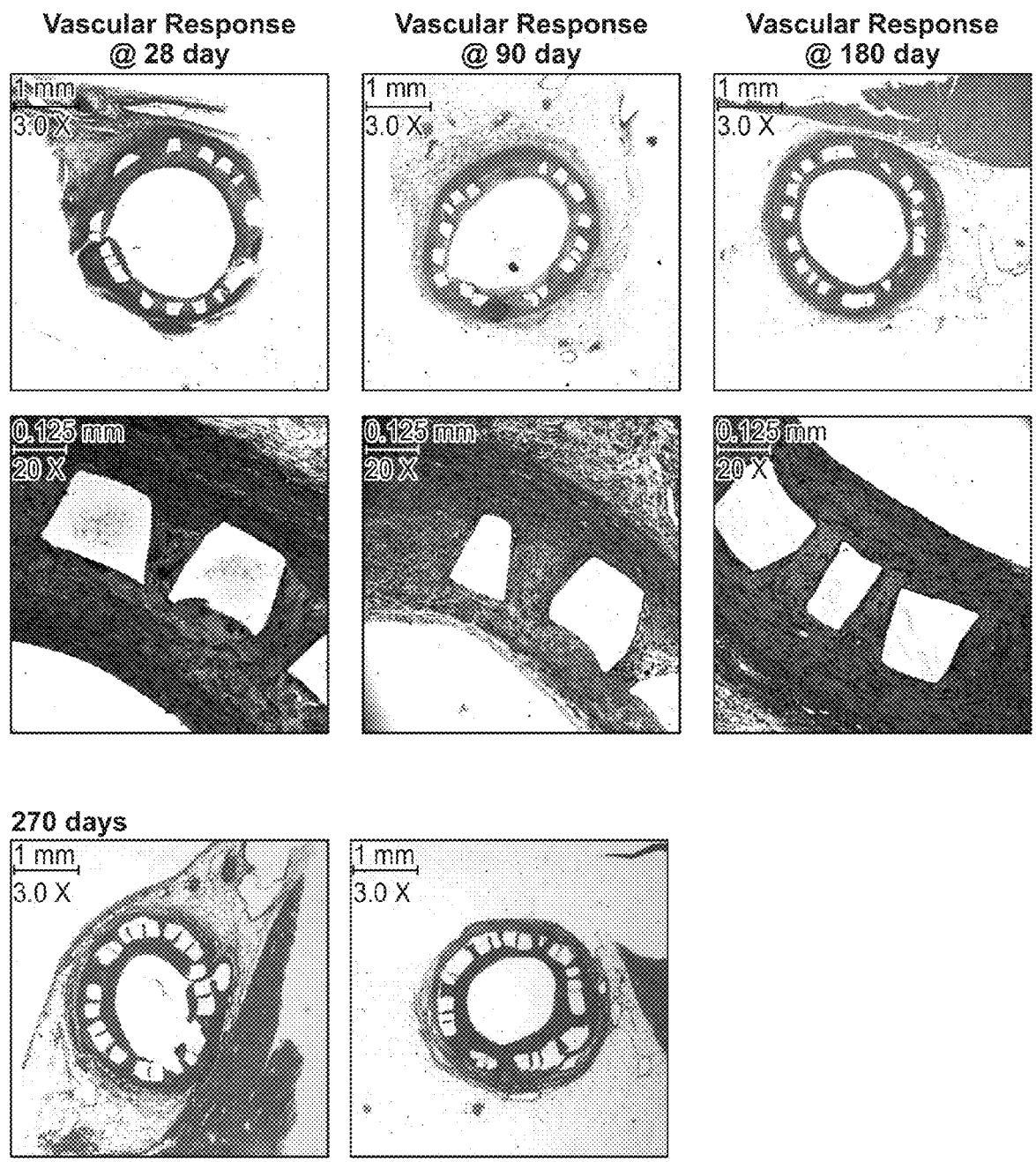
FIG. 10 shows an example of vascular response at 180 days following implant of an embodiment of a device in a porcine model.
Figure 11:
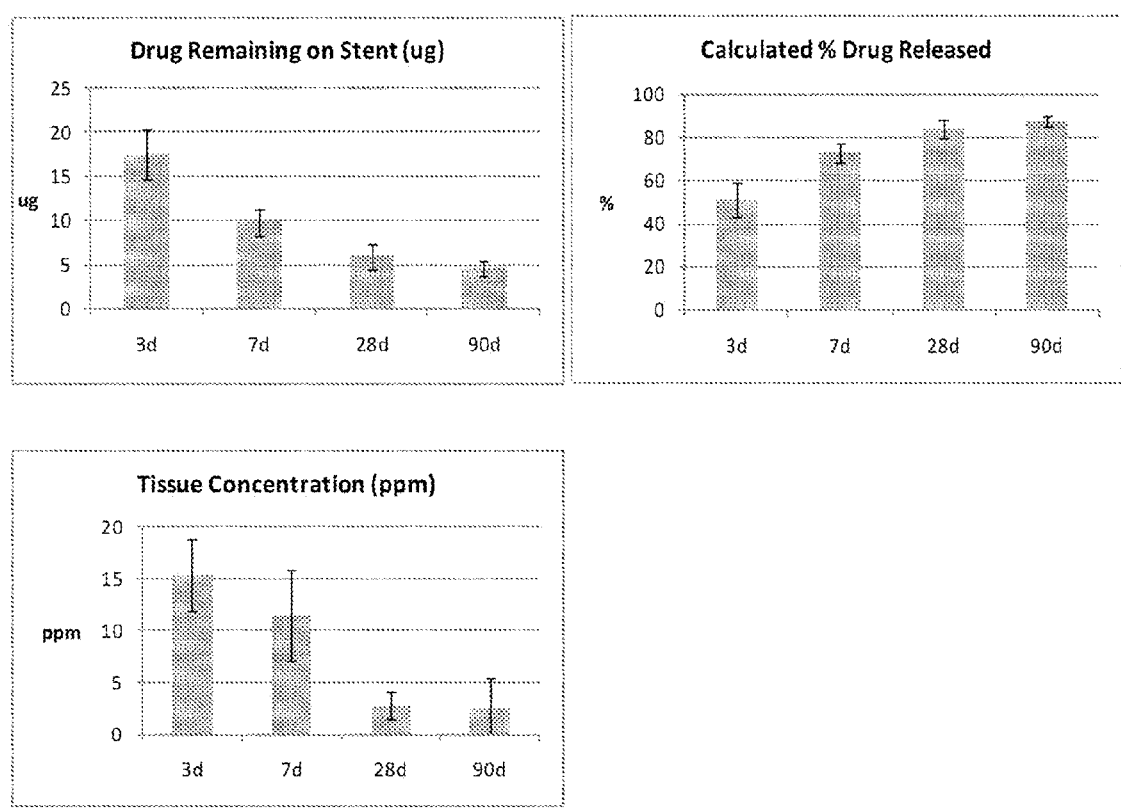
FIG. 11 shows the PK results following implant of an embodiment of a device in a porcine model.
Figure 12A:
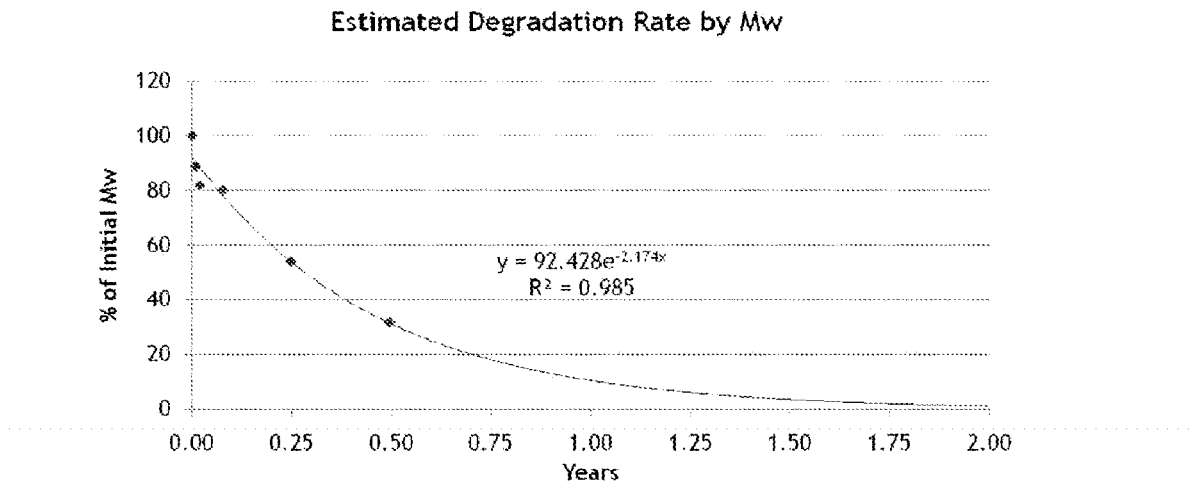
FIGS. 12A, 12B, and 12C show the degradation of the implant in a porcine model of an embodiment.
Figure 12B:
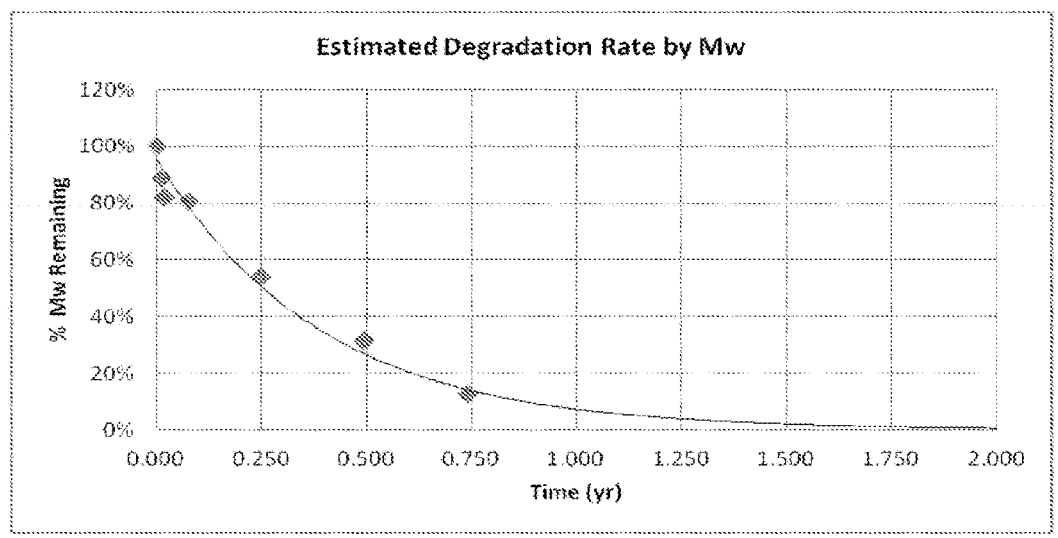
Figure 12C:
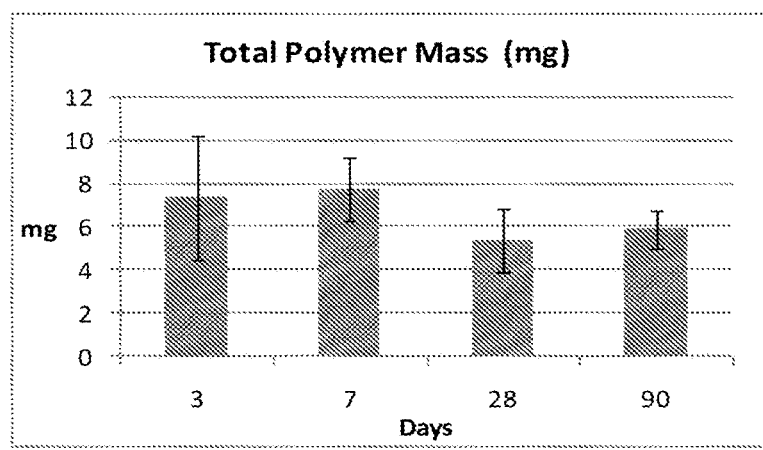

Results: FIG. 6 shows a typical series of OCT images from the implant. FIG. 7 shows the stent and lumen diameter at various time points. The acute and end of implant stent diameter were similar, indicating minimal recoil. The mean lumen diameter was at least maintained or increased over time. FIG. 8 depicts the method used to calculate % stenosis and FIG. 9 shows the observed % stenosis and it can be seen that the % stenosis was maintained to 270 d. Table 9 shows the histopathology results and FIG. 10 shows the vascular response up to 270 days. FIG. 11 shows the Pharmacokinetic results from the study. FIG. 12 shows the degradation of the implant—the trendline supports approximately 1-2 yr degradation by Mw. FIG. 12 A shows in vivo sample degradation rate of biodegradable polymer stent material through 180 days and calculated degradation rate by MW and FIG. 12B shows in vivo sample degradation rate of biodegradable polymer stent material through 270 days and calculated degradation rate by MW. FIG. 12C shows polymer mass decrease over time.

TABLE 9

Histopathology results

| Pathology Score | 28 day | 90 day | 180 day | 270 day |
| --- | --- | --- | --- | --- |
| Injury Score | 0.42 ± 0.22 | 1.31 ± 1.01 | 0.69 ± 0.54 | 0.67 ± 0.19 |
| Inflammation Score | 0.68 ± 0.26 | 1.5 ± 1.31 | 0.82 ± 1.13 | 0.25 ± 0.17 |
| Fibrin Score | 1.79 ± 0.32 | 0.32 ± 0.19 | 0.13 ± 0.04 | 0.09 ± 0.05 |
| Endothelialzation Score | 2.03 ± 0.81 | 1.67 ± 0.37 | 1.78 ± 0.69 | 1.67 ± 0.34 |

Below in Table 10 is an example of in vivo QCA measurement of recoil after expansion of the stent using two measurements techniques the first based on mean stent diameter and the other based on mean minimum diameter of the stent.

TABLE 10

Example of in vivo QCA measurement of recoil after expansion of the stent
Animal study of Biodegradable polymer stent of present invention
Coronary arteries

| Animal Number | Artery | Location | Pre-Stent Mean (mm) | Balloon Mean (mm) | End of implant Mean (mm) | End of implant Min (mm) | Recoil Based on Mean diam | Recoil Based on Min diam |
| --- | --- | --- | --- | --- | --- | --- | --- | --- |
| D28-01 | LAD | mid | 2.60 | 2.50 | 2.46 | 2.20 | 1.6% | 12.0% |
| D28-01 | RCA | dist | 2.76 | 3.02 | 2.75 | 2.43 | 8.9% | 19.5% |
| D28-02 | LAD | mid | 2.75 | 2.88 | 2.59 | 2.38 | 10.1% | 17.4% |
| D28-02 | RCA | mid | 2.72 | 2.62 | 2.59 | 2.28 | 1.1% | 13.0% |
| D180-01 | LAD | mid | 2.44 | 2.66 | 2.70 | 2.51 | −1.5% | 5.6% |
| D180-01 | RCA | mid | 2.66 | 2.58 | 2.78 | 2.59 | −7.8% | −0.4% |
| D180-02 | LAD | mid | 2.76 | 2.93 | 2.98 | 2.72 | −1.7% | 7.2% |
| D180-03 | LAD | mid | 2.52 | 2.57 | 2.65 | 2.45 | −3.1% | 4.7% |
| D180-03 | LCx | mid | 2.61 | 2.65 | 2.64 | 2.30 | 0.4% | 13.2% |
| D180-03 | RCA | dist | 2.57 | 2.91 | 2.73 | 2.50 | 6.2% | 14.1% |
| D180-04 | LAD | mid | 2.57 | 2.57 | 2.80 | 2.64 | −8.9% | −2.7% |
| D180-04 | LCx | dist | 2.85 | 3.18 | 3.06 | 2.70 | 3.8% | 15.1% |
| D180-04 | RCA | dist | 2.71 | 2.50 | 2.97 | 2.72 | −18.8% | −8.8% |
| | | | | | | Ave | −0.7% | 8.4% |
| | | | | | | Max | 10.1% | 19.5% |
| | | | | | | Min | −18.8% | −8.8% |
| | | | | | | SD | 7.8% | 8.5% |
| | | | | | | n | 13 | 13 |

Below in Tables 11, 12 and 13 are examples of different animal studies of biodegradable polymer of present invention with implantation procedures similar to Example 4 with follow-up at 28 days, 90 days, 180 days, and 270 days.

TABLE 11

Results of animal study of biodegradable polymer (90 days, 180 days, 270 days).

|  | At 90 days | | | At 180 days | | | At 270 days | | |
|---|---|---|---|---|---|---|---|---|---|
| OCT measurement | Mean | SD | n | Mean | SD | n | Mean | SD | n |
| Scaffold Diameter (mm) | 2.8 | 0.5 | 13 | 2.6 | 0.5 | 7 | 3.0 | 0.9 | 5 |
| Lumen Diameter (mm) | 2.2 | 0.4 | 13 | 2.2 | 0.4 | 9 | 2.4 | 0.6 | 5 |
| Scaffold Area ($mm^2$) | 6.6 | 1.8 | 10 | 6.8 | 2.3 | 7 | 7.4 | 3.8 | 4 |
| In-Scaffold Intimal Area ($mm^2$) | 2.4 | 0.9 | 10 | 2.9 | 1.6 | 7 | 3.2 | 2.1 | 4 |
| Lumen Area ($mm^2$) | 3.8 | 1.4 | 10 | 4.0 | 1.6 | 9 | 4.6 | 2.4 | 5 |
| % stenosis (Intimal Area/Scaffold Area) | 37% | 9% | 10 | 41% | 10% | 7 | 41% | 5% | 4 |

TABLE 12

Results of animal study of biodegradable polymer (28 days, 90 days, 180 days).

|  | At 28 days | | | At 90 days | | | At 180 days | | |
|---|---|---|---|---|---|---|---|---|---|
| OCT measurement | Mean | SD | n | Mean | SD | n | Mean | SD | n |
| Scaffold Diameter (mm) | 2.6 | 0.1 | 3 | 3.0 | 0.4 | 8 | 4.1 | 1.3 | 8 |
| Lumen Diameter (mm) | 2.1 | 0.2 | 3 | 2.2 | 0.2 | 8 | 2.4 | 0.2 | 8 |
| Scaffold Area ($mm^2$) | 6.4 | 0.7 | 3 | 8.4 | 1.9 | 8 | 8.9 | 1.8 | 8 |
| In-Scaffold Intimal Area ($mm^2$) | 2.5 | 0.2 | 3 | 4.1 | 1.7 | 8 | 4.1 | 1.3 | 8 |
| Lumen Area ($mm^2$) | 3.4 | 0.5 | 3 | 3.8 | 0.7 | 8 | 4.5 | 0.8 | 8 |
| % stenosis (Intimal Area/Scaffold Area) | 40% | 3% | 3 | 47% | 10% | 8 | 45% | 6% | 8 |

TABLE 13

Results of animal study of biodegradable polymer (28 days, 90 days, 180 days).

|  | At 28 days | | | At 90 days | | | At 180 days | | |
|---|---|---|---|---|---|---|---|---|---|
| OCT measurement | Mean | SD | n | Mean | SD | n | Mean | SD | n |
| Scaffold Diameter (mm) | 2.7 | 0.1 | 7 | 2.8 | 0.2 | 7 | 3.0 | 0.3 | 7 |
| Lumen Diameter (mm) | 2.2 | 0.3 | 7 | 1.9 | 0.3 | 7 | 2.2 | 0.3 | 7 |
| Scaffold Area ($mm^2$) | 6.9 | 0.7 | 7 | 7.5 | 1.3 | 5 | 8.5 | 1.5 | 7 |
| In-Scaffold Intimal Area ($mm^2$) | 2.5 | 4.0 | 7 | 4.0 | 1.9 | 5 | 4.4 | 1.5 | 7 |
| Lumen Area ($mm^2$) | 4.0 | 1.2 | 7 | 2.8 | 1.0 | 7 | 3.7 | 1.0 | 7 |
| % stenosis (Intimal Area/Scaffold Area) | 36% | 11% | 7 | 52% | 19% | 5 | 52% | 13% | 7 |

Example 5

Processing of Stents and Tubes

This example illustrates processing of stents and tubes utilizing some embodiments. Various other embodiments may be incorporated in these examples or other examples and are within the scope of the disclosed present invention.

A. Processing of a Polymeric Stent

Example 5A

A stent is patterned from a tube formed using extrusion (or optionally using spraying, dip coating, molding, or 3D printing) from polylactide material, more preferably, Poly(L-lactide) (or optionally from a co-polymers such as Polylactide-co-polyglycolide or polylactide-co-polycaprolactone; or blends of polylactides, polyglycolides, and polycaprolactones; or combination thereof; in various polymer or co-polymer ratios such as 80:20 to 99:01). The tubular body has an initial inner diameter of about 0.5 mm (0.020") but optionally can have an initial diameter ranging from about 0.25 mm (0.01") to 2 mm (0.079"). The tube is treated by at least one of heat, pressure, and drawing at temperature above Tg of the material and below Tm for duration ranging from a fraction of a second to one hour to expand the tube to a second uniform inner diameter of about 3 mm (0.118") which is about the diameter of the intended deployment diameter of a the stent when the stent is deployed to about 3 mm or to at least the intended deployment diameter when the stent is deployed to about 3 mm or above in this example (intended deployment diameter can also be the nominal labeled diameter of the stent or deploying balloon or the actual deployed diameter of the stent). Optionally, the second inner diameter of the tube or the stent can range from 0.9-1.5 times an intended deployment diameter of the stent. The tube or the stent is optionally treated by heating at about Tg or above Tg (for example 90° C.), ranging from a fraction of second to 24 hours when the tube is at the second inner diameter. Optionally a mandrel is inserted inside the tube while the heat treatment is applied and also optionally the tube is held into position over the mandrel to control shrinkage of the tube. The tube is cooled after heat treatment or optionally quenched quickly to a temperature below Tg or below the crystallization temperature or to ambient temperature or below ambient temperature. The tube is patterned into a stent at about the second inner diameter or optionally below the second inner diameter. The patterned stent is coated with the drug Novolimus (e.g. 5 micrograms/mm) or optionally with a mixture of Novolimus and a polymer or co-polymer such as a PLLA polymer or PLLA-PGA co-polymer. The coated stent is optionally placed in a vacuum for a total of 36 hours and then crimped to a diameter smaller than the intended deployment diameter using a gradual heat (at about Tg or below Tg) and pressure or mechanical force from about 10 seconds to about 30 minutes. The stent is crimped onto the delivery system or optionally crimped and then mounted or fitted onto a delivery system such as a balloon catheter. After crimping, the stent delivery system is packaged in a sterile barrier (i.e., in a foil pouch) and can be sterilized by ebeam or ethylene oxide cycle. The mounted stent and delivery system in the example are sterilized using E-beam sterilization. The sterilized stent is subjected optionally to one additional treatment by heating the packaged stent to a temperature below Tg (example 30° C.) for a duration ranging from 1 minute to 7 days). The stent material Tg after treatment is above 35° C. and below 55° C. The crystallinity of the stent material after treatment ranges from about 0% to 60%. (Optionally the crystallinity after treatment can range from 0% to 30% or 0% to 40% or 0% to 55%). The stent is capable of radial expansion at body temperature and have sufficient radial strength to support a body lumen, or optionally 3 psi or greater. The stent optionally has recoil from an expanded condition of less than 10%.

Other embodiments are:

Example 5A.1

A stent prosthesis as in example A wherein the heat treatment of the tubular body or stent at about Tg or above Tg for a duration ranging from a fraction of a second to about 24 hours takes place when the tube diameter is 0.9-1.5 times the intended deployment diameter.

Example 5A.2

A stent prosthesis as in example A wherein the heat treatment of the tubular body or stent at about Tg or above Tg for duration ranging from a fraction of a second to about 24 hours takes place when the tube diameter is 0.9-1.5 times the intended deployment diameter and optionally a treatment by heat of the tubular body below Tg takes place when the tube diameter is below 0.9 times the intended deployment diameter.

Example 5A.3

A stent prosthesis as in example A wherein the heat treatment of the tubular body or stent when the tube diameter is 0.9-1.5 times the intended deployment diameter is always about Tg or below Tg for a duration ranging from a fraction of a second to about 24 hours.

Example 5A.4

A stent prosthesis as in example A wherein the second inner diameter of the tube or the stent is 0.95-1.5 times an intended deployment diameter, or 1-1.5 times an intended deployment diameter, or 1.05-1.5 times an intended deployment diameter, or 1.1-1.5 times an intended deployment diameter.

Example 5A.5

A stent prosthesis as in example A wherein the treatment by heat at about Tg or above Tg for the tube or stent when the diameter is 0.9-1.5 times an intended deployment diameter is for a short duration ranging from a fraction of a second to less than one hour, preferably from a fraction of a second to less than 30 minutes, and more preferably from a fraction of a second to less than 15 minutes.

Example 6

Securing the Stent on Delivery System

As a means to retain the stent on the balloon of a delivery catheter, a blockade-like bump on the proximal end, distal end or both ends of the stent can be formed on the balloon or part of the balloon (FIG. 2). The bump can be deflated partially or fully by means of a vacuum on the catheter lumen as part of the deflation port of the balloon or a separate/independent deflation port. The bumps deflate or shrink or become smaller upon inflation of the balloon or upon deflation of the balloon or upon pulling vacuum on the balloon or upon pulling vacuum on the separate bump port. The bump prevents or minimizes the movement of the stent during introduction and delivery of the stent to the lesion.

Another means for retaining the stent is by the presence of a cap on the proximal end, distal end, or both ends of the stent. Each cap covers a portion of the stent, preferably from approximately 0.1 to 2 millimeter of the stent. The cap can be made from a solid tube, spongy tube, weave or braided tube, or laser cut tube with patterning, or a portion of the balloon material itself and affixed to one end of the catheter. The cap can fit snuggly or tightly around the stent. The inner diameter of the cap can be slightly larger than the crimped diameter of the stent, preferably same as the crimped diameter, and more preferably, smaller than the diameter of the crimp diameter. The remaining cap may cover the balloon material adjacent to the stent and may extend further to cover outer member (proximal cap) or the tip (distal cap) of the delivery catheter. The cap can have uniform diameter (inner diameter same throughout the length of the cap), it can have a larger inner diameter on the side where it covers the stent and smaller inner diameter on the side where it covers the outer member/tip of the delivery catheter. One or more exposed edges of the cap can be beveled. Preferably the cap is glued to the delivery catheter (affixed) when it is not in contact with the stent or balloon so as to prevent it from flowing away. Upon expansion of the balloon and ensuing expansion of the stent, the cap retracts or releases from the stent and at a certain balloon diameter, no longer covers the stent and allows the stent to expand freely.

Another means for retaining the stent is the use of an adhesive such as waterproof permanent adhesive, non permanent adhesive, or solvent such as tetrahydrofuran, dichloromethane, chloroform, or the like. The adhesive is applied on the balloon or catheter such that there is one or more tongue or groove formed within the adhesive mass. The tongue or groove can be the same or smaller than a stent feature such as a link, strut, marker tab or hole, crown, tab, flap or other which serves as the groove or tongue (reverse of the adhesive shape). The shape of the tongue or groove is dependent on the stent feature. The depth of the tongue or groove can be greater than the stent thickness, same as the stent thickness, or less than the stent thickness. The adhesive can be positioned at either or both end of the intended stent or elsewhere within the confines of the stent. A crimped stent is then placed onto the adhesive and the feature of the stent is snapped into the tongue or groove of the adhesive mass as a means to retain the stent. When the balloon is expanded, the stent feature snaps out of the groove.

Another means for retaining the stent is the use of heat to heat seal the stent onto the balloon surface. A stent inside a sheath is inserted over the balloon. The stent is heated to about or below the Tg of the coating of the stent or the stent and then the balloon is pressurized causing the stent to be heat sealed to the balloon. In another means, the stent with or without a sheath on a balloon can be placed inside a heated crimper set at about or below the Tg of the coating on the stent or the stent and the crimper is allowed to closed. The balloon is pressured causing the stent to be heat sealed to the balloon. Stent coating can be such that the coating itself or an added top layer of coating is made from a material that has a lower Tg than the stent itself. Examples of such a layer can be made of 70:30 PLLA-co-CL or 85:15 PLLA-co-CL or higher ratios of CL, or PGA, PLLA-GA with higher ratio of GA, PDLLA, polymers with Tg at or below 55 degrees Celsius, or the like or combination thereof.

Another means for retaining the stent is the use of an adhesive such as waterproof permanent adhesive or non permanent adhesive to affix an anchoring device. The anchoring device has a grooves or tongue that can be the same or smaller that a stent feature such as a link, strut, marker tab or hole, crown, tab, flap, or other groove or tongue (reverse of the anchor device). The shape of the tongue or groove is dependent on the stent feature. The depth of the tongue or groove can be greater than the stent thickness, same as the stent thickness, or less than the stent thickness. One or more anchoring device is snapped onto the stent feature or features. The stent can be crimped before or after attachment to the anchoring device. The stent is mounted over the balloon and the anchoring device is attached mechanically to the balloon or by use of adhesives or welding means. The anchoring device can have an elastic band which goes around the balloon as a means to be attached mechanically to the balloon. This band stretches as the balloon is expanded. As the stent and the band expand, the grip of the tongue or groove will release the stent.

Another example of securing the stent is to apply or modify the surface of the catheter or balloon catheter is such a way to retain or hinder the stent from longitudinal movement upon delivery of the stent into a body lumen and allows the stent to expand or deploy in the body lumen at body temperature.

Another example of securing the stent is to apply an adhesive to at least one side of the stent (abluminal or luminal) which when crimping the stent onto the catheter or the balloon catheter creates a bond sufficient to minimize or prevent the stent from moving in the longitudinal direction or expanding in the radial direction prior to active deployment by the operator.

Another means to secure the stent on delivery system is to incorporate a sheath over the stent that is retracted to deploy the stent to an intended deployment diameter or to a partial deployment diameter below an intended deployment diameter.

Example 7

Methods to Control Tg to a Desired Tg Between 35° C. To 50° C. Or Above 37° C. To 45° C.

To control Tg of stent material to allow expansion at body temperature or other desired temperatures. For example, a desired Tg between 35° C. and 50° C. to allow the stent to expand at body temperature can be achieved through one or more sequence of treatments to control the Tg starting from forming the tube to the final product where the desired Tg is achieved. A polymer or co-polymer tube such as PLLA-PCL or PLLA-PGA where the tube is formed using extrusion, spraying, dip coating, molding, or 3D printing and having a Tg after forming about 55° C. The tube is treated by at least one of heating, solvent removal or introduction, additive removal or introduction, pressurizing, stretching, vacuum, sterilization, and patterning, in a certain configuration or sequence to achieve a desired Tg for the stent material after treatment to be between 35° C. and 50° C. (optionally greater than 37° C. and below 45° C.) such that the stent is capable of radial expansion in a body lumen and have sufficient radial strength to support a body lumen.

Another example is a stent with a transitional temperature, Tg, between 37° C. to 55° C.—one method to control the stent Tg is by using a copolymer, terpolymer, or the like for making the stent. For example, a copolymer made from 70:30 to 95:05 of L-lactide and epsilon-caprolactone molar ratios, can result in a stent having a range of Tg from 37° C. to 55° C., respectively. Another method is to fabricate tube using a heatless process such as dipping or spraying to form a tube. For example, a tube, which can be patterned into a stent, can be fabricated by dipping a mandrel onto a concentrated solution of material having a Tg less than 55° C. For example, a tube can be made by spraying a solution onto a mandrel. After dipping or spraying, the solvent is allowed to evaporate by vacuuming and or exposure to carbon dioxide at high pressures (such as 700 psi for 24 hours). The use of this heatless spraying or dipping process minimizes the formation of crystalline structures within the polymer, thereby resulting in the minimum possible Tg. Another method is to add one or more molecules into the polymer used to fabricate the stent. Molecules can be a solvent such as methylene chloride, DMSO, or others, plasticizers such as lactide, caprolactone, lactic acid, L-lactic acid, D-lactic acid, DL-lactic acid, p-dioxanone, epsilon-caprolic acid, alkylene oxalate, cycloalkylene oxalate, alkylene succinate, $\beta$.-hydroxybutyrate, substituted or unsubstituted trimethylene carbonate, 1,5-dioxopan-2-one, 1,4-dioxepan-2-one, glycolide, glycolic acid, L-lactide, D-lactide, DL-lactide, meso-lactide, combination thereof, or others, low Tg polymers such as polyvinylpyrrolidone, polyethylene glycol, polyethylene oxide, castor oil, combination thereof, or others.

A further method of controlling the Tg of the polymer is by processing such as heating, laser cutting, crimping, irradiation, or the like. Exposing the stent or tube used to pattern the stent to these processes can decrease or increase the Tg of the material.

Examples of processing a tube or a stent at a diameter ranging from 0.9-1.5 times intended deployment diameter where the stent is expanded at temperature above 37° C. in a body lumen are shown below.

A stent is patterned from a tube made from Poly(L-lactide-co-glycolide) material, preferably having a lactide to glycolide comonomer ratio of 83:17 to 88:12. The tube can be formed by spraying. Before it is patterned into a stent, the tube has an inner diameter that is 90 to 150% of the intended stent deployment diameter. As a further example, for a 3 mm stent intended deployment diameter, the tube inner diameter can range from 2.7 millimeter (0.106") to 4.5 millimeter (0.177"). Another example is for a 3.5 mm intended deployment diameter stent. The tube inner diameter can range from 3.15 millimeter (0.124") to 5.25 millimeter (0.207"). The tube is heat treated optionally below Tg such as at 10° C. below the Tg for 30 minutes. Alternatively or optionally, the tube is heated above Tg ranging from a fraction of a second to 5 hours (for example at 90° C. for 1 hour). The Tg of the tube after heat treatment is between 30° C. to 55° C. (optionally between 35° C. to 55° C.). The tube is then patterned into a stent, coated with a drug matrix such as Poly(L-lactide) based copolymer and Novolimus. The coated stent is vacuumed for 36 hours at approximately 1 torr. The stent is then crimped at 45° C. (optionally between 30° C. and 45° C., or optionally lower than Tg) onto the balloon of a delivery catheter. The stent delivery system is packaged in a sterile barrier and sterilized by ebeam. After sterilization, the stent delivery system is optionally stabilized at 29° C. for 48 hours. Prior to or during stent deployment, the stent is heated to a temperature greater than 37° C. but below 50° C. (optionally above 37° C. and below 45° C.) to expand the stent to its intended deployment diameter. (Optionally by a heated catheter or balloon, RF balloon, heated contract agent injected into the artery, heated coil on the catheter shaft proximal to the balloon, or by other means). This provides sufficient radial strength to support a body lumen and/or have a recoil from an expanded state of less than 10%.

Another example is a stent patterned from a tube made from Poly(L-lactide-co-glycolide) material, preferably having a lactide to glycolide comonomer ratio of 80:20 to 95:05. The tube can be formed by spraying. Before it is patterned into a stent, the tube has an inner diameter that is 90 to 150% of the intended stent deployment diameter. As a further example, for a 3 mm stent, the tube inner diameter can range from 2.7 millimeter (0.106") to 4.5 millimeter (0.177"). Another example is a 3.5 mm stent. The tube inner diameter can range from 3.15 millimeter (0.124") to 5.25 millimeter (0.207"). The tube is heat treated below Tg for example at 10° C. below the Tg for 30 minutes. The Tg of the tube after treatment is between 35° C. to 55° C. The tube is then patterned into a stent, coated with a drug matrix such as Poly(L-lactide) based copolymer and Novolimus. The coated stent is vacuumed for 36 hours at approximately 1 torr. The stent is then crimped at 45° C. onto the balloon of a delivery catheter. The stent delivery system is packaged in a sterile barrier and sterilized by ebeam. After sterilization, the stent delivery system is optionally stabilized at 29° C. for 48 hours. The final stent material after treatment is substantially amorphous. Before or during stent deployment, the stent is heated to a temperature greater than 37° C. and below 50° C. (optionally above 37° C. and below 45° C.) to expand it to its intended deployment diameter by means such as a heated balloon, RF balloon, heated contract agent injected into the artery, heated coil on the catheter shaft proximal to the balloon, or by other means. The expanded stent has sufficient strength to support a body lumen and/or recoil from an expanded state of less than 10%.

Another example is a stent is patterned from a tube made from Poly(L-lactide-co-caprolactone) material, preferably having a lactide to caprolactone ratio of 80:20 to 99:01. The tube can be formed by spraying. Before it is crimped, the tube has an inner diameter that is 90 to 150% of the intended stent deployment diameter. As a further example, for a 3 mm stent, the tube inner diameter can range from 2.7 millimeter (0.106") to 4.5 millimeter (0.177"). Another example is a 3.5 mm stent. The tube inner diameter can range from 3.15 millimeter (0.124") to 5.25 millimeter (0.207"). The tube is heat treated above Tg for example at 120° C. for 2 hours (optionally fraction of a second to 5 hours). The Tg of the tube after treatment is between 35° C. to 55° C. The tube is patterned into a stent, coated with a drug matrix such as Poly(L-lactide) based copolymer and Novolimus. The coated stent is vacuumed for 36 hours at approximately 1 torr. The stent is then crimped at 35° C. onto the balloon of a delivery catheter. The stent delivery system is packaged in a sterile barrier and sterilized by ebeam. The final stent material after treatment has a crystallinity of 25% (optionally between 10% and 50%). Before or during stent deployment, the stent is heated to a temperature greater than 37° C. and below 50° C. (optionally above 37° C. and below 45° C.) to expand it to its intended deployment diameter by means such as a heated balloon, RF balloon, heated contract agent injected into the artery, heated coil on the catheter shaft proximal to the balloon, or by other means. The expanded stent has sufficient strength to support a body lumen and/or recoil from an expanded state of less than 10%.

Example 8

Methods of Fabricating a Stent or a Tube with Radiopaque Material

One method to fabricate a stent with radiopacity is to have cup or hole features in the stent design. These cup or hole features are for holding radiopaque markers that can be higher in thickness, same thickness, or lower thickness as the stent. One or more cup or hole features can be on the stent. For example, 2 cups can be located at each end of the stent and can be 90 degrees apart. Markers can be made from metals such as gold, tungsten, tantalum, platinum, iridium, alloys of these metals, combination thereof, or other. Markers can also be made from stent material filled with radiopaque agents such as nanoparticles/microparticles/fibers/others made from metal like gold, tungsten, tantalum, platinum, iridium, alloys of these metals, combination thereof, or others; barium compounds like barium sulfate; or contrast media. The loading of these agents can be from 1 to 80% by weight.

Another method to fabricate a stent with radiopacity is to add radiopaque agent fillers during the spraying, dipping, molding, 3D printing, extrusion, or the like. The radiopaque fillers can be nanoparticles/microparticles/fibers/others made from metal like gold, tungsten, tantalum, platinum, iridium, alloys of these metals, combination thereof, or others; barium compounds like barium sulfate at 1 to 80% by weight filling; or contrast media such as iodinated contrast agents like diatrizoate, metrizoate, ioxaglate, iopamidol, iohexyl, ixolian, iopromide iodixanol; Ipodate sodium; sodium iopodate; gadolinium; potassium iodide; or other. The loading of these contrast agents can be from 10 to 80% by weight.

Yet another method is to add molecules that contain iodine, barium, platinum, or heavy metal to the material used to fabricate the stent. These molecules can covalently attached to the material by grafting onto the polymer chains or crosslinking more than one polymer chains. These molecules contain one or more iodine, barium, platinum, or heavy metals. The percent of these molecules can vary from 1 to 50% by weight.

Yet another method for making the stent radiopaque is to crimp the stent onto the balloon of an infusion catheter. As the stent is being expanded, contrast agents are infused into the artery at high pressure, making the artery radiopaque at the site of deployment. Depending on the hydrophobicity and lipophilicity of the contrast agents, these agents will wash out and the artery will no longer be radiopaque.

Yet another method for making the stent radiopaque is to have a thin radiopaque metal or alloy structure within the stent. This thin radiopaque structure can be made from made from metal like gold, tungsten, tantalum, platinum, iridium, alloys of these metals, combination thereof, or others. The thickness of the structures can range from 0.0001" to 0.001". They can have circular, square, trapezoidal, rectangular, triangular, or other cross-sections. The structures can be small corrugated rings, part of or a whole stent, crowns, filaments. A tube of some thickness is first formed by partially dipping or spraying coating solutions of the stent material onto a mandrel. After coating, the thin radiopaque structures are placed in contact, pressed into place, or crimped into place on the partially dipped or spray tube. The tube with the radiopaque structure is then further dipped or sprayed until the final desired thickness has been reached. The tube is then patterned into a stent such that the radiopaque structures are partially or fully embedded in the stent.

Yet another method for making the stent radiopaque is to have a thin radiopaque metal or alloy structure within the stent. This thin radiopaque structure can be made from metal like gold, tungsten, tantalum, platinum, iridium, molybdenum, iron, magnesium, alloys of these metals, combination thereof, or others. The thickness of the structures can range from 0.0005" to 0.001". They can have circular, square, trapezoidal, rectangular, triangular, or other cross-sections. This structure is then coated with a coating of bioresorbable material such as polylactide, poly(lactide-co-caprolactone), poly(lactide-co-glycolide), or the like.

Example of a stent capable to expand to at least 120% or 1.2 times an intended deployment diameter while keeping an intact stent structure integrity and optionally having a recoil of less than 15% from an expanded state (optionally less than 10%, or less than 5%) is shown below.

A stent is patterned from a tube made from Poly(L-lactide-co-epsilon caprolactone) material, preferably having a lactide to epsilon caprolactone comonomer ratio of 82:10 to 98:02, more preferably at 88:12 to 92:08. The tube can be formed using extrusion, molding, dipping, or spraying and treated. The glass transitional temperature, Tg, of the polymeric material after treatment is greater than 35° C. and less than approximately 55° C. The tube is patterned into a stent. Before crimping the stent or the tube has an inner diameter that can range from 0.9 to 1.5 times its intended deployment diameter. As an example, for a 3 mm intended deployment diameter stent, the inner diameter of the tube or the patterned stent is between 2.7 millimeter (0.106") to 4.5 millimeter (0.177"). For a 3.5 mm stent, the inner diameter is between 3.15 millimeter (0.124") to 5.25 millimeter (0.207"). The crimped stent is mounted onto a delivery system, packaged, and sterilized. The stent is expandable at body temperature to at least 120% of an intended deployment diameter (nominal diameter) with sufficient strength to support a body lumen and without breakage (fracture) in any of the stent struts (optionally while maintaining structural integrity of the stent) and optionally with a % recoil of less than 15% from an expanded state.

Example 9

Method to Treat Above Tg at an Expanded Diameter

A tube is formed by spraying or extrusion at diameter x where x is 0.8-1.5 times (80 to 150%) an intended deployment diameter, treatment of the tubular body to temperature above Tg, patterning at x diameter, crimping, and sterilizing.

A stent is patterned from a tube made from Poly(L-lactide-co-epsilon caprolactone) material, preferably having a lactide to epsilon caprolactone comonomer ratio of 82:18 to 98:02, more preferably at 88:12 to 92:08. The tube can be formed by extrusion, molding, dipping, or spraying. Before it is patterned into a stent, the tube has an inner diameter that is 80 to 150% of the intended stent deployment diameter. As a further example, for a 3 mm intended deployment diameter for the stent, the tube inner diameter can range from 2.4 millimeter (0.094") to 4.5 millimeter (0.177"). Another example is an intended deployment diameter of at least 3.5 mm stent. The tube inner diameter can range from 2.8 millimeter (0.110") to 5.25 millimeter (0.207"). The tube is then heat treated above the Tg of material to increase the crystallinity of the stent by at least 5%. The temperature can range from 60° C. to 100° C. for 1 minutes to 24 hours. For example, the tube can be heated treated at 90° C. for 2 hours. The tube is patterned into a stent, coated with a drug matrix such as Poly(L-lactide) based copolymer and Novolimus, and crimped at 45° C. onto the balloon of a delivery catheter. The stent delivery system is the packaged in a sterile barrier and sterilized by ebeam. The stent is radially expandable at body temperature having sufficient radial strength to support a body lumen.

Example 10

Tube or Stent with Amorphous Crystallinity after Modification

A polymeric material is sprayed to form tube at x (x is 0.8-1.5 times intended deployment diameter), treated at about 75° C. for 15 minutes, patterned, crimped, sterilized, post stabilized (optional), wherein the polymeric material after treatment is amorphous.

A stent is patterned from a tube made from Poly(L-lactide-co-epsilon caprolactone) material, preferably having a lactide to epsilon caprolactone comonomer ratio of 88:12 to 92:08. The tube can be formed by spraying. Before it is patterned into a stent, the tube has an inner diameter that is 80 to 150% of the intended stent deployment diameter. As a further example, for at least a 3 mm intended deployment diameter for the stent, the tube inner diameter can range from 2.7 millimeter (0.106") to 4.5 millimeter (0.177"). Another example is a 3.5 mm stent. The tube inner diameter can range from 3.15 millimeter (0.124") to 5.25 millimeter (0.207"). The tube is patterned into a stent, coated with a drug matrix such as Poly(L-lactide) based copolymer and Novolimus. The coated stent is vacuumed for 36 hours at approximately 1 torr. The stent is optionally heat treated at 70° C. for 15 minutes. The stent is then crimped at 30° C. onto the balloon of a delivery catheter over 30 minutes (optionally 1 minute to 1 hour). The stent delivery system is packaged in a sterile barrier and sterilized by ebeam. After sterilization, the stent delivery system is optionally stabilized at 29° C. for 48 hours. The final stent material is substantially amorphous with a percent crystallinity of less than approximately 25%. In one example, the intended deployment diameter is 3.0 mm. In another example it is 3.25 mm. In a third example it is 3.5 mm, and in a forth example it is 4.0 mm.

Example 11

Crystallinity of Tube or Stent Between 10%-50% after Modification

The tube is made by extrusion, a higher temperature than 75° C. is used for longer duration, wherein the crystallinity of polymeric material after treatment is between 10% and 50%.

A stent is patterned from a tube made from Poly(L-lactide-co-epsilon caprolactone) material, preferably having a lactide to epsilon caprolactone comonomer ratio of 85:15 to 95:05. The tube can be formed by extrusion. Before crimping, the tube or the stent has an inner diameter that is 90 to 150% of the intended stent deployment diameter. As a further example, for an intended deployment diameter of at least 3 mm stent, the tube inner diameter can range from 2.7 millimeter (0.106") to 4.5 millimeter (0.177"). Another example is a 3.5 mm stent. The tube inner diameter can range from 3.15 millimeter (0.124") to 5.25 millimeter (0.207"). The tube is heat treated at 180° C. for 2 hours and quenched to at or below ambient temperature. The tube is patterned into a stent, coated with a drug matrix such as Poly(L-lactide) based copolymer and Novolimus. The coated stent is optionally vacuumed for 36 hours at approximately 1 torr. The stent is then crimped at 40° C. onto the balloon of a delivery catheter. The stent delivery system is packaged in a sterile barrier and sterilized by ebeam. After sterilization, the stent delivery system is optionally stabilized at 25° C. for 5 hours. The final stent material has crystallinity less than 50% (optionally between 0 and 50%). The stent is radially expandable at body temperature.

Example of a stent capable to expand to at least 130% or 1.3 times an intended deployment diameter while keeping an intact stent structure integrity and optionally having a recoil of less than 15% from an expanded state (optionally less than 10%, or less than 5%) is shown herein.

Example 12

Crystallinity of Stent Lower than Crystallinity of the Formed Tubular Body

The tube is made by extrusion, wherein the crystallinity of polymeric material after forming is between 30% and 55%. The stent is treated and is patterned from a tube made from Poly(L-lactide-co-epsilon caprolactone) material, preferably having a lactide to epsilon caprolactone comonomer ratio of 85:15 to 95:05. The tube can be formed by extrusion. Before crimping, the tube or the stent has an inner diameter that is greater than the intended deployment diameter to 150% of the intended stent deployment diameter. As a further example, for an intended deployment diameter of at least 3 mm stent, the tube inner diameter can range from greater than 3.0 millimeter to 4.5 millimeter. Another example is a 3.5 mm stent. The tube inner diameter can range from greater than 3.5 millimeter to 5.25 millimeter. The tube is heat treated at 90° C. for 2 hours and quenched to below ambient temperature. The tube is patterned into a stent, coated with a drug matrix such as Poly(L-lactide) based copolymer and Novolimus. The coated stent is optionally vacuumed for 36 hours at approximately 1 torr. The stent is then crimped at 45° C. onto the balloon of a delivery catheter. The stent delivery system is packaged in a sterile barrier and sterilized by ebeam. After sterilization, the stent delivery system is optionally stabilized at 25° C. for 5 hours. The stent material has crystallinity less than 30%. The stent is radially expandable at body temperature and has sufficient strength.

Example 13

Stent or Tube with the Ability Expand Above 1.3 Times Intended Deployment Diameter, while Maintaining Structural Integrity or No Breakage (Fracture) in the Struts, Links, or Crowns A tubular stent is made as described above and at the end state the stent is expanded under physiologic conditions (or 37° C. in water) unconstrained or constrained inside a tube and expanded to 1.3 times the labeled or intended deployment diameter without breakage/fracture in any of the stent struts, links, or crowns.

A stent is patterned from a tube made from Poly(L-lactide-co-epsilon caprolactone) material, preferably having a lactide to epsilon caprolactone comonomer ratio of 82:18 to 98:02, more preferably at 88:12 to 92:08. The tube can be formed by extrusion, molding, dipping, or spraying. The glass transitional temperature, Tg, of the polymeric material is greater than approximately 35° C. and less than approximately 55° C. Before it is patterned into a stent or before it is crimped, the tube has an inner diameter of 0.9 to 1.5 times an intended deployment diameter. As an example, for an intended deployment diameter of at least 3 mm stent, the expanded inner diameter is between 2.7 millimeter (0.106") to 4.5 millimeter (0.177"). For a 3.5 mm stent, the expanded inner diameter is between 3.15 millimeter (0.124") to 5.25 millimeter (0.207"). The tube is treated below the Tg of the material, ranging from 40° C. to 55° C., or heated at a temperature between the glass transitional temperature and its ambient temperature. A mandrel about the size of the inner diameter of the tube or the stent or smaller is optionally placed inside the tube and the tube is optionally heated above the Tg of the material or optionally treated below Tg of the material for duration ranging from a fraction of a second to 5 hours. The tubing can either be slowly cooled or quickly quenched quickly to a temperature below the crystallization temperature or the glass transitional temperature.

For example, an extruded tubing is made from 90:10 Poly (L-lactide-co-epsilon-caprolactone) material. The tube is expanded from an inside diameter of 1 millimeter (0.041") to 3.1 millimeter (0.122") at a temperature of 100° C. A 3 millimeter mandrel is placed inside the expanded tube. The tube on a mandrel is placed in an oven at 70° C. for a duration of about 1 hour. After heating, the tube is allowed to cool slowly to ambient temperature. The tube is patterned into a stent. The stent is coated with a drug matrix consisting of Poly(L-lactide) based copolymer and a macrocyclic lactone drug such as Novolimus. The coated stent is placed in a vacuum for a total of 36 hours. It is then heated to a 70° C. which is above the Tg of the Poly(L-lactide) based copolymer coating for approximately 15 to 30 minutes. The coated and treated stent is then crimped onto a balloon catheter at a temperature below the glass transitional temperature of the stent material, preferably between 10° C. to 40° C. below the Tg of the stent material. After crimping, the stent delivery system is packaged in a sterile barrier (i.e., in a foil pouch) and sterilized by ebeam or cold ethylene oxide cycle. The stent delivery system is then placed in an oven or incubator at 25° C. to 30° C. for 24 to 168 hours, preferably at 29° C. for 48 hours. The stent can then be deployed to or above 130 percent of an intended deployment diameter without fracture/breakage of stent struts, links, or crowns under physiologic conditions or in a simulated conditions unconstrained or constrained within a tube. The stent is expandable at body temperature and optionally have recoil of less than 15% from an expanded condition. In this example, 15% recoil is the mean recoil measurement.

Example 14

Physical Properties of a Bioresorbable Polymeric Stent

The physical properties of a biodegradable material of claimed invention stent was compared to a bare metal stent in the following manner:

A. Example of Radial Strength (Radial Compression) Measurement

The test specimen is placed into a fixture which applies radial compression. The fixture has compression dies or blades that are oriented in an iris-like configuration. These blades are actuated by a tensile force measurement machine through a mechanical linkage connected to a force gauge, which varies the opening of the fixture. The force versus displacement is constantly measured. The force is normalized to a force per unit measurement so that test specimens of various designs and dimensions may be conveniently compared. Other means to measure radial compression can be applied as well. Radial strength examples can be the mean value measurement of radial strength for multiple samples or a single measurement of radial strength for a single sample.

B. Recoil

This is one example of measuring recoil. Other measurement techniques can apply as well. The test specimen is expanded per the instructions for use and the diameter is measured at one or more locations while the device is inflated (Diameter-Initial) using an appropriate instrument. The test specimen is then measured at similar locations at one or more time intervals after device deflation (Diameter-Final), and the recoil is calculated as the percent change in diameter, or (Diameter-Initial−Diameter-Final)/Diameter-Initial*100%. As one skilled in the art, recoil can be measured using various method for bench testing of recoil, QCA measurement for recoil, OCT measurements for recoil. An example of recoil is a single measurement at a single location, or mean measurement at a single or multiple locations for the same stent.

C. Crimped Flexibility and Expanded Conformability

In this example, the test specimen is placed into a fixture which applies a 3 point bend load. The test specimen may be as-manufactured or prepared in a clinically-relevant manner, such as soaking the device in fluid at body temperature prior to testing, or expanding the device per the instructions for use. The 3 point bend fixture has a span that is a fixed distance appropriate for the sample, such as 13 mm of a sample that is greater than 13 mm. An anvil is aligned to the center of the span and connected to the force gauge on a tensile force measurement machine, which lowers the anvil and in turn applies a force to the test specimen, which is centered across the span. The force versus displacement is constantly measured to a fixed displacement, such as 15% of the span. The force per unit displacement is calculated.

Figure 13:
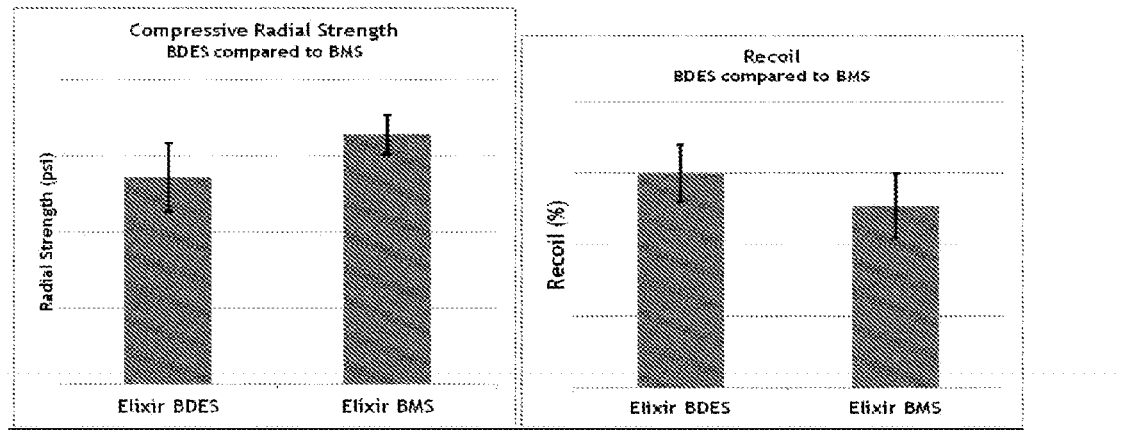
FIG. 13 shows embodiments of compressive radial stress and recoil of bioresorbable, drug eluting stent (BDES) versus bare metal stent (BMS)
Figure 14:
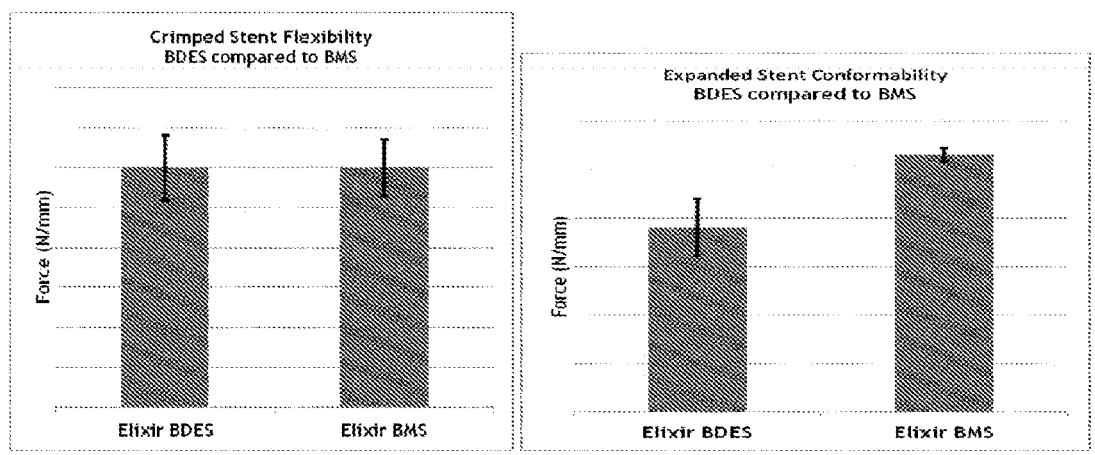
FIG. 14 shows embodiments of flexibility, and conformability of BDES vs. BMS.

The results are shown in FIGS. 13 and 14. BDES stands for bioresorbable, drug eluting stent, while BMS stands for bare metal stent.

D. In Vitro Testing

Figure 15:
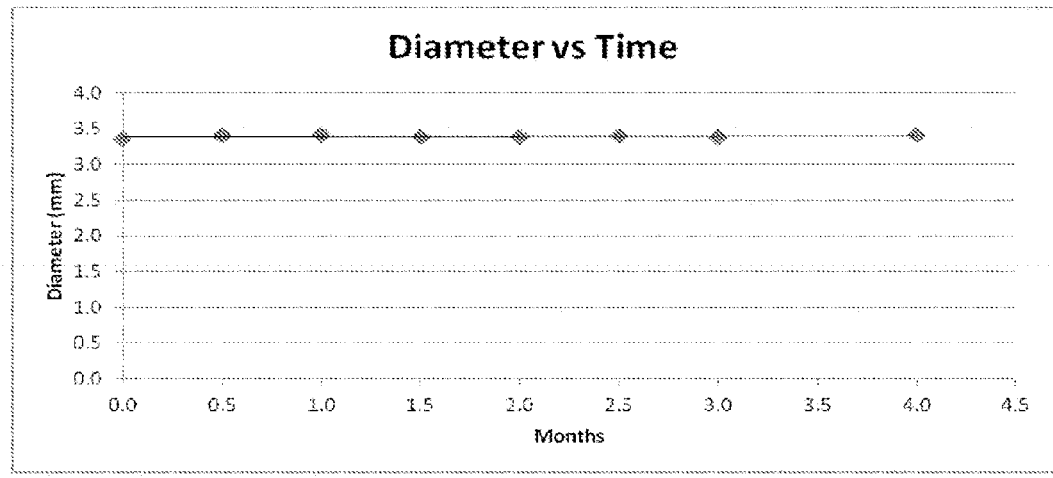
FIG. 15 shows a plot of a stent diameter over time in a water bath at 37° C. in one embodiment.

FIG. 15 shows an example of in vitro testing of an expanded sample stent to approximately 3.0 mm internal diameter (ID) with an outer diameter (OD) of about 3.3 mm (prior to approximately less than 10% recoil from an expanded state). The stent diameter is at least maintained or grows over time (approximately within 15 days) to approximately at least 3.0 mm and substantially maintain the stent over a period of time such as over 1 month, 2 month, 3 month, or 4 months. This experiment was conducted in a saline tube submerged in a water bath at 37° C. The diameters of the stents were measured at approximately the middle of the stent using an optical comparator.

Figure 16:
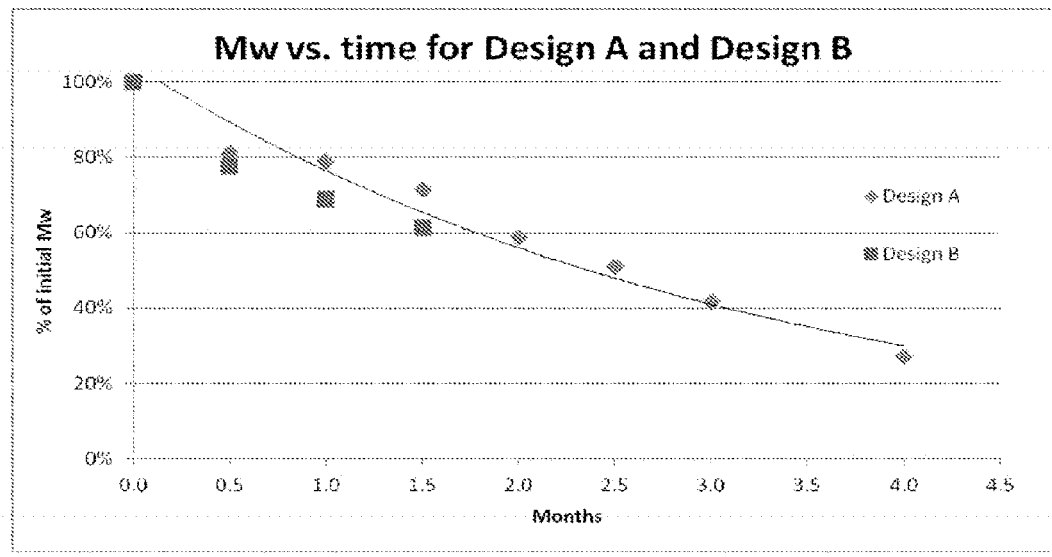
FIG. 16 shows a plot of $M_w$ of stents of Design A and Design B embodiments over time in a water bath at 37° C.

FIG. 16 shows an example of in vitro testing for MW over time for design A and design B submerged in a saline at 37° C. showing MW decreasing over time. MW was measured using GPC. Design A and Design B were stents with different patterning designs and treatments.

Figure 17:
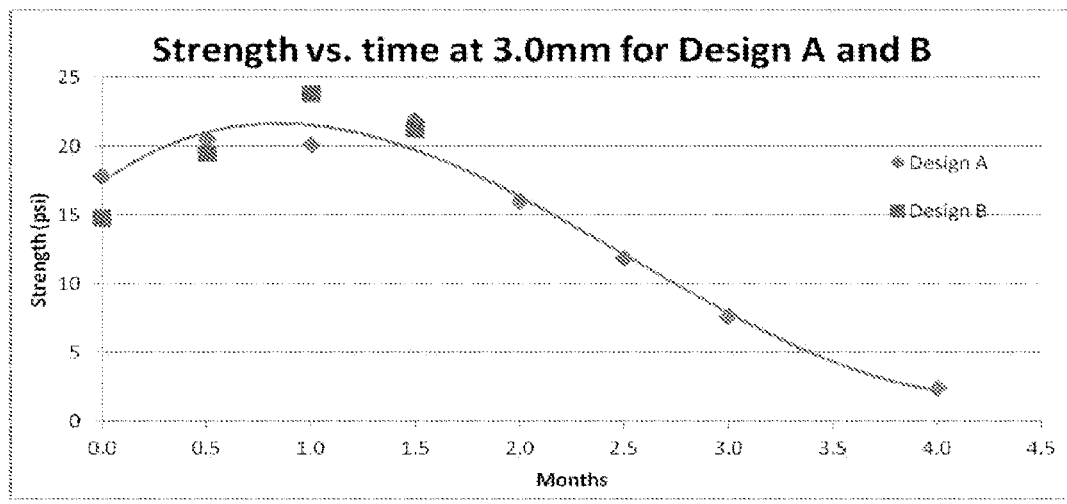
FIG. 17 shows a plot of strength of stents of Design A and Design B embodiments over time in a water bath at 37° C.
Figure 18:
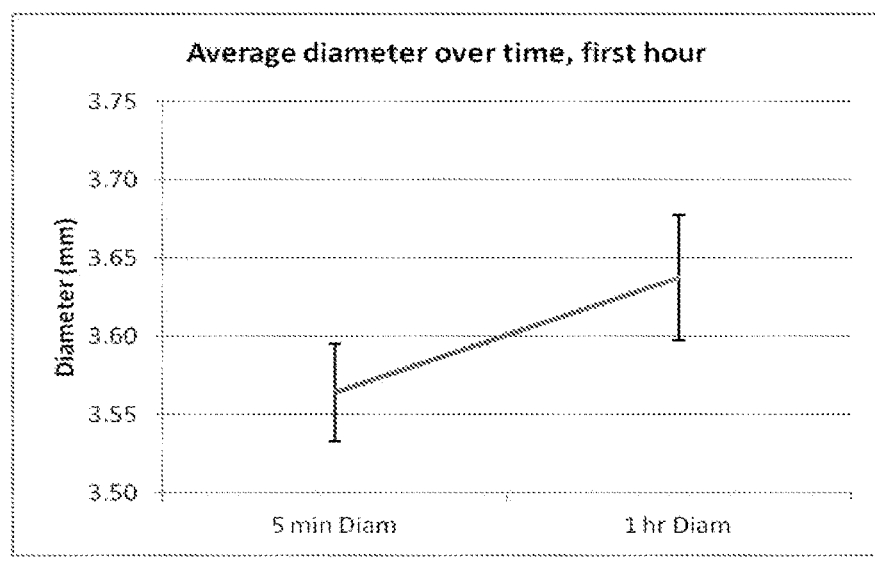
FIG. 18 shows a stent balloon expanded to about 3.6 mm outer diameter (OD) wherein the stent further self expands within one hour by at least 0.1 mm.

FIG. 17 shows an example of in vitro testing of sample design A and design B submerged in a saline at 37° C. showing that the stent radial strength after expansion of the stent increases by at least 5%, or at least 10%, or at least by 15% over time (within approximately 30 days or within approximately 15 days) and maintains sufficient strength to support a body lumen for at least one month, or at least two months, or at least three months, or at least four months. A stent deployed to nominal diameter increased in strength over initial period followed by a decrease in strength. Radial strength was measured using the radial compression iris method. FIG. 18 shows a stent balloon expanded to around 3.6 mm OD wherein the stent further self expands within one hour by at least 0.1 mm.

Example 15

Biodegradable Stent

A stent is patterned from a tube made from Poly(L-lactide-co-epsilon caprolactone) material blended with 0.1%-10% by weight ratio polyglycolide polymer or glycolide monomer, preferably having a lactide to epsilon caprolactone comonomer ratio of 82:18 to 98:02 blended with 0.1%-10% polyglycolide or glycolide by weight ratio, more preferably at 88:12 to 92:08 and 5% or under by weight ratio polyglycolide polymer or glycolide monomer. The tube can be formed by extrusion, molding, dipping, printing, or spraying. The glass transitional temperature, Tg, of the polymeric material optionally is greater than approximately 35° C. and less than approximately 55° C. Before it is patterned into a stent or before it is crimped, the tube has optionally an inner diameter of 0.9 to 1.5 times an intended deployment diameter. As an example, for an intended deployment diameter of at least 3 mm stent, the expanded inner diameter is between 2.7 millimeter (0.106") to 4.5 millimeter (0.177"). For a 3.5 mm stent, the expanded inner diameter is between 3.15 millimeter (0.124") to 5.25 millimeter (0.207"). The tube is treated below the Tg of the material, ranging from 40° C. to 55° C., or heated at a temperature between the glass transitional temperature and its ambient temperature, or treated by heat above Tg. A mandrel about the size of the inner diameter of the tube or the stent or smaller is optionally placed inside the tube and the tube is optionally heated above the Tg of the material or optionally treated below Tg of the material for duration ranging from a fraction of a second to 5 hours. The tubing can either be slowly cooled or quickly quenched quickly to a temperature below the crystallization temperature or the glass transitional temperature. The stent prosthesis is crimped onto a delivery system. The stent is capable of radial expansion under physiologic environment and/or 37 C to a deployed diameter from a crimped diameter. The stent has sufficient strength to support a body lumen at an expanded diameter, the stent optionally has % acute recoil of under 10%, the stent substantially degrades under 2 years, preferably substantially degrades under 1.5 years.

A tubular stent is made as described above and at the end state the stent is expanded under physiologic conditions (or 37° C. in water) unconstrained or constrained inside a tube and expanded to >1.1 times the labeled or intended deployment diameter without breakage/fracture in any of the stent struts, links, or crowns.

A. In Vitro Testing, Diameter, Strength, and Degradation Study

Figure 19A:
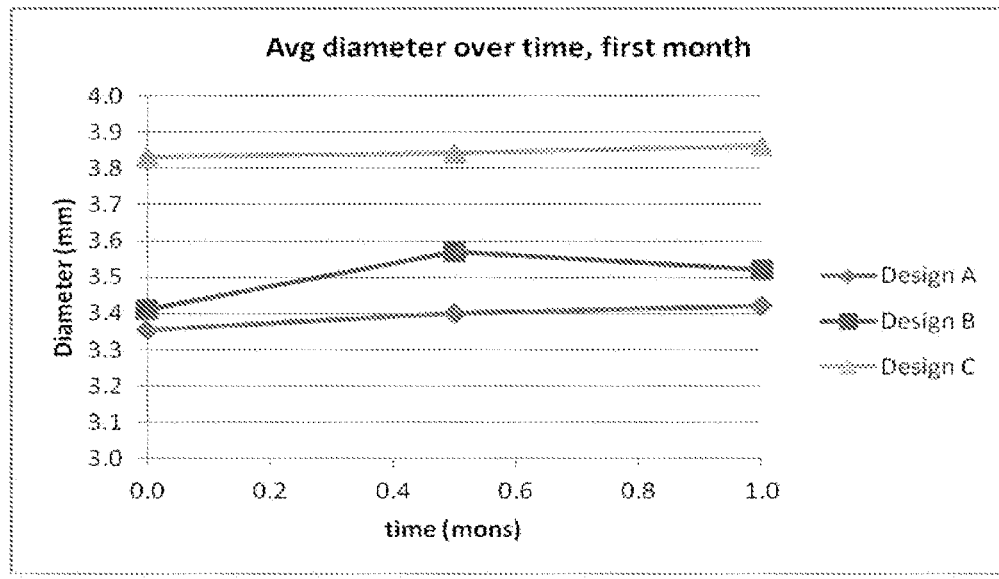
FIGS. 19A and 19B show balloon expanded stents at least maintain the diameter of tubular stents of design A, design B, and design C, embodiments over time (1 month and 6 months, respectively)
Figure 19B:
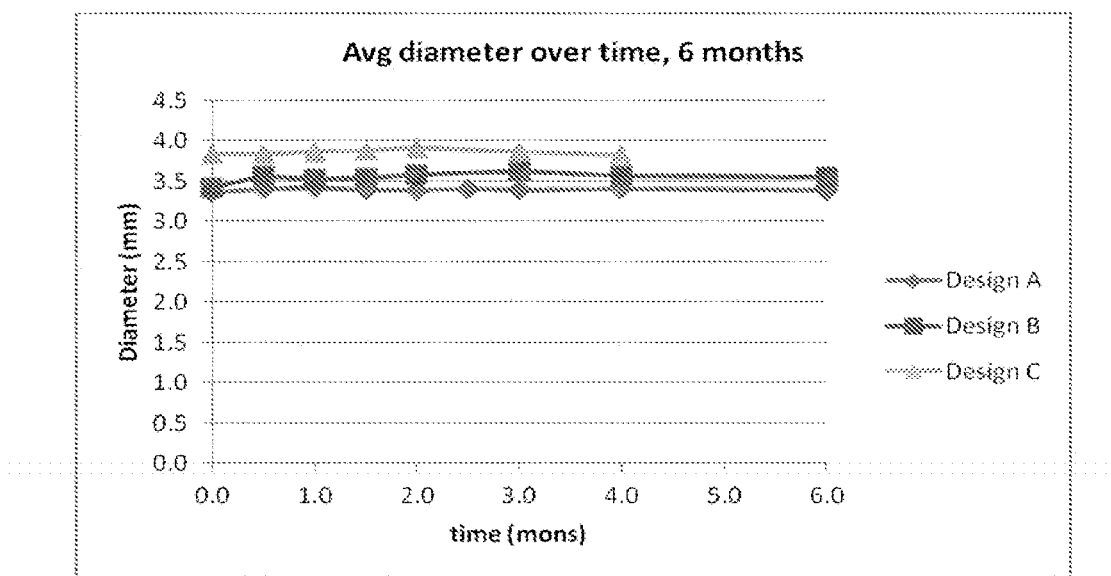
Figure 20:
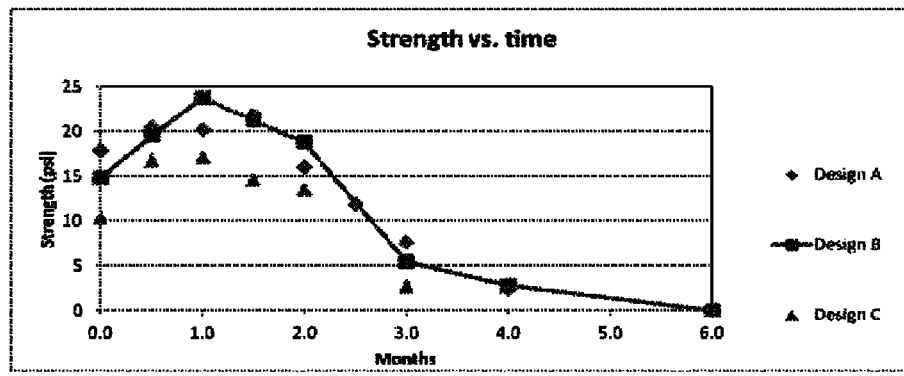
FIG. 20 shows changes in the strength of tubular stents of design A, design B, and design C embodiments over time.

A stent prosthesis was fabricated in accordance with an embodiment of the invention. Samples of three designs were produced and expanded to a deployed diameter using indeflator. An initial diameter measurement was taken and strength was measured at time zero. The units were tested in environment simulating physiologic environment (and/or 37 C in water) such as placed into a single capped 250 mL bottle filled with saline (0.85% Sodium Chloride solution, Sigma Aldrich) and maintained at 37° C. in a static water bath for the duration of the test. At regular intervals the diameter, strength, and molecular weight were measured. FIGS. 19A and 19B show balloon expanded stents at least maintain the diameter of tubular stents of design A, design B, and design C, over time (1 month and 6 months, respectively). FIG. 20 shows changes in the strength of tubular stents of design A, design B, and design C over time.

B. Scaffold Implantation in Porcine Model

The scaffold was implanted in the internal mammary artery in a porcine model per standard implantation techniques. The scaffold and the artery were explanted at different timepoints and the scaffold material molecular weight was measured using analytical techniques.

The scaffold molecular weight decreases by 50% in less than six months. The molecular weight decreases to less than 25% in less than 6 months. The molecular weight decreases to less than 10% in less than 18 months.

Figure 21:
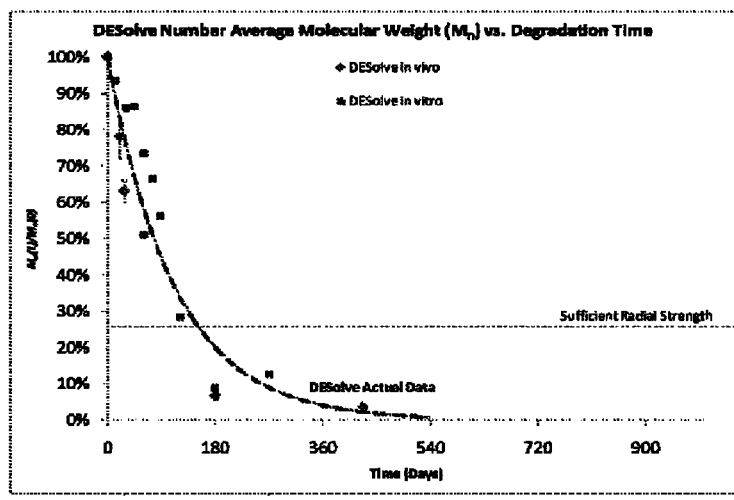
FIG. 21 shows the decrease of molecular weight of stent over one to two years with radial strength sufficient to support a blood vessel for at least 2 months.

The in vitro and in vivo molecular weight over time was plotted on a graph and demonstrated that the in vitro and in vivo degradation was similar. FIGS. 21A and 21B show the decrease of molecular weight of stent over one to two years with radial strength sufficient to support a blood vessel for at least 2 months.

C. Underdeployed Stent Scaffold Apposition Testing

Figure 22A:
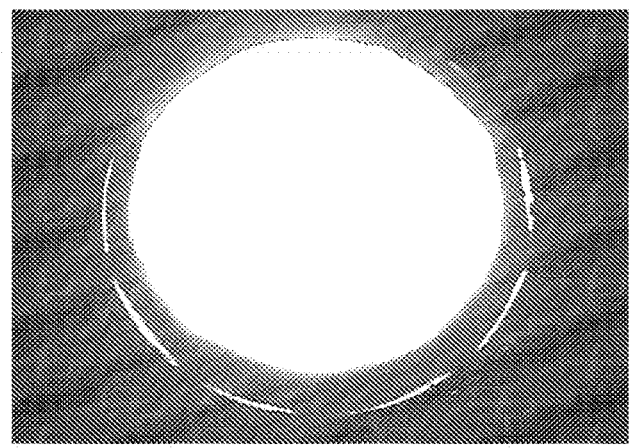
FIG. 22A illustrates a stent scaffold deployed in a block, with a final diameter smaller than block simulating malapposed struts.
Figure 22B:
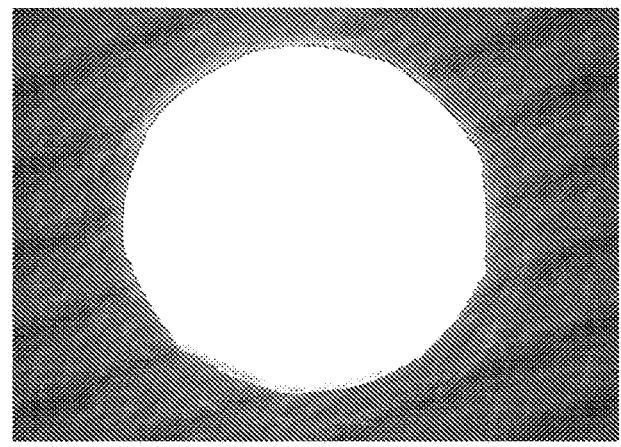
FIG. 22B illustrates stent scaffold within 5-10 minutes of soaking in water at 37 C, with gaps "resolved", or opposed to the wall and no malapposition present.

A sample unit of the present invention was underdeployed in a mock artery, which was a plastic block with a 3.2 mm hole. The scaffold diameter was recorded as 3.12 mm Backlighting was employed to visually identify gaps between the scaffold outer diameter and the block inner diameter. The block with the scaffold in the hole was then placed in a 37° C. water bath and the presence of gaps was noted. After 5-10 minutes, the gaps were no longer present. The scaffold was removed and measured to be equal or greater than 3.2 mm, confirming that the malapposition between scaffold and mock artery fixture had been resolved. FIG. 22A illustrates a stent scaffold deployed in a block, with a final diameter smaller than block simulating malapposed struts. FIG. 22B illustrates stent scaffold within 5-10 minutes of soaking in water at 37° C., with gaps "resolved" and no longer present. The example shows a balloon expanded stents, where in the stent further self expands to a larger diameter or transverse dimension, or until the stent apposes the vessel wall.

D. Scaffold Strut Malapposition Testing

Figure 23A:
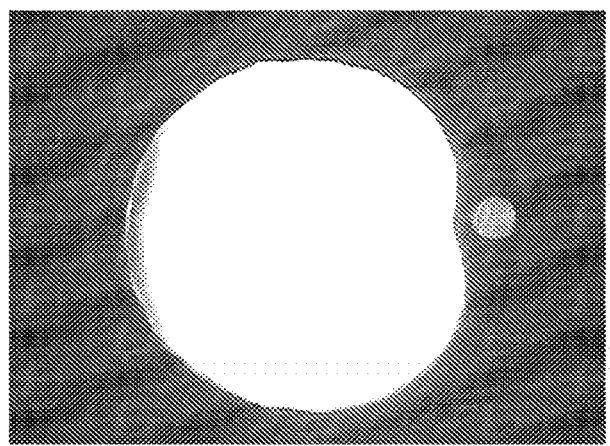
FIG. 23A illustrates a stent scaffold expanded in a mock artery with a 0.3 mm mandrel on the side.
Figure 23B:
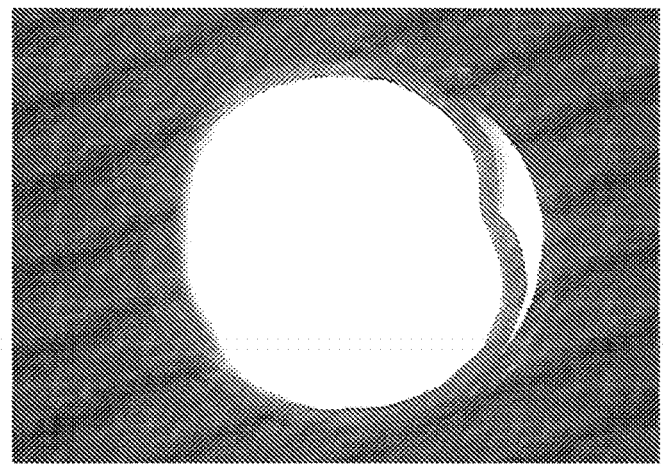
FIG. 23B illustrates a stent scaffold with mandrel removed, confirming that a gap is still present.
Figure 23C:
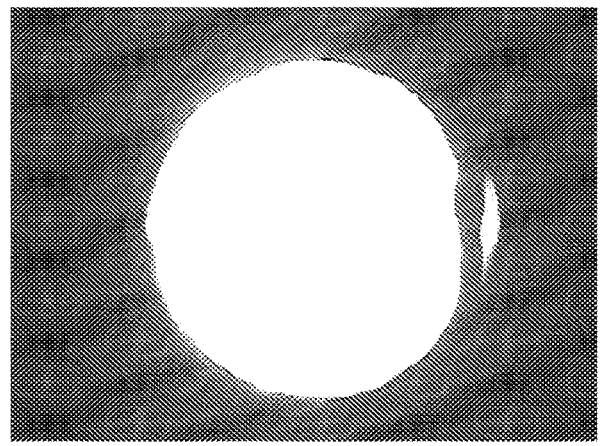
FIG. 23C illustrates a stent scaffold shows a stent scaffold after 10 minutes of soaking in water at 37° C.
Figure 23D:
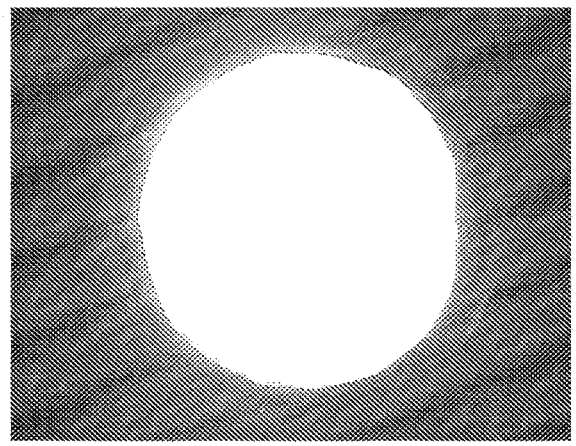
FIG. 23D illustrates a stent scaffold after 20 minutes of soaking in water where in the stent is apposed against the vessel wall.

A sample unit of the present invention was deployed in a mock artery, which was a plastic block with a 3.2 mm hole, with a 0.3 mm mandrel on one side creating an eccentric deployment cross-section. The mandrel was removed and created a malapposition between the scaffold and the surface of the mock artery. Backlighting was employed to visually identify the gap between the scaffold and the block inner diameter. The block with the scaffold in the hole was then placed in a 37° C. water bath and the presence or absence of the malapposition was noted over time. After 20 minutes, the gap was no longer visually present. FIG. 23A illustrates a stent scaffold expanded in a mock artery with a 0.3 mm mandrel on the side. FIG. 23B illustrates a stent scaffold with mandrel removed, confirming that a gap is still present. FIG. 23C illustrates a stent scaffold shows a stent scaffold after 10 minutes of soaking in water, and FIG. 23D illustrates a stent scaffold after 20 minutes of soaking in water where in the stent is apposed against the vessel wall. This also provides an example of stent strut self expanding to appose against the vessel wall during a side branch treatment procedure of kissing balloon technique where in the guidewire has to be pulled out from under the expanded stent in the vessel leaving behind unapposed struts. The Stent struts in the present invention after the procedure will self expand by at least 0.1 mm and appose to the vessel wall.

E. Scaffold Overexpansion Study

Figure 24:
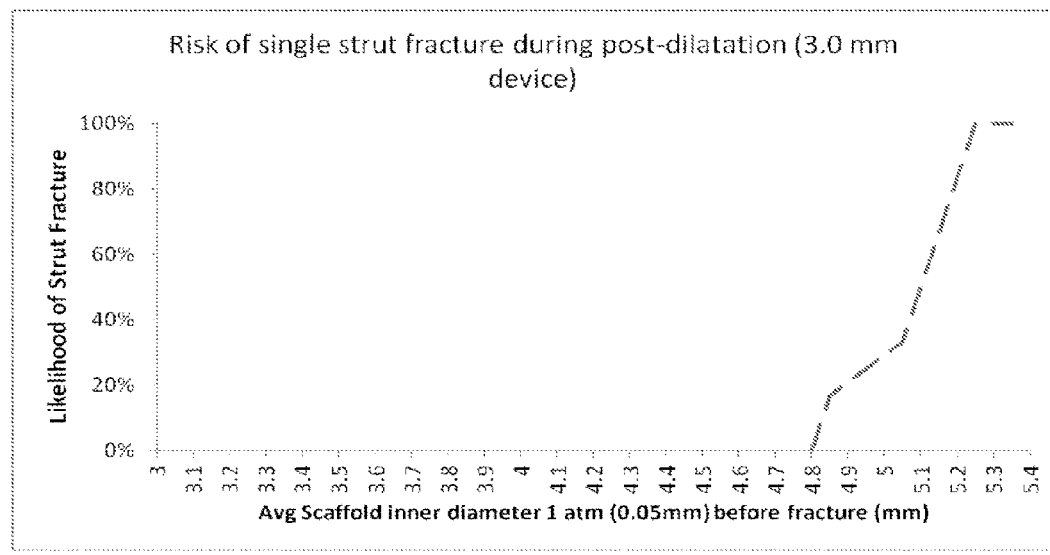
FIG. 24 shows a plot illustrating the first occurrence of fracture after dilating the stent/scaffold to diameters substantially larger than the nominal/labeled stent/scaffold diameter of 3.0 mm.
Figure 25A:
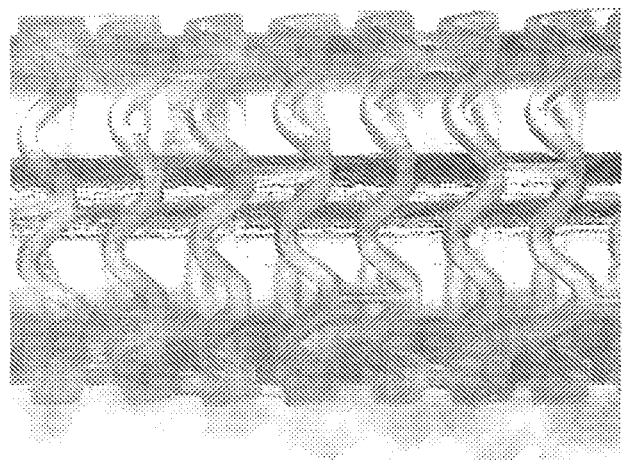
FIG. 25A depicts a scaffold (another name for a stent) at 3.0 mm nominal/labeled diameter.
Figure 25B:
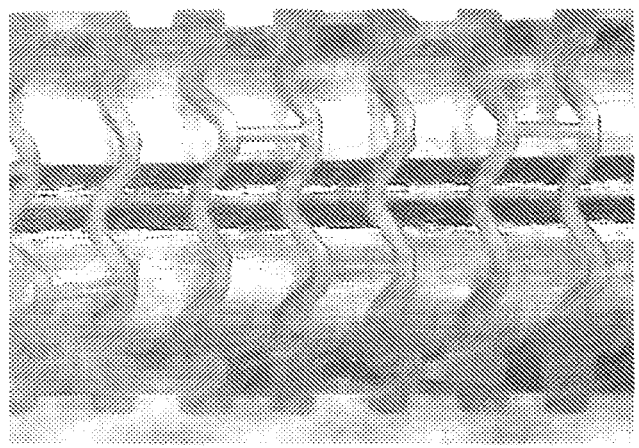
FIG. 25B depicts a scaffold deployed at nominal and further balloon expanded to about 3.8 mm without fracture.
Figure 25C:
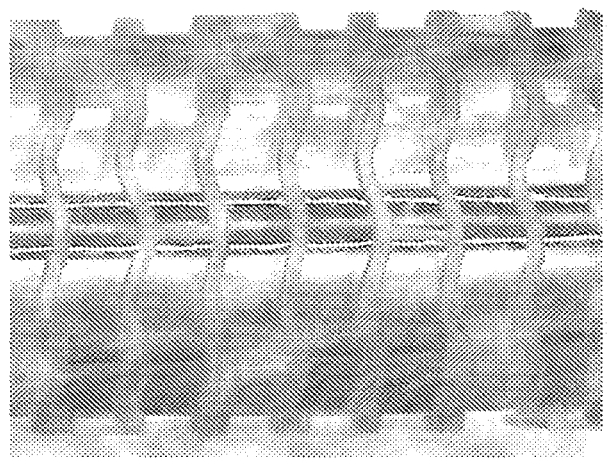
FIG. 25C depicts a scaffold deployed at nominal and further balloon expanded to about 4.0 mm without fracture.
Figure 25D:
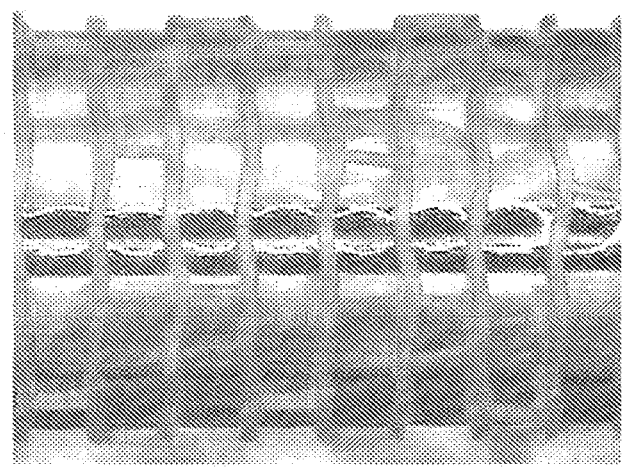
FIG. 25D depicts a scaffold deployed at nominal and further balloon expanded to 4.4 mm diameter without fracture.
Figure 25E:
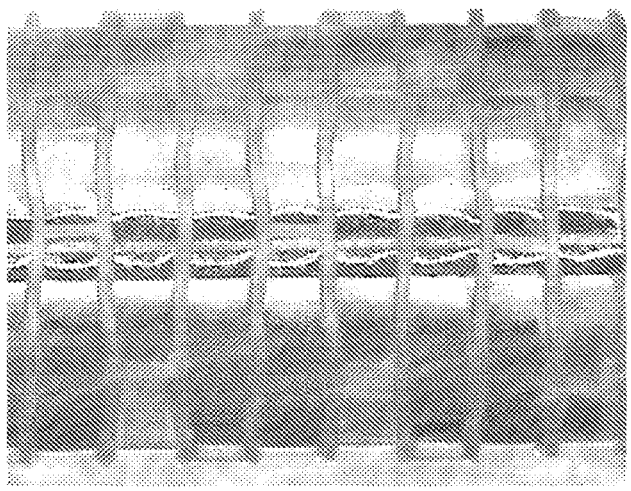
FIG. 25E depicts a scaffold deployed at about nominal and further balloon expanded to about 4.75 mm diameter without fracture.
Figure 25F:
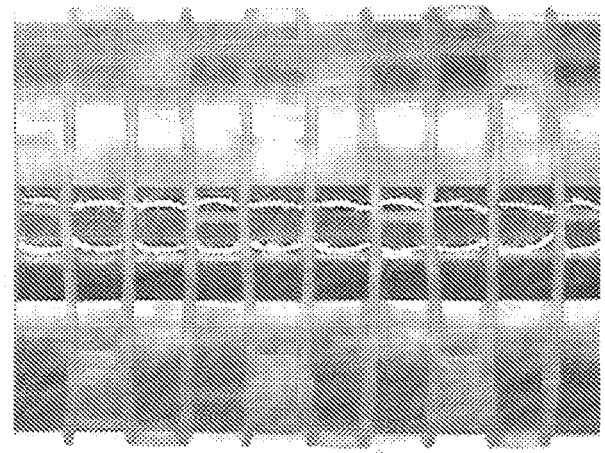
FIG. 25F depicts a scaffold deployed at about nominal or labeled 3.0 mm and further balloon expanded to about 5.1 mm diameter without fracture.

Sample units of the present invention were deployed in a 37° C. water bath to nominal diameter of 3.0 mm using standard inflation techniques. The scaffolds were then post-dilated to multiple diameters and inspected at regular intervals until a fracture was noted. The diameter at fracture was recorded. Pictures were also taken at regular intervals. By testing several units, the number of units with fractures at a given diameter was calculated and plotted. FIG. 24 shows a plot illustrating the likelihood of fracture against post-dilated scaffold diameter for (e.g., a balloon expanded stent at nominal diameter of 3.0 mm and further balloon expanded to 4.8 mm diameter, 1.6 times the nominal deployed diameter, survives without fracture). FIG. 25A depicts a scaffold at 3.0 mm nominal diameter, and FIG. 25B depicts a scaffold deployed at nominal and further balloon expanded at 3.8 mm overexpanded diameter. FIG. 25C depicts a scaffold deployed at nominal and further balloon expanded to 4.0 mm overexpanded diameter, FIG. 25D depicts a scaffold deployed at nominal and further balloon expanded to 4.4 mm overexpanded diameter, FIG. 25E depicts a scaffold deployed at nominal and further balloon expanded to a 4.75 mm overexpanded diameter, and FIG. 25 F depicts a scaffold deployed at nominal and further balloon expanded to a 5.1 mm overexpanded diameter. The figures shows the undulating rings of the stent overexpanded to substantially circular rings without fracture.

Example 16

Bioresorbable Polymeric Stent+Myolimus @ 3 μg Per mm Stent Length (DESolve First in Man Study)

The DESolve I trial is a first in man study enrolling 15 patients evaluating the Myolimus Eluting Bioresorbable Coronary Scaffold System (CSS) with a PLLA based polymer. The principal imaging endpoints include: in-stent late lumen loss assessed by QCA at 6 months, stent and vessel assessment using IVUS, OCT at baseline and 6 months, and multi-slice computed tomography (MSCT) at 12 and 24 months to provide long-term assessment of the vessel. The principal safety endpoint is the composite of major adverse cardiac events (MACE) comprised of cardiac death, target vessel myocardial infarction (MI) and clinically-indicated target vessel revascularization (TLR) at 30 days, 6, 12 months, and 2-5 years. The stent size used is 3.0×14 mm and myolimus drug dose is 3 μg per mm of stent length. A portion of the available results as measured and analyzed by the principal investigators lab are shown in the Table 14 below A complete analysis of the results from the core laboratory are presented later in Part II.

A. Stent or Tube with the Ability Expand Above 1.1 Times Deployment Diameter, while Maintaining Structural Integrity or No Breakage/Fracture in the Struts, Links, or Crowns; and have Accelerated Degradation Period Below 2 Years, Preferably Below 1 Year

TABLE 14

Acute stent recoil in the DESolve ™ I group of patients

|  | n |
|---|---|
| Number of patients | 12 |
| Age (years) | 72.0 ± 6.9 |
| Gender (males) | 6 (50%) |

TABLE 14-continued

Acute stent recoil in the DESolve ™ I group of patients

| | n |
|---|---|
| Target vessel | 12 |
| LAD | 2 (20%) |
| LCX | 4 (30%) |
| RCA | 6 (50%) |
| Stent size (mm) | |
| 3.0 | 12 (100%) |
| Stent length (mm) | |
| 14 | 12 (100%) |
| Maximum pressure (atm) | 13.7 ± 2.5 |
| Predicted ID (mm) | 3.2 ± 0.1 |
| QCA measurements | |
| Pre-PCI | |
| Reference vessel diameter (mm) | 2.5 ± 0.5 |
| Minimum lumen diameter (mm) | 1.1 ± 0.3 |
| Diameter stenosis (%) | 49.2 ± 13.8 |
| Post-PCI | |
| Reference vessel diameter (mm) | 2.6 ± 0.5 |
| Minimum lumen diameter (mm) | 2.1 ± 0.3 |
| Diameter stenosis (%) | 9.0 ± 10.5 |
| Last inflated balloon at the highest pressure MinD (mm) | 2.1 ± 0.4 |
| Last inflated balloon at the highest pressure MaxD (mm) | 2.9 ± 0.2 |
| Last inflated balloon at the highest pressure MeanD (mm) (X) | 2.6 ± 0.3 |
| Stent immediately after last balloon MinD (mm) | 2.1 ± 0.3 |
| Stent immediately after last balloon MaxD (mm) | 3.0 ± 0.4 |
| Stent immediately after last balloon MeanD (mm) (Y) | 2.6 ± 0.3 |
| IVUS post-intervention measurements at MSA site | |
| IVUS MinSD (mm) | 2.1 ± 0.3 |
| IVUS MaxSD (mm) | 2.8 ± 0.3 |
| IVUS MeanSD (mm) | 2.5 ± 0.2 |
| IVUS MSA (mm$^2$) | 4.7 ± 0.8 |
| OCT post-intervention measurements at MSA site | |
| OCT MinSD (mm) | 2.1 ± 0.4 |
| OCT MaxSD (mm) | 2.9 ± 0.5 |
| OCT MeanSD (mm) | 2.5 ± 0.4 |
| OCT MSA (mm$^2$) | 5.0 ± 1.5 |
| Recoil calculations | |
| Acute absolute recoil QCA (X − Y) | 0.02 ± 0.2 |
| Acute percent recoil QCA (X − Y)/X (%) | 0.8 ± 8.9 |
| IVUS MinSD/predicted ID ratio | 0.60 ± 0.2 |
| OCT MinSD/predicted ID ratio | 0.66 ± 0.1 |

The mean acute absolute recoil measurement by QCA in the example above were calculated using the measurement technique as described in Tanimoto et al, CCI 70:515-523 (2007).

Example 17

Clinical Trial Data for DESolve Study

Figure 28:
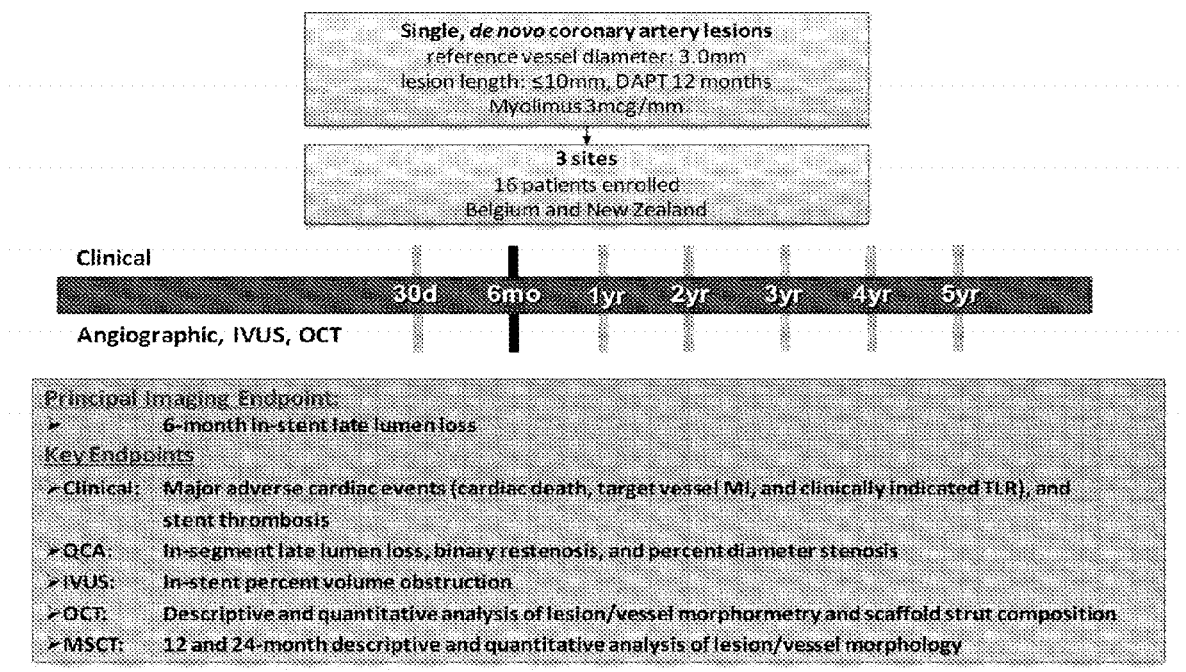
FIG. 28 schematically depicts the DESolve™ First-in-Man (FIM) study design.

FIGS. 26A and 26B depict the DESolve™ Bioresorbable Coronary Stent Scaffold used in the DESolve 1 clinical trial. FIG. 27 depicts preclinical optical coherence tomography (OCT) images of the scaffold at different time points. FIG. 28 schematically depicts the DESolve™ First-in-Man (FIM) study design.

Figure 29:
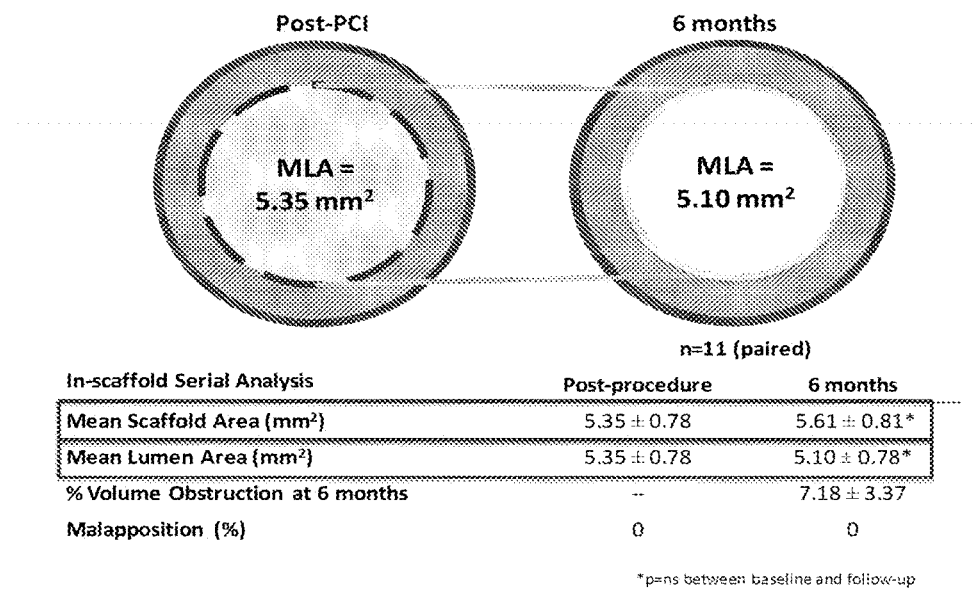
FIG. 29 depicts Intravascular Ultrasound (IVUS) results from the DESolve™ FIM study.
Figure 30:
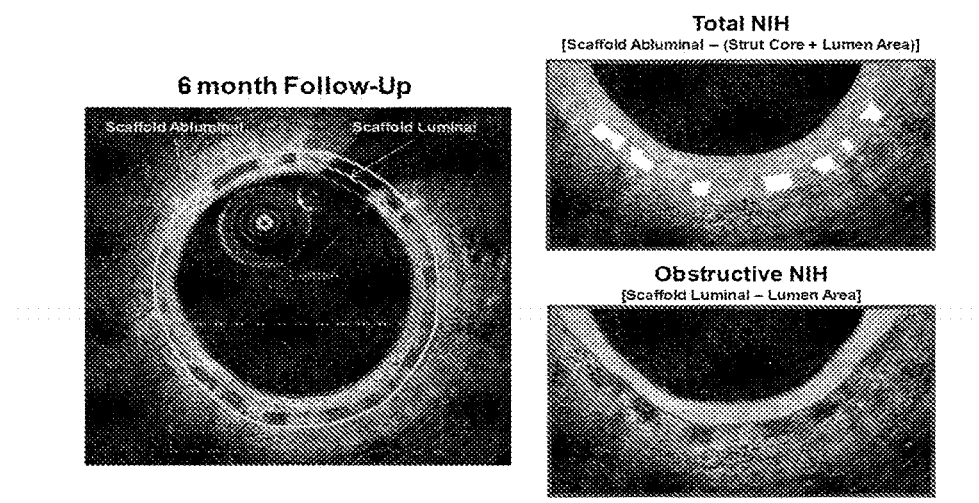
FIG. 30 depicts the methodology of OCT analysis where NIH stands for neointimal hyperplasia.

Table 15 describes patient characteristics and angiographic results. FIG. 29 depicts Intravascular Ultrasound (IVUS) results from the DESolve™ FIM study. FIG. 30 depicts the methodology of OCT analysis where NIH stands for neointimal hyperplasia.

TABLE 15

Baseline and angiographic characteristics and angiographic results at baseline and 6 month follow-up in patients

| Baseline Characteristics | |
|---|---|
| Patient Characteristics, % (n) | (n = 15 Patients*) |
| Age, years (±SD) | 70 ± 8.6 |
| Male | 66.7 (10/15) |
| Diabetes mellitus | 6.7 (1/15) |
| Current/former smoker | 7.33 (11/15) |
| Hypercholesterolemia | 7.33 (11/15) |
| Hypertension | 66.7 (10/15) |
| Previous myocardial infarction | 26.7 (4/15) |
| Previous target vessel CABG or PCI | 6.7 (1/15) |

| Angiographic Characteristics | |
|---|---|
| Baseline Characteristics, % (n) | n = 14 (paired) |
| RVD (mm) | 2.65 ± 0.32 |
| MLD (mm) | 0.81 ± 0.29 |
| % DS | 70.0 ± 10.5 |
| Lesion Length (mm) | 8.95 ± 2.64 |
| Target Vessel, % (n) | |
| LAD | 21.4 (3/14) |
| LCX | 35.7 (5/14) |
| RCA | 42.9 (6/14) |
| Lesion Class (ACC/AHA), % (n) | |
| A | 35.7 (5/14) |
| B1/B2 | 64.3 (9/14) |
| C | 0.0 (0/14) |

| Angiographic Results | |
|---|---|
| In-scaffold Analysis | n = 14 (paired) |
| RVD (mm) | |
| post-procedure | 2.84 ± 0.23 |
| at 6 months | 2.78 ± 0.27 |
| MLD (mm) | |
| post-procedure | 2.60 ± 0.19 |
| at 6 months | 2.41 ± 0.28 |
| % Diameter Stenosis | |
| post-procedure | 8.05 ± 7.90 |
| at 6 months | 12.63 ± 11.37 |
| Acute Recoil (%) | 6.4 ± 4.6 |
| Late Lumen Loss (mm) at 6 months | 0.19 ± 0.19 |
| Binary Restenosis (%) at 6 months | 0.0 |

Table 16 includes OCT results of the DESolve FIM Study. The results show the mean scaffold area was maintained between baseline and 6 month. There was minimal neointimal growth leading to a low % neointimal obstruction within the vessel lumen. Table 17 includes clinical outcomes of the DESolve FIM study at 0 to 30 days. Table 18 includes clinical outcomes of the DESolve FIM study at 31 to 180 days showing clinical safety of the DESolve scaffold.

TABLE 16

DESolve FIM: OCT Results

| | Baseline | 6-month Follow-up n = 10 (paired) |
|---|---|---|
| In-scaffold Cross Section Level Serial Analysis | | |
| Mean Scaffold area (mm²) | 6.57 ± 0.68 | 6.80 ± 0.85* |
| Mean NIH Area (obstructive) (mm²) | — | 0.71 ± 0.36 |
| Mean NIH Obstruction (%) | — | 13.16 ± 5.59 |
| In-scaffold Strut Level Serial Analysis | | |
| Total number of Analyzed Struts | 2,984 | 2,575 |
| Frequency of covered Struts/patient (%) | — | 98.68 ± 2.44 |
| Mean NIH Thickness over Covered Struts (mm) | — | 0.12 ± 0.04 |

*p = ns between baseline and follow-up

TABLE 17

Clinical Outcomes: 0 to 30 days.

| 0 to 30 days | (n = 15) |
|---|---|
| Hierarchical Events, % (n) | |
| Cardiac Death | 0/15 |
| Target Vessel MI | 0/15 |
| Clinically-Indicated TLR | 0/15 |
| Major Adverse Cardiac Events | 0/15 |
| Other Events | |
| Stent Thrombosis (ARC$^f$) | 0/15 |
| Definite | 0/15 |
| Probable | 0/15 |
| Clinically-Indicated TVR | 1/15$^§$ |

$^§$one patient underwent emergent CABG for a procedurally-related spiral dissection; there was no stent thrombosis in the scaffold area or within the 5 mm segment proximal or distal to the scaffold
$^f$Cutlip, D, Windecker, S, Mehran, R, et al. Clinical Endpoints in Coronary Stent Trials: A Case for Standardized Definitions. Circ 2007; 115; 2344-2351

TABLE 18

Clinical Outcomes: 31 to 180 days.

| 31 to 180 days | (n = 15) |
|---|---|
| Hierarchical Events, % (n) | |
| Cardiac Death | 0/15 |
| Target Vessel MI | 0/15 |
| Clinically-Indicated TLR | 1/15* |
| Major Adverse Cardiac Events | 1/15 |
| Other Events | |
| Stent Thrombosis (ARC$^f$) | 0/15 |
| Definite | 0/15 |
| Probable | 0/15 |
| Clinically-Indicated TVR | 0/15 |

*one patient underwent PCI for a stenosis in the proximal 5 mm segment to the scaffold; the scaffold area was widely patent
$^f$Cutlip, D, Windecker, S, Mehran, R, et al. Clinical Endpoints in Coronary Stent Trials: A Case for Standardized Definitions. Circ 2007; 115; 2344-2351

Example 18

Stent Fabrication

Figure 34:
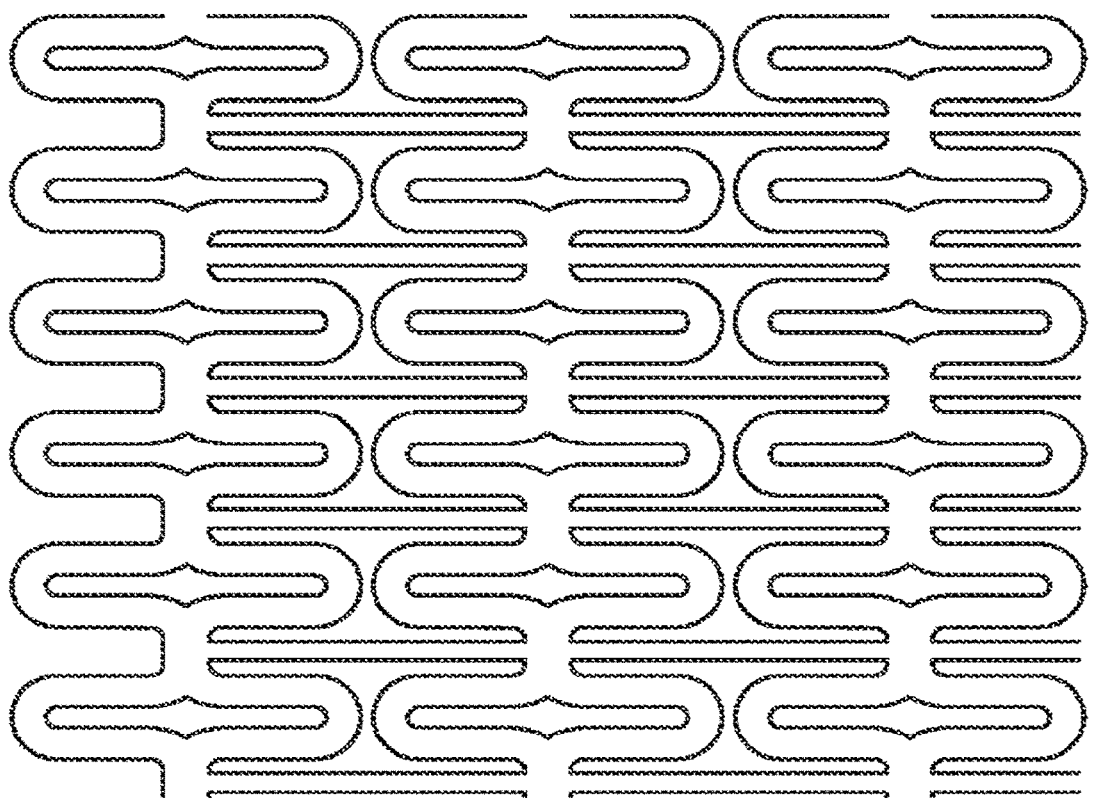
FIG. 34 illustrates a stent pattern utilized in an Example of the present application.
Figure 35:
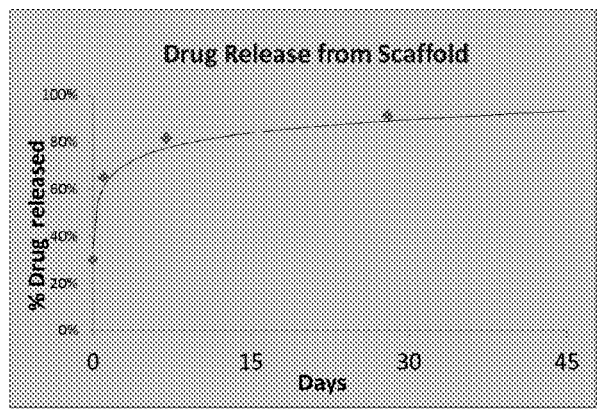
FIG. 35 illustrates a pharmacokinetic release profile of novolimus from a stent demonstrating that over 85% of the drug released in one month and that a therapeutic tissue drug concentration of 0.5 ng/mg at 90 days.
Figure 36:
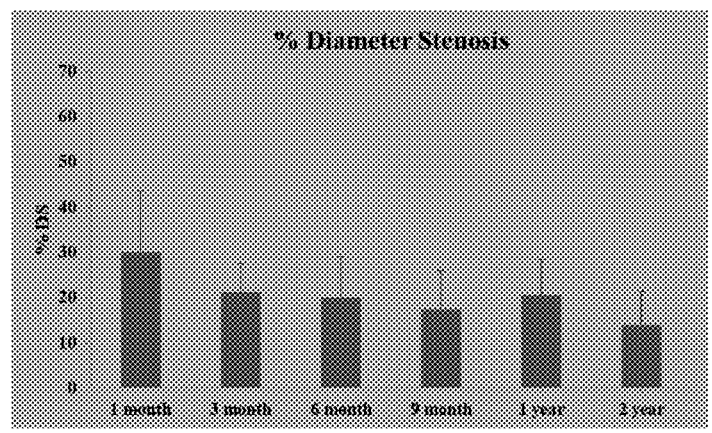
FIG. 36 shows a percent diameter stenosis of the novolimus-stent treated blood vessel measured by quantitative coronary angiography (QCA) over two years.
Figure 37:
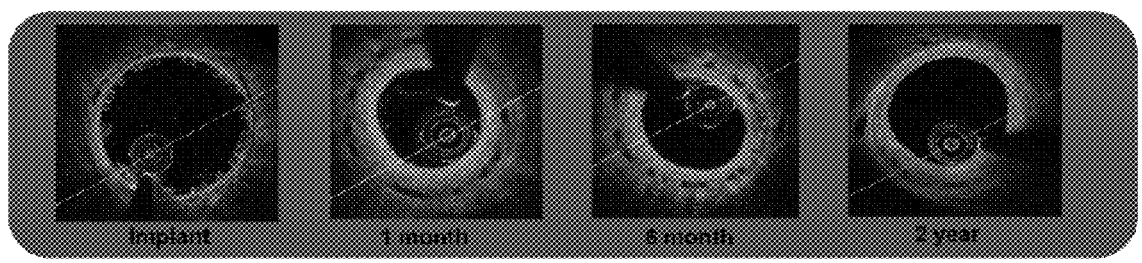
FIG. 37 provides optical coherence tomography (OCT) images of the novolimus-stent treated blood vessel measured by quantitative coronary angiography (QCA) over two years.
Figure 38:
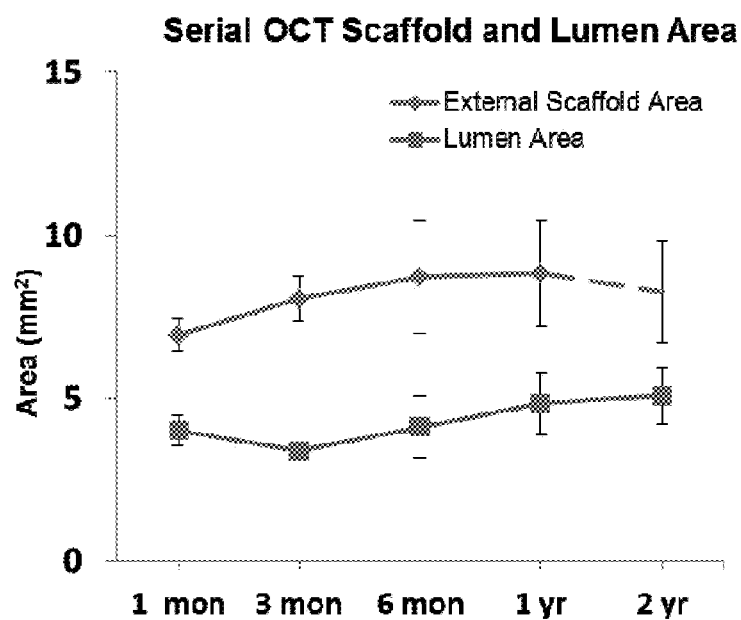
FIG. 38 is a graph of the external scaffold area luminal areas derived from the OCT images of FIG. 37.
Figure 39:
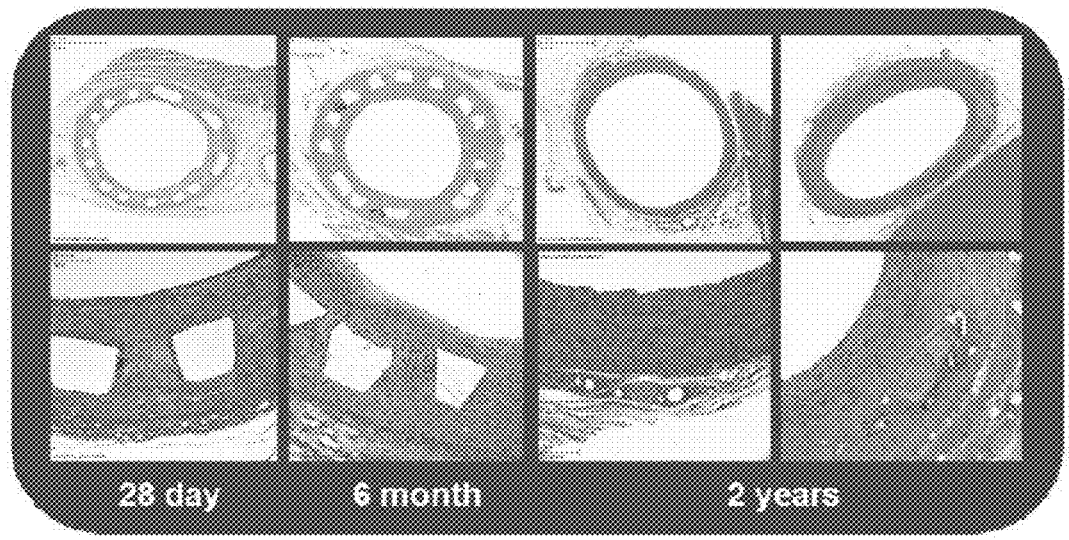
FIGS. 39 and 40 show a histopathology analysis of alcain blue stained the novolimus-stent treated blood vessel.
Figure 40:
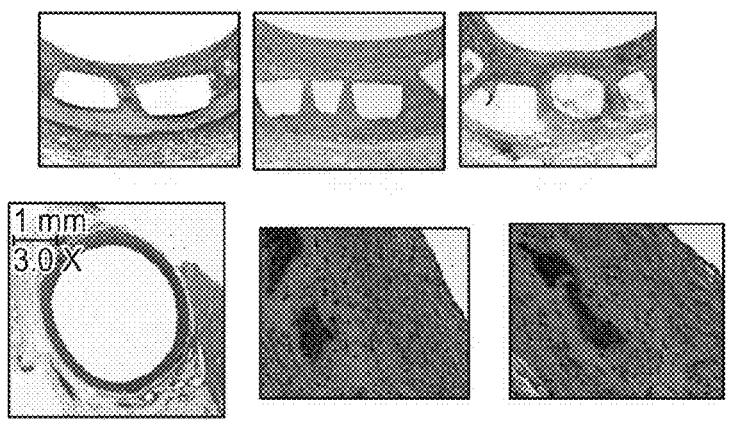

A tube is made by spraying an amorphous copolymer poly (L-lactide-co-glycolide) with 85% lactide and 15% glycolide. The polymer and rapamycin analog can be dissolved in a solvent and can be sprayed together to incorporate the rapamycin into the polymer stent. A mandrel is placed underneath an ultrasonic spray nozzle (Micromist System with Ultrasonic Atomizing Nozzle Sprayer, Sono-Tek, N.Y.) which is rotating at 80 rpm and move longitudinally at a rate of 0.050 inches/minutes. A solution of 11 to 1 ratio of poly (L-lactide-co-glycolide) and rapamycin analog on the mandrel. The resulting tube has a thickness of 0.17 mm. The tube is heated at 45° C. for about 60 hours, annealed at 90° C. for 2 hours, and cooled to ambient or room temperature within 10 seconds. The annealed tube is then cut with a UV laser to the design shown in FIG. 34 (shown in its crimped state). The cut stent is annealed at 90° C. and slowly cooled from the annealing temperature to ambient temperature within eight hours. The stent delivery system is then packaged in a pouch and sterilized by gamma radiation.

The heat treated stent has higher radial strength than the non-treated stent (Table 19).

TABLE 19

Comparison of Radial Strength of Treated and Non-treated Stent.

| Type | No Heat Treatment | Heat Treatment |
|---|---|---|
| Radial Strength After Laser Cutting Stent | 7 Psi | 14 Psi |
| Radial Strength After Crimping Stent | 6 Psi | 9 Psi |
| Radial Strength After 30 kGy Ebeam Sterilization | 3 Psi | 8 Psi |
| Radial Strength when expanded at Tg | n/a | 12.5 Psi |

Figure 31:
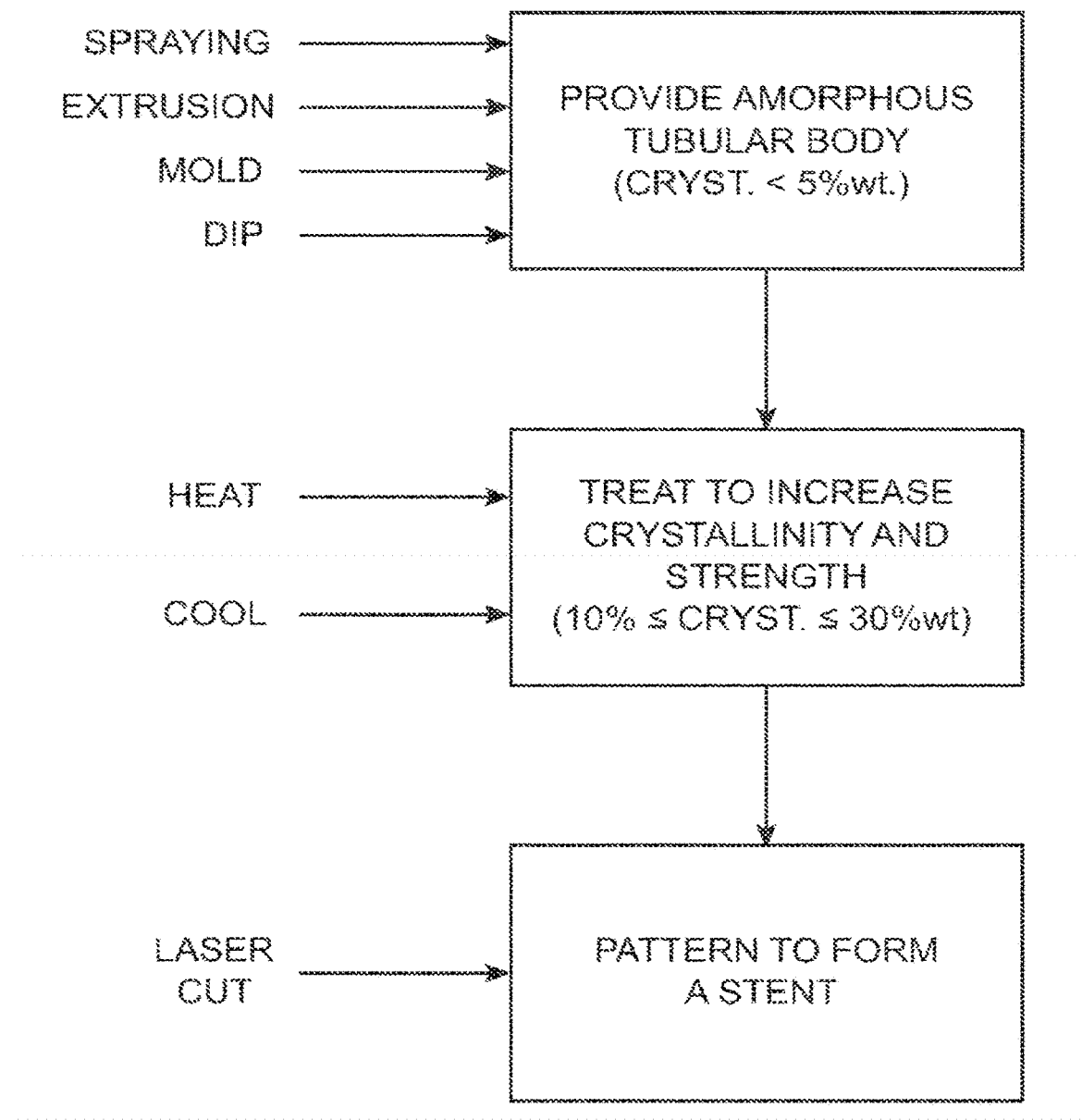
FIG. 31 is a block diagram illustrating the principal steps of the methods of the present invention in one embodiment.

Thus, as shown in FIG. 31, methods according to the present invention initially provide for a tubular body comprised of an amorphous polymer, where the tubular body may be formed by extrusion, molding, dipping, or the like, but is preferably formed by spraying onto a mandrel. The tubular body is annealed to increased crystallinity and strength, usually by the heating and cooling processes described above. The tubular body is then patterned to form a stent or other endoprosthesis, typically by laser cutting, usually after at least one annealing treatment. Optionally, the tubular body may be treated both before and after patterning, and may be treated by annealing more than once both before and after the patterning.

Figure 32A:
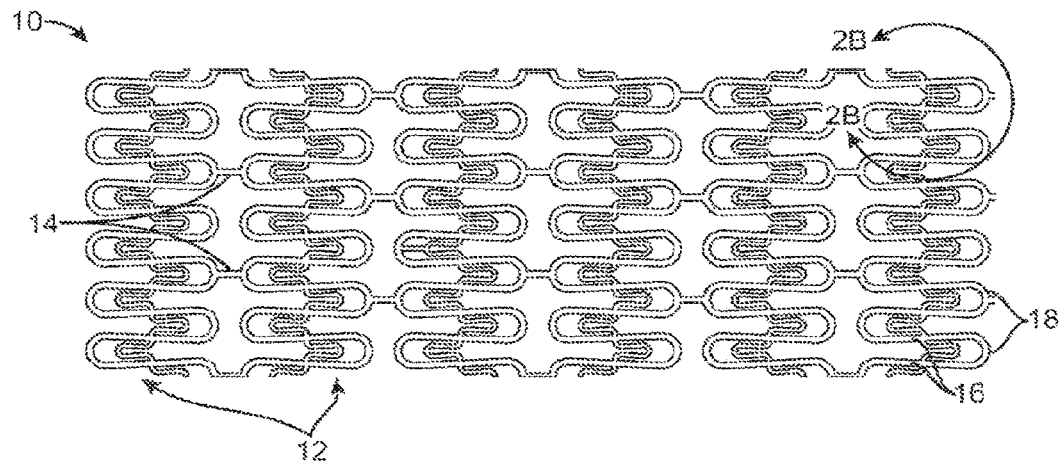
FIGS. 32A and 32B illustrate an exemplary stent structure which may be fabricated using the methods of the present invention.
Figure 32B:
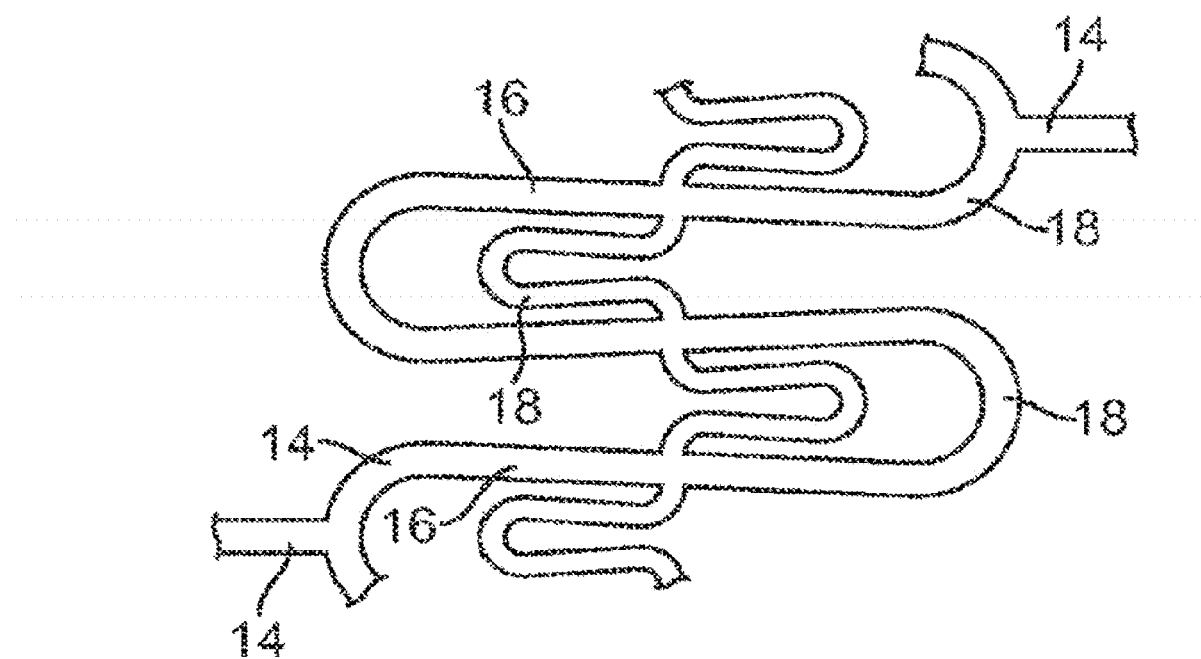
Figure 33:
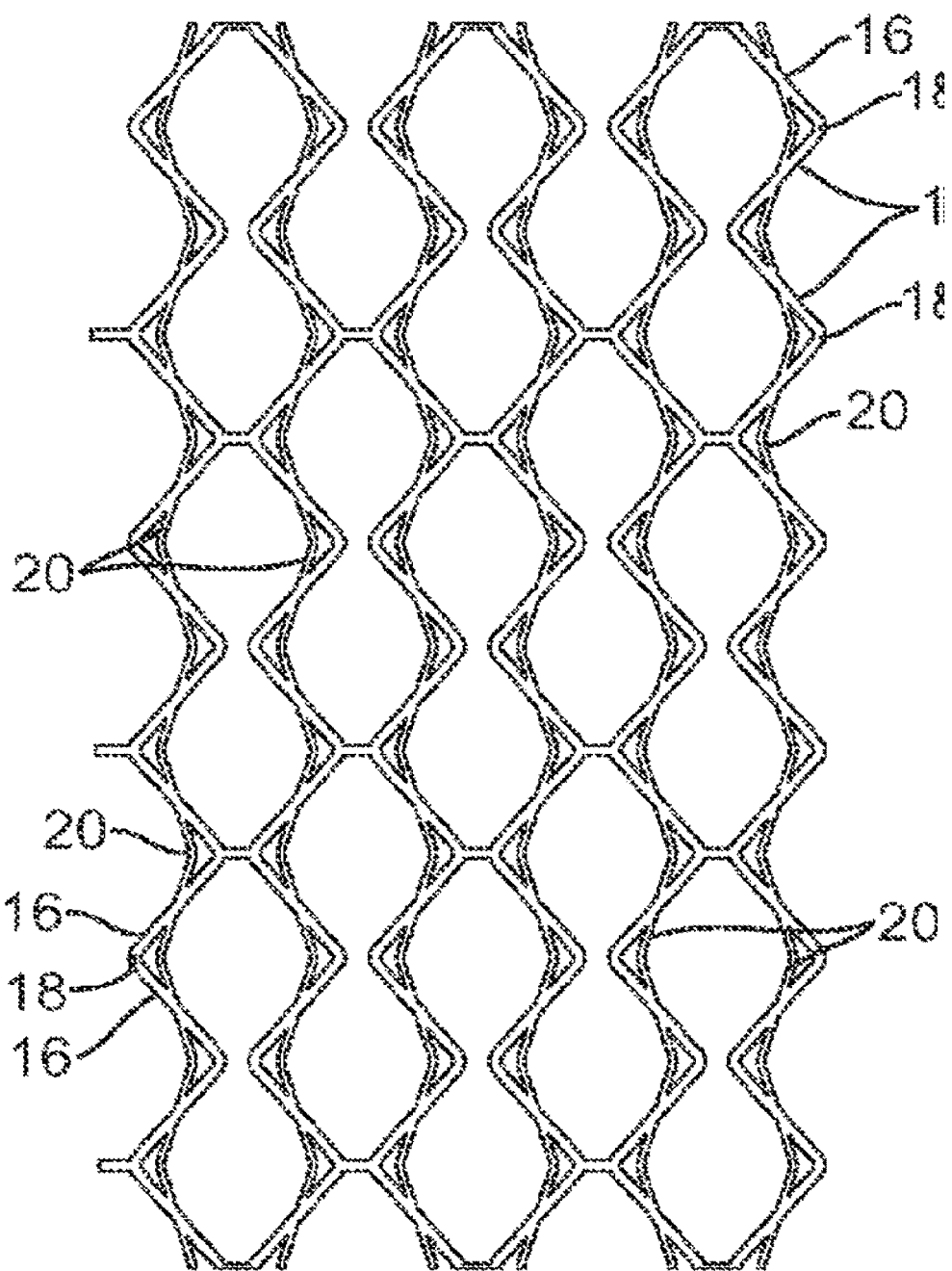
FIG. 33 illustrates the stent of FIGS. 32A and 32B in a radially expanded configuration.

Referring now to FIGS. 32A and 32B, a stent 10 suitable for modification by the present invention has base pattern including a plurality of adjacent serpentine rings 12 joined by axial links 14. As illustrated, the stent 10 includes six adjacent serpentine rings 12, where each ring includes six serpentine segments comprising a pair of axial struts 16 joined by a hinge-like crown 18 at one end. The number of rings and segments may vary widely depending on the size of the desired size of the stent. According to the present invention, a supporting feature 20 is disposed between adjacent axial struts 16 and connected so that it will expand, usually elongate, circumferentially with the struts, as shown in FIG. 3. The supporting features 20 are in a generally closed U-shaped configuration prior to expansion, as shown in FIGS. 32A and 32B, and open into a shallow V-shape along with the opening of the axial struts 16 about the crowns 18 during radial expansion of the serpentine rings 12, as shown in FIG. 33. Supporting features 20 enhance the hoop strength of the stent after radial expansion, help resist recoil after expansion is completed, and provide additional area for supporting the vascular or other luminal wall and optionally for delivering drugs into the luminal wall.

Example 33

Novolimus Eluting Bioresorbable Stent in a Clinical Trial

DESolve Nx was a prospective, multicenter international trial evaluating the DESolve Nx Novolimus Eluting Coronary Scaffold System of the present invention. The trial was conducted at 13 international centers across Europe, Brazil and New Zealand with enrollment of 126 patients. The trial was designed to evaluate single de novo coronary artery lesions with a reference vessel diameter between 2.75 and 3.0 mm and lesion length <12 mm Scaffold sizes available were 3.0, 3.25, 3.5 mm diameters and 14 and 18 mm lengths. Study follow up for clinical events was scheduled for 30 days, six months, 12 months and yearly until five years. Imaging endpoint assessments were planned for six month follow up (QCA for all patients and intravascular ultrasound (IVUS) OCT in a subset of patients) and 12 month follow up (Multi-slice computed tomography (MSCT) in a subset of patients).

The primary endpoint of the study was in-scaffold late lumen loss assessed at the six month time point. Key secondary endpoints included:

Clinical: (30 days, 6 m, 12, 2-5 years)
MACE (Major Adverse Cardiac Events) a composite of Cardiac Death, Target Vessel MI or Clinically-Indicated Target Lesion Revascularization
Scaffold Thrombosis
QCA (6 m)
In Segement late lumen loss
Binary Restenosis
% Diameter Stenosis
IVUS (6 m)
In scaffold % Volume Obstruction
Malapposition
OCT (6 m)
In scaffold % obstruction
Strut Coverage
MSCT (12 m)
% DS
Lumen Area
Patient Disposition and Follow Up:

A total of 126 patients (126 lesions) were enrolled. 6 m follow up was available on:

Clinical Follow Up: 120 patients (98%)
Serial QCA Follow Up: 113 patients (92%)
Serial IVUS Subset Follow Up: 40 patients (87%)
Serial OCT Subset Follow Up: 38 patients (83%)
Key Baseline Characteristics:

TABLE 21

| Patient Characteristics, % unless stated | N = 126 |
|---|---|
| Age, years (mean ± SD) | 62.0 ± 9.8 |
| Male | 68.3% |
| Diabetes mellitus | 21.4% |
| Hypercholesterolemia | 70.6% |
| Hypertension | 70.6% |
| Previous MI | 44.4% |
| Previous PCI | 35.7% |
| Unstable Angina | 12.7% |

| Patient Characteristics, % unless stated | N = 126 |
|---|---|
| Age, years (mean ± SD) | 62.0 ± 9.8 |
| Male | 68.3% |
| Diabetes mellitus | 21.4% |
| Hypercholesterolemia | 70.6% |
| Hypertension | 70.6% |
| Previous MI | 44.4% |
| Previous PCI | 35.7% |
| Unstable Angina | 12.7% |

Lesion Characteristics (QCA):

TABLE 22

| Lesion Characteristics | N = 126<br>$N_L$ = 126 |
|---|---|
| Target-vessel | |
| LAD | 28% (48) |
| LCX | 31% (39) |
| RCA | 31% (39) |
| Calcium (moderate/severe) | 18% (23) |
| Eccentricity | 44% (55) |
| Pre-TIMI 3 flow | 97% (122) |
| Lesion length, mm | 11.20 ± 3.77 |
| Reference diameter (int.), mm | 3.06 ± 0.31 |
| MLD, mm | 0.92 ± 0.40 |
| % DS | 69.9 ± 12.3 |

| | N = 126<br>NL = 126 |
|---|---|
| Target-vessel | |
| LAD | 28% (48) |
| LCX | 31% (39) |
| RCA | 31% (39) |
| Calcium (moderate/severe) | 18% (23) |
| Eccentricity | 44% (55) |
| Pre-TIMI 3 flow | 97% (122) |
| Lesion length, mm | 11.20 ± 3.77 |
| Reference diameter (int.), mm | 3.06 ± 0.31 |
| MLD, mm | 0.92 ± 0.40 |
| % DS | 69.9 ± 12.3 |

6 m Clinical Outcomes:

TABLE 23

| Hierarchical Events<br>0 to 180 days, n (%) | (N = 122)* |
|---|---|
| Major Adverse Cardiac Events | 3.28% |
| Cardiac Death (Probable ST)[+] | 1 (0.8%) |
| Target vessel MI** | 1 (0.8%) |
| Q-wave MI | 0 (0.0%) |
| Non-Q-wave MI | 1 (0.8%) |
| Clinically Indicated-TLR PCI | 2 (1.6%) |
| Definite Stent Thrombosis[+] | 0 (0.0%) |

*Modified Intent To Treat = those patients in which a scaffold was implanted;
[+]ARC-defined;
ST = stent thrombosis;
**MI during follow up attributed to multi modality imaging procedure.

6 m Diabetes Sub Analysis:

TABLE 24

| Hierarchical Events<br>0 to 180 days, % (n) | Diabetes<br>(N = 26)* | Non Diabetes<br>(N = 96) |
|---|---|---|
| Major Adverse Cardiac Events | 1/26 | 3/96 |
| Cardiac Death (Probable ST)* | 0 | 1/96 |
| Target vessel MI[+] | 1/26 | 0 |
| Q-wave | 0 | 0 |
| Non-Q-wave | 1/26[+] | 0 |
| Clinically Indicated-TLR PCI | 0 | 2/96 |
| Definite Stent Thrombosis* | 0 | 0 |

Serial QCA outcomes Post Procedure and at 6 m: (N = 126, post procedure N = 113 at 6 m):

TABLE 25

Post-Procedure QCA

| Variable | N = 126 |
|---|---|
| IN-SCAFFOLD | |
| Reference diameter (int.), mm | 3.09 ± 0.26 |
| MLD, mm | 2.67 ± 0.28 |
| % DS | 13.5 ± 7.8 |
| Acute gain, mm | 1.73 ± 0.45 |
| IN-SEGMENT | |
| Reference diameter (int.), mm | 3.04 ± 0.30 |
| MLD, mm | 2.59 ± 0.30 |
| % DS | 14.5 ± 7.9 |
| Acute gain, mm | 1.66 ± 0.44 |
| Balloon:artery ratio | 1.11 ± 0.08 |

Values are presented as mean ± standard deviation

TABLE 26

Acute Recoil: Measured at Post-Procedure (Final) Angiogram

| Variable | N = 126 |
|---|---|
| % Acute recoil | 6.6 ± 6.2 |

Values are presented as mean ± standard deviation

TABLE 27

QCA at 6 Months FU

| Variable | N = 113 |
|---|---|
| IN-SCAFFOLD | |
| Reference diameter (int.), mm | 3.01 ± 0.29 |
| MLD, mm | 2.45 ± 0.44 |
| % DS | 18.3 ± 13.6 |
| Late lumen loss, mm | 0.21 ± 0.34 |
| Median late lumen loss, mm*) | 0.11 [0.04, 0.21] |
| IN-SEGMENT | |
| Reference diameter (int.), mm | 2.98 ± 0.31 |
| MLD, mm | 2.34 ± 0.44 |
| % DS | 2.13 ± 13.0 |
| Late lumen loss, mm | 0.25 ± 0.34 |
| Binary Restenosis | 3.5% (4) |

Values are presented as mean ± standard deviation or percentage of total, median and interquartile range [25%, 75%]

TABLE 28

Edge Analysis

| Variable | Post-Procedure N = 126 | 6-Month FU N = 113 |
|---|---|---|
| Proximal Edge | | |
| MLD, mm | 2.93 ± 0.36 | 2.70 ± 0.44 |
| % DS | 8.2 ± 7.3 | 13.1 ± 10.4 |
| Late lumen loss, mm | — | 0.22 ± 0.30 |
| Distal Edge | | |
| MLD, mm | 2.77 ± 0.35 | 2.58 ± 0.38 |
| % DS | 7.0 ± 6.3 | 11.3 ± 8.8 |
| Late lumen loss, mm | — | 0.20 ± 0.25 |

Values are presented as mean ± standard deviation

Figure 41:
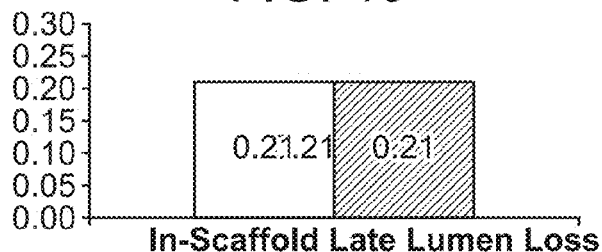
FIG. 41 shows 6 m diabetes subset QCA outcomes.

FIG. 41 shows 6 m diabetes subset QCA outcomes.

Figure 42:
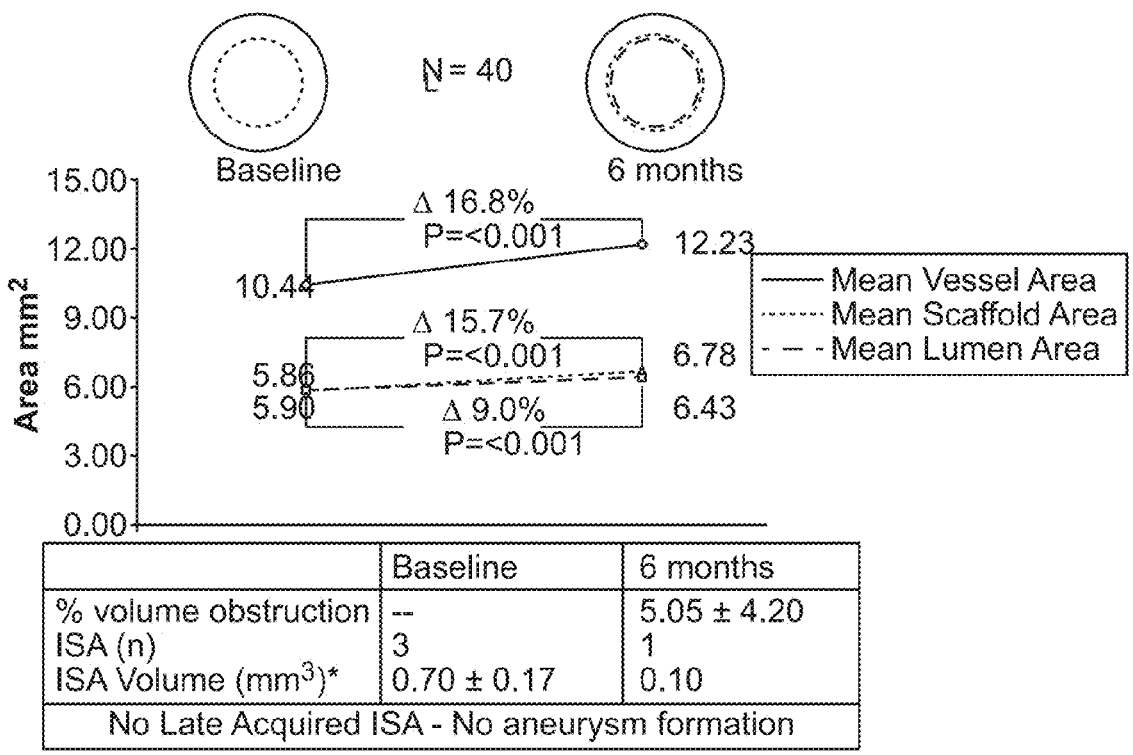
FIGS. 42 and 43 show serial IVUS outcomes at baseline (post procedure) and at 6 m: (N=40).
Figure 43:
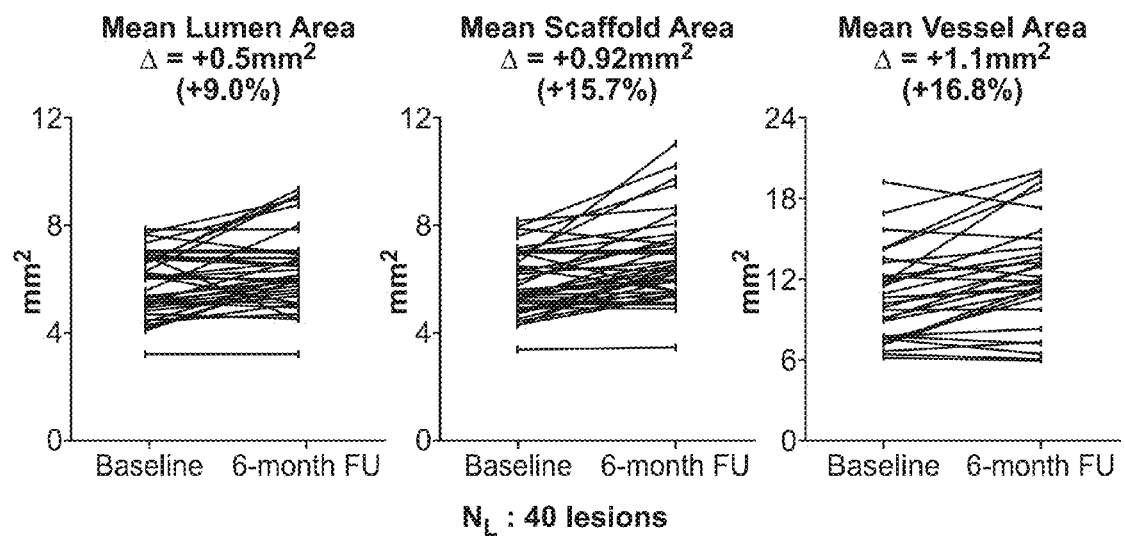

FIGS. 42 and 43 show serial IVUS outcomes at baseline (post procedure) and at 6 m: (N=40).

Figure 44:
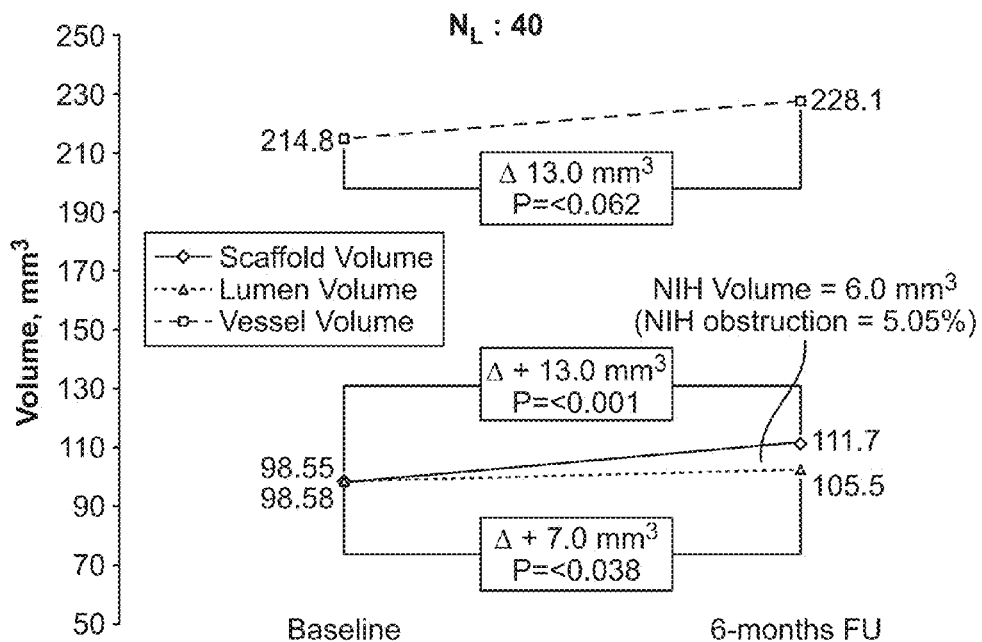
FIG. 44 shows vessel, scaffold, and lumen areas and volumes.

FIG. 44 shows vessel, scaffold, and lumen areas and volumes.

Figure 45:
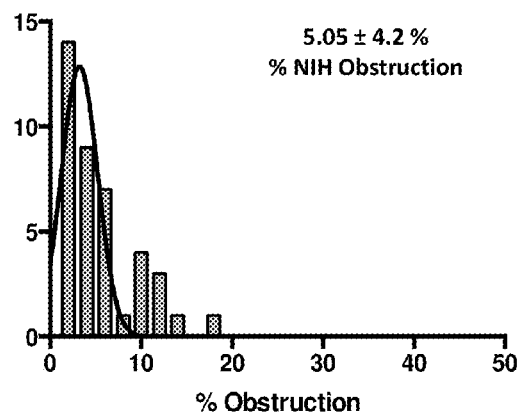
FIG. 45 shows the distribution of % NIH obstruction.

FIG. 45 shows the distribution of % NIH obstruction.

Figure 46:
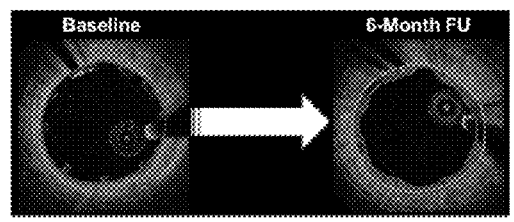
FIG. 46 shows serial OCT outcomes at (scaffold and lumen area) baseline (post-procedure) and at 6 m: (N=38).

FIG. 46 shows serial OCT outcomes at (scaffold and lumen area) baseline (post-procedure) and at 6 m: (N=38).

Figure 47:
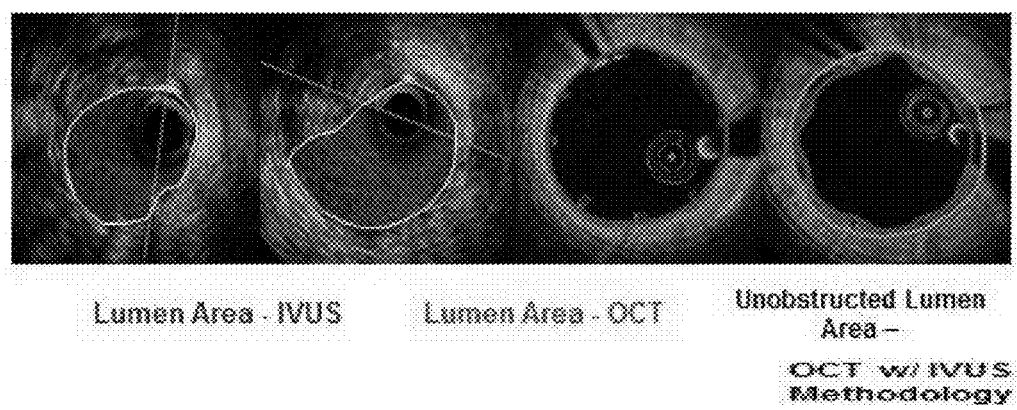
FIG. 47 is a series of IVUS/OCT images which provide a lumen area comparison analysis FIG. 48 provides a graphical lumen area comparison analysis.
Figure 48:
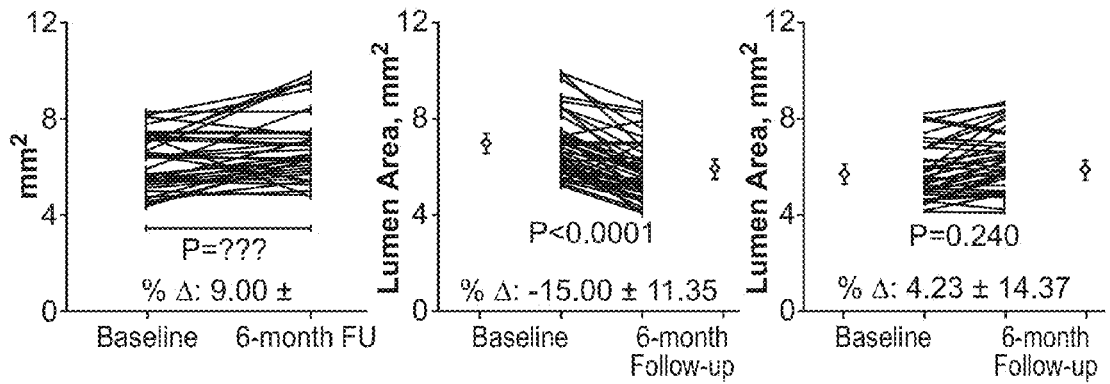

FIG. 47 is a series of IVUS/OCT images which provide a lumen area comparison analysis FIG. 48 provides a graphical lumen area comparison analysis.

| In-scaffold Strut | $N_S = 14.261$ | | |
|---|---|---|---|
| Level Analysis | Baseline | 6 m | P value |
| ISA (n) | 15 | 5 | |
| ISA Area (mm$^2$) | 0.19 ± .015 | 0.35 ± .015* | 0.33 |

$N_S$ Number of Struts;
$N_L$ Number of Lesions
*One patient with post baseline ISA (area 0.30 mm$^2$) due to resolution of thrombus visible on OCT FIGS. 49 and 50 provides an NIH quantification by OCT.

FIGS. 51 and 52 provide an NIH thickness and distribution analysis.

FIGS. 53 and 54 provide a strut coverage (safety surrogate) analysis.

Example 19

Tapered Main Artery and Bifurcation

An artery may be tapered such that the proximal segment is larger in diameter than the distal segment. This typically occurs at a bifurcation of a main artery and a sidebranch. The current embodiment of the device may be expanded such that the sizing is appropriate for the distal segment of the main artery, and somewhat smaller in diameter than the proximal segment of the main artery. In a normal balloon expandable scaffold or stent expanded in such a manner, the proximal segment would then be malapposed to the vessel wall.

The malapposition may be resolved by expanding the proximal segment of the scaffold with a post-dilatation balloon to a larger diameter positioned appropriately at the proximal segment. The current embodiment of the device has the ability to be expanded to a large diameter at the proximal segment such that the scaffold does not fracture.

Because the current embodiment of the device has the ability to self-expand over time, the malapposition would be resolved and the scaffold would self-appose to the artery wall.

For example, a scaffold is manufactured from a 4.0 mm tube. The scaffold is deployed in an artery that is tapered from 3.5 mm to 2.75 mm (proximal to distal). The device is crimped onto a delivery system, delivered to the tapered deployment site, and expanded to 3.0 mm. The 2.75 mm distal segment is well apposed, and the proximal 3.5 mm segment is malapposed. The malapposition is resolved by either post-dilating the proximal segment with a larger 3.5 mm balloon without fracturing the scaffold, or allowed to resolve over a period of time by the ability of the device to self-resolve malapposition.

Example 20

Balloon Expansion Followed by Self Expansion

A biodegradable stent is fabricated from a polymeric sheet comprising lactide-co-caprolactone (or a blend of lactide and caprolactone) wherein the sheet is joined at its ends via solvent bonding, ultrasonic bonded, inductive heating bonded, or heat welding. The polymeric sheet has an initial diameter of 4.5 mm. The stent is treated, and crimped without fracture onto a balloon catheter and sterilized at 30 kGy. After sterilization, the stent at body temperature is balloon expanded from a crimped configuration to a first expanded diameter of 3.5 mm and wherein the stent further self expands to a second larger diameter of 3.75 within 24 hours. The stent does not have fractures (completely broken struts) at the first or second expanded diameters and has sufficient strength to support a body lumen. The stent is patterned before the sheet is joined or after.

Example 21

Self Expansion Followed by Balloon Expansion

A biodegradable stent comprising a polymeric material comprising lactide-co-glycolide (or a blend of lactide and glycolide) which is molded into an initial diameter that is 0.9-1.5 times the nominal/labeled deployed stent diameter. The initial diameter is 4.5 mm and the nominal deployment/labeled diameter is 3.5 mm. The stent is crimped to a smaller diameter of about 1.5 mm onto a catheter without fracture and sterilized at 30 kGy. The stent at body temperature (about 37 C) self expands from the crimped configuration to a first expanded diameter of about 3.75 mm within about 30 minutes and further expanded by balloon to a second expanded diameter of 4.75 mm without fracture and have sufficient strength to support a body lumen. The stent is patterned by the mold or after the mold or the mold forms a tubular body that is subsequently patterned.

Example 22

Incorporation of at Least One Solvent to Allow Expansion of a Stent without Fracture A biodegradable stent comprising a polymeric material formed into a tubular body wherein the polymeric material comprises lactide-co-caprolactone (or a blend of lactide and caprolactone). The tubular body is formed by spraying the polymeric material onto a mandrel. DCM is incorporated into the solution to such that the amount of DCM after treatment is 1.5% by weight of the polymeric material. The tubular body is treated, is patterned, and is crimped onto a delivery system without fracture and sterilized. The stent at body temperature (about 37 C) is expandable from the crimped configuration to an expanded diameter that is 1.2 times the nominal deployment diameter (labeled diameter) of the stent without fracture and having sufficient strength to support a body lumen.

Example 23

Incorporation of Monomer in Amounts Sufficient to Allow Expansion of the Stent without Fracture A biodegradable stent is formed by 3-D printing of polymeric material comprising polylactide-co-glycolide blended with about 30000 ppm of ε-caprolactone monomer. The stent is treated and crimped to a smaller diameter of about 1 mm without fracture, and sterilized. The stent at body temperature is expanded from the crimped configuration to the expanded diameter of nominal or higher without fracture and having sufficient strength to support a blood vessel.

Example 24

Crimping without Fracture

A biodegradable stents having the pattern of FIG. 1 were laser cut from polymeric tubes made by spraying polymeric material comprising poly(L-lactide-co-ε-caprolactone) copolymers or blends and treated, and patterned into stents. Five stents having an initial inner diameter of 2.5 mm are subjected to crimping at 45° C. After crimping, the inner diameters of the stents are 2.0 mm, 1.8 mm, 1.4 mm, 1.6 mm, and 1.2 mm, 1.0, 0.8 mm respectively. None of the five stents exhibit significant cracks or any fractures.

Example 25

Pressure Treatment to Control Crystallinity

A biodegradable stent comprising a polymeric material is formed by spraying a solution of 85% L-lactide to 15% glycolide onto a mandrel. The material has crystallinity of 40% The material is then placed in a high pressure stainless steel vessel, sealed, and subjected to carbon dioxide at a pressure of 700 psi for 24 hours. After the exposure to carbon dioxide, the crystallinity is about 25% by XRD.

Example 26

Expansion of a Biodegradable Stent Above Nominal Deployment without Fracture

A biodegradable stent comprising poly(L-lactide-co-ε-caprolactone) polymer is molded into a tubular body, is treated, and is patterned. The stent has an initial diameter of 3.8 mm. The stent is crimped to a 1 mm diameter without fracture and mounted on a 3.0 mm nominal/labeled balloon of a catheter and sterilized at 30 kGy. The stent at body temperature is balloon expanded to above the nominal/labeled deployment diameter of 3.0 mm by expanding it to 4.8 mm without fracture and have sufficient strength to support a blood vessel.

Example 27

Drug Incorporation into the Polymeric Material or Tubular Body for Extended Delivery 180 mg Poly-DL-lactide is dissolved in 60 ml of dichloromethane and 1 mg of rapamycin is added to the solution. The mixture is mixed for 10 minutes. The mixture is then sprayed onto a mandrel to form a tubular body. After dichloromethane evaporates, the mandrel is removed from the tube and tube is allowed to air-dried for 48 hours. The tubular body is patterned into a stent. The stent is crimped without fracture and mounted on a balloon of a catheter and sterilized at 30 kGy. The stent body temperature is expanded from a crimped configuration to deliver the drug over an extended period of time between 3 months and 2 years.

Example 28

Treatment to Control of One or More of Crystallinity, Tg, and $M_W$

A biodegradable stent as in any of the examples from A though H wherein the polymeric material is treated to control at least one of crystallinity, Tg, or MW, wherein the crystallinity ranges from 1% to 50%, Tg ranges from >37 C to 50 C, and MW ranges from 30 Kda to 700 Kda wherein the stent is capable to be crimped and expanded from a crimped condition to a deployed condition without fracture and have sufficient strength to support a body lumen.

Example 29

Biodegradable Stent Properties

A biodegradable stent as in Examples 20 through 28 comprising a polymeric material wherein the material has at least one of elastic modulus of 0.35 GPa or higher, strength of 2 psi or higher, recoil from an expanded diameter of 10% or less; wherein the stent is capable to be crimped from an expanded condition to a crimped condition without fracture and wherein the stent is capable at body temperature to be expanded to nominal diameter or higher without fracture.

The invention provides polymeric materials, including biodegradable stents, and methods of their fabrication. Various aspects of the invention described herein may be applied to any of the particular applications set forth below or in any other type of setting. The invention may be applied as a standalone system or method, or as part of an integrated system or method. It shall be understood that different aspects of the invention can be appreciated individually, collectively, or in combination with each other.

Numerous modifications, variations, alternatives and equivalents to the present disclosure, as set forth in the embodiments and illustrative examples described herein, will be apparent to persons of ordinary skill in the art. All such modifications, variations, alternatives and equivalents are intended to be within the scope of the present disclosure and the appended claims.

Example 30

Fabricating a Stent and Treatment of Stent by Heat at a Temperature Above Tg Before Patterning, and then Crimping the Stent onto a Delivery System at a Temperature Below Tg A biodegradable stent comprising a polymeric material formed optionally into a tubular body wherein the polymeric material comprises lactide-co-caprolactone (or a blend of lactide and caprolactone). The tubular body is formed optionally by spraying the polymeric material onto a mandrel. DCM (or other suitable solvent capable of dissolving completely the polimeric material) is incorporated into the solution to such that the amount of DCM after treatment is less than 1.5% by weight of the polymeric material. The tubular body is treated by heating at a temperature above Tg of the polimeric material for a time period ranging from 10 seconds to 5 hours, and/or cooling at a temperature below Tg of the polymeric material, is patterned at substantially the same diameter as the formed diameter, and is crimped onto a delivery system at a temperature below Tg of the polymeric material. The stent at body temperature (about 37 C) is expandable from the crimped configuration to an expanded diameter that is 1.2 times the nominal deployment diameter (labeled diameter) of the stent without fracture and having sufficient strength to support a body lumen.

Example 31

Fabricating a Stent and Treatment of Stent at Substantially the Same Diameter of the Formed Polymeric Tube Outer Diameter, by Pressure, Heat at a Temperature Above Tg, and Optionally Stretching; Before Patterning; and then Crimping the Stent onto a Delivery System at a Temperature Below Tg A 4.00 mm outer diameter and 3.70 mm inner diameter polymeric tube comprising 85:15 poly(L-lactide-co-glycolide) formed by extrusion, spraying, dipping, or the like. This tube is placed inside a metal (or glass mold) mold with approximately 4.0 mm diameter cylindrical hole (inner diameter of the mold), (or optionally 4.0 mm inner diameter mold, or optionally less than 4.0 mm ID mold, or optionally 4.1 mm ID mold, or optionally a mold ID with 0.9-1.15 times the formed OD of the polymeric material, or optionally a mold ID with 0.9-1.1, times the formed OD of the polymeric material. The mold optionally could be composed of two halve for ease of tube placement and removal. The mold and/or the polymeric material is heated to above the polymeric materialTg. The ID of the polymeric material is pressurized at pressure(s) ranging from 100 PSi to 5000 psi in a fraction of a second to 5 minutes, and the polymeric material is optionally stretched by an amount ranging from 10% to 500% of the polymeric material length in a time ranging from a fraction of a second to 5 minutes. The polymeric material is optionally cooled at a temperature below Tg in a time ranging from a fraction of a second to 50 minutes. The compressed polymeric tubing with approximately 4.00 mm outer diameter (+/−0.1 mm) and an Inner diameter ranging from 3.8 to approximately 3.6 mm inner diameter is then removed. The wall of the polymeric tube in this example is compressed approximately 0.0005". The modified tube is patterned at substantially the same diameter, and subsequently coated with a drug/or drug-polymer and subsequently crimped onto a delivery system at a temperature below Tg of the polymeric material and then sterilized. The stent at body temperature (about 37 C) is expandable from the crimped configuration to an expanded diameter having sufficient strength to support a body lumen.

Example 32

Novolimus Eluting Bioresorbable Coronary Stent System in the Porcine Model

Studies were performed in a porcine model with the Novolimus Eluting Bioresorbable Coronary Stent System which combines a polymer stent coated with a thin topcoat layer of polymer with Novolimus. The stents in the studies comprised PLLA, PLLAPGA, PLLAPCL, Poly(L lactide-co-Glycolide) and poly(L lactide-co-caprolactone). At least one of the studies is described below. The nominal drug dose in the coating on the 18 mm length stent is 85 µg of Novolimus and coating is poly(L-lactide-co-glycolide).

The purpose of the studies are to evaluate the efficacy and safety of the polymeric degradable drug eluting stent after a period of 1 m, 3 m, 6 m, 9 m, 1 year and 2 years. The vascular response, including the arterial minimal lumen diameter and percent stenosis, will be evaluated in all vessels using quantitative vessel angiography (QCA) at 1 m, 3 m, 6 m, 9 m, 1 year and 2 years. Optical coherence tomography (OCT) will also be performed at time points to assess stent apposition and recoil. Additionally, histopathologic analysis of the coronary arteries will be performed at 1 m, 3 m, 6 m and 2 years to evaluate the cellular response to the stents. Another purpose of this study is to evaluate pharmacokinetics (PK) of the released drug at 3 days, 7 days, 28±2 days, and longer timepoints; drug release will be assessed by analysis of the drug remaining on the stents and uptake of the drug by the tissue.

A nonatherosclerotic swine model was chosen. Hybrid farm pigs (Landrance-Yorkshire) were selected for use in studies up to 3 m in length and Yucatan Mini Swine were selected for use in the 6 m and longer term studies due to starting size and growth expectations. When possible, stents are implanted in the 3 coronary arteries (left circumflex artery [LCx], left anterior descending artery [LAD] and right coronary artery [RCA]), and in the left and right internal mammary arteries (IMAs) per animal.

Upon assignment to the study and until sacrifice, animals will be monitored and observed at least twice a day. To prevent or reduce the occurrence of thrombotic events, animals are treated daily, with acetylsalicylic acid (325 mg, per os [PO]) and clopidogrel (300 mg on the first day and 75 mg daily afterwards, PO), beginning at least 3 days before intervention and continuing until sacrifice. The drugs will be crushed to powder and mixed with their food; therefore, treatment will not be administered when animals are fasted. Fasting (food, including any dietary supplements) will be conducted the morning prior to interventional procedures and scheduled sacrifice. Water will not be withheld. Animals will be tranquilized with ketamine, azaperone and atropine administered intramuscularly [IM]. Animal weight will be recorded. Anesthesia induction will be achieved with propofol injected intravenously [IV]. Upon induction of light anesthesia, the subject animal will be intubated and supported with mechanical ventilation. Isoflurane in oxygen will be administered to maintain a surgical plane of anesthesia. Intravenous fluid therapy will be initiated and maintained throughout the procedure. The rate may be increased to replace blood loss or to correct low systemic blood pressure. To prevent postoperative infection, animals will be given prophylactic antibiotic Draxxin® IM. Additional doses may be administered as deemed appropriate. In order to prevent pain sensitization and minimize postoperative pain, Torbugesic (butorphanol) will be administered IM as preemptive analgesia. After induction of anesthesia, the left or right femoral artery will be accessed through an incision made in the inguinal region. Bupivacain IM will be infiltrated into the femoral access site to achieve local anesthesia and manage pain after surgery. An arterial sheath will be introduced and advanced into the artery. An initial heparin bolus will be administered and ACT will be measured at least every 30 minutes and recorded. The device will not be introduced until ACT is confirmed to be >300 seconds. If ACT is <300 seconds, additional heparin will be administered. Under fluoroscopic guidance, a guiding catheter will be inserted through the sheath (6F) and advanced to the appropriate location. After placement of the guiding catheter, nitroglycerin will be delivered to achieve vasodilatation and angiographic images of the vessel will be obtained with contrast media to identify the proper location for the deployment site (designated pre-stent angiographies). A segment of coronary artery will be chosen and a guidewire will be inserted into the chosen artery. QCA will be performed at this time to document the reference diameter for stent placement. OCT will be performed before implantation to confirm vessel sizing at three locations per coronary vessel.

Stent Deployment Procedures: The stent will be introduced into the selected artery (diameter range of 2.6 to 3.0 mm if possible) by advancing the delivery system through the guiding catheter, over the guide wire to the deployment site. After the stent enters the guide catheter, there will be at least a one minute soak wait before deploying the stent. The stent will then be deployed. The balloon will be inflated at a slow rate: starting with 10 second intervals per atmosphere, bring the balloon to 2 atm. Further expansion completed at 3-5 second intervals for each subsequent atmosphere of pressure. This is approx. 40-50 seconds to nominal pressure. Final pressure is maintained for 20-30 seconds. An angiogram of the balloon at full inflation will be recorded (designated balloon angiography) and the inflation pressure will be noted. After the target stent to artery ratio has been achieved, vacuum will be slowly applied to the inflation device to deflate the balloon. Complete balloon deflation will be verified fluoroscopically. A second inflation may be conducted if a stent is not well apposed against arterial wall or if an animal is at risk. Injection of nitroglycerin will be repeated and a final angiogram of the treated vessel will be performed (designated post-stent angiography) to document device patency, and TIMI flow Implantation will be repeated in the other vessels.

OCT will be performed on animals to assess stent recoil. OCT will be performed before implantation to confirm vessel sizing at three locations per coronary vessel. After all implants are completed, OCT will be performed again for the same (first) stent, followed by every other stent implanted in the coronaries (designated end of implant OCT).

Following the successful deployment of stents and completion of angiography, all catheters and the sheath will be removed from the animal and the femoral artery will be ligated. The incision will be closed in layers with appropriate suture materials. An antibiotic ointment will be applied to the wound.

The fluoroscopic output from the stent implantation (pre-stent, balloon inflation, post-stent, and end of implant) and at explanation (final) was recorded in digital format. From these images, QCA measurements were obtained. OCT imaging was performed in animal after the first stent was implanted and after all implants had been completed. Several semi-quantitative parameters were employed to assess the biological response of vascular tissue to the stents by light microscopy examination of stained sections. Other organ samples were observed for any abnormal findings.

What is claimed is:

1. A biodegradable polymeric stent prosthesis, comprising:
a biodegradable polymeric material which has been formed as a substantially continuous tubular body and has an intended deployed diameter, said tubular body has been patterned at 1.1-1.5 times the intended deployed diameter, and has been crimped to a configuration having a smaller diameter than the intended deployed diameter, said stent prosthesis being expandable from the crimped configuration to a deployed configuration and having sufficient strength in the deployed configuration to support a blood vessel.

2. The biodegradable polymeric stent of claim 1, wherein the tubular body has been treated.

3. The biodegradable polymeric stent of claim 2, wherein the tubular body is patterned after treatment.

4. The biodegradable polymeric stent of claim 2, wherein the tubular body has been subjected to one or more treatments of heating after said tubular body has been patterned.

5. The biodegradable polymeric stent of claim 2, wherein the tubular body is subjected to more than one treatment.

6. The biodegradable polymeric stent of claim 2, wherein the treatment comprises at least one of pressurizing, vacuum, heating, cooling, cross-linking, exposure to radiation, and addition of additives.

7. The biodegradable polymeric stent of claim 2, wherein the treatment includes heating the tubular body above Tg and below the melting temperature of the polymeric material before crimping.

8. The biodegradable polymeric stent of claim 2, wherein the tubular body has been treated without substantially changing an outer tubular diameter.

9. The biodegradable polymeric stent of claim 1, wherein the tubular body is patterned at a diameter 1.1-1.3 times the intended deployed diameter.

10. The biodegradable polymeric stent of claim 1, further comprising one or more drugs.

11. The biodegradable polymeric stent of claim 1, wherein the biodegradable polymeric material has a molecular weight from 100 KDa to 1000 KDa.

12. The biodegradable polymeric stent of claim 1, wherein the polymeric material has an elastic modulus of at least 0.5 GPa.

13. The biodegradable polymeric stent of claim 1, wherein the polymeric material comprises one or more of polymers and copolymers.

14. The biodegradable polymeric stent of claim 1, wherein said tubular body has a concentricity of about 0.001 inch or less.

15. The biodegradable polymeric stent of claim 1, wherein said tubular body has a concentricity of at least about 90%.

16. The biodegradable polymeric stent of claim 1, wherein said tubular body has a concentricity of at least about 92%.

17. The biodegradable polymeric stent of claim 1, wherein the tubular body has been formed by spraying or dipping.

18. The biodegradable polymeric stent of claim 1, wherein the tubular body has been formed by printing.

19. The biodegradable polymeric stent of claim 1, wherein said stent further comprises radiopacity.

20. The biodegradable polymeric stent of claim 1, wherein the stent prosthesis is capable of being expanded from a crimped diameter to a deployed diameter without fracture.

21. The biodegradable polymeric stent of claim 1, wherein the intended deployed diameter is 3.5 mm.

22. The biodegradable polymeric stent of claim 1, wherein the biodegradable polymeric material comprises at least one material selected from the group consisting of poly-DL-Lactide, polylactide-co-gycolide, polylactide-co-polycaprolactone, poly(L-lactide-co-trimethylene carbonate), polytrimethylene carbonate and copolymers thereof, polyhydroxybutyrate and copolymers thereof; polyhydroxyvalerate and copolymers thereof, poly orthoesters and copolymers thereof, poly anhydrides and copolymers thereof, polylactide and copolymers thereof, polyglycolides and copolymers thereof, polycaprolactone and copolymers thereof, and polyiminocarbonates and copolymers thereof.

23. The biodegradable polymeric stent of claim 1, wherein said tubular body is formed at the patterned diameter.

24. The biodegradable polymeric stent of claim 23, wherein the stent prosthesis is capable of being expanded from a crimped diameter to a deployed diameter at body temperature.

25. The biodegradable polymeric stent of claim 23, wherein the intended deployed diameter is 3 mm.

26. The biodegradable polymeric stent of claim 1, wherein said stent has a recoil of less than 10% after expansion from the crimped configuration to the deployed configuration.

27. The biodegradable polymeric stent of claim 1, wherein said stent prosthesis is balloon expandable from the crimped configuration to the deployed configuration.

28. The biodegradable polymeric stent of claim 27, wherein said stent prosthesis self-expands prior to balloon expansion.

29. The biodegradable polymeric stent of claim 1, wherein the stent prosthesis length change after expansion from the crimped configuration to the deployed configuration is less than 15%.

30. The biodegradable polymeric stent of claim 1, wherein the patterned stent prosthesis comprises a plurality of adjacent serpentine rings formed of a plurality of crowns and struts, wherein adjacent serpentine rings are connected by a plurality of links.

31. The biodegradable polymeric stent of claim 1, wherein the longitudinal shortening of the stent prosthesis after expansion from the crimped configuration to the deployed configuration is less than 15%.

32. The biodegradable polymeric stent of claim 1, wherein the tubular body is patterned by laser.

* * * * *